United States Patent [19]
Christ et al.

[11] Patent Number: 5,843,918
[45] Date of Patent: Dec. 1, 1998

[54] ANTI-ENDOTOXIN COMPOUNDS

[75] Inventors: William J. Christ, Andover; Lynn D. Hawkins, Haverhill; Tsutomu Kawata; Daniel P. Rossignol, both of Andover, all of Mass.; Seiichi Kobayashi, Tsuchiurashi; Osamu Asano, Tsukuba, both of Japan

[73] Assignee: Eisai Co., Ltd., Tokyo, Japan

[21] Appl. No.: 472,820

[22] Filed: Jun. 7, 1995

Related U.S. Application Data

[60] Division of Ser. No. 935,050, Aug. 25, 1992, Pat. No. 5,530,113, which is a continuation-in-part of Ser. No. 776,100, Oct. 11, 1991, abandoned.

[51] Int. Cl.[6] .................. A61K 31/715; A61K 31/72; A61K 31/73
[52] U.S. Cl. .................. 514/53; 514/885; 536/123.13
[58] Field of Search ............. 514/53, 885, 889; 536/123.13

[56] References Cited

U.S. PATENT DOCUMENTS

| | | | |
|---|---|---|---|
| 4,495,346 | 1/1985 | Anderson et al. | 536/18.5 |
| 4,844,894 | 7/1989 | Ribi | 424/88 |
| 4,912,094 | 3/1990 | Myers et al. | 514/54 |
| 4,918,163 | 4/1990 | Young et al. | 530/387 |
| 4,929,604 | 5/1990 | Munford et al. | 514/53 |
| 5,013,661 | 5/1991 | Munford et al. | 435/197 |
| 5,041,427 | 8/1991 | Takayama et al. | 514/53 |
| 5,057,598 | 10/1991 | Pollack et al. | 530/387 |
| 5,066,794 | 11/1991 | Shiba | 536/55.3 |
| 5,134,230 | 7/1992 | Kusama et al. | 536/117 |
| 5,158,939 | 10/1992 | Takayama et al. | 514/53 |
| 5,158,941 | 10/1992 | Jadhav et al. | 514/62 |
| 5,191,072 | 3/1993 | Hasegawa et al. | 536/117 |

FOREIGN PATENT DOCUMENTS

| | | |
|---|---|---|
| 902875-A | 7/1984 | Belgium . |
| 905010-A | 12/1986 | Belgium . |
| 172581-A2 | 2/1986 | European Pat. Off. . |
| 330715-A1 | 9/1989 | European Pat. Off. . |
| 536969A2 | 11/1993 | European Pat. Off. . |
| 3833319-A | 9/1987 | Germany . |
| 1221387-A | 2/1988 | Japan . |
| 3135990-A | 10/1989 | Japan . |
| 881430 | 2/1988 | South Africa . |
| 2179945 | 3/1987 | United Kingdom . |
| 2220211 | 1/1990 | United Kingdom . |
| 91/01134 | 2/1991 | WIPO . |

OTHER PUBLICATIONS

Brinder et al., "123, Glycosylphosphonates of 2–Amino–2–Deoxy–Aldoses. Synthesis of a Phosphonate Analogue of Lipd $X^{1}$", Helvetica Chimica Acta 70:1341–1357, 1987.

Bone et al., "A Controlled Clinical Trial of High–Dose Methylprednisolone in the Treatment of Severe Sepsis and Septic Shock", The New England Journal of Medicine 317:653–658, 1987.
Hampton et al., "Lipid A Binding Sites in Membranes of Macrophage Tumor Cells", J. of Biol. Chem. 263:14802–14807, 1988.
Hinshaw et al., "Effect of High–Dose Glucocorticoid Therapy on Mortality in Patents with Clinical Signs of Systemic Sepsis", The New England Journal of Medicine 317:659–665, 1987.
Kinzy et al., "Synthesis of Glycopeptides of the Mucin Type Containing A β–D–GlepNAc–(1→3)–D–GalpNAc Unit", Carbohydrate Research 193:33–47, 1989.
Kirkland et al., "Diphosphoryl Lipid A Derived from Lipopolysaccharide (LPS) of *Rhodopseudomonas sphaeroides* Inhibits Activation", Infection and Immunity 59:131–136, 1991.
Krauss et al., "Structural Analysis of the Nontoxic Lipid A of Thodobacter Capsulatus 37b4", Eur. J. Biochem. 180:519–526, 1989.
Lei et al., "I. Detection of Lipopolysaccahride–Binding Sites on Splenocytes and Splenocyte Subpopulations", J. of Immunology 996–1005, 1988.
Lei et al., "II. Membrane Localization and Binding Characteristics", The J. of Immunology 141:1006–1011, 1988.
Qureshi et al., "Diphosphoryl Lipid A Obtained from the Nontoxic Lipopolysaccharide of *Rhodopseudomonas Sphaeroides* is an Endotoxin Antagonist in Mice", Infection and Immunity 59:441–444, 1991.
Roeder et al., "Endotoxic–Lipopolysaccharide–Specific Binding Proteins on Lymphoid Cells of Various Animal Species: Association with Endotoxin Susceptibility", Infection and Immunity 57:1054–1058, 1989.
Takayama et al., "Diphosphoryl Lipid A from *Rhodopseudomonas Sphaeroides* ATCC 17023 Blocks Induction of Cachectin in Macrophages by Lipopolysaccharide", Infection and Immunity 57:1336–1338, 1989.
Toepfer et al., "Muramic Acid Derivatives as Glycosyl Donors for the Synthesis of Muramyl–Containing Glycosphingolipids and Fatty Acids", Carbohydrate Resarch 202:193–205, 1990.
Wright et al., "CR3 (CD11b/CD18) Expresses One Binding Site for Arg–Gly–Asp–Containing Peptides and a Second Site for Bacterial Lipopolysaccharide", J. Exp. Med. 169:175–183, 1989.
Ziegler et al., "Treatment of Gram–Negative Bacteremia and Shock with Human Antiserum to a Mutant *Escherichia Coli*", The New England Journal of Medicine 307:1225–1230, 1982.

*Primary Examiner*—John Kight
*Assistant Examiner*—Howard C. Lee
*Attorney, Agent, or Firm*—Clark & Elbing LLP

[57] ABSTRACT

Disclosed are lipid A analogs useful for the treatment of septic shock and LPS-mediated activation of viral infection.

1 Claim, No Drawings

ANTI-ENDOTOXIN COMPOUNDS

This is a divisional of application Ser. No. 07/935,050 filed on Aug. 25, 1992, now U.S. Pat. No. 5,530,113; which is a continuation-in-part of application Ser. No. 07/776,100, filed Oct. 11, 1991, now abandoned.

BACKGROUND OF THE INVENTION

The invention relates to compounds which are useful as anti-endotoxic drugs, particularly analogs of lipid A.

The incidence of gram negative bacteremia in the United States has been estimated to be approximately 100,000 to 300,000 cases per year, with a mortality rate of 30–60% (Dudley, *Am. J. Hosp. Pharm.* 47, Supp. 3:S3, 1990). Antibiotics are commonly used as the primary chemotherapy for this disease; however, their bactericidal action results in disruption of the bacterium and concomitant release of endotoxin, i.e., the lipopolysaccharide (LPS) moiety of the bacterial outer membrane. The liberated LPS induces a number of pathophysiological events in mammals (collectively referred to as gram-negative endotoxemia or sepsis syndrome): these include fever, generalized inflammation, disseminated intravascular coagulation (DIC), hypotension, acute renal failure, acute respiratory distress syndrome (ARDS), hepatocellular destruction, and cardiac failure (Dudley, supra; Braunwald et al., eds., *Harrison's principles of Internal Medicine,* 11th ed., McGraw-Hill Book Co., New York, 1987).

Although the endotoxin initiates sepsis, it has little or no direct effect on tissues; instead, it triggers a cascade of biologic mediators which lead to sepsis and septic shock. Endotoxin stimulates monocytes and macrophages to produce tumor-necrosis factor and interleukin-1, two major primary mediators. These mediators then cause the sepsis syndrome by stimulating inflammatory or other cells, such as endothelial cells, to secrete a cascade of secondary mediators (e.g., prostaglandins, leukotrienes, interferons, platelet-activating factor, endorphins, and colony-stimulating factors). These inflammatory mediators influence vasomotor tone, microvascular permeability, and the aggregation of leukocytes and platelets. Although the actions and interactions of these substances appear to be complex, their net effect in initiating septic shock appears to be very significant (Braunwald et al., supra).

As reported by DiPiro (*Am. J. Hosp. Pharm.* 47, Supp.3:S6, 1990), the bacterial lipopolysaccharide molecule has three main regions: a long-chain polysaccharide (O Antigen) region, a core region, and a lipid A region. The entire lipopolysaccharide molecule and some of its components have toxic effects. Most of these toxic effects, however, are believed to be attributable to the lipid A portion. Structurally, lipid A is composed of a disaccharide and acylated by long-chain fatty acids.

Therapies for endotoxin-related diseases have generally been directed toward controlling the inflammatory response. Such therapies include: corticosteroid treatment, suggested to ameliorate endotoxin-mediated cell membrane injury and to reduce production of certain biologic mediators (Bone, *N. Eng. J. Med.* 1:653, 1987; Veterans Administration Systemic Sepsis Cooperative Study Group, *N. Eng. J. Med.* 37:659, 1987; Braunwald et al., supra); administration of antibodies designed to neutralize the bacterial LPS endotoxin (see, e.g., Ziegler et al., *N. Eng. J. Med.* 307:1225, 1982); treatment with naloxone, which apparently blocks the hypotensive effects associated with the sepsis syndrome (Sheagren et al., Shock Syndromes Related to Sepsis. In: Wyngaarden and Smith, eds., *Cecil Textbook of Medicine,* 18th ed. Philadelphia, 1988, pp. 1538–41); and treatment with non-steroidal anti-inflammatory drugs, purported to block cyclo-oxygenases and thereby decrease the production of certain secondary mediators such as prostaglandins and thromboxane (DiPiro, supra).

SUMMARY OF THE INVENTION

In general, the invention features a compound of the formula:

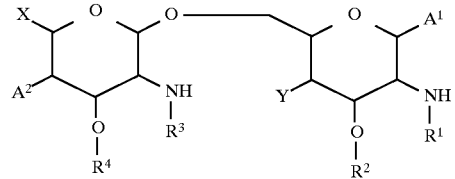

wherein at least one $R^1$, $R^2$, $R^3$, or $R^4$ is:

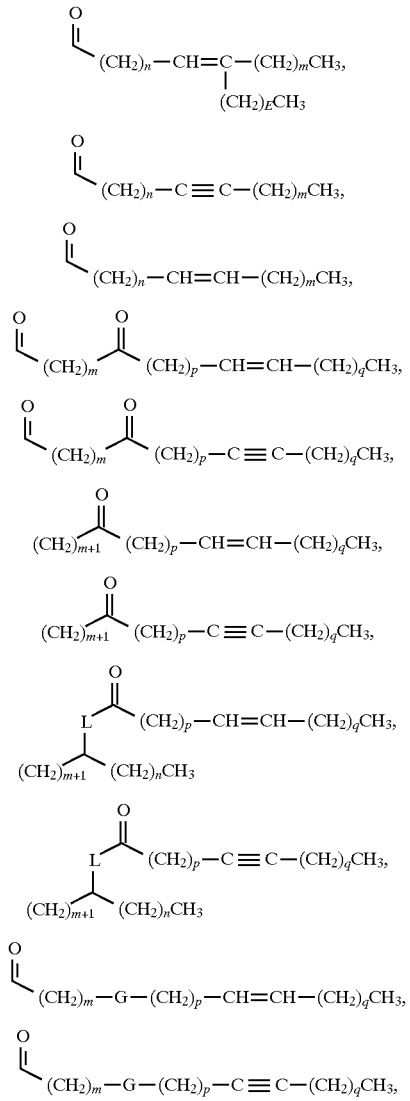

-continued

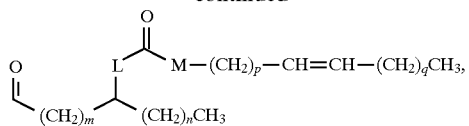

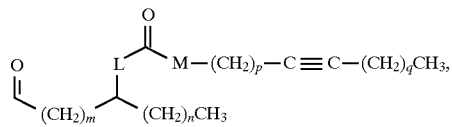

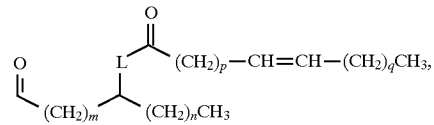

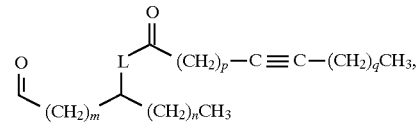

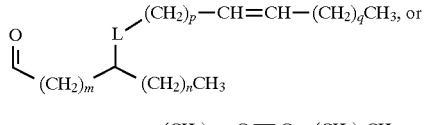

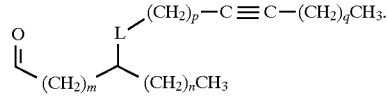

wherein each L is O, N, or C; each M is O or N; each E, independently, is an integer between 0 and 14 inclusive; each G, independently, is N, O, S, SO, or $SO_2$; each m, independently, is an integer between 0 and 14 inclusive; each n, independently, is an integer between 0 and 14 inclusive; each p, independently, is an integer between 0 and 10 inclusive; and each q, independently, is an integer between 0 and 10 inclusive;

each of the remaining $R^1$, $R^2$, $R^3$, and $R^4$, independently, is:

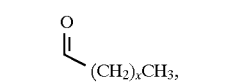

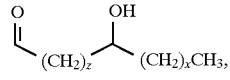

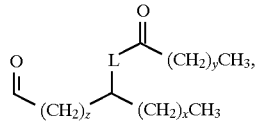

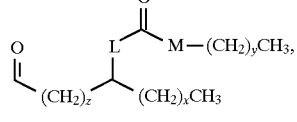

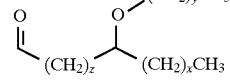

-continued

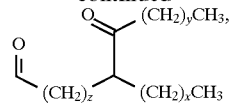

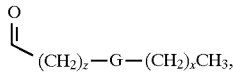

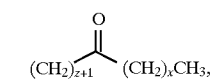

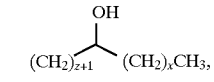

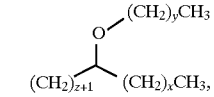

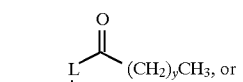

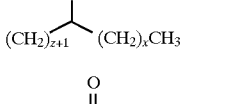

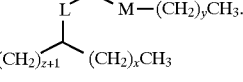

wherein each L is O, N, or C; each M is O or N; each x, independently, is an integer between 0 and 14 inclusive; each y, independently, is an integer between 0 and 14 inclusive; each z, independently, is an integer between 0 and 10 inclusive; and each G, independently, is N, O, S, SO, or $SO_2$;

each $A^1$ and $A^2$, independently, is H, OH, $OCH_3$,

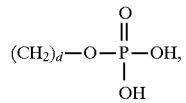

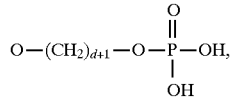

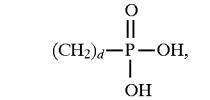

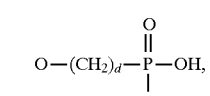

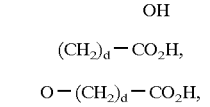

-continued

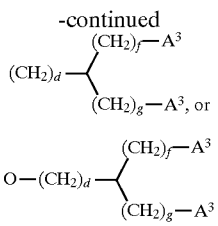, or

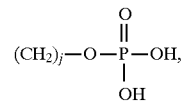

wherein each d, independently, is an integer between 0 and 5 inclusive; each f, independently, is an integer between 0 and 5 inclusive; each g, independently, is an integer between 0 and 5 inclusive; and each $A^3$, independently, is:

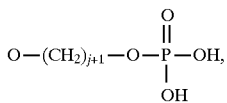

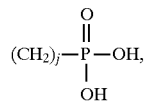

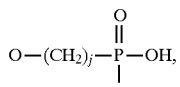

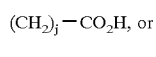

$(CH_2)_j-CO_2H$, or $O-(CH_2)_j-CO_2H$ wherein each j, independently, is an integer between 0 and 14 inclusive;

X is H, $(CH_2)_tCH_3$, $(CH_2)_tOH$, $(CH_2)_tO(CH_2)_vCH_3$, $(CH_2)_tOPO(OH)_2$, $(CH_2)_t-CH=CH-(CH_2)_vCH_3$, $(CH_2)_t-O-R^5$,

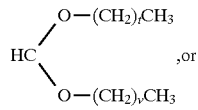, or

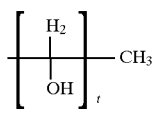

wherein each t and v, independently, is an integer between 0 and 14 inclusive; and $R^5$ is any of the possibilities listed above for $R^1$–$R^4$; and Y is H, OH, $O(CH_2)_wCH_3$, a halo group,

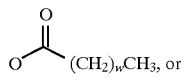, or

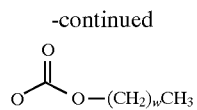

wherein w is an integer between 0 and 14 inclusive.

Preferably, at least one $R^1$, $R^2$, $R^3$, or $R^4$ is:

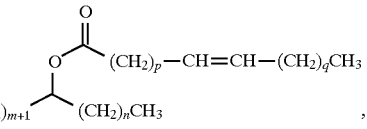,

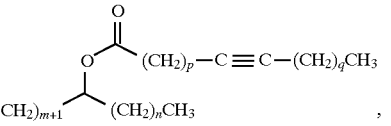,

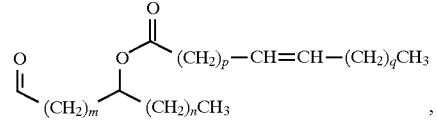,

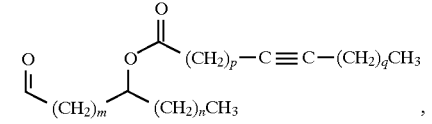,

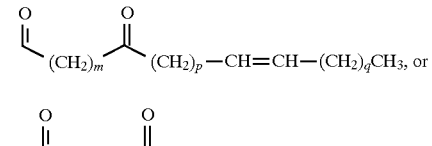

wherein each m, independently, is an integer between 0 and 10 inclusive; each n, independently, is an integer between 0 and 10 inclusive; and for each p and q, independently, $0 \leq (p+q) \leq 12$;

each of the remaining $R^1$, $R^2$, $R^3$, and $R^4$, independently, is:

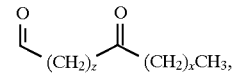,

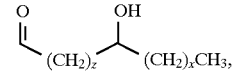,

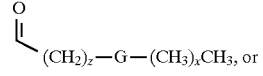, or

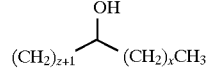

wherein each x, independently, is an integer between 0 and 10 inclusive; each z, independently, is an integer between 0 and 3 inclusive; and each G, independently, is SO or $SO_2$;

each $A^1$ and $A^2$, independently, is:

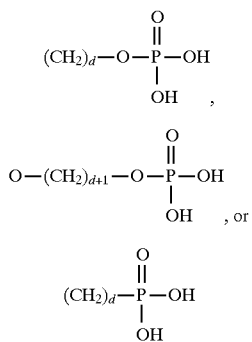

wherein each d, independently, is an integer between 0 and 2 inclusive;
X is H, $(CH_2)_tOH$, $(CH_2)_tO(CH_2)_vCH_3$ or $(CH_2)_tCH_3$, wherein t is an integer between 0 and 6 inclusive and v is an integer between 0 and 6; and
Y is a halo group or OH.
More preferably, at least one $R^1$, $R^2$, $R^3$, or $R^4$ is:

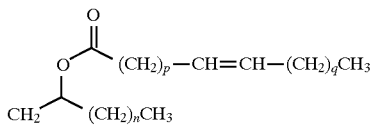

wherein each n, independently, is an integer between 6 and 10 inclusive, most preferably 6; and $6 \leq (p+q) \leq 10$, and most preferably, q is 5;
each of the remaining $R^1$, $R^2$, $R^3$, and $R^4$, independently, is:

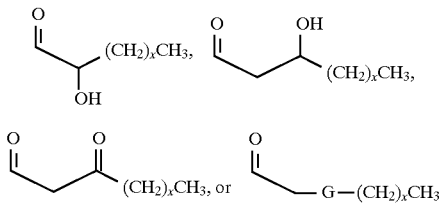

wherein each x, independently, is an integer between 6 and 11 inclusive, most preferably 6 or 10; and each G, independently, is SO or $SO_2$;
each $A^1$ and $A^2$, independently, is:

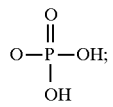

X is $CH_2OH$, $CH_2OCH_3$, or $CH_2O(CH_2)_vCH_3$, wherein v is an integer between 1 and 3 inclusive; and
Y is OH.
Most preferably, the above compounds are formulated as a lysine salt, a Tris salt, an ammonium salt, or a sodium salt; and include lipid A analogs B274, B276, B286, B288, B313, B314, B379, B385, B387, B388, B398, B400, B479, B214, B218, B231, B235, B272, B287, B294, B300, B318, B377, B380, B406, B410, B425, B426, B427, B442, B451, B452, B459, B460, B464, B465, B466, B531, B415, B718, B587, B737, B736, B725, and B763 (described herein).

Of the compounds of the first aspect (above), those which may be isolated from natural sources (e.g., from *Rhodopseudomonas capsulata* or *Rhodopseudomonas sphaeroides*) are less preferred in the invention.

In a second aspect, the invention features a compound of the formula:

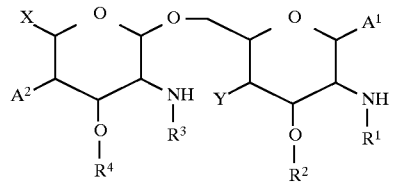

wherein at least one $R^1$, $R^2$, $R^3$, or $R^4$ is:

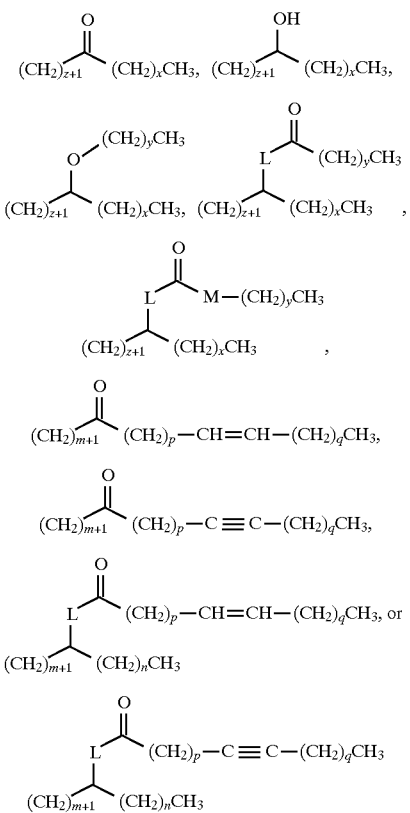

wherein each L is O, N, or C; each M is O or N; each m, independently, is an integer between 0 and 14 inclusive; each n, independently, is an integer between 0 and 14 inclusive; each p, independently, is an integer between 0 and 10 inclusive; and each q, independently, is an integer between 0 and 10 inclusive; each x, independently, is an integer between 0 and 14; each y, independently, is an integer between 0 and 14 inclusive; and each z, independently, is an integer between 0 and 10 inclusive;
each of the remaining $R^1$, $R^2$, $R^3$, and $R^4$, independently, is:

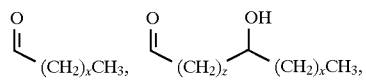

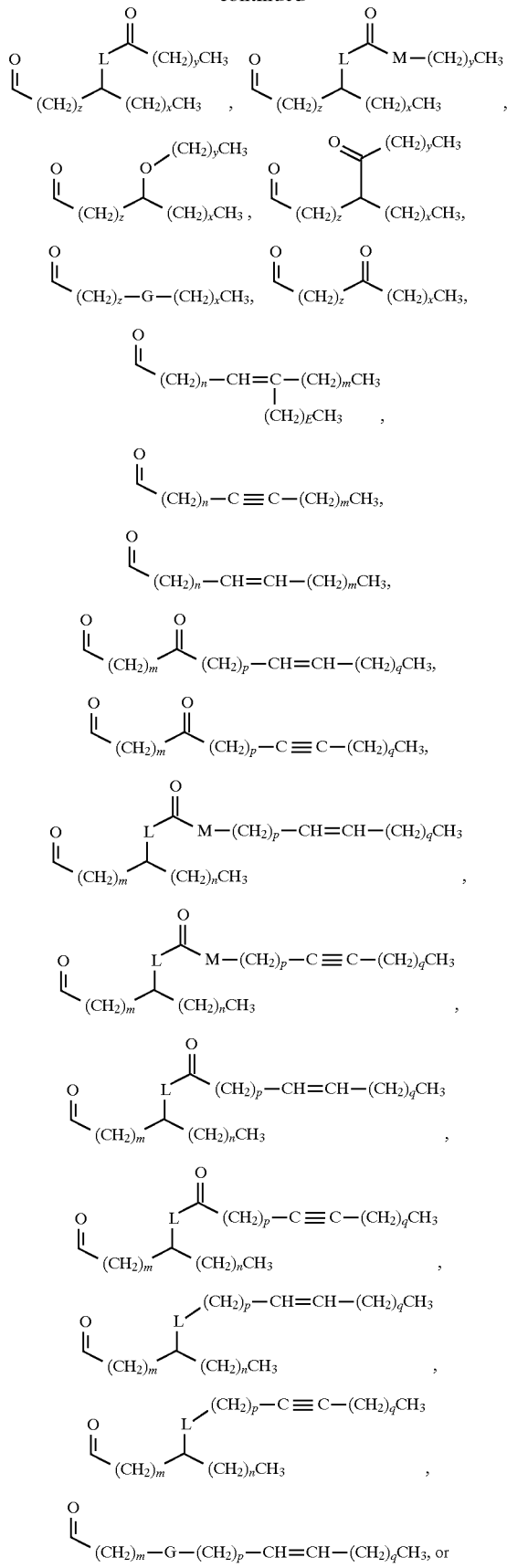

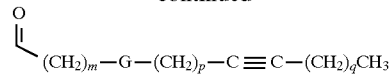

wherein each L is O, N, or C; each M is O or N; each E, independently, is an integer between 0 and 14 inclusive; each m, independently, is an integer between 0 and 14 inclusive; each n, independently, is an integer between 0 and 14 inclusive; each p, independently, is an integer between 0 and 10 inclusive; and each q, independently, is an integer between 0 and 10 inclusive; each x, independently, is an integer between 0 and 14 inclusive; each y, independently, is an integer between 0 and 14 inclusive; each z, independently, is an integer between 0 and 10 inclusive; and each G, independently, is N, O, S, SO, or $SO_2$;

each $A^1$ and $A^2$, independently, is H, OH,

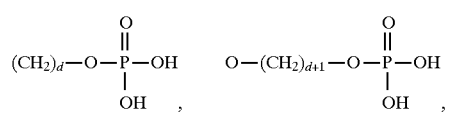

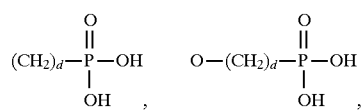

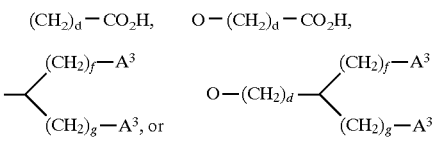

wherein each d, independently, is an integer between 0 and 5 inclusive; each f, independently, is an integer between 0 and 5 inclusive; each g, independently, is an integer between 0 and 5 inclusive; and each $A^3$, independently, is:

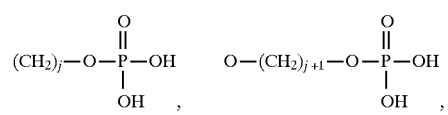

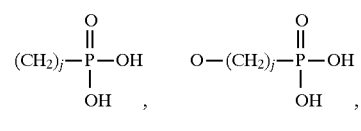

wherein each j, independently, is an integer between 0 and 14 inclusive;

X is H, $(CH_2)_tCH_3$, $(CH_2)_tOH$, $(CH_2)_tO(CH_2)_vCH_3$,

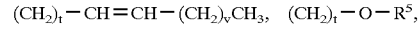

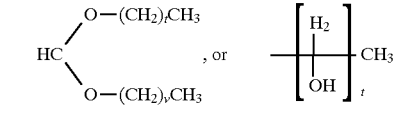

wherein each t and v, independently, is an integer between 0 and 14 inclusive; and $R^5$ is any of the possibilities listed above for $R^1$–$R^4$; and Y is H, OH, O(CH$_2$)$_w$CH$_3$, a halo group,

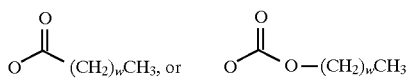

wherein w is an integer between 0 and 14 inclusive.
Preferably, at least one R$^1$, R$^2$, R$^3$, or R$^4$ is:

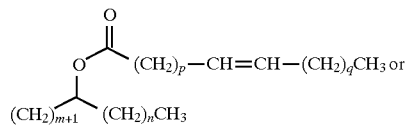

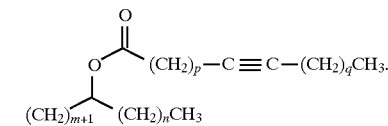

wherein each m, independently, is an integer between 0 and 10 inclusive; each n, independently, is an integer between 0 and 10 inclusive, most preferably 6; and for each p and q, independently, $0 \leq (p+q) \leq 12$, and most preferably, q is 5;

each of the remaining R$^1$, R$^2$, R$^3$, and R$^4$, independently, is:

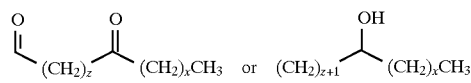

wherein each x, independently, is an integer between 0 and 10 inclusive, most preferably 6 or 10; and each z, independently, is an integer between 0 and 3 inclusive;

each A$^1$ and A$^2$, independently, is:

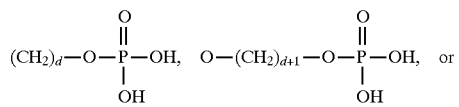

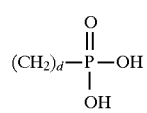

wherein each d, independently, is an integer between 0 and 2 inclusive;

X is H, (CH$_2$)$_t$OH, (CH$_2$)$_t$O(CH$_2$)$_v$CH$_3$ or (CH$_2$)$_t$CH$_3$, wherein t is an integer between 0 and 6 inclusive and v is an integer between 0 and 6; and Y is OH.

Most preferably, the compounds of the second aspect are formulated as a lysine salt, a Tris salt, an ammonium salt, or a sodium salt; and include lipid A analogs: B415, B459, B460, B465, B466, B477, B479, B510, B427, B464, and B531 (described herein).

In a third aspect, the invention features a therapeutic composition which includes, as an active ingredient, a compound according co to the invention formulated in a physiologically-acceptable carrier.

In a fourth aspect, the invention features a compound of formula:

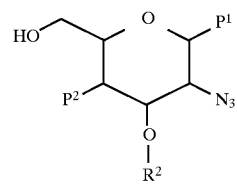

wherein R$^2$ is:

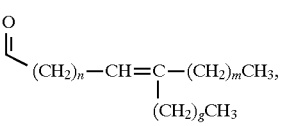

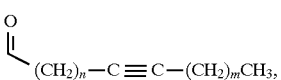

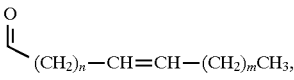

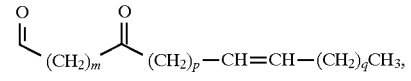

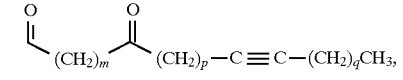

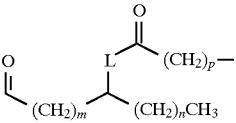

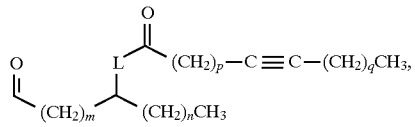

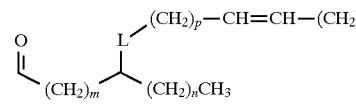

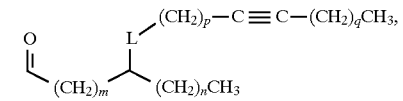

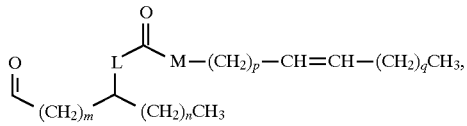

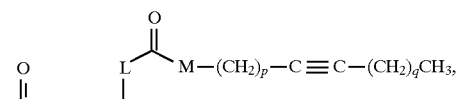

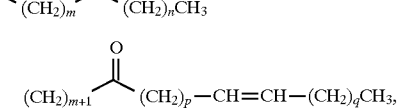

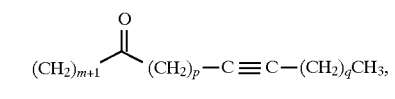

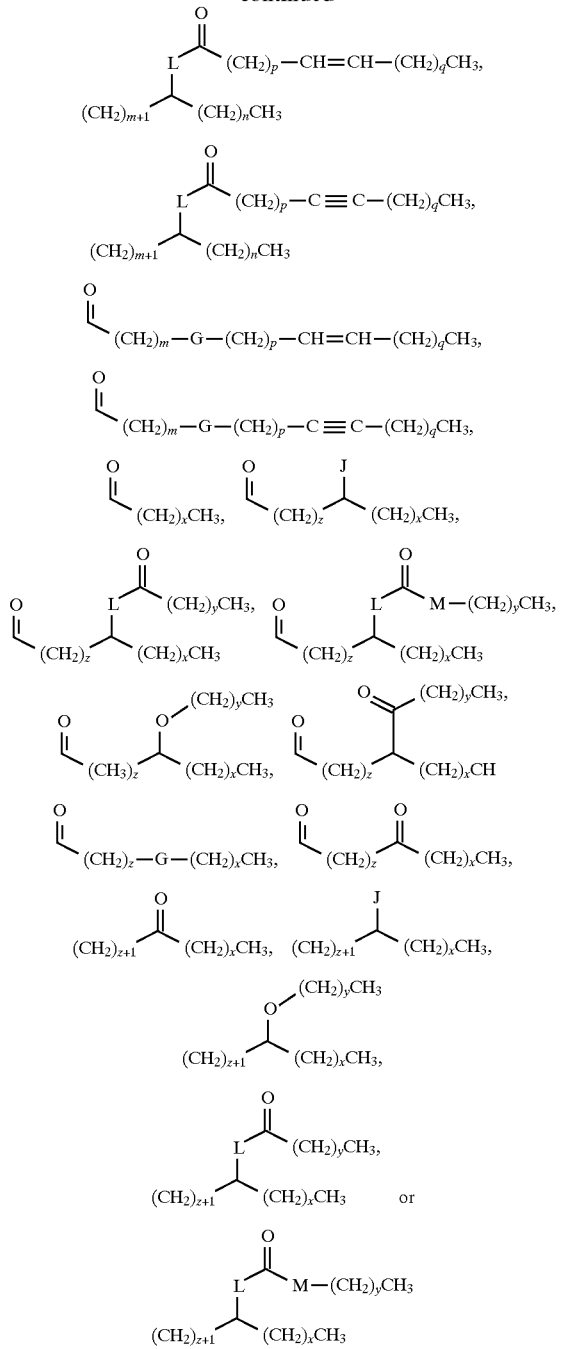

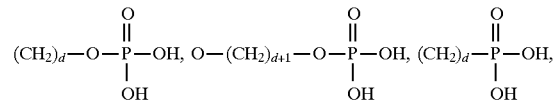

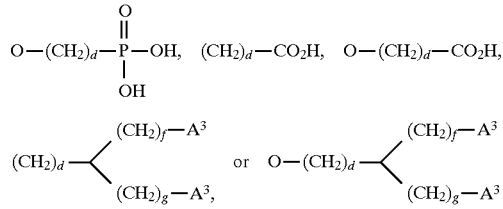

wherein each J, independently, is OH or a protected OH; each L is O, N, or C; each M is O or N; each E, independently, is an integer between 0 and 14 inclusive; each m, independently, is an integer between 0 and 14 inclusive; each n, independently, is an integer between 0 and 14 inclusive; each p, independently, is an integer between 0 and 10 inclusive; each q, independently, is an integer between 0 and 10 inclusive; each x, independently, is an integer between 0 and 14 inclusive; each y, independently, is an integer between 0 and 14 inclusive; each z, independently, is an integer between 0 and 10 inclusive; and each G, independently, is N, O, S, SO, or $SO_2$;

$P^1$ is OH, a protected OH, or a protected $A^1$ group, wherein $A^1$ is:

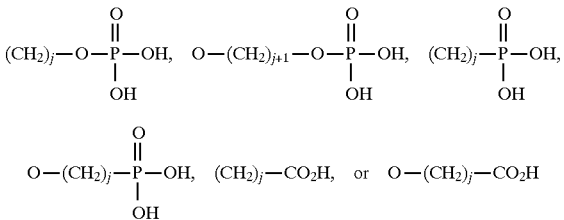

wherein each d, independently, is an integer between 0 and 5 inclusive; each f, independently, is an integer between 0 and 5 inclusive; each g, independently, is an integer between 0 and 5 inclusive; and each $A^3$, independently, is:

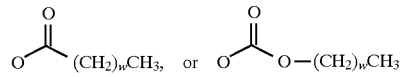

wherein in each j, independently, is an integer between 0 and 14 inclusive; and $P^2$ is H, a halo group, OH, a protected OH, $O(CH_2)_wCH_3$,

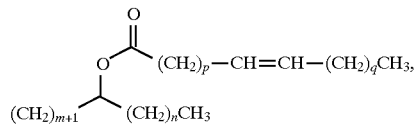

wherein w is an integer between 0 and 14 inclusive. Preferably, $R^2$ is:

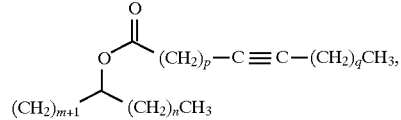

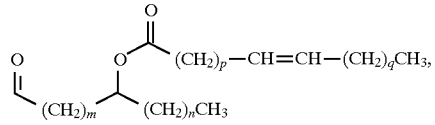

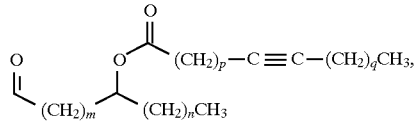

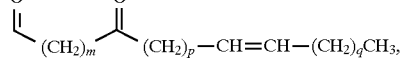

-continued

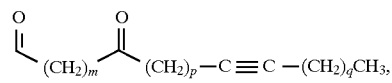
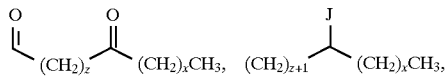
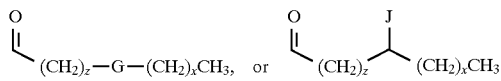

wherein each J, independently, is OH or a protected OH; each m, independently, is an integer between 0 and 10 inclusive; each n, independently, is an integer between 0 and 10 inclusive; each x, independently, is an integer between 0 and 10 inclusive; each z, independently, is an integer between 0 and 3 inclusive; each G, independently, is SO or $SO_2$; and for each p and q, independently, $0 \leq (p+q) \leq 12$;

$P^1$ is OH, a protected OH, or a protected $A^1$ group, wherein $A^1$ is:

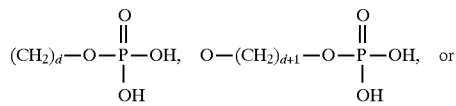

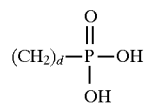

wherein each d, independently, is an integer between 0 and 2 inclusive; and $P^2$ is H, OH, a protected OH, or $O(CH_2)_w CH_3$, wherein w is an integer between 0 and 3 inclusive.

Most preferably, $R^2$ is

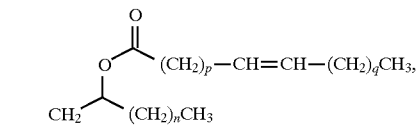

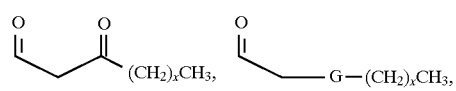

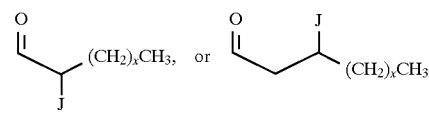

wherein each J, independently, is OH or a protected OH; each x, independently, is an integer between 6 and 11 inclusive; and each G, independently, is SO or $SO_2$; each n, independently, is an integer between 6 and 10 inclusive; and $6 \leq (p+q) \leq 10$;

$P^1$ is OH, a protected OH, or a protected $A^1$ group, wherein $A^1$ is:

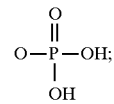

and $P^2$ is H, OH, a protected OH, or $OCH_3$.

In a fifth aspect, the invention features a compound of the formula:

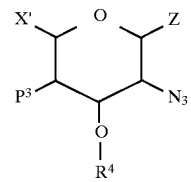

wherein $R^4$ is:

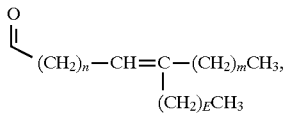

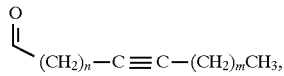

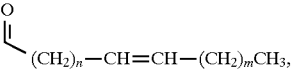

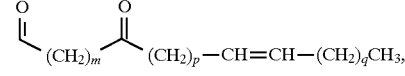

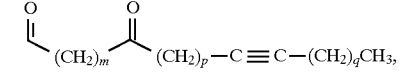

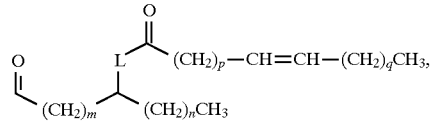

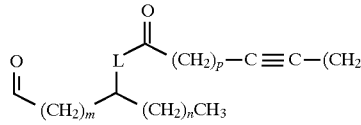

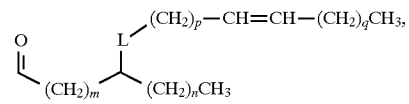

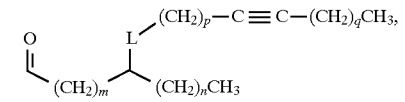

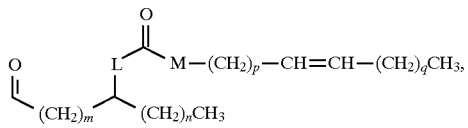

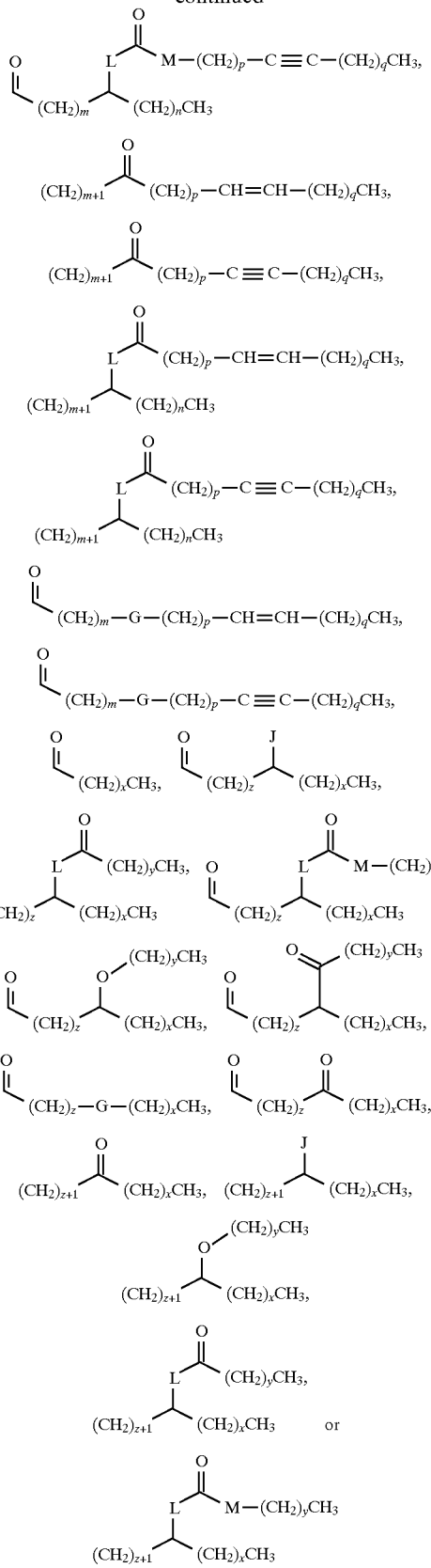

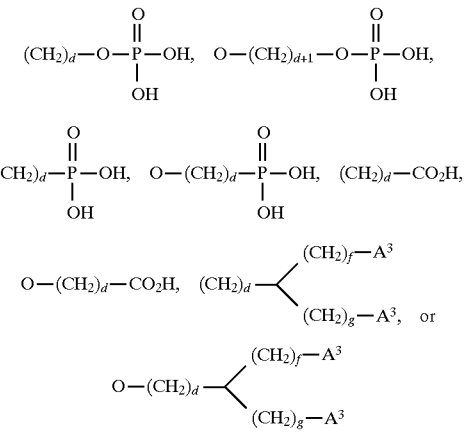

independently, is an integer between 0 and 14 inclusive; each m, independently, is an integer between 0 and 14 inclusive; each n, independently, is an integer between 0 and 14 inclusive; each p, independently, is an integer between 0 and 10 inclusive; each q, independently, is an integer between 0 and 10 inclusive; each x, independently, is an integer between 0 and 14 inclusive; each y, independently, is an integer between 0 and 14 inclusive; each z, independently, is an integer between 0 and 10 inclusive; and each G, independently, is N, O, S, SO, or $SO_2$;

$P^3$ is OH, a protected OH, $OCH_3$, an $A^{2'}$ group, or a protected $A^{2'}$ group, wherein $A^{2'}$ is:

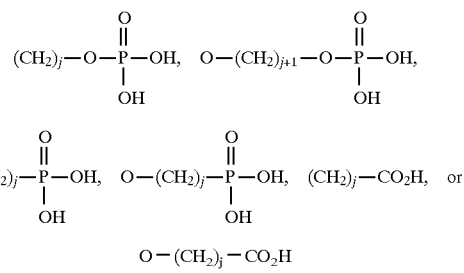

wherein each d, independently, is an integer between 0 and 5 inclusive; each f, independently, is an integer between 0 and 5 inclusive; each g, independently, is an integer between 0 and 5 inclusive; and each $A^3$, independently, is:

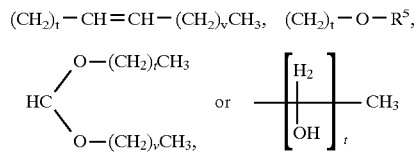

wherein each j, independently, is an integer between 0 and 14 inclusive; and

Z is OH, a protected OH, an activated OH, or a displaceable leaving group; and

X' is X or a protected x group, wherein the X group is H, $(CH_2)_t CH_3$, $(CH_2)_t OH$, $(CH_2)_t O(CH_2)_v CH_3$, $(CH_2)_t OPO(OH)_2$, $(CH_2)_t-CH=CH-(CH_2)_v CH_3$, $(CH_2)_t-O-R^5$, wherein each J, independently, is OH or a protected OH; each L is O, N, or C; each M is O or N; each E, wherein each t and v, independently, is an integer between 0 and 14 inclusive; and $R_5$ is any of the possibilities listed above for $R^1$–$R^4$.

Preferably, $R^4$ is:

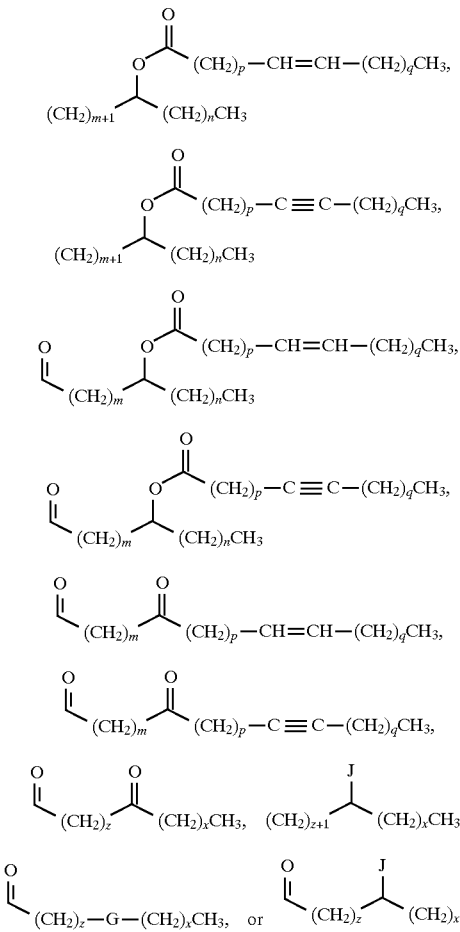

wherein each J, independently, is OH or a protected OH; each m, independently, is an integer between 0 and 10 inclusive; each n, independently, is an integer between 0 and 10 inclusive; each x, independently, is an integer between 0 and 10 inclusive; each z, independently, is an integer between 0 and 3 inclusive; each G, independently, is SO or $SO_2$; and for each p and q, independently, $0 \leq (p+q) \leq 12$;

$P^3$ is H, OH, a protected OH, an $A^{2'}$ group, or a protected $A^{2'}$ group, wherein $A^{2'}$ is:

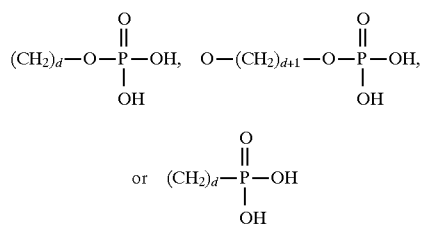

wherein each d, independently, is an integer between 0 and 2 inclusive; and

X' is H, $(CH_2)_tOH$, $(CH_2)_tO(CH_2)_vCH_3$ or $(CH_2)_tCH_3$, wherein t is an integer between 0 and 6 inclusive and v is an integer between 0 and 6.

Most preferably, $R^4$ is:

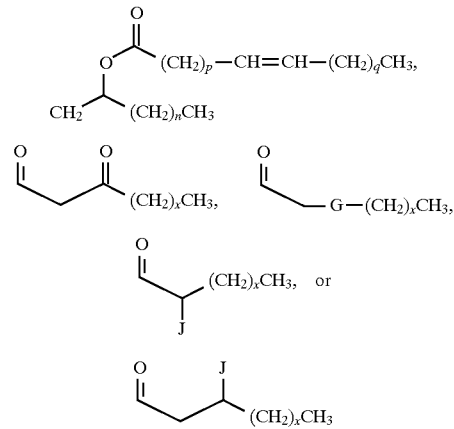

wherein each J, independently, is OH or a protected OH; each x, independently, is an integer between 6 and 11 inclusive; and each G, independently, is SO or $SO_2$; each n, independently, is an integer between 6 and 10 inclusive; and $6 \leq (p+q) \leq 10$;

$P^3$ is OH, a protected OH, an $A^{2'}$ group, or a protected $A^{2'}$ group, wherein $A^{2'}$ is:

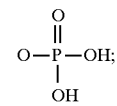

X' is $CH_2OH$, $CH_2OCH_3$, or $CH_2O(CH_2)_vCH_3$, wherein v is an integer between 1 and 3 inclusive.

In a sixth aspect, the invention features a compound of the formula:

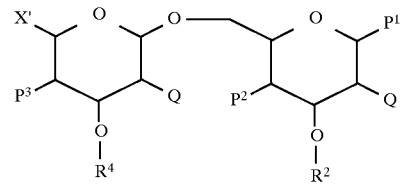

wherein each $R^2$ and $R^4$, independently is:

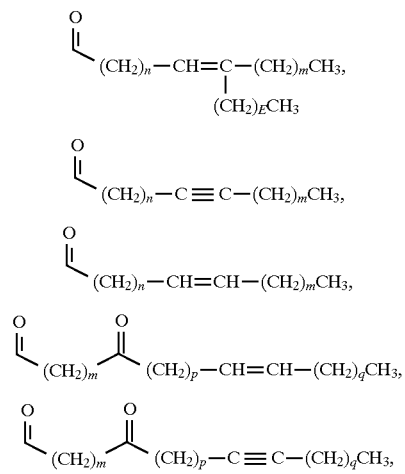

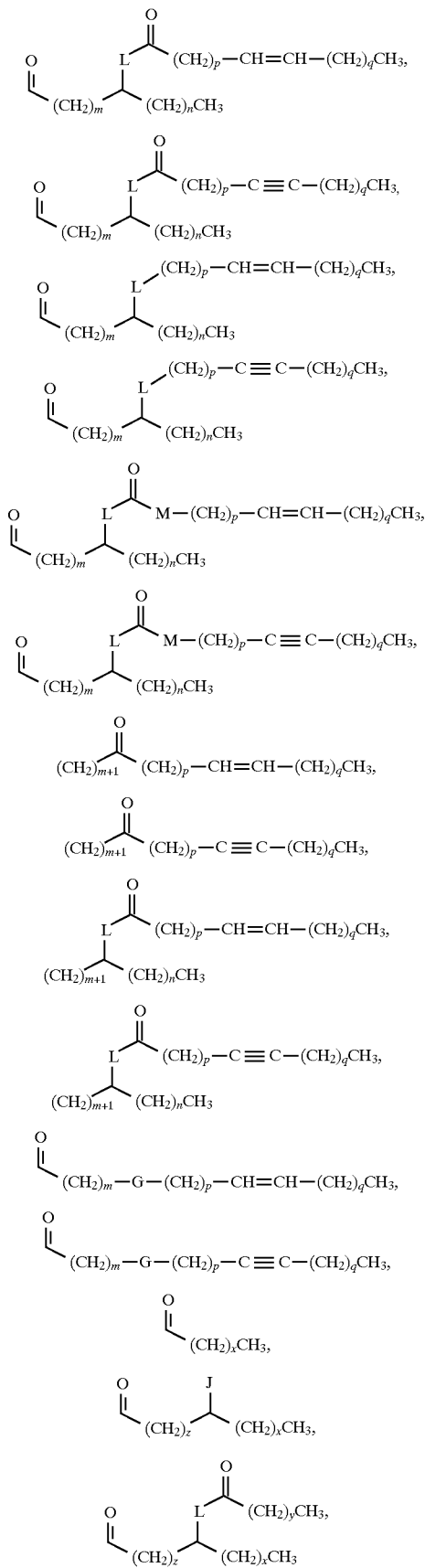
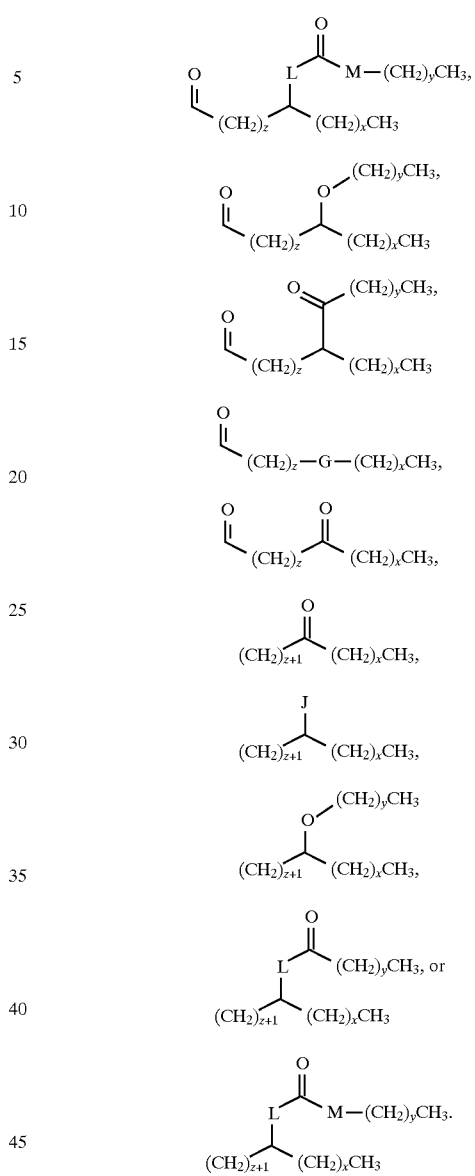

wherein each J, independently, is OH or a protected OH; each L is O, N, or C; each M is O or N; each E, independently, is an integer between 0 and 14 inclusive; each m, independently, is an integer between 0 and 14 inclusive; each n, independently, is an integer between 0 and 14 inclusive; each p, independently, is an integer between 0 and 10 inclusive; each q, independently, is an integer between 0 and 10 inclusive; each x, independently, is an integer between 0 and 14 inclusive; each y, independently, is an integer between 0 and 14 inclusive; each z, independently, is an integer between 0 and 10 inclusive; and each G, independently, is N, O, S, SO, or $SO_2$;

$P^1$ is OH, a protected OH, or a protected $A^1$ group; and $P^3$ is OH, a protected OH, an $A^{2'}$ group, or a protected $A^{2'}$ group, wherein each $A^1$ and $A^{2'}$ group, independently, is:

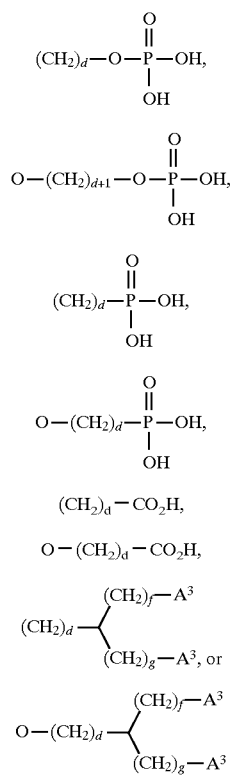

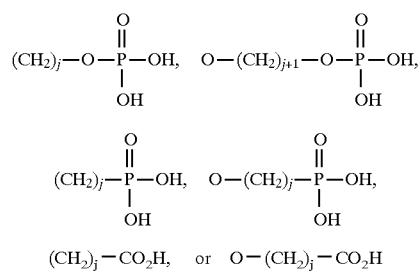

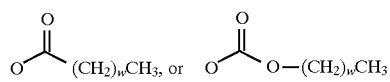

wherein each d, independently, is an integer between 0 and 5 inclusive; each f, independently, is an integer between 0 and 5 inclusive; each g, independently, is an integer between 0 and 5 inclusive; and each $A^3$, independently, is:

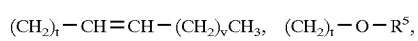

wherein each j, independently, is an integer between 0 and 14 inclusive; and $P^2$ is H, a halo group, OH, a protected OH, $O(CH_2)_wCH_3$,

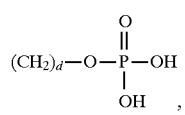

wherein w is an integer between 0 and 14 inclusive;

Q, independently, is $N_3$ or $NH_2$; and

X' is X or a protected X group, wherein the X group is H, $(CH_2)_tCH_3$, $(CH_2)_tOH$, $(CH_2)_tO(CH_2)_vCH_3$, $(CH_2)_t-CH=CH-(CH_2)_vCH_3$, $(CH_2)_t-O-R^5$,

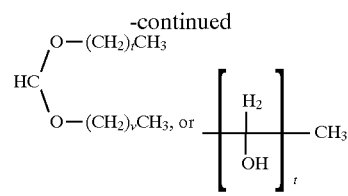

wherein each t and v, independently, is an integer between 0 and 14 inclusive; and $R^5$ is any of the possibilities listed above for $R^1$–$R^4$.

Preferably, each $R^2$ and $R^4$, independently, is:

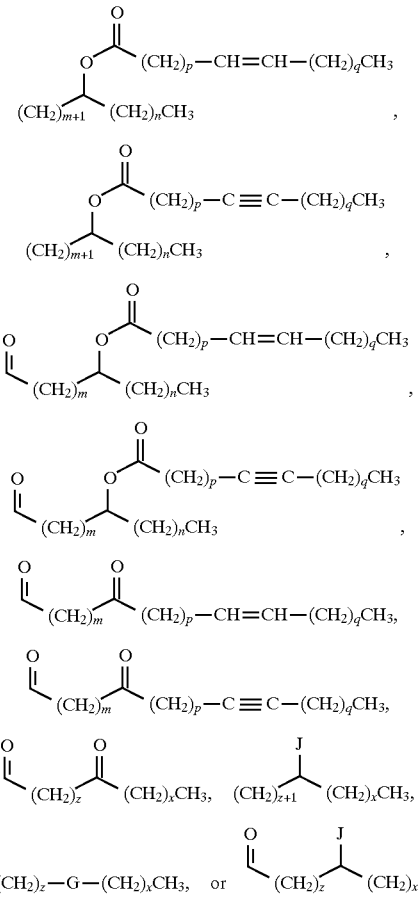

wherein each J, independently, is OH or a protected OH; each m, independently, is an integer between 0 and 10 inclusive; each n, independently, is an integer between 0 and 10 inclusive; each x, independently, is an integer between 0 and 10 inclusive; each z, independently, is an integer between 0 and 3 inclusive; each G, independently, is SO or $SO_2$; and for each p and q, independently, $0 \leq (p+q) \leq 12$;

$P^1$ is OH, a protected OH, or a protected $A^1$ group; and $P^3$ is OH, a protected OH, an $A^{2'}$ group, or a protected $A^{2'}$ group, wherein each $A^1$ and $A^{2'}$ group, independently, is:

-continued

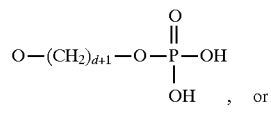, or

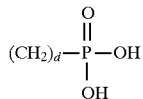

wherein each d, independently, is an integer between 0 and 2 inclusive;

$P^2$ is H, OH, a protected OH, or $O(CH_2)_w CH_3$, wherein w is an integer between 0 and 3 inclusive; and X' is H, $(CH_2)_t OH$, $(CH_2)_t O(CH_2)_v CH_3$ or $(CH_2)_t CH_3$, wherein t is an integer between 0 and 6 inclusive and v is an integer between 0 and 6.

Most preferably, each $R^2$ and $R^4$, independently, is

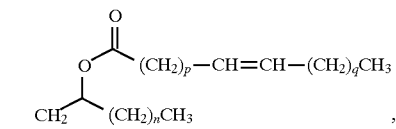,

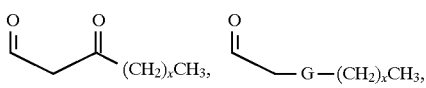

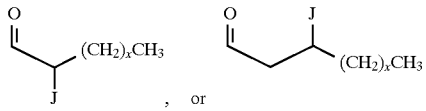, or wherein each J, independently, is OH or a protected OH; each x, independently, is an integer between 6 and 11 inclusive; and each G, independently, is SO or $SO_2$; each n, independently, is an integer between 6 and 10 inclusive; and $6 \leq (p+q) \leq 10$;

$P^1$ is OH, a protected OH, or a protected $A^1$ group; and $P^3$ is OH, a protected OH, an $A^{2'}$ group, or a protected $A^{2'}$ group, wherein each $A^1$ and $A^{2'}$ group, independently, is:

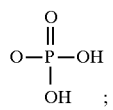;

$P^2$ is OH; and

X' is $CH_2OH$, $CH_2OCH_3$, or $CH_2O(CH_2)_v CH_3$, wherein v is an integer between 1 and 3 inclusive.

In a seventh aspect, the invention features a compound of the formula:

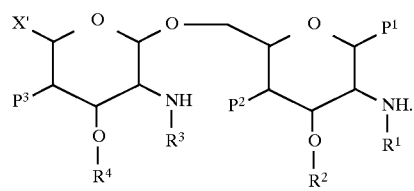

wherein each $R^1$, $R^2$, $R^3$, and $R^4$, independently is:

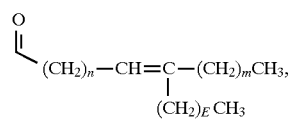

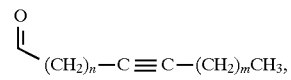

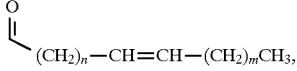

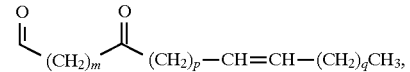

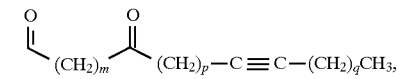

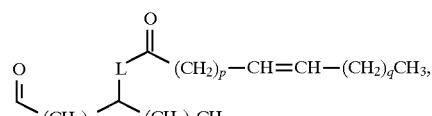

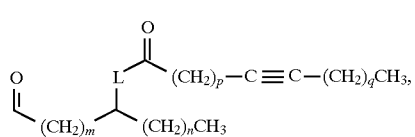

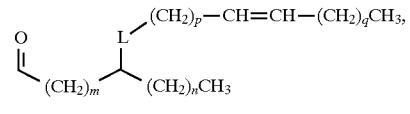

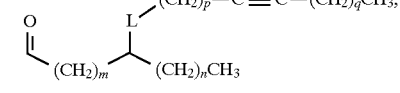

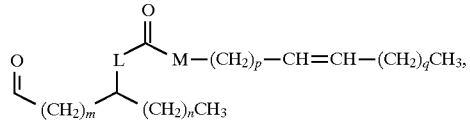

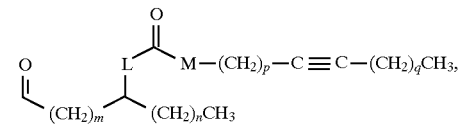

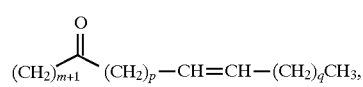

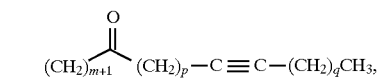

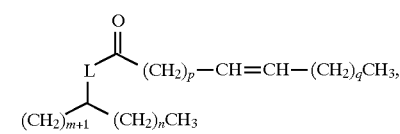

-continued

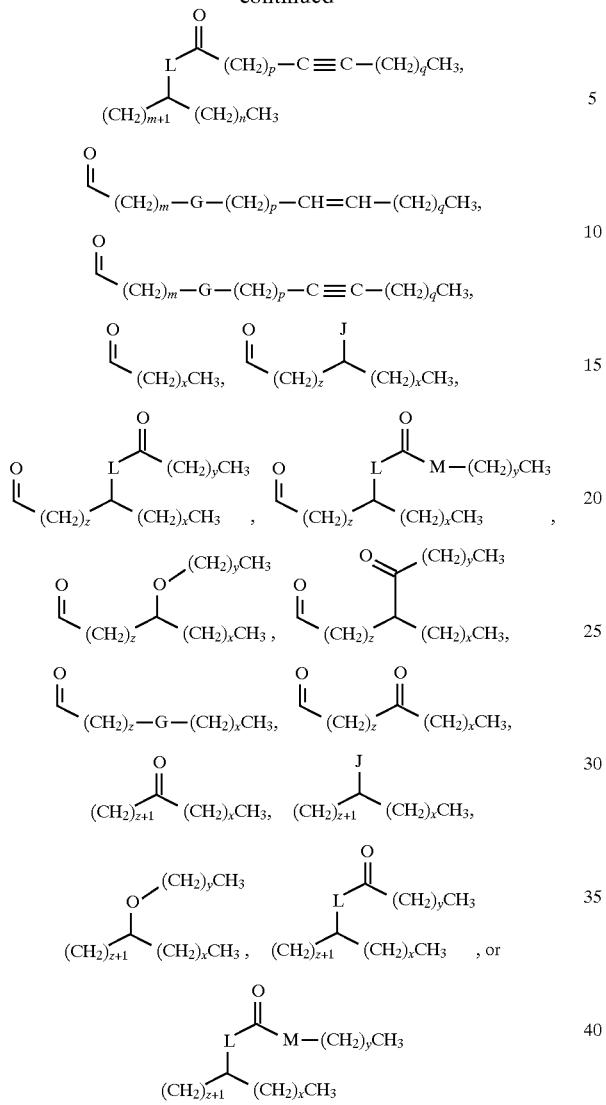

wherein each J, independently, is OH or a protected OH; each L is O, N, or C; each M is O or N; each E, independently, is an integer between 0 and 14 inclusive; each m, independently, is an integer between 0 and 14 inclusive; each n, independently, is an integer between 0 and 14 inclusive; each p, independently, is an integer between 0 and 10 inclusive; each q, independently, is an integer between 0 and 10 inclusive; each x, independently, is an integer between 0 and 14 inclusive; each y, independently, is an integer between 0 and 14 inclusive; each z, independently, is an integer between 0 and 10 inclusive; and each G, independently, is N, O, S, SO, or $SO_2$;

$P^1$ is OH, a protected OH, or a protected $A^1$ group; and
$P^3$ is OH, a protected OH, an $A^{2'}$ group, or a protected $A^{2'}$ group, wherein each $A^1$ and $A^{2'}$ group, independently, is:

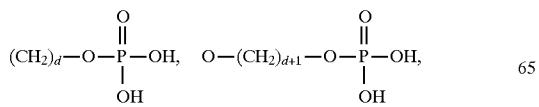

-continued

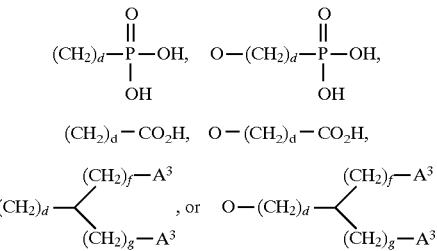

wherein each d, independently, is an integer between 0 and 5 inclusive; each f, independently, is an integer between 0 and 5 inclusive; each g, independently, is an integer between 0 and 5 inclusive; and each $A^3$, independently, is:

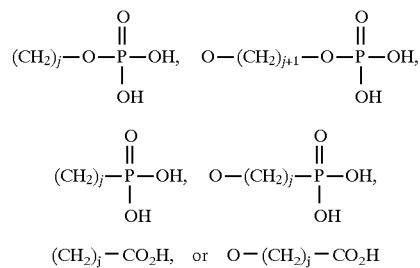

wherein each j, independently, is an integer between 0 and 14 inclusive; and
$P^2$ is H, a halo group, OH, a protected OH, $O(CH_2)_w CH_3$,

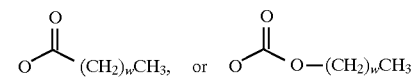

wherein w is an integer between 0 and 14 inclusive; and
X' is X or a protected X group, wherein the X group is H, $(CH_2)_t CH_3$, $(CH_2)_t OH$, $(CH_2)_t O(CH_2)_v CH_3$,

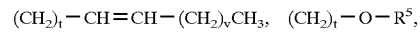

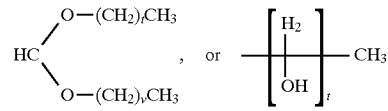

wherein each t and v, independently, is an integer between 0 and 14 inclusive; and $R^5$ is any of the possibilities listed above for $R^1$–$R^4$.

Preferably, each $R^1$, $R^2$, $R^3$, and $R^4$, independently, is:

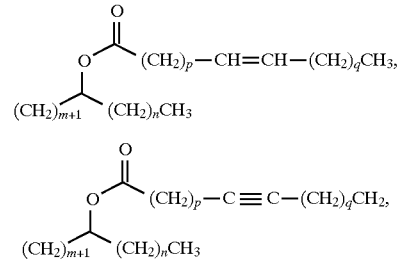

-continued

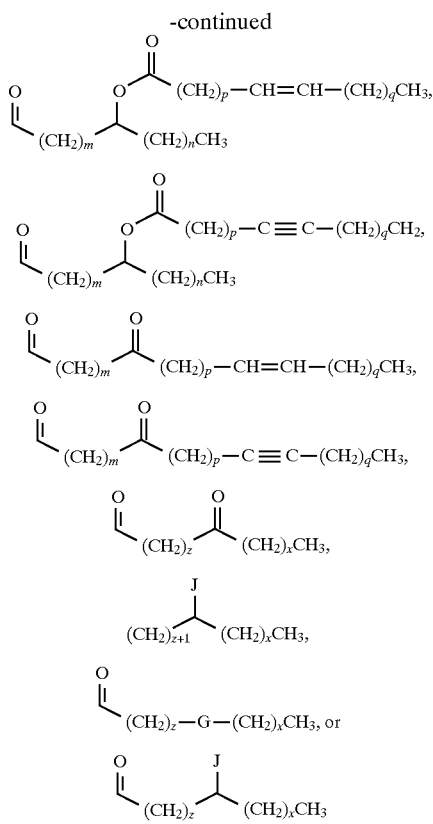

wherein each J, independently, is OH or a protected OH; each m, independently, is an integer between 0 and 10 inclusive; each n, independently, is an integer between 0 and 10 inclusive; each x, independently, is an integer between 0 and 10 inclusive; each z, independently, is an integer between 0 and 3 inclusive; each G, independently, is SO or $SO_2$; and for each p and q, independently, $0 \leq (p+q) \leq 12$;

$P^1$ is OH, a protected OH, or a protected $A^1$ group; and
$P^3$ is OH, a protected OH, an $A^{2'}$ group, or a protected $A^{2'}$ group, wherein each $A^1$ and $A^{2'}$ group, independently, is:

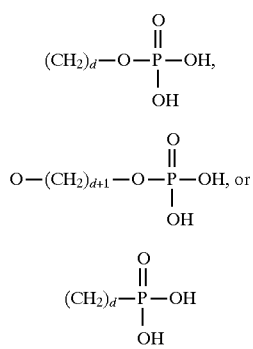

wherein each d, independently, is an integer between 0 and 2 inclusive;
$P^2$ is H, OH, a protected OH, or $O(CH_2)_w CH_3$, wherein w is an integer between 0 and 3 inclusive; and
X' is H, $(CH_2)_t OH$, $(CH_2)_t O(CH_2)_v CH_3$ or $(CH_2)_t CH_3$, wherein t is an integer between 0 and 6 inclusive and v is an integer between 0 and 6.

Most preferably, each $R^1$, $R^2$, $R^3$, and $R^4$, independently, is

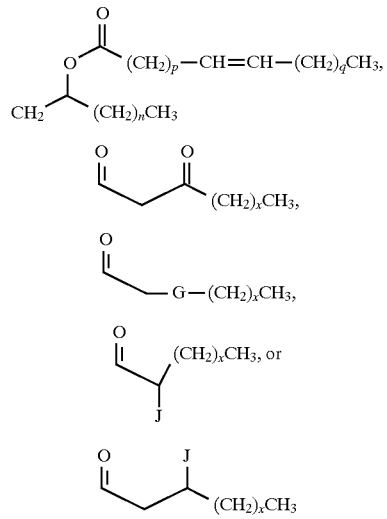

wherein each J, independently, is OH or a protected OH; each x, independently, is an integer between 6 and 11 inclusive; and each G, independently, is SO or $SO_2$; each n, independently, is an integer between 6 and 10 inclusive; and $6 \leq (p+q) \leq 10$;

$P^1$ is OH, a protected OH, or a protected $A^1$ group; and
$P^3$ is OH, a protected OH, an $A^{2'}$ group, or a protected $A^{2'}$ group, wherein each $A^1$ and $A^{2'}$ group, independently, is:

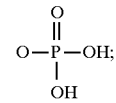

$P^2$ is OH; and
X' is $CH_2OH$, $CH_2OCH_3$, or $CH_2O(CH_2)_v CH_3$, wherein v is an integer between 1 and 3 inclusive.

In an eighth aspect, the invention features a method of making a compound of the formula

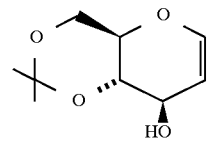

involving the steps of (a) providing a mannopyranoside of the formula

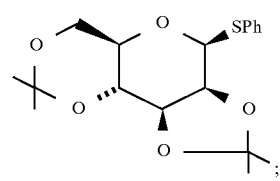

(b) reacting said mannopyranoside with a catalytic, amount of napthalene in the presence of lithium.

In an ninth aspect, the invention features a method of making a compound of the formula

31

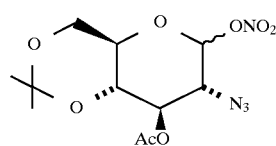

involving the steps of (a) providing a compound of the formula

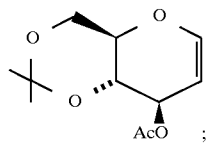

(b) reacting the compound with ammonium cerium nitrate and an azide alkali metal salt, preferably, sodium azide.

In a preferred embodiment, the method further involves the step of reacting

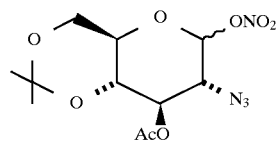

with sodium nitrate to form

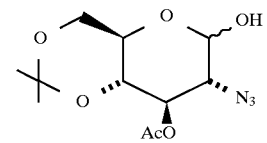

In a tenth aspect, the invention features a method of selectively making the α-stereoisomer of the compound of formula

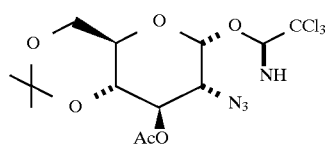

involving the steps of:

32

(a) providing a compound of formula

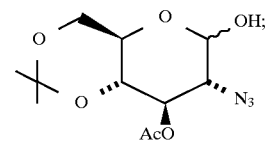

(b) dissolving the compound in trichloroacetonitrile; and
(c) reacting the dissolved compound with lithium bis(trimethylsilyl)amide.

In an eleventh aspect, the invention features a method of coupling a 3,4-dimethoxybenzyl protecting group to an activated azido saccharide involving reacting the azido saccharide first with dimethoxybenzyl alcohol and then with boron trifluoride etherate. In a preferred embodiment, the azido saccharide is

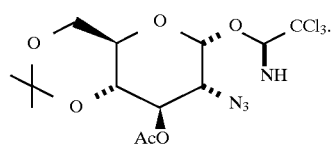

In a twelfth aspect, the invention features a method of coupling an allyloxycarbonate protecting group to a hydroxyl sidechain of a saccharide involving reacting the saccharide first with phosgene and then with allyl alcohol.

In preferred embodiments, the saccharide is an azido saccharide; the saccharide is of the formula

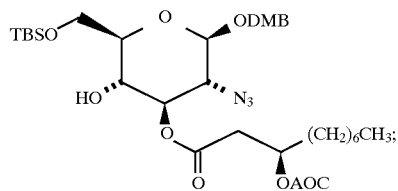

the saccharide is of the formula

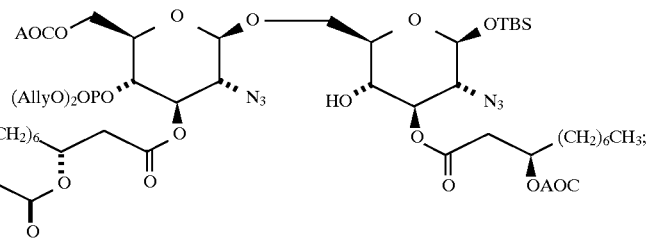 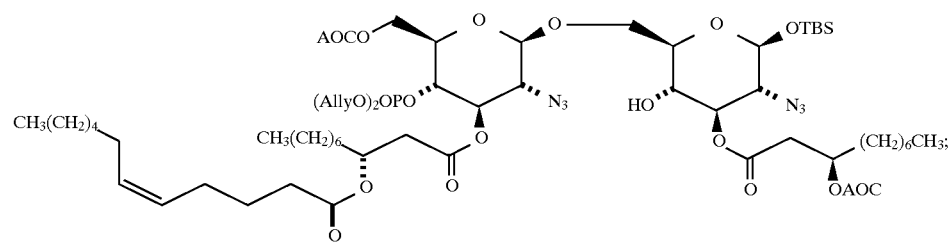

and the saccharide is of the formula

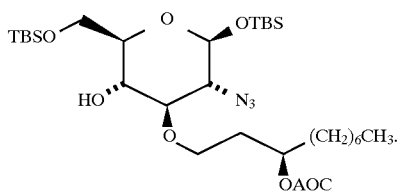

In a thirteenth aspect, the invention features a method of selectively removing a t-butyldimethylsilyl protecting group from an acyl-protected saccharide involving reacting the saccharide with hydrofluoric acid.

In preferred embodiments, the saccharide is a disaccharide; the acyl protecting group is an allyloxycarbonate group; the acyl-protected saccharide is the acyl-protected saccharide further includes a 3,4-dimethoxybenzyl protecting group; and the acyl-protected saccharide is

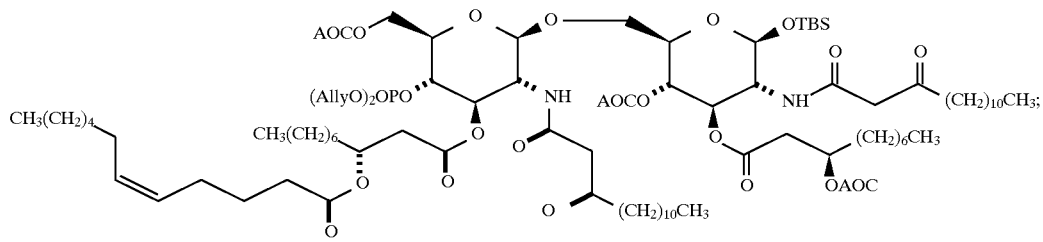

the acyl-protected saccharide is

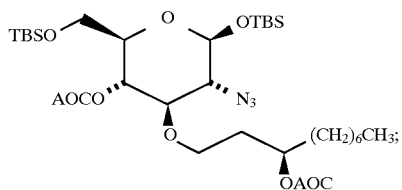

the acyl-protected saccharide is

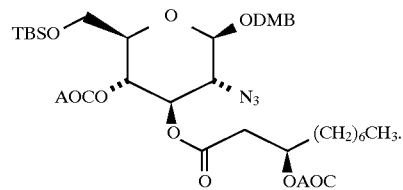

In a fourteenth aspect, the invention features a method of coupling a bis(alkoxy)phosphonyl sidechain to a saccharide involving reacting the saccharide first with a bis (alkoxy) (diisopropylamino) phosphine and tetrazole and then with an oxidant.

In preferred embodiments, the bis(alkoxy)phosphonyl sidechain is an allyloxy-protected phosphate group; the oxidant is m-chloroperoxybenzoic acid; the saccharide is a disaccharide, preferably, an azido saccharide; the azido saccharide is of the formula

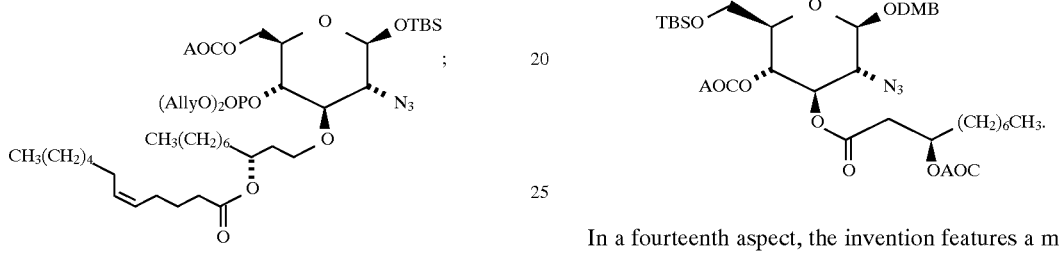

the acyl-protected saccharide is

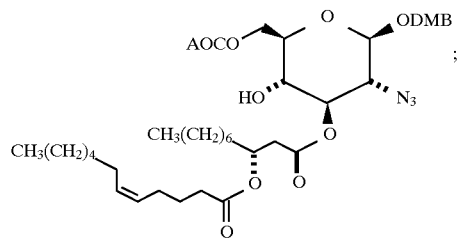

the acyl-protected saccharide is

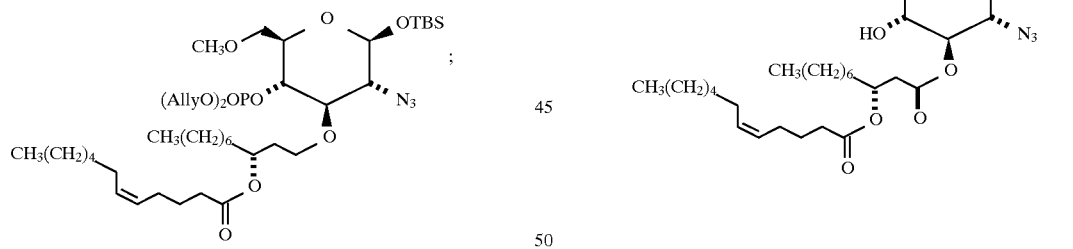

the acyl-protected saccharide is

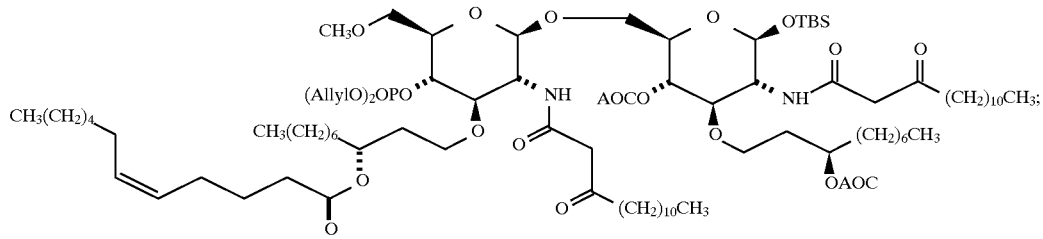

the azido saccharide is of the formula

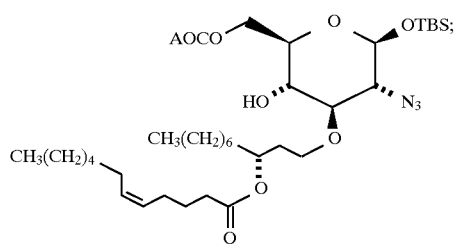

the azido saccharide is of the formula

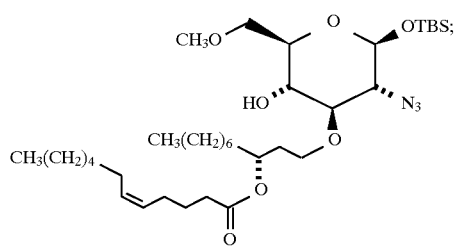

and the azido saccharide is of the formula

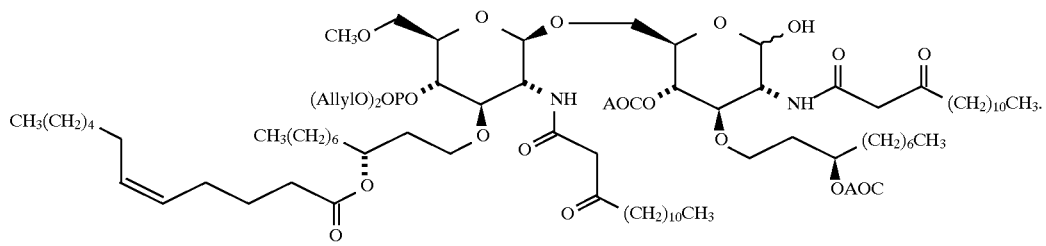

In a fifteenth aspect, the invention features a method of removing a 3,4-dimethoxybenzyl protecting group from an azido saccharide involving reacting the azido saccharide with 2,3-dichloro-5,6-dicyano-1,4-benzoquinone in the dark under anaerobic conditions.

In a sixteenth aspect, the invention features a method of removing a 3,4-dimethoxybenzyl protecting group from an azido saccharide involving reacting the azido saccharide with ammonium cerium nitrate.

In a preferred embodiment of the fifteenth and sixteenth aspects, the azido saccharide is

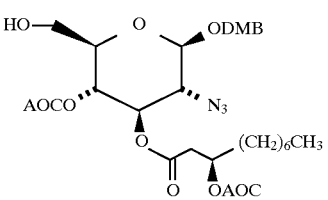

In a seventeenth aspect, the invention features a method for selectively coupling an α-trichloroimidate activating group to an azido sugar involving reacting the azido sugar with trichloroacetonitrile and cesium carbonate. In a preferred embodiment, the azido sugar is of the formula

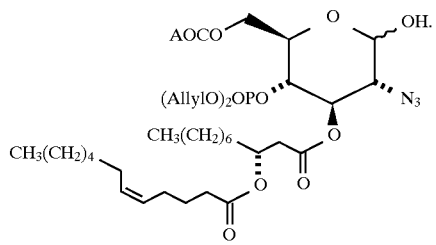

In an eighteenth aspect, the invention features a method for making a disaccharide involving the steps: (a) providing an azido monosaccharide having a 3,4-dimethoxybenzyl protecting group and a free hydroxyl group; and (b) reacting the 3,4-dimethoxybenzyl-protected azido monosaccharide with a second activated azido monosaccharide under an argon atmosphere in the presence of boron trifluororide etherate or trimethylsilyl trifluoromethanesulfonate.

In preferred embodiments, the azido monosaccharides are

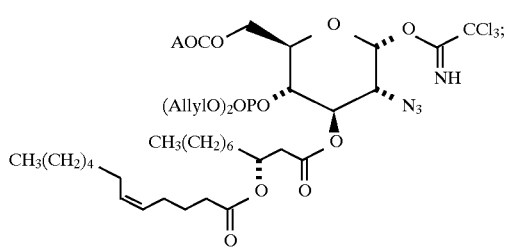

and and the azido monosaccharides are

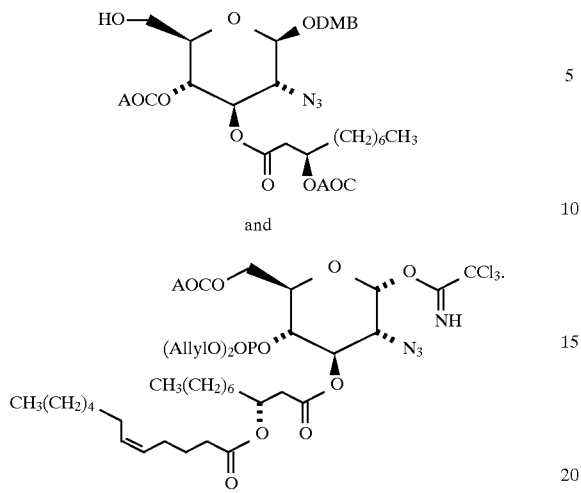

and

In a nineteenth aspect, the invention features a method for reducing an azido sidechain of a saccharide without reducing an unsaturated sidechain involving reacting the azido saccharide with a tin(II)tris-arylthiolate trialkylamine complex in the dark under anaerobic conditions.

In preferred embodiments, the tin(II)tris-benzenethiolate trialkylamine is tin(II)tris-benzenethiolate triethylamine; the azido saccharide is a disaccharide; the disaccharide is of the formula

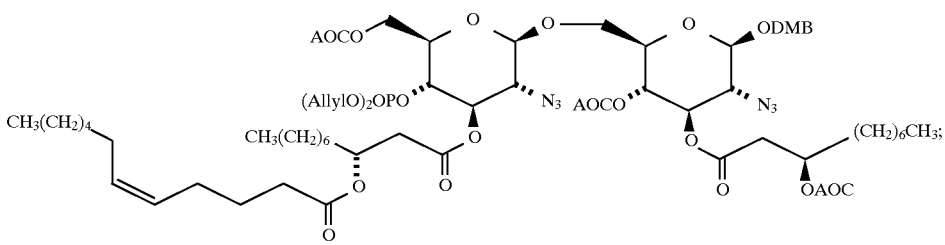

the disaccharide is of the formula

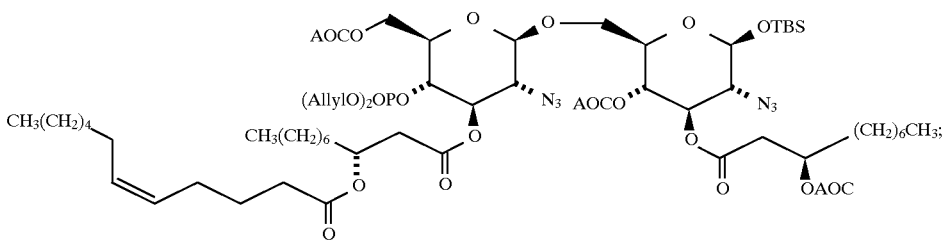

and the disaccharide is of the formula

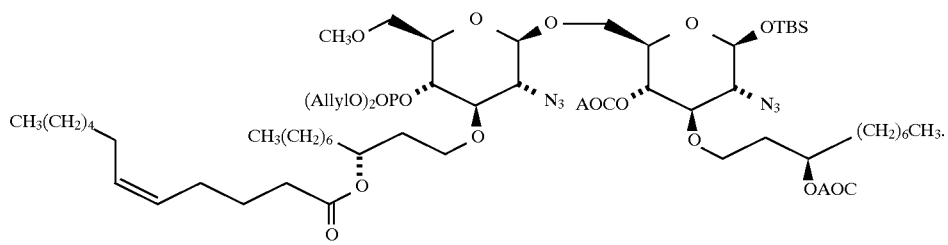

In a twentieth aspect, the invention features a method for removing an allyloxy protecting group from a saccharide molecule involving the steps: (a) providing a saccharide having an allyloxy-protected hydroxyl group; and (b) reacting the protected saccharide with a palladium complex.

In preferred embodiments, the palladium complex is tetrakis(triphenylphosphine)palladium(O); the saccharide is of the formula In a twenty-second aspect, the invention features a method of phosphorylating the $C_1$ carbon of a saccharide having an amido sidechain including a β-sulfoxy group involving reacting the amido saccharide first with a lithium base under anaerobic conditions in the cold and then with dialkyl chlorophosphate.

In preferred embodiments, the lithium base is lithium bis(trimethylsilyl)amide; the dialkyl chlorophosphate is diallyl chlorophosphate; and the saccharide is of the formula

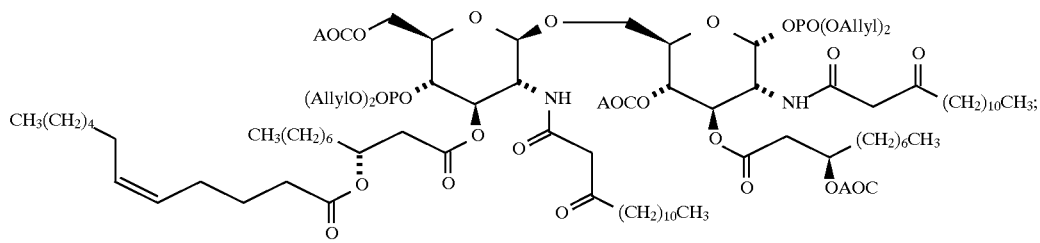

and the saccharide is of the formula

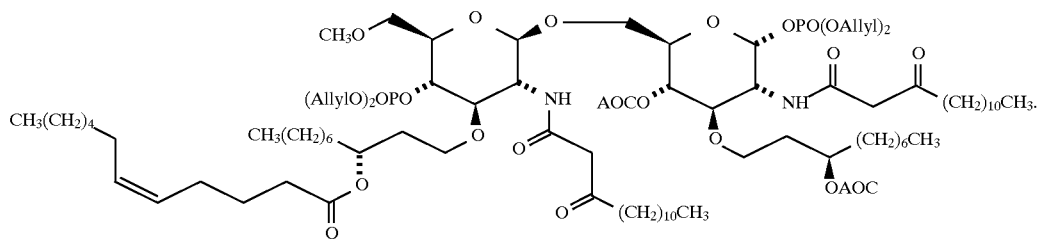

In a twenty-first aspect, the invention features a method for alkylating the $C_6$ hydroxyl of a hexose without alkylating other free hydroxyl groups involving reacting the hexose with a silver salt and an alkyl halide.

In preferred embodiments, the silver salt is silver oxide or silver carbonate; the alkyl halide is methyl iodide; and the hexose is of the formula

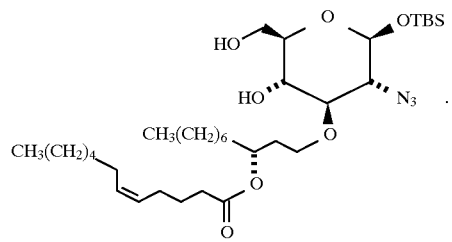

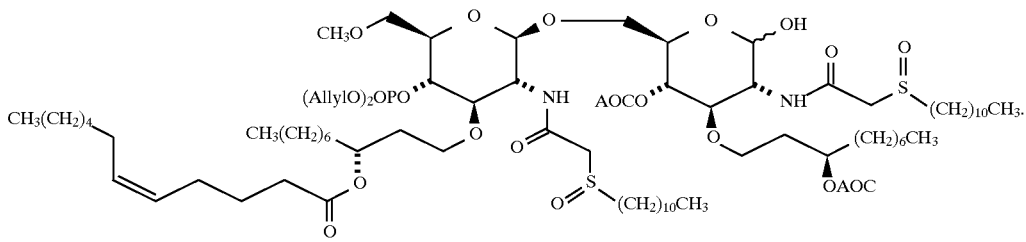

In a twenty-third aspect, the invention features a method of making a $C_1$ dialkylphosphonate saccharide involving (a) first reacting the saccharide with trichloroacetonitrile and carbonate under anaerobic conditions; and then (b) treating with a Lewis acid and a trialkylphosphite under anaerobic conditions.

In preferred embodiments, the carbonate is cesium carbonate; the trialkylphosphite is triallylphosphite; and the saccharide is of the formula

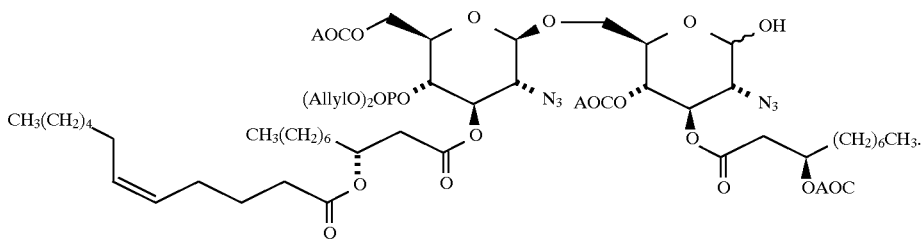

In a twenty-fourth aspect, the invention features a method for coupling an alkyl sidechain to an azido saccharide having a free hydroxyl involving reacting the azido saccharide with an alkali metal salt and a sulfonyl mono-activated alkyl diol under anaerobic conditions.

In preferred embodiments, the alkali metal salt is sodium hydride; and the sulfonyl mono-activated alkyl diol is monotosyl alkyl diol.

In a twenty-fifth aspect, the invention features a method for treating a disease in a mammal for which a lipid A receptor antagonist is effective involving administering to the mammal a therapeutic composition of the invention in a dosage effective to reduce the binding of LPS to a lipid A receptor.

In a twenty-sixth aspect, the invention features a method for treating septic shock in a mammal involving administering to the mammal a therapeutic composition of the invention in a dosage effective to antagonize LPS-mediated target cell activation.

In a twenty-seventh aspect, the invention features a method for treating LPS-mediated activation of a viral infection in a mammal involving administering to the mammal a therapeutic composition of the invention in a dosage effective to antagonize LPS-mediated target cell activation.

In preferred embodiments, the virus includes an NF-κB binding site in a replication control sequence; the virus is a human immunodeficiency virus, for example, HIV-1 or HIV-2; the virus is a herpes virus, for example, a Herpes simplex virus; and the virus is an influenza virus.

A "protected" group, as used herein, means a group (e.g., a hydroxyl group attached to an intermediate compound of the invention) which is prevented from undergoing a chemical reaction; the particular reaction which is blocked and the conditions under which the protecting group is removed are particular to each intermediate compound and are made obvious to those skilled in the art by the synthetic procedures described herein. Examples of preferred protecting groups include, but are not limited to, methyl, benzyl, substituted benzyl, silyl, alkylsilyl, methoxymethyl, alkylacyl, alky oxy carbonyl, and aromatic acyl groups.

By "activated" is meant having a carbon center which is adjacent to a "displaceable leaving group". The choice of an appropriate leaving group is made obvious to one skilled in the art by the synthetic procedures described herein. Examples of preferred leaving groups include, but are not limited to, acyl oxy, iminoether oxy, iminocarbonate oxy, phenoxy, sulfonyl oxy, alkyl thio, and aryl thio, aryl oxy, Se alkyl, and halo groups.

By "mono activated" is meant a compound (e.g., an intermediate compound of the invention) which has only one activated group (as defined above) attached.

The lipid A analogs described herein provide particularly potent therapeutics for the treatment or prevention of LPS-mediated disorders. Without being held to any particular theory, the analogs likely act by blocking access to LPS target sites on mediator molecules, thereby competing directly with bacterial LPS. Because this block occurs at a very early step in the mediator cascade, the therapy is unusually effective and is accompanied by few or no side effects. In addition, because the lipid A analogs of the instant invention are synthesized chemically, they are relatively inexpensive to manufacture and are of unusually high purity and defined chemical constitution, resulting in low immunoreactivity.

Other features and advantages of the invention will be apparent from the following description of the preferred embodiments and from the claims.

DESCRIPTION OF THE PREFERRED EMBODIMENTS

There now follow examples of synthetic compounds which are particularly useful in the invention. These examples are designed to illustrate, not limit, the invention.

Table 1 provides abbreviations which are used throughout the specification.

TABLE 1

| | |
|---|---|
| Ac | Acetate |
| | ![acetate structure: CH3-C(=O)-R] |
| Sph | thiophenyl |
| | ![thiophenyl structure: phenyl-S-R] |
| DMB | 3,4-dimethoxybenzyl |
| | ![DMB structure: R-CH2-C6H3(OCH3)2] |
| AOC | allyloxycarbonate |
| | ![AOC structure: R-C(=O)-O-CH2-CH=CH2] |
| TBS | t-butyldimethylsilyl |
| | ![TBS structure] |
| AllylO | allyloxy |
| | ![allyloxy structure: R-O-CH2-CH=CH2] |
| MPM | p-methoxybenzyl |
| | ![MPM structure: R-CH2-C6H4-OCH3] |

EXAMPLE 1

This example illustrates the synthesis of the lipid A analogs described herein as well as the synthesis of novel product intermediates, also claimed in the invention.

PART A

Preparation of Monosaccharides and Disaccharides

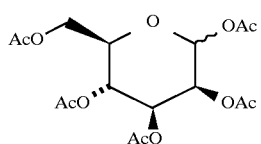

2

To a 0° C. solution of D-mannose (i.e., Compound 1; 1.5 kg, 8.33 mol; Lancaster Chemical Co., Windham, N.H.) dissolved in anhydrous pyridine (3.5 kg, 126.0 mol, Aldrich Chemical Co., Milwaukee, Wis.) was added 5.6 kg (54.9 mol) acetic anhydride (Aldrich Chemical Co.), over four hours at a rate to maintain the reaction temperature between 20°–40° C. The resulting solution was then stirred at room temperature overnight; 5.0 g (40.9 mmol) of 4-dimethylaminopyridine (Aldrich Chemical Co.) was added; the resulting mixture was stirred for an additional 48 hours. The reaction mixture was then poured into 14.0 L of ice-water under vigorous stirring, and extracted with 12.0 L dichloromethane (J.T. Baker, Inc., Phillipsburg, N.J.). The organic layer was washed first with 1N hydrochloric acid (10.0 L; Fisher Scientific Co., Pittsburgh, Pa.), then with saturated aqueous sodium bicarbonate solution (20.0 L; Fisher Scientific Co.), and finally with 5.0 L saturated aqueous sodium chloride solution and dried over 3 kg sodium sulfate (Fisher Scientific Co.). The solution was then filtered through a glass fritted funnel and concentrated under reduced pressure at 40° C. to provide 3.5 kg of Compound 2 {$R_f$: 0.39 [ethyl acetate (J.T. Baker, Inc.): hexanes (J.T. Baker, Inc), 1:1 (v/v)]} as a brown oil which was utilized in the next step without purification.

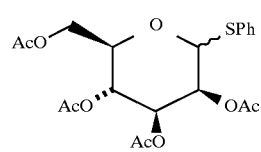

3

Compound 2 (3.0 kg, 7.3 mol) was mixed with thiophenol (Aldrich Chemical Co.) (1.5 L, 11.0 mol), dissolved in 8.0 L of chloroform (J.T. Baker, Inc.), and boron trifluoride etherate (1.6 L, 12.9 mol, Aldrich Chemical Co.) was added at such a rate that the reaction temperature remained below 40° C. Upon complete consumption of the starting material [as measured by thin layer chromatographic analysis using hexanes:ethyl acetate, 1:1 (v/v)], the mixture was cooled to room temperature and slowly poured, with rapid mechanical stirring, into 15.0 L of saturated aqueous sodium bicarbonate solution. The resulting mixture was extracted with 18.0 L of dichloromethane, and the organic layer washed first with 15.0 L of saturated aqueous sodium bicarbonate solution and then 10.0 L of saturated aqueous sodium chloride solution, and the resultant solution dried over 3 kg sodium sulfate and filtered through a glass fritted funnel. The filtrate was concentrated under reduced pressure at 40° C. to provide 4.99 kg of Compound 3 {$R_f$: 0.63 [ethyl acetate:hexanes, 1:1 (v/v)]; as a dark brown oil which was utilized in the next step without further purification.

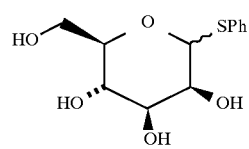

4

To a mechanically stirred solution of Compound 3 (6.28 kg, 4.3 mol) dissolved in methyl alcohol (13.0 L; Aldrich Chemical Co.) was gradually added 750.0 mL (3.28 mol) of a 25% (wt/v) sodium methoxide/methyl alcohol solution (Aldrich Chemical Co.), maintaining a reaction temperature below 40° C. The resulting mixture was stirred at 40° C. until completion, i.e., until only material having an $R_f$ of 0.05 (by thin layer chromatography analysis using ethyl acetate) was detected. The mixture was then cooled to room temperature and neutralized by addition of Dowex acidic 50X 8-200 ion exchange resin (Aldrich Chemical Co.). The neutralized reaction mixture was filtered through a glass fritted funnel and then concentrated under reduced pressure at 40° C. to yield a brown oil. The oil was partially purified by the addition, with stirring, of two 10.0 L aliquots of 5:1 (v/v) ethyl acetate/hexanes; the supernatant was discarded after each wash. The product, Compound 4 {$R_f$: 0.05 [ethyl acetate]}, was obtained as a brown oil after drying under vacuum.

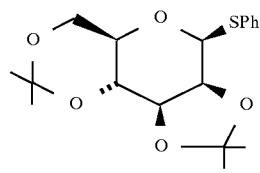

5

Compound 4 (3.0 kg) was dissolved in anhydrous N,N-dimethylformamide (6.0 L; Aldrich Chemical Co.) at room temperature. To this solution was first added 1.0 kg (4.3 mol) (±)-10-camphorsulfonic acid (Aldrich Chemical Co.), and next added (slowly, over 48 hours) 8.0 L of 2,2-dimethoxypropane (Aldrich Chemical Co.). Thin layer chromatographic analysis [ethyl acetate:hexanes, 1:4 (v/v)] indicated completion of the reaction. The completed reaction mixture was poured into 10.0 L of saturated aqueous sodium bicarbonate solution and extracted with 12.0 L dichloromethane. The organic layer was washed first with 5.0 L water and then with 10.0 L saturated aqueous sodium chloride solution, and dried over 3.0 kg sodium sulfate. The dried solution was filtered through a glass fritted funnel and concentrated under reduced pressure at 40° C. to provide Compound 5 as a black oil. The crude oil was dissolved in 10.0 L of boiling ethyl acetate, cooled to room temperature, and allowed to crystallize overnight. The crystalline mass was cooled to 5° C., filtered, and washed with 5.0 L of hexanes at 0° C. to provide 2.0 kg of partially purified Compound 5 as light brown needles. The remaining filtrate was concentrated under reduced pressure at 40° C., the resultant oil dissolved in 2.0 L dichloromethane, and the solution applied to a short pad of silica gel (2.0 kg; J.T. Baker, Inc.) and eluted with 1:4 (v/v) ethyl acetate/hexanes. The filtrate was concentrated and crystallized from ethyl acetate, yielding an additional 1.5 kg of crystalline product. The combined crystals were recrystallized from ethly acetate to provide a total of 2.8 kg of Compound 5 {$R_f$: 0.60 [ethyl acetate:hexanes, 1:4 (v/v)]} in 66% overall yield from Compound 1.

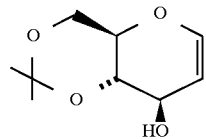

6

Compound 5 (1.98 kg, 6.0 mol) was dissolved in anhydrous tetrahydrofuran (6.0 L; Aldrich Chemical Co.), and 40.0 g (0.31 mol) of naphthalene (Aldrich Chemical Co.) was added at room temperature under a nitrogen atmosphere. To the solution was next added 20.0 g (2.9 mol) of lithium wire (3.2 mm diameter, 0.01% sodium; Aldrich Chemical Co.), cut into 20 cm long pieces, and the resulting mixture was subjected to rapid mechanical stirring. Upon completion of the reaction {as monitored by thin layer chromatographic analysis [ethyl acetate:hexanes, 1:1 (v/v)]}, excess lithium wire was removed, and the reaction mixture was poured into 10.0 L of saturated aqueous ammonium chloride solution (Fisher Scientific Co.). The mixture was then extracted with 10.0 L of dichloromethane; the organic layer was washed with 7.0 L of saturated aqueous sodium chloride solution, dried over 2.0 kg sodium sulfate, filtered through a fritted glass funnel, and concentrated under reduced pressure at room temperature to provide 1.4 kg of crude Compound 6 {$R_f$: 0.50 [ethyl acetate:hexanes, 1:1 (v/v)]}.

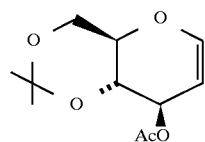

7

Compound 6 (3.5 kg) was slowly added to a mechanically stirred mixture of 0.5 L acetic anhydride and 4.5 L anhydrous pyridine. The addition was carried out in an ice-water bath in order to maintain a reaction temperature under 25° C. Forty-eight hours later the reaction mixture was concentrated to dryness under reduced pressure at room temperature to yield a syrupy, crystalline mass, which was filtered on a fritted glass funnel and washed with 1.0 L hexanes (at 0°) to provide 2.25 kg of Compound 7 as white needles {$R_f$: 0.5 [ethyl acetate:hexanes, 1:4 (v/v)]}.

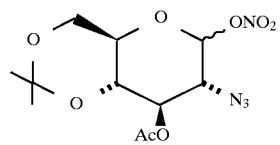

8

Compound 7 (50.6 g, 0.22 mol) was dissolved in 1.3 L anhydrous acetonitrile (Aldrich Chemical Co.), and a mixture of finely powdered ammonium cerium nitrate (550.0 g, 1.0 mol. Aldrich Chemical Co.) and sodium azide (40.0 g, 0.62 mol, Aldrich Chemical Co.) was added at −30° C., using a solid additional funnel. During the addition, the reaction temperature rose to −26° C. After stirring at −28° C. for four hours, the reaction mixture was poured slowly into 4.0 L ice water. Evolution of gas was observed during this process. The mixture was then diluted with 4.0 L ethyl acetate, and the two layers were separated. The organic layer was washed first with a 1.0 L portion of water, then with 2.0 L saturated aqueous sodium bicarbonate solution, and finally with 1.0 L saturated aqueous sodium chloride solution; the resulting solution was then dried over 500.0 g sodium sulfate, filtered through a fritted glass funnel, and concentrated to dryness under reduced pressure, at room temperature to provide approximately 70.0 g of crude product as a light yellow oil. The oil was passed through a short pad of silica gel (1.0 kg) with a mixture of 1:2 (v/v) ethyl acetate:hexanes. Evaporation of solvent from the product-containing fractions (as identified by thin layer chromatographic analysis) under reduced pressure at room temperature and drying overnight under vacuum at room temperature provided 56.0 g (0.169 mol) of (Compound 8) as a colorless foam in 77% yield.

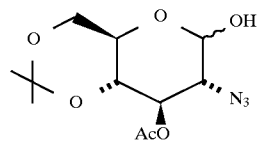

9

Compound 8 (56.0 g, 0.168 mol) was dissolved in a mixture of dioxane (1.47 L; Aldrich Chemical Co.) and water (600.0 mL), and 64.5 g (0.93 mol) sodium nitrite (Aldrich Chemical Co.) was added. The reaction mixture was refluxed for one hour, cooled to room temperature, and diluted with ethyl acetate (2.0 L). The two layers were separated, and the aqueous layer extracted with 2.0 L ethyl acetate. The combined organic layers were washed first with 1.0 L water, then with 1.0 L saturated aqueous sodium bicarbonate solution, and finally with 1.0 L saturated aqueous sodium chloride solution; the solution was dried over 500.0 g sodium sulfate, filtered through a fritted glass funnel, and concentrated under reduced pressure at room temperature to yield a yellow oil. The oil was passed through a short pad of silica gel (1.0 kg) with a mixture of 1:1 (v/v) ethyl acetate/hexanes. Evaporation of solvent from the product-containing fractions (as identified by thin layer chromatographic analysis) under reduced pressure at room temperature and drying overnight under vacuum at room temperature provided 55.0 g (0.168 mol) of Compound 9 {$R_f$: 0.14 [ethyl acetate:hexanes, 1:4 (v/v)]} as a colorless foam in a near quantitative yield.

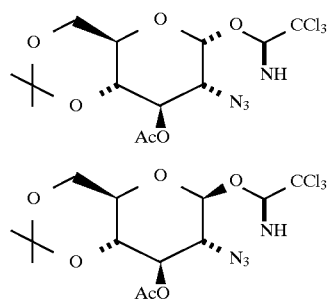

Compound 9 (1.50 g, 5.20 mmol) was dissolved in anhydrous tetrahydrofuran (20.0 mL) and trichloroacetonitrile (14 mL, 0.14 mol; Aldrich Chemical Co.). To this solution was added 1.8 mL (1.8 mmol) of a 1.0 M solution of lithium bis(trimethylsilyl)amide (Aldrich Chemical Co.) in hexanes added at 0° C. over four hours. The reaction was quenched with 10.0 mL saturated aqueous ammonium chloride solution and extracted with 200.0 mL ethyl acetate. The organic layer was washed with 100.0 mL saturated aqueous sodium chloride solution, dried over 50.0 g sodium sulfate, filtered, and concentrated under reduced pressure at room temperature. The crude product was purified on a silica gel (150.0 g) column, eluting with 1:3 (v/v) ethyl acetate/hexanes to provide 1.40 g (3.2 mmol) of the α-trichloroimidate, i.e., Compound 10a {$R_f$: 0.37 [hexanes:ethyl acetate, 3:1 (v/v)]}, as a syrup, in 67% yield, and 0.47 g (1.09 mmol) of the β-trichloroimidate, i.e., Compound 10b {$R_f$: 0.45 [hexanes:ethyl acetate, 3:1 (v/v)]}, as crystalline needles, in 25% yield.

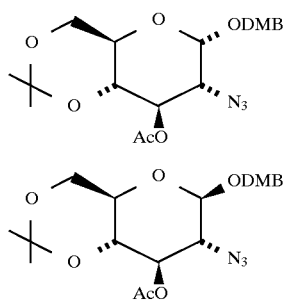

Compound 10a (130.0 mg, 0.30 mmol) was mixed with 3,4-dimethoxybenzyl alcohol (65.0 mL, 0.45 mmol; Aldrich Chemical Co.) and anhydrous dichloromethane (5.0 mL). To this mixture was added 200.0 mg of finely powdered AW-300 molecular sieves (Aldrich Chemical Co.). The mixture was stirred for one hour at room temperature, cooled to −78° C., and 1.0 mL of a 0.02 M dichloromethane solution of boron trifluoride etherate added over a period of six hours. The reaction was quenched with 1.0 L saturated aqueous sodium bicarbonate solution and extracted with 50.0 mL dichloromethane. The organic layers were dried over 25.0 g sodium sulfate, filtered through a fritted glass funnel, and concentrated under reduced pressure at room temperature. Purification on a silica gel column by eluting with 2:1 (v/v) hexanes/ethyl acetate provided a 6:1 mixture of Compound 11b {$R_f$: 0.28 [hexanes:ethyl acetate, 3:1 (v/v)]} and Compound 11a {$R_f$: 0.31 [hexanes:ethyl acetate, 3:1 (v/v)]} as a crystalline solid. The solid was recrystallized from 2:1 (v/v) hexanes/ethyl acetate as described above. Evaporation of solvent from the product-containing fractions (as identified by thin layer chromatographic analysis) under reduced pressure at room temperature and drying overnight under vacuum at room temperature provided 91.9 mg (0.21 mmol) of pure Compound 11b in 70% yield.

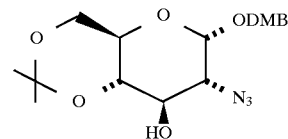

To a solution of Compound 11b (18.48 g, 0.04 mol) in methyl alcohol (200.0 mL) was added 2.0 mL of a 25% (w/v) sodium methoxide/methyl alcohol solution; the resulting mixture was stirred at room temperature for four hours. The reaction mixture was neutralized with 10.0 mL saturated aqueous ammonium chloride solution and extracted with 500.0 mL ethyl acetate. The organic layer was washed first with 100.0 mL water, and then with 100.0 mL saturated aqueous sodium chloride solution, and dried over 50.0 g sodium sulfate. Filtration through a cotton plug and evaporation of the solvent under reduced pressure at room temperature yielded a crude product which was applied to a silica gel (2.0 kg) column and eluted with 2:1 (v/v) hexanes/ethyl acetate to provide 15.1 g (0.038 mol) of Compound 12 {$R_f$: 0.19 [hexanes:ethyl acetate, 2:1 (v/v)]} in a 90% yield.

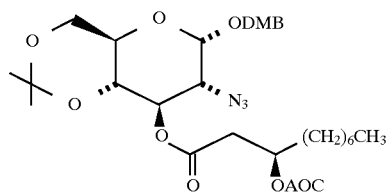

Compound 12 (15.1 g, 0.038 mol) was dissolved in anhydrous dichloromethane (200.0 mL). To this solution were sequentially added 12.4 g (0.038 mol) of Compound A6 (see below), 9.5 g (0.046 mol) 1,3-dicyclohexylcarbodiimide (Aldrich Chemical Co.), and 50.0 mg (0.41 mmol) of 4-dimethylaminopyridine, at 0° C., with magnetic stirring. After 30 minutes, the mixture was diluted with 100.0 mL hexanes and filtered through 100.0 g Celite 545 (Aldrich Chemical Co.). The filtrate was evaporated under reduced pressure at room temperature and the residue purified on a silica gel (2.0 kg) column by elution with 1:4 (v/v) ethyl acetate/hexanes. Evaporation of solvent from the product-containing fractions (as determined by thin layer chromatographic analysis) under reduced pressure at room temperature provided 22.1 g (0.034 mol) Compound 13 {$R_f$: 0.41 [ethyl acetate:hexanes, 1:2 (v/v)]} in an 89% yield.

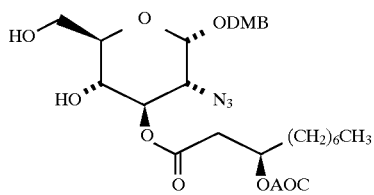

14

Compound 13 (22.0 g, 0.034 mol) was dissolved in glacial acetic acid (90.0 mL; Fisher Scientific Co.) and water (10.0 mL), and magnetically stirred at room temperature for 36 hours. The mixture was then evaporated under reduced pressure at room temperature and azeotroped three times with 50.0 mL portions of toluene (J.T. Baker, Inc.). The residue was purified on a silica gel (2.0 kg) column by elution with a linear gradient of 1:99 (v/v) to 5:95 (v/v) methyl alcohol/chloroform to provide 22.7 g (0.037 mol) of Compound 14 {$R_f$: 0.15 [chloroform:methyl alcohol, 98:2 (v/v)]} in quantitative yield. Compound 14 was used for the next step without further purification.

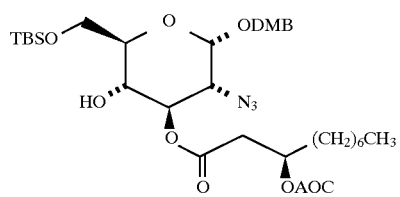

15

Compound 14 (20.6 g, 0.034 mol) was dissolved in N,N-dimethylformamide (33.9 mL), under a nitrogen atmosphere, at 0° C. To this solution was added 11.5 g (0.17 mol) of imidazole (Aldrich Chemical Co.) followed by 5.5 g (0.037 mol) of tert-butyldimethylsilyl chloride (Lithco Corporation of America, Gastonia, N.C.). The resulting mixture was stirred for one hour, diluted with 500.0 mL ethyl acetate, and poured into 500.0 mL saturated aqueous sodium bicarbonate solution. The organic layer was washed first with 200.0 mL saturated aqueous sodium bicarbonate solution, then with 200.0 mL water, and finally with 100.0 mL saturated aqueous sodium chloride solution. The organic layer was dried over 200.0 g sodium sulfate, filtered through a cotton plug, and evaporated under reduced pressure at room temperature. The residue was then purified by silica gel (2.0 kg) column chromatography, eluting with 1:4 (v/v) ethyl acetate/hexanes. Evaporation of solvent from the product-containing fractions (as determined by thin layer chromatographic analysis) provided 24.2 g (0.033 mol) of Compound 15 {$R_f$: 0.76 [ethyl acetate:hexanes, 1:1 (v/v)]} in 98% yield.

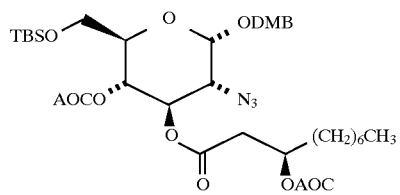

16

Compound 15 (24.1 g, 0.033 mol) was dissolved in anhydrous toluene (300.0 mL) and anhydrous pyridine (30.0 mL), at 0° C., under a nitrogen atmosphere. To this solution was slowly added (i.e., over 10 min) 24.1 mL (0.046 mol) of a 1.93 M solution of phosgene in toluene (Fluka Chemical Corp., Ronkonkoma, N.Y.). Thirty minutes later, 24.0 mL (0.353 mol) of allyl alcohol (Fluka Chemical Corp., Ronkonkoma, N.Y.) was added over a five-minute period, and the resulting reaction mixture was stirred for an additional 10 minutes. The reaction was quenched by addition of 100.0 mL saturated aqueous sodium bicarbonate solution, and diluted with 1.0 L ethyl acetate. The organic layer was washed first with 500.0 mL water, then with 500.0 mL saturated aqueous sodium chloride solution, dried over 500.0 g sodium sulfate, filtered through a cotton plug, and then evaporated under reduced pressure at room temperature. The residue was purified by silica gel (2.0 kg) column chromatography, eluting with 1:4 (v/v) ethyl acetate/hexanes to provide 25.3 g (0.031 mol) of Compound 16 {$R_f$: 0.60 [ethyl acetate:hexanes, 1:2 (v/v)]} in 94% yield.

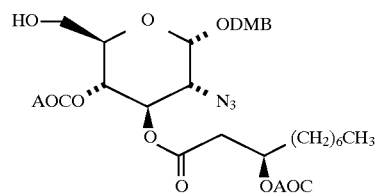

17

In a 250.0 mL polypropylene tube, 25.3 g (0.031 mol) of Compound 16 was dissolved in 100.0 mL of acetonitrile (Aldrich Chemical Co.). To the solution, at room temperature with magnetic stirring, was added 100.0 mL of a 4 M solution of hydrofluoric acid (Aldrich Chemical Co.) in acetonitrile. After 30 minutes, the reaction was quenched with 100.0 mL saturated aqueous sodium bicarbonate solution and extracted with 500.0 mL chloroform. The organic layer was washed with 100.0 mL water followed by 100.0 mL saturated aqueous sodium chloride solution, and then dried over 100.0 g sodium sulfate, filtered through a cotton plug, and the solvent evaporated under reduced pressure at room temperature. The residue obtained was purified by silica gel (2.0 kg) column chromatography, eluting with 2:3 (v/v) ethyl acetate/hexanes to provide 19.9 g (0.029 mol) of Compound 17 {$R_f$: 0.53 [ethyl acetate:hexanes, 1:1 (v/v)]} in 91% yield.

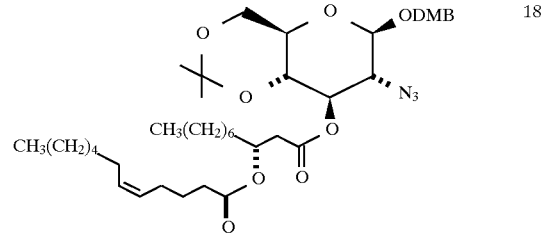

18

Compound 12 (20.0 g, 50.1 mmol) was dissolved in anhydrous dichloromethane (500.0 mL) at 0° C., and 19.4 g (52.7 mmol) of Compound B6 (see below), 20.8 g (100.9 mmol) of 1,3-dicyclohexycarbodiimide, and 120.0 mg (0.98 mmol) of 4-dimethylaminopyridine were added. After stirring for 20 minutes at room temperature the reaction mixture was diluted with 500.0 mL hexanes, filtered through 100.0 g Celite 545, and the solids washed with 100.0 mL hexanes. The combined filtrates were then concentrated under reduced pressure at room temperature, and the residue obtained was purified by silica gel (2.0 kg) column chromatography, eluting with 1:3 (v/v) ethyl acetate/ hexanes. Evaporation of solvent from the product containing fractions (as determined by thin layer chromatographic analysis) under reduced pressure at room temperature provided 35.0 g (47.0 mmol) of Compound 18 {$R_f$: 0.54 [ethyl acetate:hexanes, 1:4 (v/v)]} in 93% yield.

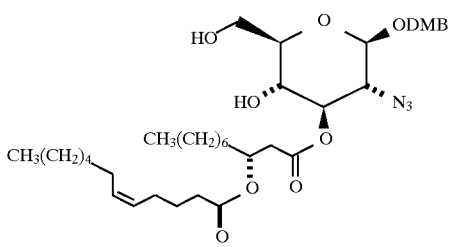

A solution of 35.0 g (47.0 mmol) of Compound 18 in a mixture of 240.0 mL of glacial acetic acid and 60.0 mL of water was magnetically stirred for 14 hours at room temperature. The reaction mixture was then concentrated under reduced pressure at room temperature, and the crude product azeotroped with three 50.0 mL portions of toluene. The product was purified by silica gel (3.0 kg) column chromatography, eluting first with 1:1 (v/v) hexanes/diethyl ether (Mallinckrodt Chemical Co., St. Louis, Mo.) followed by elution with ethyl acetate to provide 29.3 g (41.6 mmol) of Compound 19 {$R_f$: 0.62 [dichloromethane:methyl alcohol, 95:5 (v/v)]} in an 89% yield.

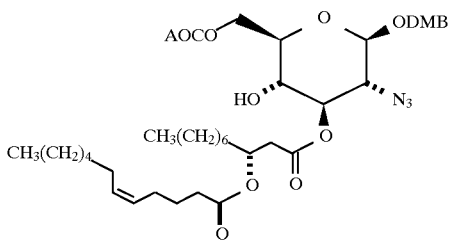

Compound 19 (4.9 g, 6.94 mmol) was dissolved in anhydrous toluene (50.0 mL) and anhydrous pyridine (12.0 mL) at 0° C., under a nitrogen atmosphere. To this solution was added 1.31 mL (12.3 mmol) allylchloroformate (Aldrich Chemical Co.). After seven and a half hours, the mixture was diluted with 100.0 mL ethyl acetate and washed, first with 100.0 mL saturated aqueous sodium bicarbonate solution, then with 100.0 mL water, and finally with 100.0 mL saturated aqueous sodium chloride solution. The mixture was then dried over 50.0 g sodium sulfate, and the solvents evaporated under reduced pressure at room temperature. The residue was dissolved in 10.0 mL dichloromethane, loaded onto a silica gel (500.0 g) column, and eluted with 1:2 (v/v) ethyl acetate:hexanes. Evaporation of solvent from the product-containing fractions (as determined by thin layer column chromatographic analysis) under reduced pressure at room temperature provided 4.2 g (5.32 mmol) of Compound 20 {$R_f$: 0.70 [ethyl acetate:hexanes, 1:1 (v/v)]} in 77% yield.

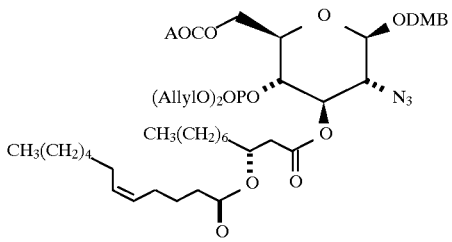

To a magnetically stirred solution of 18.26 g (0.02 mol) of Compound 20 in 200.0 mL anhydrous tetrahydrofuran, 17.02 mL (0.069 mol) bis(allyloxy) (diisopropylamino) phosphine (prepared by the method of Brannwarth and Kung, *Tetrahedron Lett.* 30, 4219, 1989) and 14.58 g (0.208 mol) 1H-tetrazole (Amresco Chemical Co., Solon, Ohio) were added at room temperature under a nitrogen atmosphere. After one hour, the mixture was cooled to −78° C., and a solution of 11.95 g 3-chloroperoxybenzoic acid (Aldrich Chemical Co.) in 80.0 mL anhydrous dichloromethane was added. The reaction temperature was adjusted to 0° C., and the mixture stirred for 20 minutes. The reaction was quenched with 50.0 mL of a 10% aqueous sodium thiosulfate solution; and following 10 minutes of stirring at room temperature, the mixture was warmed to room temperature. The mixture was then poured into 200.0 mL saturated aqueous sodium bicarbonate solution and extracted with 500.0 mL dichloromethane. The organic layer was washed first with 100.0 mL water, and then with 100.0 mL saturated aqueous sodium chloride solution, dried over 200.0 g sodium sulfate, and the solvents evaporated under reduced pressure at room temperature. The residue was purified on a silica gel (2.0 kg) column eluting with ethyl acetate:hexanes [1:2 (v/v)]. Evaporation of solvent from the product-containing fractions (as determined by thin layer chromatographic analysis) under reduced pressure at room temperature provided 17.64 g (0.0186 mol) of Compound 21 {$R_f$: 0.32 [ethyl acetate:hexanes, 1:2 (v/v)]} in an 80.5% yield.

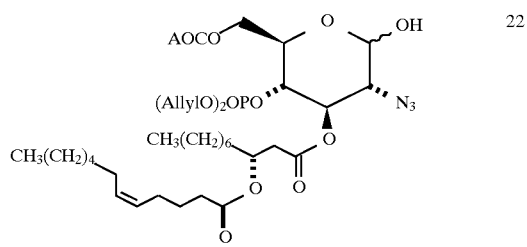

Compound 21 (35.0 g, 0.0369 mol) was dissolved in 40.0 mL tert-butylalcohol (Aldrich Chemical Co.), 40.0 mL pH 7.0 phosphate buffer concentrate (Fisher Scientific Co.) and 200.0 mL dichloromethane. To this solution, 33 g (0.145 mol) 2,3-dichloro-5,6-dicyano-1,4-benzoquinone (Aldrich Chemical Co.) was added at room temperature under a nitrogen atmosphere. The mixture was stirred in the dark at room temperature for 14 hours. The reaction was quenched with 200.0 mL 10% sodium thiosulfate solution (Fisher Scientific Co.), poured into 100.0 mL saturated aqueous sodium bicarbonate solution, and extracted with 1.0 L chloroform. The organic layer was washed first with 200.0 mL water and then with 200.0 mL saturated aqueous sodium chloride solution, dried over 500.0 g sodium sulfate, and the solvents evaporated under reduced pressure at room temperatures. The mixture was purifies on a silica gel (3.0 kg) column, eluting with 98:2 (v/v) dichloromethane/methyl alcohol. Evaporation of solvent from the product-containing fractions (as determined by thin layer chromatographic analysis) under reduced pressure at room temperature provided 27.5 g (0.0344 mol) of Compound 22 {$R_f$: 0.57 [dichloromethane:methyl alcohol, 95:5 (v/v)]} in a 94% yield.

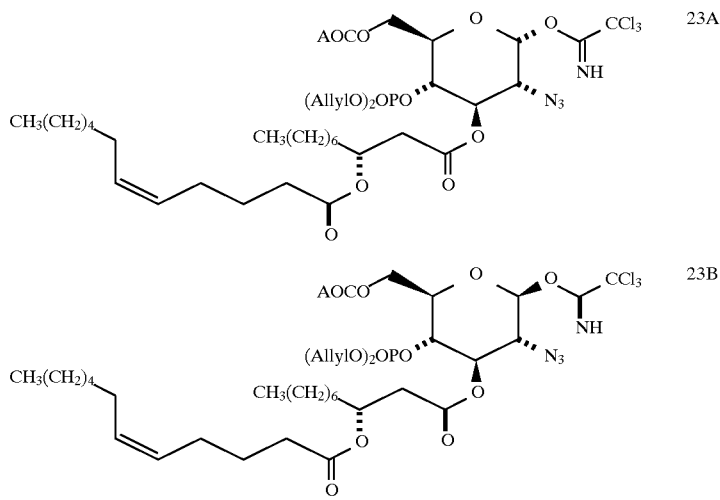

To a mechanically-stirred solution of 52.8 g (0.066 mol) of Compound 22 in 1.32 L trichloroacetonitrile, 53.0 g (0.163 mol) of cesium carbonate (Aldrich Chemical Co.) was added at room temperature under a nitrogen atmosphere. After eight hours, the mixture was filtered through 100.0 g Celite 545, washed with 500.0 mL dichloromethane, and the solvent evaporated under reduced pressure at room temperature. The residue was purified on a silica gel (3.0 kg) column eluted with 95:5 (v/v) dichloromethane/diethyl ether. Evaporation of solvent from the product-containing fractions (as determined by thin layer chromatographic analysis) under reduced pressure at room temperature provided 30.0 g (0.03 mol) of Compound 23A (α-isomer) {$R_f$: 0.79 [dichloromethane:diethyl ether, 9:1 (v/v)]} and 10.0 g (0.01 mol) of Compound 23B (β-isomer) {$R_f$: 0.76 [dichloromethane:diethyl ether, 9:1 (v/v)]}. Compound 23B was subjected again to the above reaction and subsequent purification to yield a second crop of Compound 23A. The two crops were combined to provide a total of 32.2 g (0.034 mol) of pure Compound 23A in 52% yield.

stirred for one hour at room temperature, under argon. The mixture was cooled to −23° C., and 9.45 mL (1.89 mmol) of a 0.2 M boron trifluoride etherate:dichloromethane solution [prepared by dissolving 0.25 mL (2.03 mmol) of boron trifluoride etherate in 10.0 mL of anhydrous dichloromethane and stirring with 200.0 mg powdered AW-300 molecular sieves for one hour at room temperature] was added using a syringe pump over a six-hour period. The reaction was quenched with 30.0 mL of saturated aqueous sodium bicarbonate solution, diluted with 500.0 mL dichloromethane, and filtered through 50.0 g Celite 545. The filtrate was washed first with 200.0 mL saturated aqueous sodium bicarbonate solution, then with 200.0 mL water, and finally with 200.0 mL saturated aqueous sodium chloride solution; the filtrate was then dried over 300.0 g sodium sulfate, filtered through a cotton plug, and the solvents evaporated under reduced pressure at room temperature. The resultant residue was purified on a silica gel (1.0 kg) column

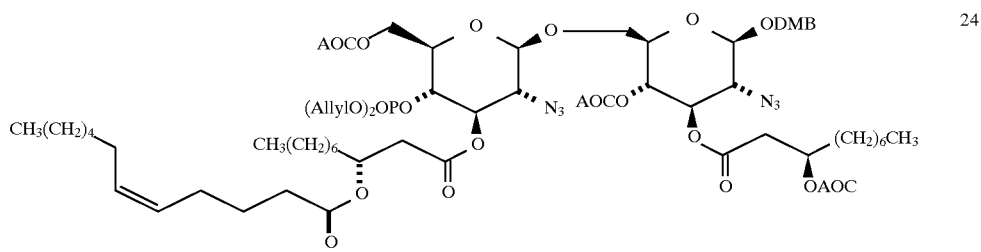

A mixture of 6.0 g (6.3 mmol) of Compound 23A and 4.5 g of Compound 17 (6.5 mmol) were dried under vacuum for 14 hours and dissolved in 100.0 mL of anhydrous dichloromethane. To this solution was added 10.0 g of powdered AW-300 molecular sieves (which had been flame-dried under vacuum), and the resulting mixture magnetically by elution with 1:3 (v/v) ethyl acetate/hexanes. Evaporation of solvent from the product-containing fractions (as determined by thin layer chromatographic analysis) under reduced pressure at room temperature provided 5.42 g (3.67 mmol) of Compound 24 {$R_f$: 0.34 [ethyl acetate:hexanes, 1:2 (v/v)]} in 59% yield.

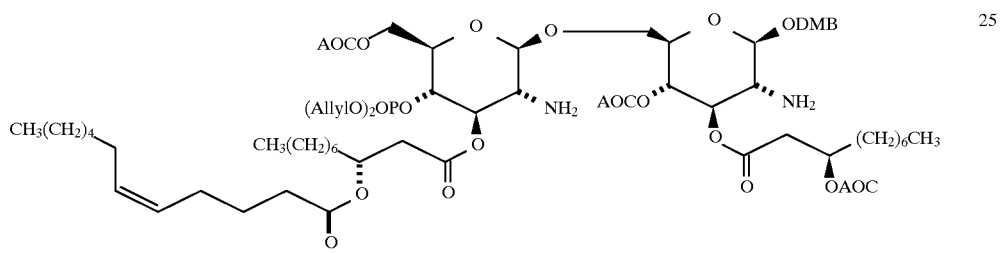

25

Compound 24 (2.11 g, 1.43 mmol) was dissolved in anhydrous dichloromethane (22.0 mL), and 1.9 g of tin(II) tris-benzenethiolate triethylamine complex (prepared by the method of Barta et al., *Tetrahedron Lett.* 47, 5941, 1987) was added. The resultant mixture was stirred for eight hours at room temperature under a nitrogen atmosphere in the absence of light. Thin layer chromatographic analysis [hexanes:ethyl acetate, 1:1 (v/v)] demonstrated that all starting material was consumed. The reaction mixture was loaded directly onto a silica gel (200.0 g) column and eluted first-with 4:1 (v/v) hexanes/ethyl acetate to remove reagent by-products, and then with 200.0 mL ethyl acetate. Evaporation of solvent from the product-containing fractions (as determined by thin layer chromatographic analysis) under reduced pressure at room temperature provided 0.91 g (1.34 mmol) of Compound 25 {$R_f$: 0.34 [ethyl acetate:hexanes, 1:1 (v/v)]} in 93.5% yield.

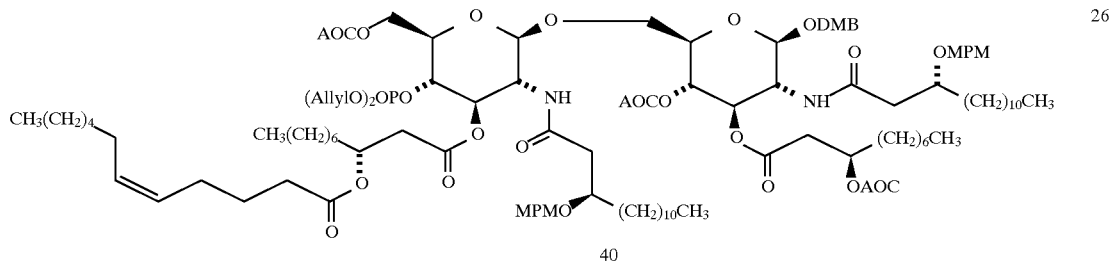

26

Compound 25 (1.91 g, 1.34 mmol) was dissolved in 10.0 mL anhydrous dichloromethane. To this mixture was added 1.7 g (4.65 mmol) of Compound C6 (see below) and 1.98 g (9.60 mmol) of 1,3-dicyclohexylcarbodiimide at room temperature. Fourteen hours later, thin layer chromatographic analysis [hexanes:ethyl acetate, 1:1 (v/v)] indicated that the reaction was complete. The reaction mixture was diluted with 50.0 mL ethyl acetate and filtered through 10.0 g Celite 545, the solids washed with 20.0 mL ethyl acetate, and the filtrate evaporated under reduced pressure at room temperature, yielding a syrupy residue. The syrup was dissolved in 5.0 mL dichloromethane, loaded onto a silica gel (100.0 g) column, and eluted, initially with 1:2 (v/v) ethyl acetate/hexanes and then with 1:1 (v/v) ethyl acetate/hexanes. Evaporation of solvent from the product-containing fractions (as determined by thin layer chromatographic analysis) under reduced pressure at room temperature provided 2.0 g (0.95 mmol) of Compound 26 {$R_f$: 0.5 [ethyl acetate:hexanes, 1:1 (v/v)]} in 71% yield.

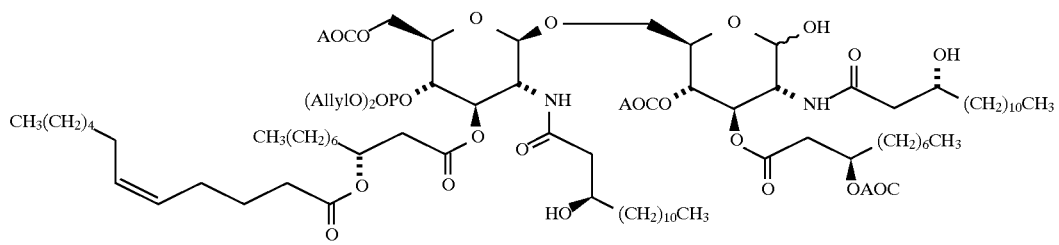

27

Compound 26 (817.0 mg, 0.386 mmol) was mixed with 13.5 mL of dichloromethane, 1.4 mL of tert-butyl alcohol and 1.4 mL of pH 7.0 phosphate buffer concentrate. To the mixture was added 439.0 mg (1.9 mmol) of 2,3-dichloro-5,6-dicyano-1,4-benzoquinone. The resulting mixture was magnetically stirred under a nitrogen atmosphere in the dark until thin layer chromatographic analysis [dichloromethane:methyl alcohol, 95:5 (v/v)] indicated the complete consumption of starting material (approximately four and a half hours). The reaction was then quenched with 10.0 mL 10% aqueous sodium thiosulfate solution, diluted with 100.0 mL dichloromethane, and poured into 50.0 mL saturated aqueous sodium bicarbonate solution. The organic layer was separated, washed with 50.0 mL saturated aqueous sodium chloride solution, dried over sodium sulfate, and filtered through a cotton plug. The crude reaction mixture was loaded directly onto a silica gel (100.0 g) column and eluted with 95:5 (v/v) dichloromethane/methyl alcohol to provide 606.0 mg (0.35 mmol) of Compound 27 {$R_f$: 0.42 [dichloromethane:methyl alcohol, 95:5 (v/v)]} in 91% yield.

To produce Lipid A Analog B274–32, Compound 27 was deprotected generally as described below for the preparation of Compound 31, and the free acid product was reacted with L-lysine as described below for analog B214–32.

hexanes was added slowly under a nitrogen atmosphere, at −78° C., with stirring. After five minutes, 0.71 mL (0.355 mirlol) of 0.5 M diallyl chlorophosphate (prepared by the method of Hayakawa et al.,*Tetrahedron Lett.* 28, 2259, 1987) in anhydrous toluene was added, and the mixture was stirred for 10 min. The mixture was then warmed to 0° C. stirred 15 minutes, and the reaction quenched with 0.1 mL of glacial acetic acid. The reaction mixture was poured into a 20.0 mL saturated aqueous sodium bicarbonate solution and extracted with 100 mL dichloromethane. The organic layer was washed with 20 mL saturated aqueous sodium bicarbonate solution and then 20.0 mL saturated aqueous sodium chloride solution, dried over 50.0 g sodium sulfate, filtered through a cotton plug, and the solvents evaporated under reduced pressure at room temperature. The residue obtained was purified on a silica gel (100.0 g) column by elution with 1:1 (v/v) dichloromethane/ethyl acetate, to provide 298.2 mg (0.158 mmol) of Compound 28 {$R_f$: 0.38 [dichloromethane:methyl alcohol, 95:5 (v/v)]} in 66.8% yield.

To produce Lipid A Analogs B231–31 and B231–32, Compound 28 was deprotected generally as described below for the preparation of Compound 31. Lipid A Analog B231–32 was produced by reacting the free acid product

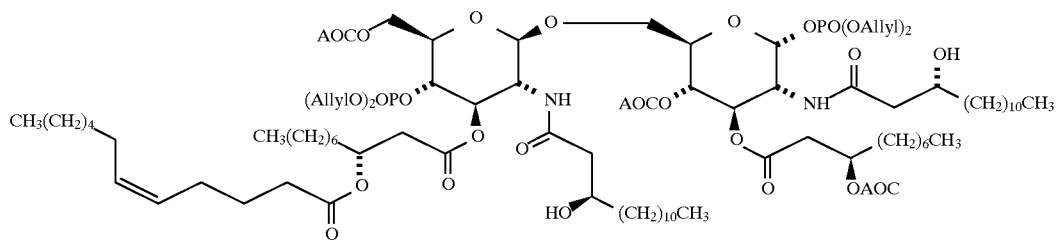

28

To a solution of 408.4 mg (0.237 mmol) of Compound 27 in anhydrous tetrahydrofuran (5.0 mL), 0.265 mL (0.262 mmol) of 0.99 M n-butyllithium (Aldrich Chemical Co.) in with L-lysine as described below for analog B214–32. Lipid A Analog B231–31 was produced by reacting the free acid product with Tris as described below for B214–31.

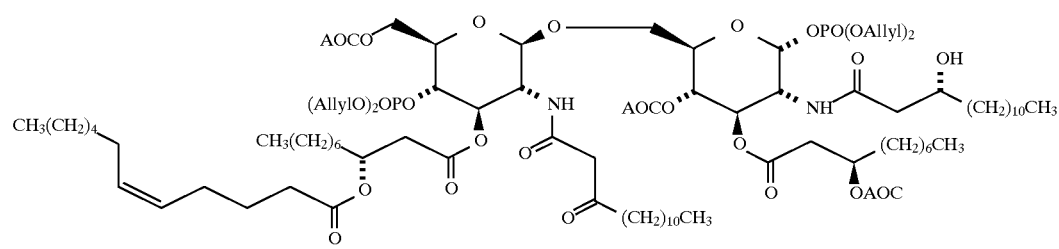

29

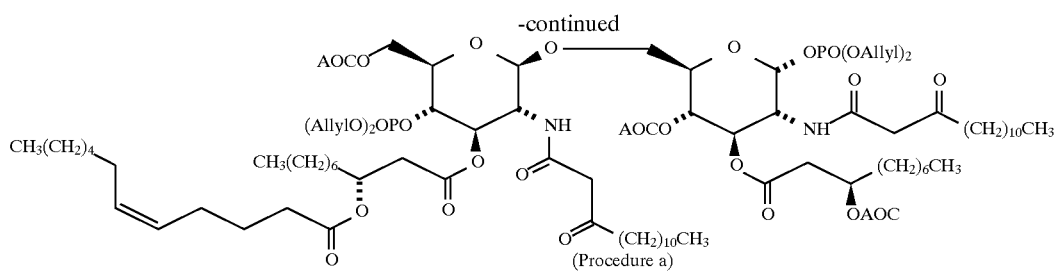
(Procedure a)

389.0 mg (0.92 mmol) 1,1,1-tris(acetoxy)-1,1-dihydro-1,2-zenziodoxol-3(1H)-one (prepared by the method of Dess and Martin, *J. Org. Chem.* 48:4156, 1983) was dissolved in 9.1 mL of anhydrous dichloromethane, and 600.0 mg of flame-dried powdered 4 Å molecular sieves (Aldrich Chemical Co.) were added. To this reaction mixture was then slowly added a solution of 287.2 mg (0.15 mmol) of Compound 28 dissolved in 2.9 mL dichloromethane, at 0° C., under argon. Two hours later, 5.0 mL (0.50 mmol) of a 0.1 M dichloromethane solution of 1,1,1-tris(acetoxy)-1,1-dihydro-1,2-benziodoxol-3(1H)-one was slowly added, and the reaction mixture was stirred for an additional two hours. The reaction mixture was then diluted with 10.0 mL diethyl ether, and 20.0 mL of a 1:1 (v/v) mixture of 10% aqueous sodium thiosulfate solution and saturated aqueous sodium bicarbonate solution was added. The resultant mixture was extracted with 100.0 mL dichloromethane. The organic layer was washed with 50.0 mL saturated aqueous sodium chloride solution, dried over 50.0 g sodium sulfate, and the solvents evaporated under reduced pressure at room temperature. The residue was purified on six 0.5 mm silica gel preparative thin layer chromatography plates (E.M. Science, Gibbstown, N.J.) using, as the elution solvent, 95:5 (v/v) dichloromethane/methyl alcohol. The product bands were eluted from the silica gel with ethyl acetate to provide 110.0 mg (0.058 mmol) of Compound 29 {$R_f$: 0.59 [dichloromethane:methyl alcohol, 95:5 (v/v)]} in 38.2% yield and 120.0 mg (0.064 mmol) of Compound 30 {$R_f$: 0.53 [dichloromethane:methyl alcohol, 95:5 (v/v)]} in 42% yield.

To produce Lipid A Analogs B218–31 and B218–32, Compound 29 was deprotected generally as described below for the preparation of Compound 31. Lipid A Analog B218–32 was produced by reacting the free acid product with L-lysine as described below for analog B214–32. Lipid A Analog B218–31 was produced by reacting the free acid product with Tris as described below for B214–31.

Compound 30 (332.0 mg, 0.176 mmol) was dissolved in 40.0 mL anhydrous tetrahydrofuran:96% formic acid (Aldrich Chemical Co.) [10:1 (v/v)], under a nitrogen atmosphere in the dark. To this solution was added tetrakis (triphenylphosphine)palladium(O) (2.07 g, 1.76 mmol (Aldrich Chemical Co.) and triphenylphosphine (1.45 g, 5.28 mmol, Aldrich Chemical Co.). The mixture was stirred at room temperature for two hours, the solvents evaporated under reduced pressure at room temperature, and the resulting residue azeotroped with 5.0 mL toluene three times. The residue was then dissolved in 10.0 mL methyl alcohol, and hydrogen sulfide gas was bubbled through the solution for five minutes. The solvent was then removed by evaporation under reduced pressure at room temperature. The crude product was purified on a DEAE-cellulose (100.0 g; Sigma Chemical Co., St. Louis, Mo.) column using a 0 to 0.1 M ammonium acetate (Aldrich Chemical Co.) salt gradient in a 3:2:1 (v/v/v) mixture of methyl alcohol/chloroform. Fractions containing product (as determined by thin layer chromatographic analysis) were combined and an equal volume of chloroform added. The organic layer was separated and concentrated under reduced pressure at room temperature, yielding the product in its ammonium salt form. The product was then dissolved in 100.0 mL water, and the excess ammonium acetate was removed by lyophilization. This product obtained is Lipid A Analog B214–33.

The lyophilized product was converted to the free acid by passage through a CM-cellulose (Sigma Chemical Co., St. Louis, Mo.) column, eluting with 3:2:1 (v/v/v) methyl alcohol/chloroform/water. The solution of free acid product was evaporated to dryness under reduced pressure at room temperature and an accurate weight obtained.

The product was then dissolved in 5.0 mL methyl alcohol, and 73 mg (0.49 mmol) L-lysine (Sigma Chemical Co., "Cell culture grade") dissolved in 5.0 mL water was added. The resulting mixture was evaporated to dryness under reduced pressure at room temperature, the product obtained redissolved in 300.0 mL pyrogen free deionized water, filtered through a 0.2 μm pore size Teflon HPLC filter (Rainin Instruments, Woburn, Mass.), and lyophilized to provide 256.7 mg (0.64 mmol) of a tetralysine salt {i.e., Compound 31; $R_f$: 0.64 [chloroform:methyl alcohol:glacial acetic acid:water, 125:75:10:20 (v/v/v/v)]} as a white hydroscopic foam in 71% yield. This product, Compound 31, is Lipid A Analog, B214–32.

Lipid A Analog B214–31 was produced by reacting the free acid product obtained above with tris[hydroxymethyl] aminomethane (Sigma Chemical Co.). The resulting mixture was evaporated to dryness under reduced pressure at room temperature, the product obtained redissolved in pyrogen

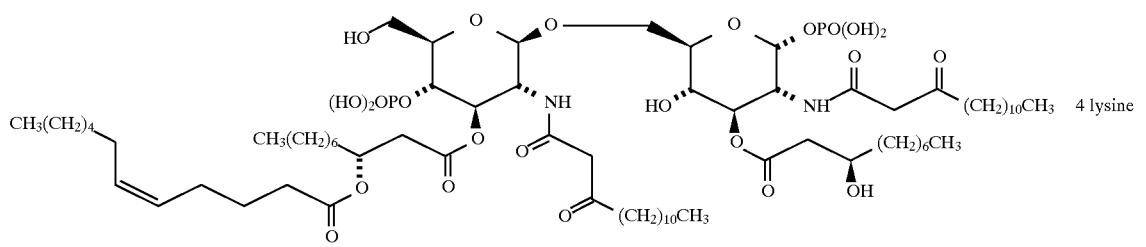

free deionized water, filtered through a 0.2 μm pore size Teflon HPLC filter (Rainin Instruments, Woburn, Mass.), and lyophilized to provide the tris[hydroxymethyl] amino methane salt, B214–31.

concentrate, followed by 957.0 mg (4.2 mmol) of 2,3-dichloro-5,6-dicyano-1,4-benzoquinone. The resultant heterogeneous mixture was magnetically stirred under a nitrogen atmosphere in the dark for about 12 hours or until

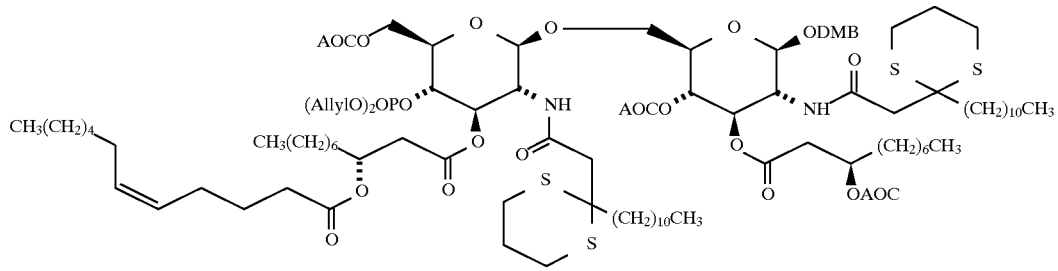

32

Compound 25 (3.90 g, 2.74 mmol) was dissolved in 40.0 mL anhydrous dichloromethane at room temperature. To this solution, at room temperature, was added 3.6 g (10.9 mmol) of Compound C8 (see below) and 4.50 g (21.9 mmol) of 1,3-dicyclohexylcarbodiimide. The reaction was allowed to proceed for 14 hours, at which time the reaction was determined to be complete by thin layer chromatographic analysis [hexanes:ethyl acetate, 1:1 (v/v)]. The reaction mixture was then diluted with 100.0 mL hexanes and filtered through 20.0 g Celite 545, the solids washed with 100.0 mL ethyl acetate, and the filtrate evaporated under reduced pressure at room temperature to yield a syrupy residue. The syrup was dissolved in 5.0 mL dichloromethane, applied to a silica gel (400.0 g) column and eluted first with 1:4 (v/v) ethyl acetate/hexanes, and then with 1:1 (v/v) ethyl acetate/hexanes to provide 3.36 g (1.64 mmol) of Compound 32 {$R_f$: 0.51 [ethyl acetate:hexanes, 1:1 (v/v)]} in 60% yield.

completion [as indicated by thin layer chromatographic analysis using dichloromethane:methyl alcohol, 19:1 (v/v)]. The reaction was quenched with 30.0 mL 10% aqueous sodium thiosulfate solution, diluted with 200.0 mL dichloromethane, and poured into 100.0 mL saturated aqueous sodium bicarbonate solution. The organic layer was separated, washed with 100.0 mL saturated aqueous sodium chloride solution, dried over 100.0 g sodium sulfate, and filtered through a cotton plug. The crude reaction mixture was then applied directly to a silica gel (400.0 g) column and eluted with a dichloromethane:methyl alcohol step gradient [99:1–50:1–19:1–4:1 (v/v)]. Evaporation of solvent from the product-containing fractions (as determined by thin layer chromatographic analysis) under reduced pressure at room

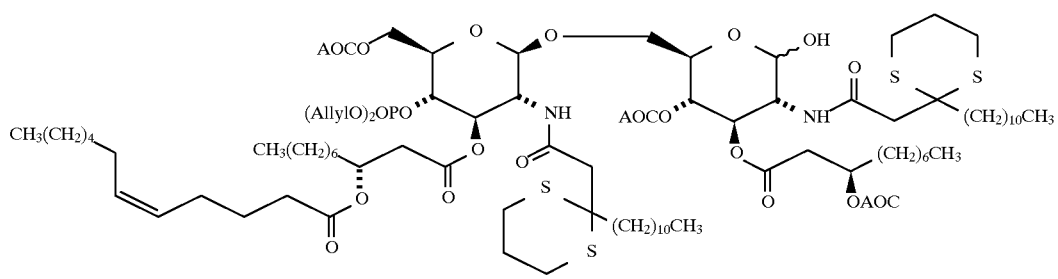

33

Compound 32 (3.46 g, 1.69 mmol) was dissolved in 35.0 mL dichloromethane and 3.5 mL tert-butyl alcohol. To this solution was added 3.5 mL of pH 7.0 phosphate buffer temperature provided 2.8 g (1.47 mmol) of Compound 33 {$R_f$: 0.32 [dichloromethane:methyl alcohol, 19:1 (v/v)]} in 87% yield.

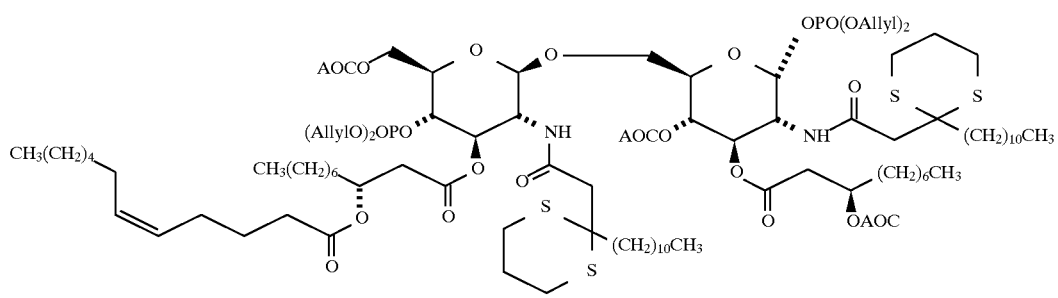

34

To a solution of Compound 33 (716.4 mg, 0.377 mmol) in anhydrous tetrahydrofuran (71 mL), 1.1 M n-butyllithium (377.0 µL, 0.415 mmol) in hexanes was added slowly with stirring, under a nitrogen atmosphere, at −78° C. After five minutes, 0.5 M diallyl chlorophosphate (1.13 mL; 0.566 mmol) in anhydrous toluene was added, and the mixture was stirred for 10 min. The mixture was then warmed to 0° C., stirred for an additional 10 minutes, and quenched with glacial acetic acid (716.0 L). The reaction mixture was poured into 100.0 mL of a saturated aqueous sodium bicarbonate solution and extracted with 500.0 mL dichloromethane. The organic layer was washed first with 100.0 mL saturated aqueous sodium bicarbonate solution and then with 100.0 mL saturated aqueous sodium chloride solution, dried over 300.0 g sodium sulfate, filtered through a cotton plug, and the solvents evaporated under reduced pressure at room temperature. The residue obtained was purified by elution from a silica gel (100.0 g) column with 3:1 (v/v) toluene/ethyl acetate. Evaporation of solvent from the product-containing fractions (as determined by thin layer chromatographic analysis) under reduced pressure at room temperature provided 450.4 mg (0.219 mmol) of Compound 34 {$R_f$: 0.50 [dichloromethane:methyl alcohol, 19:1 (v/v)]} in 58% yield.

To a magnetically stirred solution of Compound 9 (380.0 g; 1.3 mol) dissolved in 1.5 L of N,N-dimethylformamide was first added 227.0 g (3.25 mol) of imidazole under nitrogen, at 0° C., and then added 263.0 g (1.7 mol) of tert-butyldimethylsilyl chloride.. The solution was stirred for one and a half hours, diluted with 2.0 L ethyl acetate and poured into 2.0 L saturated aqueous sodium bicarbonate solution. The organic layer was separated and washed first with 2.0 L saturated aqueous sodium bicarbonate solution, then with 2.0 L water, and finally with 1.0 L saturated aqueous sodium chloride solution. The organic layer was then dried over 500.0 g sodium sulfate, filtered through a glass fritted funnel and concentrated under reduced pressure, at room temperature. The residue was then purified on a silica gel [4.0 kg] column and eluted with ethyl acetate:hexanes [1:4 (v/v)]. Evaporation of solvent from the product-containing fractions (identified by use of thin layer chromatographic analysis) under reduced pressure at room temperature and drying overnight under vacuum at room temperature provided 411.0 g (1.0 mol) of Compound 36 [ethyl acetate:hexanes, 1:4 (v/v)]} in 78% yield.

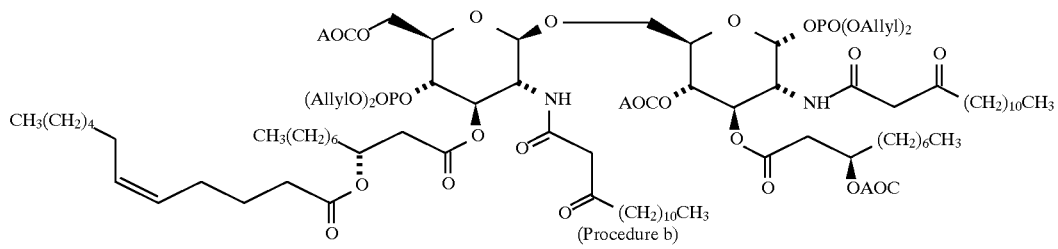

30

(Procedure b)

Compound 34 (810.0 mg, 0.40 mmol) was dissolved in acetonitrile (10.0 mL), and 1.0 mL water was added. To the resultant solution was added mercury(II)oxide red (693.0 mg, 3.20 mmol, Aldrich Chemical Co.), followed by mercury(II)chloride (434.4 mg, 1.60 mmol, Aldrich Chemical Co.), and the resulting mixture stirred at room temperature under a nitrogen atmosphere for one hour. The reaction mixture was then diluted with 20.0 mL methyl alcohol; hydrogen sulfide was bubbled through the mixture for five minutes; and the solution was filtered through a pad of silica gel (10.0 g) which had been preconditioned with 4:1 (v/v) dichloromethane/methyl alcohol. The filtrate was evaporated to dryness under reduced pressure at room temperature and purified on a silica gel (100.0 g) column, eluting first with 7:4 (v/v) hexanes/diethyl ether and then with 4:1 (v/v) dichloromethane/methyl alcohol. Evaporation of solvent from the product-containing fractions (as determined by thin layer chromatographic analysis) under reduced pressure at room temperature provided 539.0 mg (0.287 mmol) of Compound 30 {$R_f$: 0.53 [dichloromethane:methyl alcohol, 95:5 (v/v)]} in a 72% yield.

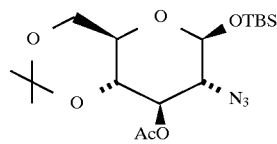

36

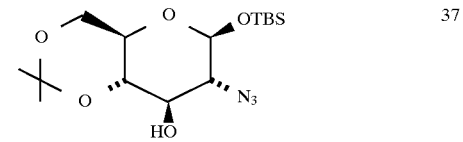

37

To a solution of Compound 36 (411.0 g; 1.0 mol) dissolved in 8.0 L methyl alcohol was added 50.0 mL of a 25% (wt/v) sodium methoxide in methyl alcohol solution, and the resulting mixture was stirred at room temperature for six hours. The reaction mixture was then neutralized with 1.0 L saturated aqueous ammonium chloride solution and extracted with 8.0 L ethyl acetate. The organic layer was separated, washed first with 1.0 L water, then with 1.0 L saturated aqueous sodium chloride solution, dried over 1.5 kg sodium sulfate, filtered, and concentrated under reduced pressure at room temperature. The crude product was purified on a silica gel [4.0 kg] column and eluted with a step gradient, beginning with a 5:1 (v/v), followed by a 4:1, a 3:1, and finally with a 2:1 mixture of hexanes:ethyl acetate. Evaporation of solvent from the product-containing fractions (as identified by use of thin layer chromatographic analysis) under reduced pressure at room temperature and drying overnight under vacuum at room temperature provided 339.8 g (0.95 mol) of Compound 37 [hexanes:ethyl acetate, 2:1 (v/v)] in a 93% yield.

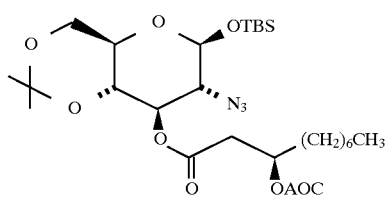

38

To a solution of Compound 37 (0.5 g; 1.4 mmol) in 10.0 mL of anhydrous dichloromethane was added: 0.38 g (1.4 mmol) of Compound A6 (see below), 0.35 g (1.7 mmol) 1,3-dicyclohexylcarbodiimide, and 1.8 mg (0.02 mmol) of 4-dimethylaminopyridine sequentially, at 0° C., with magnetic stirring. The mixture was stirred for an additional three hours, diluted with 20.0 mL hexanes, and filtered through 5.0 g Celite 545. The filtrate was concentrated under reduced pressure, at room temperature, and the residue purified on a silica gel (100.0 g) column and eluted with ethyl acetate:hexanes[1:7 (v/v)]. Evaporation of solvent from the product-containing fractions (as identified by thin layer chromatographic analysis) under reduced pressure at room temperature and drying overnight under vacuum, at room temperature provided 0.63 g (1.02 mmol) of Compound 38 {$R_f$: 0.64 [ethyl acetate:hexanes, 1:4 (v/v)]} in a 73% yield.

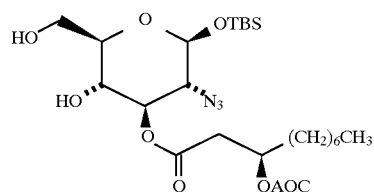

39

Compound 38 (0.63 g; 1.02 mmol) was dissolved in 8.0 mL of glacial acetic acid and 2.0 mL of water by magnetic stirring at room temperature for 12 hours. The mixture was concentrated under reduced pressure at room temperature and azeotroped three times with 10.0 mL portions of toluene. The residue was purified on a silica gel (100.0 g) column and eluted with 1:2 (v/v) ethyl acetate:hexanes. Evaporation of solvent from the product-containing fractions (as identified by thin layer chromatographic analysis) under reduced pressure at room temperature and drying overnight under vacuum at room temperature provided 0.57 g (0.99 mmol) of Compound 39 {$R_f$: 0.22 [ethyl acetate:hexanes, 1:2 (v/v)]} in 98% yield.

A mixture of Compound 23A (113.4 mg; 0.134 mmol) and Compound 39 (321.5 mg; 0.61 mmol) was dried under vacuum for 14 hours and dissolved in 10.0 mL of anhydrous toluene. To this solution was added 300.0 mg of powdered AW-300 molecular sieves which were flame-dried under vacuum, and the resulting mixture magnetically stirred for one hour at room temperature under an argon atmosphere. The mixture was then cooled to −35° C. and 8.0 mL (0.32 mmol) of a 0.04 M boron trifluoride etherate:toluene solution [prepared by dissolving 200.0 μL (1.6 mmol) of boron trifluoride etherate in 40.0 mL of toluene and stirring with 200.0 mg powdered AW-300 molecular sieves for one hour at room temperature] was added over a two and a half hour period using a syringe pump. The reaction was quenched with 10.0 mL of saturated aqueous sodium bicarbonate solution, diluted with 100.0 mL dichloromethane, and filtered through 20.0 g Celite 545. The filtrate was washed first with 100.0 mL of saturated aqueous sodium bicarbonate solution, then with 100 mL of water, and finally with 100 mL of saturated aqueous sodium chloride solution, dried over 50.0 g sodium sulfate, filtered through a glass fritted funnel, and concentrated under reduced pressure at room temperature. The residue was purified on a silica gel (100.0 g) column and eluted with ethyl acetate:hexanes [1:2 (v/v)]. Evaporation of solvent from the product-containing fractions (as identified by thin layer chromatographic analysis) under reduced pressure at room temperature and drying overnight under vacuum at room temperature provided 119.1 g (0.094 mmol) of Compound 40 {$R_f$: 0.44 [ethyl acetate:hexanes, 1:2 (v/v)]} in 70% yield.

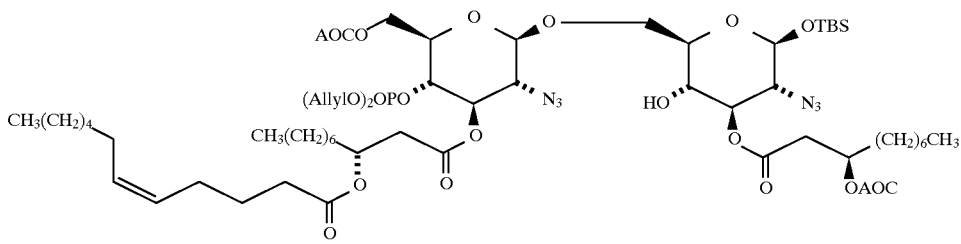

40

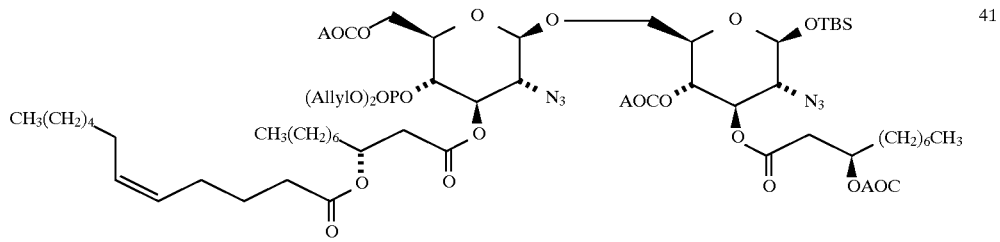

41

To a magnetically stirred solution of Compound 40 (110.0 mg; 0.09 mmol) dissolved in 1.0 mL anhydrous toluene and 33.0 μL (0.34 mmol) anhydrous pyridine, at 0° C., was added 68.0 μL (0.13 mmol) 1.93 M phosgene in toluene dropwise, and the reaction mixture was stirred for an additional 15 minutes. To this solution, 100.0 μL (1.47 mmol) of allyl alcohol was added dropwise, the reaction was stirred for an additional 30 minutes, the reaction quenched by addition, at 0° C., of 10.0 mL saturated sodium bicarbonate solution and warming to 25° C. The reaction mixture was then extracted with 100.0 mL ethyl acetate, the organic layer washed with 10.0 mL saturated aqueous sodium chloride solution, dried over 25.0 g sodium sulfate, filtered through a glass fritted funnel, and concentrated under reduced pressure at room temperature. The residue obtained was purified on a silica gel (100.0 g) column and eluted with 1:3 (v/v) mixture of ethyl acetate:hexanes. Evaporation of solvent from the product-containing fractions (as identified by thin layer chromatographic analysis) under reduced pressure at room temperature and drying overnight under vacuum at room temperature provided 75.0 mg (0.06 mmol) of Compound 41 {$R_f$: 0.75 [hexanes:ethyl acetate, 3:1 (v,v)]} in 64% yield.

and eluted first with a 4:1 (v/v) mixture of hexanes:ethyl acetate and then with ethyl acetate. Evaporation of solvent from the product-containing fractions (as identified by thin layer chromatographic analysis) under reduced pressure at room temperature and drying under vacuum at room temperature for 30 minutes provided 64.4 mg (0.05 mmol) of Compound 42 {$R_f$: 0.57 [ethyl acetate:hexanes, 1:1 (v/v)]} in 90% yield.

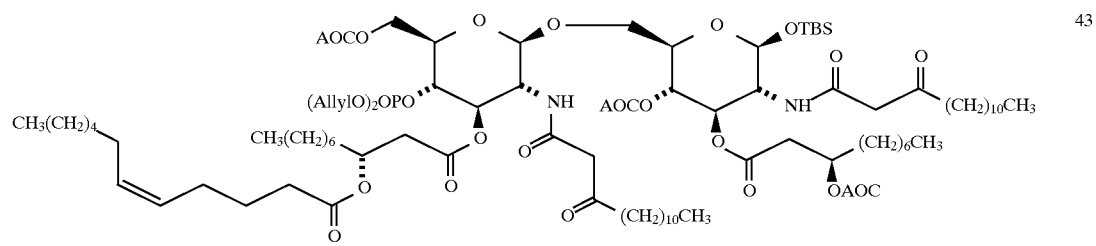

43

To a magnetically stirred 0° C. solution of Compound 42 (64.4 mg; 0.05 mmol) in 3.0 mL anhydrous dichloromethane was added 67.0 mg (0.28 mmol) of Compound D2 and 70.0 mg (0.34 mmol) of 1,3-dicyclohexylcarbodiimide. After one hour, when thin layer chromatographic analysis [hexanes:ethyl acetate, 1:1 (v/v)] indicated completion of the reaction had occurred, the reaction mixture was diluted with 50.0 mL ethyl acetate and filtered through 10.0 g Celite 545. The solids obtained were washed with 20.0 mL ethyl acetate and the filtrate concentrated under reduced pressure at room temperature yielding a syrupy residue. The syrup

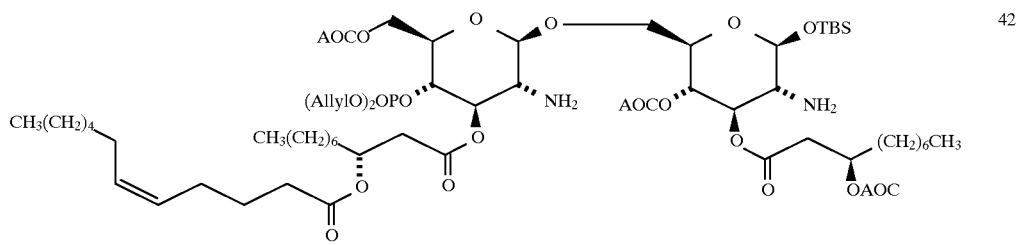

42

To a magnetically stirred solution of Compound 41 (75.0 mg; 0.056 mmol) dissolved in 4.0 mL of anhydrous dichloromethane, was added 250.0 mg (0.45 mmol) of tin(II)tris-benzenethiolate triethylamine complex and the resulting mixture stirred at room temperature under nitrogen in the dark until thin layer chromatographic analysis [hexanes:ethyl acetate, 1:1 (v/v)] indicated the starting material to be consumed (i.e., for two hours). The reaction mixture was loaded directly onto a silica gel (10.0 g) column was dissolved in 1.0 mL dichloromethane, loaded onto a silica gel (10.0 g) column and eluted first with 1:9 (v/v) ethyl acetate:hexanes to remove reagent residues, and then with 1:1 (v/v) ethyl acetate:hexanes. Evaporation of solvent from the product-containing fractions (as indicated by thin layer chromatographic analysis) under reduced pressure at room temperature and drying overnight under vacuum at room temperature provided 87.0 mg (0.04 mmol) of Compound 43 {$R_f$: 0.95 [ethyl acetate:hexanes, 1:1 (v/v)]} in 85% yield.

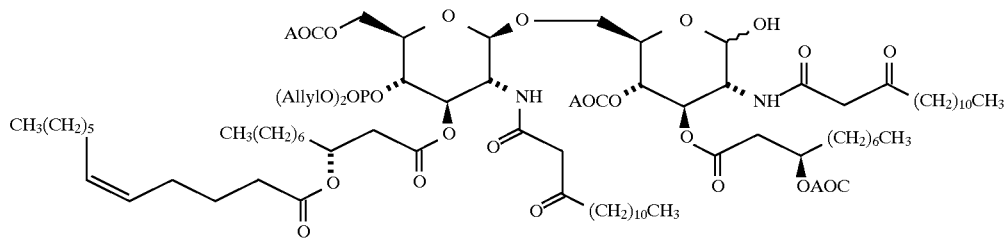

44

To a magnetically stirred solution of 12.0 mL of 2 M hydrogen fluoride in acetonitrile in a Teflon reaction vessel was added 70.0 mg (0.036 mmol) of Compound 43 dissolved in 0.5 mL of dichloromethane, at room temperature. The resulting mixture was stirred for 18 additional hours, diluted with 20.0 mL saturated aqueous sodium bicarbonate solution, and extracted with 100.0 mL dichloromethane. The organic layer was separated and washed first with 20.0 mL water and then with 10.0 mL saturated aqueous sodium chloride solution. The organic layer was dried over 25.0 g sodium sulfate, filtered through a glass fritted funnel, and concentrated under reduced pressure at room temperature. The residue was purified on a silica gel (10.0 g) column and eluted with dichloromethane:methyl alcohol [98:2 (v/v)]. Evaporation of solvent from the product-containing fractions (as indicated by thin layer chromatographic analysis) under reduced pressure at room temperature and drying overnight under vacuum at room temperature provided 60.3 mg (0.035 mmol) of Compound 44 {$R_f$: 0.78 [dichloromethane:methyl alcohol, 98:2 (v/v)]} in 97% yield.

To produce Lipid A Analog B276–32, Compound 44 was deprotected generally as described above for the preparation of Compound 31, and the free acid product was reacted with L-lysine as described above for analog B214–32.

product-containing fractions (as identified by thin layer chromatographic analysis) under reduced pressure at room temperature and drying overnight under vacuum at room temperature provided 53.0 mg (0.028 mmol) of Compound 30 {$R_f$: 0.29 [ethyl acetate:hexanes, 1:1 (v/v)]} in a 74% yield.

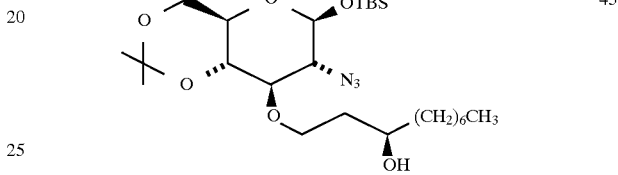

45

To a magnetically stirred solution of Compound 37 (19.0 g; 0.05 mol) dissolved in 65.0 mL anhydrous dichloromethane, under an argon atmosphere, at 0° C. was added 2.75 g (0.11 mol) 60% sodium hydride oil dispersion (Aldrich Chemical. Co.). The mixture was stirred first for fiveminutes at 0° C. and then for 15 minutes at room temperature. Under argon, a solution of 20.5 g (0.06 mol) A10 dissolved in 30.0 mL of anhydrous dichloromethane was then added dropwise to the reaction mixture through a

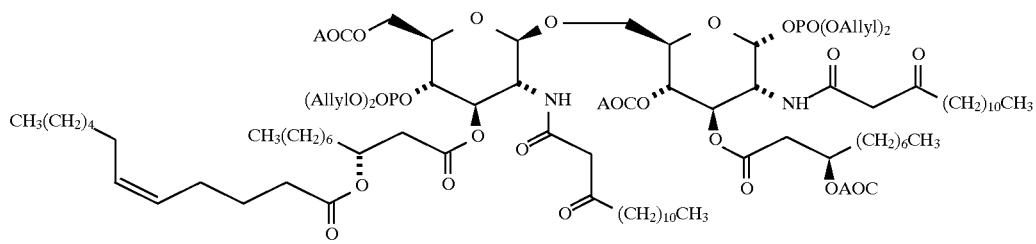

30 (Procedure c)

To a magnetically stirred solution of Compound 44 (65.0 mg; 0.038 mmol) in 5.0 mL anhydrous dichloromethane, 70.0 mg (0.28 mmol) of bis(allyloxy) (diisopropylamino) phosphine and 70.0 mg (1.0 mmol) of 1H-tetrazole was added at 0° C., under a nitrogen atmosphere. The mixture was warmed to room temperature and stirred for an additional hour. The mixture was then cooled to −78° C., and a solution of 11.95 mg (0.12 mmol) 3-chloroperoxybenzoic acid dissolved in 0.80 mL dichloromethane was added. The mixture was warmed to 0° C., stirred for 20 additional minutes, and 10.0 mL saturated aqueous sodium bicarbonate solution was added. The resultant mixture extracted with 100.0 mL dichloromethane, and the organic layer was separated and washed first with 10.0 mL water, and then with 10.0 mL saturated aqueous sodium chloride solution, and dried over 25.0 g sodium sulfate. The dried product was concentrated under reduced pressure, at room temperature purified on a silica gel (10.0 g) column, and eluted with ethyl acetate:hexanes [1:1 (v/v)]. Evaporation of solvent from the syringe-pump over a two-hour period. After stirring for 30 minutes, the reaction mixture was cooled to 0° C., 5.0 mL methyl alcohol was added dropwise to quench any unreacted sodium hydride, and the reaction mixture was diluted with 300.0 mL dichloromethane and washed first with 300.0 mL saturated aqueous ammonium chloride solution, then with 300.0 mL saturated aqueous sodium chloride solution. The organic layer was separated, dried over 100.0 g sodium sulfate and concentrated under reduced pressure to yield a crude syrupy product. The product was purified on silica gel (2.0 kg) column and eluted with a step gradient of hexanes: ethyl acetate [12:1 to 9:1 to 8:1 to 5:1 (v/v)]. Evaporation of solvent from the product-containing fractions (as identified by thin layer chromatographic analysis)-under reduced pressure at room temperature and drying overnight under vacuum at room temperature provided 20.1 g (0.04 mol) of Compound 45 {$R_f$: 0.53 [hexanes:ethyl acetate, 4:1 (v/v)]} in 68% yield.

46

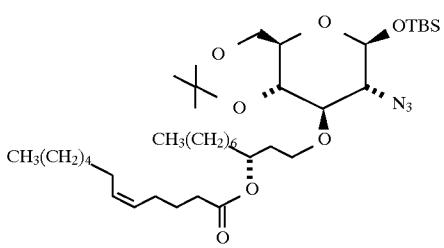

To a magnetically stirred solution of Compound 45 (13.69 g; 26.5 mmol) and Compound B4 (6.3 g; 31.8 mmol) (see below) dissolved in 76.0 mL of anhydrous dichloromethane at room temperature under a nitrogen atmosphere was added 11.0 g (53.0 mmol) of 1,3-dicyclohexylcarbodiimide. To the resulting mixture was added 5.26 mL (0.26 mmol) of 0.5 M 4-dimethylaminopyridine in anhydrous dichloromethane over a one-hour period. The reaction mixture was stirred for nine hours at room temperature, filtered through a pad of 100.0 g Celite 545, and the filtered solids washed with 200.0 mL of ethyl acetate. The combined filtrate and ethyl acetate wash were concentrated under reduced pressure at room temperature and the crude product purified on a silica gel (2.0 kg) column and eluted with hexanes:ethyl acetate [9:1 (v/v)]. Evaporation of solvent from the product-containing fractions (as identified by thin layer chromatographic analysis) under reduced pressure at room temperature and drying overnight under vacuum at room temperature provided 17.4 g (25.1 mmol) of Compound 46 {$R_f$: 0.80 [hexanes:ethyl acetate, 4:1 (v/v)]} in 94% yield.

47

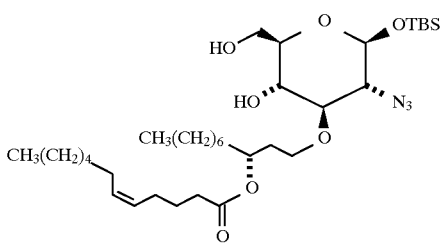

A solution of Compound 46 (17.4 g; 25.0 mmol), dissolved in 100.0 mL of a 8:1 (v/v) mixture of glacial acetic acid and water, was heated to 60° C., with magnetic stirring for 12 hours. The reaction mixture was then concentrated under reduced pressure, at 40° C., and the crude product purified on a silica gel (2.0 kg) column by elution with a step gradient of hexanes:ethyl acetate [first 6:1 (v/v) then 2:1 (v/v)]. Evaporation of solvent from the product-containing fractions (as identified by thin layer chromatographic analysis) under reduced pressure at room temperature and drying overnight under vacuum at room temperature provided 15.0 g (22.9 mmol) of Compound 47 {$R_f$: 0.13 [hexanes:ethyl acetate, 4:1 (v/v)]} in 91% yield.

48

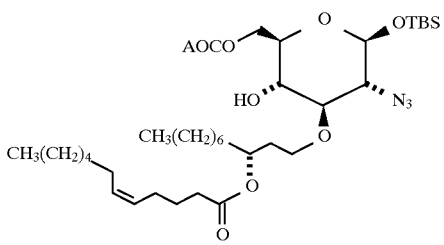

To a magnetically stirred solution of Compound 47 (8.85 g; 12.7 mmol) dissolved in 60.0 mL of a 4:1 [v/v] mixture of anhydrous toluene and anhydrous pyridine, at 0° C., under nitrogen, was added 1.75 mL (16.5 mmol) allylchloroformate dropwise over a 30-minute period. The resulting mixture was diluted with 300.0 mL ethyl acetate, washed with 100.0 mL saturated aqueous sodium bicarbonate solution, 100 mL water, and 100 mL saturated aqueous sodium chloride solution, dried over 100.0 g sodium sulfate, and concentrated under reduced pressure at room temperature. The residue was dissolved in 10.0 mL dichloromethane, loaded on a silica gel (1.0 kg) column and eluted with ethyl acetate:hexanes [1:9 (v/v)]. Evaporation of solvent from the product-containing fractions (as identified by thin layer chromatographic analysis) under reduced pressure at room temperature and drying overnight under vacuum at room temperature provided 8.1 g (10.9 mmol) of Compound 48.

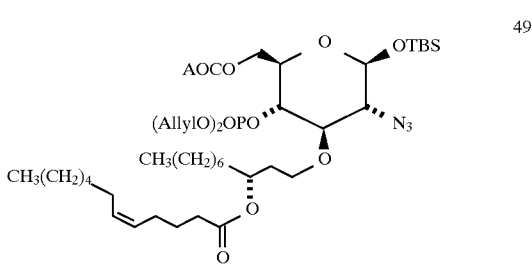

To a magnetically stirred solution of Compound 48 (1.6 g; 2.06 mmol), dissolved in 10.0 mL anhydrous dichloromethane at room temperature under a nitrogen atmosphere, was first added 757.0 mg (3.1 mmol) bis(allyloxy)(diisopropylamino) phosphine and then added (in one portion) 650.0 mg (9.3 mmol) 1H-tetrazole. After 10 minutes, the reaction mixture was cooled to −78° C., and a solution of 550.0 mg (2.2 mmol) of 55% 3-chloroperoxybenzoic acid dissolved in 5.0 mL anhydrous dichloromethane was added dropwise over a 10-minute period. The reaction was quenched at −78° C. by the addition of 50.0 mL saturated aqueous sodium bicarbonate solution. The resulting mixture was then extracted with 200.0 mL dichloromethane and the organic layer extract washed first with 50.0 mL water, then with 50.0 mL saturated aqueous sodium chloride, and dried over 50.0 g sodium sulfate. Concentration under reduced pressure at room temperature provided the crude product which was purified on a silica gel (300.0 g) column and eluted with ethyl acetate:hexanes [1:4 (v/v)]. Evaporation of solvent from the product-containing fractions (as identified by thin layer chromatographic analysis) under reduced pressure at room temperature and drying overnight under vacuum at room temperature provided 1.7 g (1.8 mmol) of Compound 49.

50

To a magnetically stirred solution of 70.0 mL of 6 M hydrogen fluoride in acetonitrile in a Teflon reaction vessel was added 10.5 g (11.6 mol) of Compound 49 dissolved in 10.0 mL of dichloromethane at room temperature. The resulting mixture was stirred for an additional 18 hours, poured into 400.0 mL of a saturated aqueous sodium bicarbonate solution at 0° C., and extracted with 500.0 mL dichloromethane. The organic layer extract was washed first with 100.0 mL water and then with 100.0 mL saturated aqueous sodium chloride solution. The organic layer was dried over 250.0 g sodium sulfate, filtered through a glass fritted funnel, and concentrated under reduced pressure at room temperature. The residue was purified on a silica gel (1.0 kg) column and eluted with hexanes:ethyl acetate [3:1 (v/v)]. Evaporation of solvent from the product-containing fractions (as identified by thin layer chromatographic analysis) under reduced pressure at room temperature and drying overnight under vacuum at room temperature provided 7.9 g (10.1 mmol) of Compound 50.

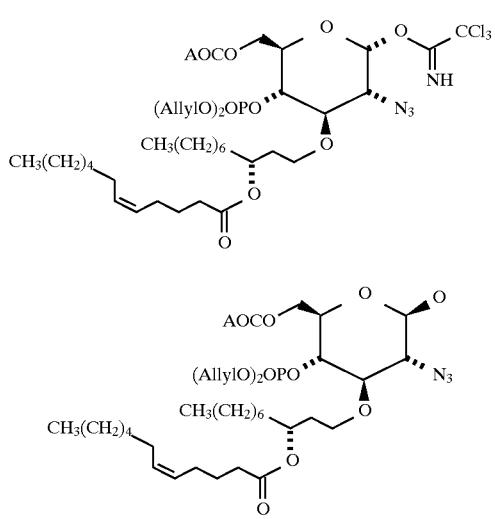

To a mechanically stirred solution of Compound 50 (1.1 g; 1.4 mmol) in 10.0 mL trichloroacetonitrile, 2.6 g (8.0 mmol) of cesium carbonate was added at room temperature under a nitrogen atmosphere. After two hours, the mixture was filtered through 25.0 g Celite 545, the filtered solids washed with 100.0 mL dichloromethane, and the combined filtrates concentrated under reduced pressure at room temperature. The crude product was purified on a silica gel (200.0 g) column and eluted with dichloromethane:diethyl ether [19:1 (v/v)]. Evaporation of solvent from the product-containing fractions (as identified by thin layer chromatographic analysis) under reduced pressure at room temperature and drying overnight under vacuum at room temperature provided 600.7 mg (0.65 mmol) of Compound 51A (αisomer) and 500.0 mg (0.54 mmol) of Compound 51B (βisomer) in a combined yield of 85%.

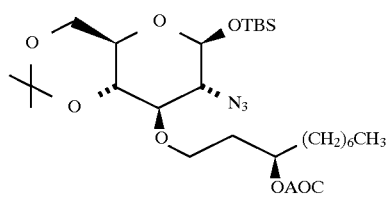

To a magnetically stirred solution of Compound 45 (13.8 g; 26.8 mmol) dissolved in 100.0 mL of a 4:1 (v/v) mixture of anhydrous toluene and anhydrous pyridine at room temperature under a nitrogen atmosphere, was added 21.0 mL (40.2 mmol) of 1.93 M phosgene in toluene dropwise over a 30-minute period. The resulting mixture was stirred for an additional 15 minutes, 16.1 mL (214.4 mmol) allyl alcohol was added and the mixture stirred for one hour longer. The reaction mixture was diluted with 100.0 mL saturated aqueous sodium bicarbonate solution and extracted with 300.0 mL ethyl acetate. The organic layer extract was washed first with 200.0 mL water, then with 100.0 mL saturated aqueous sodium chloride solution, and dried over 200.0 g sodium sulfate. The dried organic layer extract was filtered and concentrated under reduced pressure, at room temperature. The crude product obtained was dissolved in 10.0 mL dichloromethane, loaded onto a silica gel (1.0 kg) column and eluted with ethyl acetate:hexanes [1:9 (v/v)]. Evaporation of solvent from the product-containing fractions (as identified by thin layer chromatographic analysis) under reduced pressure at room temperature and drying overnight under vacuum at room temperature provided 15.6 g (26.1 mmol) of Compound 52 in 97% yield.

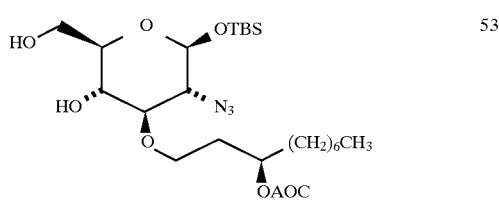

A solution of Compound 52 (15.6 g; 26.1 mmol) dissolved in 50.0 mL of glacial acetic acid and 2.0 mL of water was magnetically stirred at room temperature for 12 hours. The mixture was concentrated under reduced pressure at room temperature and azeotroped three times with 10.0 mL portions of toluene. The residue was purified on a silica gel (1.0 kg) column and eluted using a two step gradient: 1:2 (v/v) ethyl acetate:hexanes then ethyl acetate. Evaporation of solvent from the product-containing fractions (as identified by thin layer chromatographic analysis) under reduced pressure at room temperature and drying overnight under vacuum at room temperature provided 12.1 g (21.6 mmol) of Compound 53 in 83% yield.

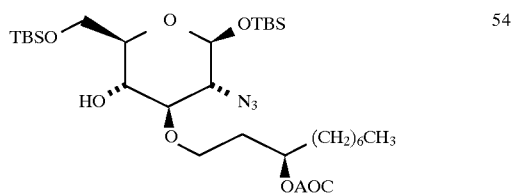

To a magnetically stirred solution of Compound 53 (10.3 g; 18.5 mmol) dissolved in 400.0 mnL of anhydrous dichloromethane, under a nitrogen atmosphere, at 0° C., was added 2.9 g (42.6 mmol) of imidazole, followed by 3.6 g (24.1 mmol) of tert-butyldimethylsilyl chloride. The resulting mixture was warmed to room temperature and stirred for three hours. The reaction mixture was poured into 1.0 L saturated aqueous ammonium chloride solution, and the product extracted with 1.0 L dichloromethane. The organic layer extract was washed first with 200.0 mL saturated aqueous sodium bicarbonate solution, then with 200.0 mL water, and finally with 100.0 mL saturated aqueous sodium chloride solution. The washed organic layer was dried over 300.0 g sodium sulfate, filtered and concentrated under reduced pressure, at room temperature. The crude product was purified on a silica gel (1.0 kg) column and eluted with ethyl acetate:hexanes [1:8 (v/v)]. Evaporation of solvent from the product-containing fractions (as identified by thin layer chromatographic analysis) under reduced pressure at room temperature and drying overnight under vacuum at room temperature provided 10.6 g (15.8 mmol) of Compound 54 {R$_f$: 0.70 [ethyl acetate:hexanes, 1:4 (v/v)]} in 85% yield.

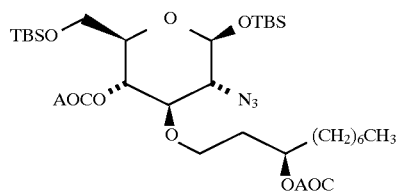

To a mechanically stirred solution of Compound 54 (8.9 g; 13.2 mmol) dissolved in 270.0 mL of anhydrous toluene and 4.2 mL of anhydrous pyridine, at 0° C., under a nitrogen atmosphere, was slowly added 10.2 mL (26.4 mmol) of 1.93 M phosgene in toluene, over a 10-minute period. Twenty minutes later, 8.0 mL (105.6 mmol) of allyl alcohol was added over a five-minute period, and the resulting reaction mixture stirred for an additional 15 minutes. The reaction mixture was quenched with 200.0 mL saturated aqueous sodium bicarbonate solution, diluted with 1.0 L ethyl acetate, and the organic layer separated, and washed with 500.0 mL water and then 500.0 mL saturated aqueous sodium chloride solution, dried over 500.0 g sodium sulfate, filtered, and concentrated under reduced pressure at room temperature. The residue was purified on a silica gel (1.0 kg) column and eluted with ethyl acetate:hexanes [1:19 (v/v)]. Evaporation of solvent from the product-containing fractions (as identified by thin layer chromatographic analysis) under reduced pressure at room temperature and drying overnight under vacuum at room temperature provided 9.5 g (12.5 mmol) of Compound 5 {$R_f$: 0.68. [ethyl acetate:hexanes, 1:9 (v/v)]} in 95% yield.

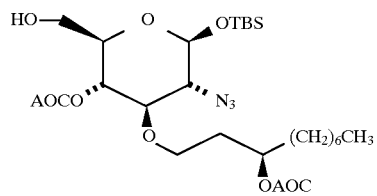

In a 1.0 L Teflon reaction vessel, Compound 55 (5.8 g; 7.6 mmol) was dissolved in 200.0 mL of dichloro-methane. To the solution at room temperature, with magnetic stirring, was added 150.0 mL of a 1 M solution of hydrofluoric acid in acetonitrile. After seven hours, the reaction mixture was quenched by pouring into 200.0 mL saturated aqueous sodium bicarbonate solution, at 0° C., and extracted with 500.0 mL dichloromethane. The organic layer was separated, washed with 100.0 mL water then with 100.0 mL saturated aqueous sodium chloride solution, dried over 300.0 g sodium sulfate, filtered, and concentrated under reduced pressure at room temperature. The residue obtained was purified on a silica gel [600.0 g] column and eluted with ethyl acetate:hexanes [1:4 (v/v)]. Evaporation of solvent from the product-containing fractions (as identified by thin layer chromatographic analysis) under reduced pressure at room temperature and drying overnight, under vacuum, at room temperature provided 4.5 g (6.7 mmol) of Compound {$R_f$: 0.33 [ethyl acetate:hexanes,1:4 (v/v)]} in 88% yield.

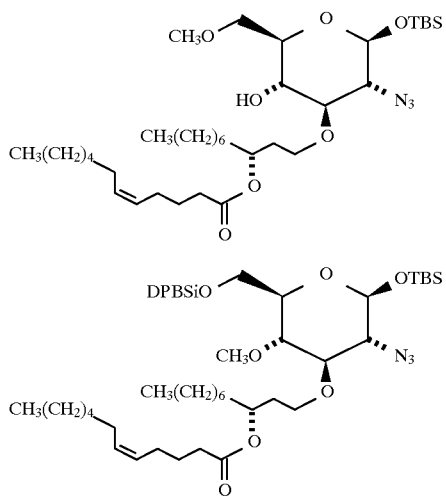

A heterogeneous mixture of 8.0 g (12.2 mmol) Compound 47, 11.3 g (48.8 mmol) silver(I) oxide (Aldrich Chemical Co.), and 120.0 mL (1.92 mol) methyl iodide (Aldrich Chemical Co.) was mechanically stirred at 39° C., for 12 hours under nitrogen in the dark. The reaction mixture was cooled, filtered through a 100.0 g Celite 545 and the filtered solids washed with 200.0 mL ethyl acetate. The combined filtrate and wash was then concentrated under reduced pressure at 43° C., yielding crude product which was then dissolved in 50.0 mL dichloromethane and cooled to 0° C. To the cooled reaction mixture was added, in one portion, 1.0 g (14.69 mmol) imidazole followed by tert-butylchlorodiphenylsilane over a five-minute period. The reaction mixture was then warmed to room temperature, stirred one hour longer, quenched with 100.0 mL saturated aqueous sodium bicarbonate solution, and extracted with 500.0 mL of dichloromethane. The organic layer was washed first with 100.0 mL water and then with 100.0 mL saturated aqueous sodium chloride solution, dried over 300.0 g sodium sulfate, filtered and concentrated under reduced pressure at room temperature. The residue obtained was purified on a silica gel (100.0 g) column by elution with ethyl acetate:hexanes [1:9 (v/v)]. Evaporation of solvent from the product-containing fractions (identified by use of thin layer chromatographic analysis) under reduced pressure at room temperature and drying overnight under vacuum at room temperature yielded 6.85 g (10.2 mmol) of Compound 57A {$R_f$: 0.63 [dichloromethane:diethyl ether, 19:1 (v/v)]} in 84% yield and 1.11 g (1.22 mmol) of Compound 57B {$R_f$: 0.90 [dichloromethane:diethyl ether, 19:1 (v/v)]} in 10% yield.

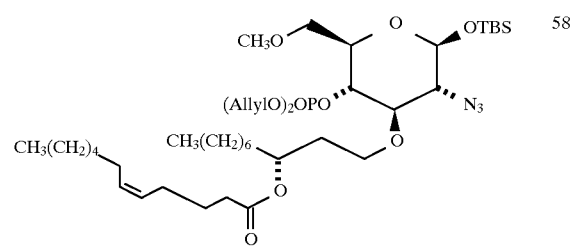

To a magnetically stirred solution of Compound 57A (8.7 g; 0.013 mol) dissolved in 46.0 mL anhydrous dichloromethane, at room temperature, under a nitrogen atmosphere, was first added 4.8 mL (0.02 mol) bis(allyloxy) (diisopropylamino) phosphine and then added (in one portion) 4.1 g (0.06 mol) 1H-tetrazole. After five minutes, the reaction mixture was cooled to −78° C., and a solution of 3.35 g (0.02 mol) 55% 3-chloroperoxybenzoic acid dissolved in 37.0 mL anhydrous dichloromethane was added dropwise over a 10 minute period. The reaction was then quenched at −78° C. by the addition of 100.0 mL saturated aqueous sodium bicarbonate solution. The resulting mixture was then extracted with 500.0 mL dichloromethane and the organic layer extract washed first with 200.0 mL water, then with 200.0 mL saturated aqueous sodium chloride solution, and dried over 300.0 g sodium sulfate. Concentration under reduced pressure at room temperature provided the crude product which was purified on a silica gel (1.0 kg) column and eluted with ethyl acetate:hexanes [1:6 (v/v)]. Evaporation of solvent from the product-containing fractions (as identified by thin layer chromatographic analysis) under reduced pressure at room temperature and drying overnight under vacuum at room temperature provided 8.8 g (0.011 mol) of Compound 58 {R$_f$: 0.28 [ethyl acetate:hexanes, 1:4 (v/v)]} in an 85% yield.

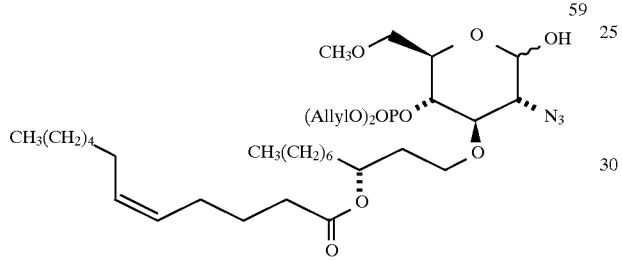

To a magnetically stirred solution of 80.0 mL 6 M hydrogen fluoride in acetonitrile in a Teflon reaction vessel was added at room temperature, 8.8 g (10.6 mmol) of Compound 58 dissolved in 30.0 mL of dichloromethane. The resulting mixture was stirred for nine hours, poured into 200.0 mL saturated aqueous sodium bicarbonate solution at 0° C., and extracted with 300.0 mL dichloromethane. The organic layer extract was washed with 100.0 mL saturated aqueous sodium chloride solution, dried over 100.0 g sodium sulfate, filtered and concentrated under reduced pressure at room temperature. The residue was then purified on a silica gel (1.0 kg) column and eluted with hexanes:ethyl acetate [1:1 (v/v)]. Evaporation of solvent from the product-containing fractions (as identified by thin layer chromatographic analysis) under reduced pressure at room temperature and drying overnight under vacuum at room temperature provided 5.7 g (7.95 mmol) of Compound 59 {R$_f$: 0.37 [dichloromethane:methyl alcohol, 95:5 (v/v)]} in 75% yield.

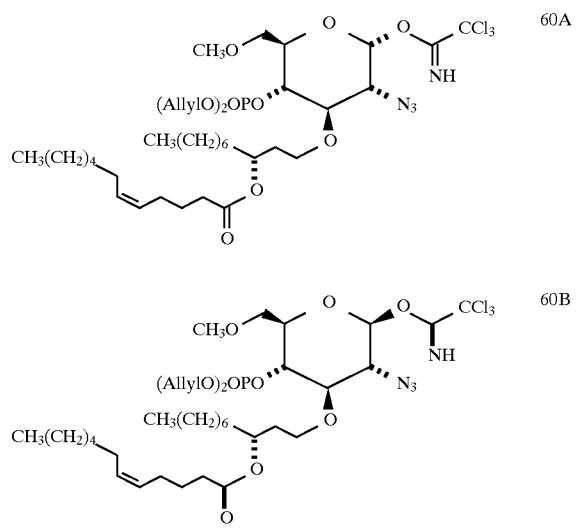

To a mechanically stirred solution of 10.32 g (14.5 mmol) of Compound 59 in 200.0 mL trichloroacetonitrile, 8.80 g (63.7 mmol) of potassium carbonate was added at room temperature under nitrogen. After 20 minutes, the mixture was filtered through 100.0 g Celite 545, the filtered solids washed with 100.0 mL dichloromethane and the combined filtrates concentrated under reduced pressure at room temperature. The crude product obtained was purified on a silica gel (10.0 g) column by elution with hexanes:ethyl acetate [1:1 (v/v)]. Evaporation of solvent from the product-containing fractions (identified by thin layer chromatographic analysis) under reduced pressure at room temperature and drying overnight under vacuum at room temperature gave 11.1 g (12.9 mmol) of 60B (βisomer) and 60A (αisomer) {R$_f$: 0.61 and 0.53 [hexanes:ethyl acetate, 1:1 (v/v)]} in a combined yield of 89%.

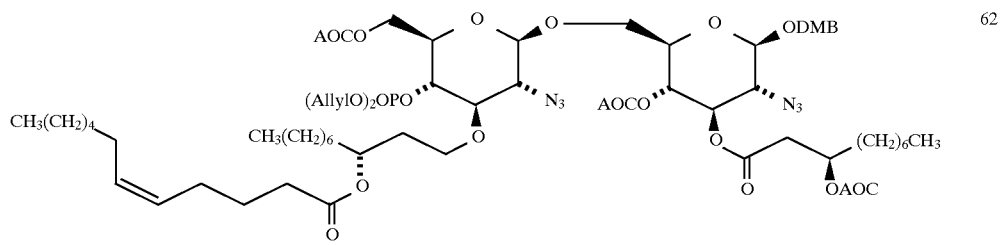

A mixture of 465.0 mg (0.492 mmol) of Compound 51A and 374.0 mg (0.541 mmol) of Compound 17 was dried under vacuum for 14 hours, dissolved in 10.0 mL of anhydrous dichloromethane, and to the solution was added 800.0 mg of powdered AW-300 molecular sieves, which had been flame-dried under vacuum. The resulting mixture was magnetically stirred for one hour at room temperature under an argon atmosphere, cooled to −23° C., and 740.0 μL (0.147 mmol) of a 0.2 M boron trifluoride etherate:anhydrous dichloromethane solution [prepared by dissolving 250.0 μL (2.03 mmol) of boron trifluoride etherate in 10.0 mL of anhydrous dichloromethane and stirring with 200 mg powdered AW-300 molecular sieves for one hour at room temperature] was slowly added over a one hour period. The reaction was quenched with 5.0 mL of saturated aqueous sodium bicarbonate solution, diluted with 100.0 mL dichloromethane, and filtered through 10.0 g Celite 545. The filtrate was washed first with 50.0 mL saturated aqueous sodium bicarbonate solution, then with 50 mL of water, and finally with 50 mL of saturated aqueous sodium chloride solution, dried over 25.0 g sodium sulfate, filtered, and concentrated under reduced pressure at room temperature. The resulting residue was purified on a silica gel (100.0 g) column and eluted with ethyl acetate:hexanes [1:3 (v/v)]. Evaporation of solvent from the produce-containing fractions (as identified by thin layer chromatographic analysis) under reduced pressure at room temperature and drying overnight under vacuum at room temperature provided 430.0 mg (0.292 mmol) of Compound 62 {R$_f$: 0.2 [ethyl acetate:hexanes, 1:2 (v/v)]} in 60% yield.

with 100.0 mL dichloromethane, and filtered through 10.0 g Celite 545. The filtrate was washed first with 50.0 mL of saturated aqueous sodium bicarbonate solution, then with 50 mL of water, and finally with 50 mL of saturated aqueous sodium chloride solution, dried over 25.0 g sodium sulfate, filtered, and concentrated under reduced pressure at room temperature. The resulting residue was purified on a silica gel (200.0 g) column and eluted with ethyl acetate and hexanes [1:3 (v/v)]. Evaporation of solvent from the product-containing fractions (as identified by thin layer chromatographic analysis) under reduced pressure at room temperature and drying overnight under vacuum, at room temperature provided 210.0 mg (0.152 mmol) of Compound 63 {R$_f$: 0.23 [ethyl acetate:hexanes, 1:2 (v/v)]} in 62% yield.

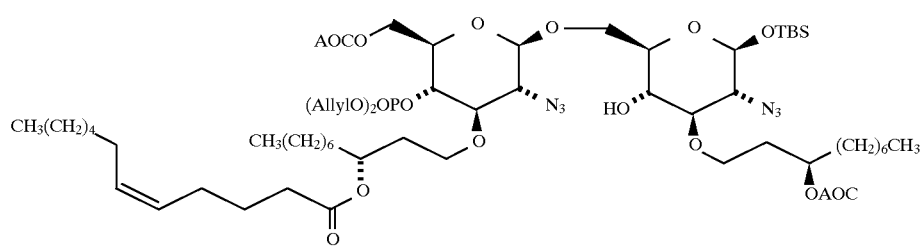

64

A mixture of 601.4 mg (0.636 mmol) of Compound 51A and 769.3 mg (1.38 mmol) of Compound 39 were dried under vacuum for 14 hours and dissolved in 40.0 mL of anhydrous toluene. To this solution was added 1.0 g of powdered AW-300 molecular sieves, which had been flame-dried under vacuum, and the resulting mixture magnetically stirred for one hour at room temperature under an argon atmosphere. The mixture was cooled to −35° C. and 10.0 mL (0.190 mmol) of a 0.02 M boron trifluoride etherate:anhydrous dichloromethane solution [prepared by dissolving 250.0 μL (2.03 mmol) of boron trifluoride etherate in 10.0 mL of anhydrous dichloromethane, diluting the resulting mixture with 91.5 mL anhydrous toluene and stirring with

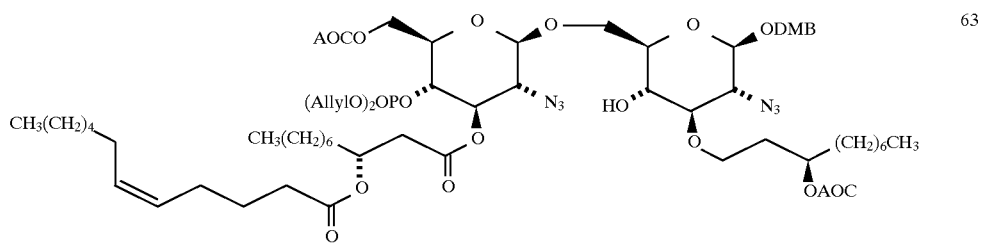

63

A mixture of 250.0 mg (0.265 mmol) of Compound 23A and 205.0 mg (0.265 mmol) of Compound 14 was dried under vacuum for 14 hours and dissolved in 15.0 mL of anhydrous dichloromethane. To this solution was added 600.0 mg of powdered AW-300 molecular sieves, which had been flame-dried under vacuum, and the resulting mixture magnetically stirred for one hour at room temperature under an argon atmosphere. The mixture was cooled to −23° C. and 400.0 μL (0.265 mmol) of a 0.2 M boron trifluoride etherate:anhydrous dichloromethane solution [prepared by dissolving 250.0 μL (2.03 mmol) of boron trifluoride etherate in 10.0 mL of anhydrous dichloromethane and stirring with 200 mg powdered AW-300 molecular sieves for one hour at room temperature] was slowly added over a 30-minute period. The reaction was quenched with 5.0 mL of saturated aqueous sodium bicarbonate solution, diluted 200 mg powdered AW-300 molecular sieves for one hour at room temperature] was slowly added over a one and a half hour period. The reaction was quenched with 10.0 mL of saturated aqueous sodium bicarbonate solution, diluted with 200.0 mL dichloromethane, and filtered through 10.0 g Celite 545. The filtrate was washed first with 50.0 mL of saturated aqueous sodium bicarbonate solution, then with 50 mL of water, and finally with 50 mL of saturated aqueous sodium chloride solution, dried over 50.0 g sodium sulfate, filtered, and concentrated under reduced pressure at room temperature. The resulting residue was purified on a silica gel (100.0 g) column and eluted with ethyl acetate:hexanes [1:2 (v/v)]. Evaporation of solvent from the product-containing fractions (as identified by thin layer chromatographic analysis) under reduced pressure at room temperature and drying overnight under vacuum at room temperature provided 297.5 mg (0.152 mmol) of Compound 64 {$R_f$: 0.42 [dichloromethane:diethyl ether, 9:1 (v/v)]} in 34% yield.

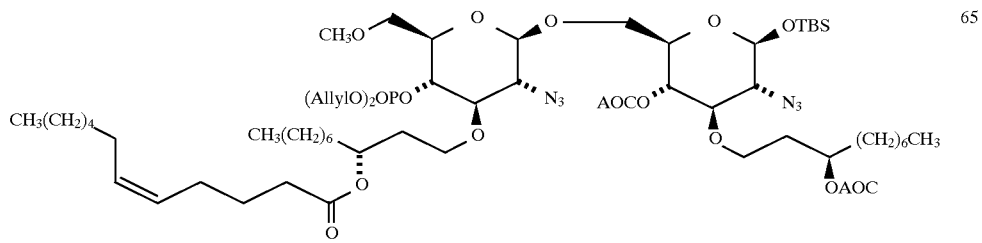

65

A mixture of 7.35 g (8.5 mmol) of Compound 60 (αβ mixture) and 5.0 g (7.4 mmol) of Compound 56 which had been dried under vacuum for 14 hours, was dissolved in 200.0 mL of anhydrous dichloromethane. To this solution was added 8.2 g of powdered AW-300 molecular sieves (previously flame-dried under vacuum) and the resulting mixture magnetically stirred for one hour at room temperature under argon. The mixture was then cooled to −35° C., and 8.7 mL (0.50 mmol) of a 0.05 M trimethylsilyl trifluoromethanesulfonate (Aldrich Chemical Co.): dichloromethane solution [prepared by dissolving 310.0 μL (2.03 mmol) of trimethylsilylmethyl trifluoromethanesulfonate in 40.0 mL of anhydrous dichloromethane and stirring with 1.0 g powdered AW-300 molecular sieves for one hour at room temperature] was slowly added over an eight hour period. The reaction was quenched with 100.0 mL of saturated aqueous sodium bicarbonate solution, then diluted with 500.0 mL dichloromethane, and filtered through 50.0 g Celite 545. The filtrate was then washed with 100.0 mL portions of saturated aqueous sodium bicarbonate solution, water, and saturated aqueous sodium chloride solution sequentially, dried over 100.0 g sodium sulfate, filtered, and then concentrated under reduced pressure at room temperature. The resulting residue was purified on a silica gel (200.0 g) column by elution with ethyl acetate and hexanes [1.4 (v/v)]. Evaporation of solvent from the product containing fractions (identified by use of thin layer chromatography analysis) under reduced pressure at room temperature and drying overnight under vacuum at room temperature gave 8.1 g (0.006 mol) of Compound 65 {$R_f$: 0.42 [ethyl acetate:hexanes, 1:2 (v/v)]} in 82% yield.

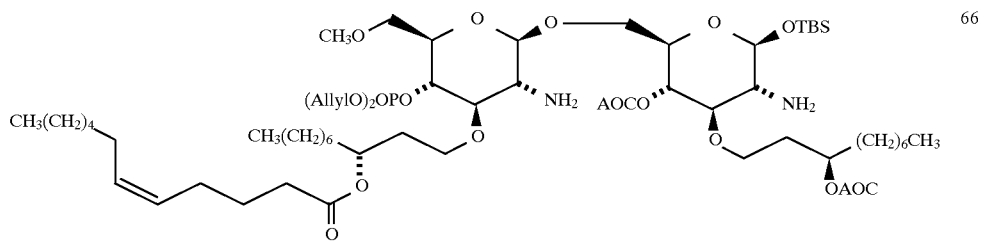

66

To a magnetically stirred solution of Compound 65 (1.99 g; 1.48 mmol) dissolved in 10.0 mL of anhydrous dichloromethane was added 250.0 mg (0.45 mmol) of tin(II)trisbenzenethiolate triethylamine complex and the resulting mixture stirred at room temperature under a nitrogen atmosphere in the absence of light for 30 minutes, at which time thin layer chromatographic analysis [hexanes:ethyl acetate, 1:1 (v/v)] indicated starting material to be consumed. The reaction mixture was loaded directly into a silica gel (10.0 g) column and eluted first with a 4:1 (v/v) mixture of hexanes:ethyl acetate to remove reagent by-products and then with ethyl acetate. Evaporation of solvent from the product-containing fractions (as identified by thin layer chromatographic analysis) under reduced pressure at room temperature and drying under vacuum at room temperature for 30 minutes provided partially purified Compound 66 [1.72 g (1.33 mmol)]{$R_f$: 0.48 [dichloromethane:methyl alcohol, 95:5 (v/v)]} which was suitable for use in subsequent reaction in 90% yield.

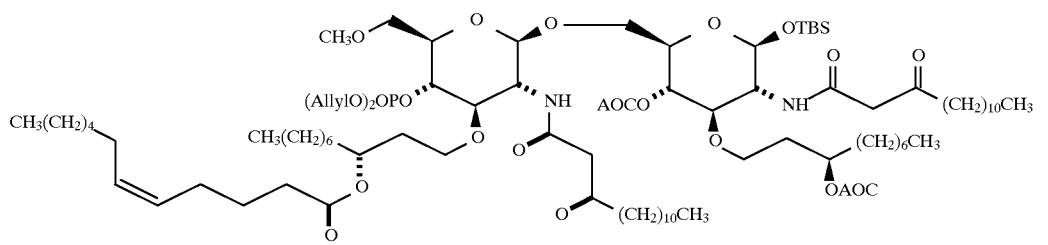

To a magnetically stirred solution of Compound 66 (1.72 g; 1.33 mmol) in 10.0 mL anhydrous dichloromethane, at 0° C., was added 1.1 g (4.44 mmol) of Compound D2 (see below) and 1.83 g (8.88 mmol) of 1,3-dicyclohexylcarbodiimide. After 30 minutes, when thin layer chromatographic analysis [dichloromethane:methyl alcohol, 95:5 (v/v)] indicated that completion of the reaction had occurred, the reaction mixture was diluted with 50.0 mL ethyl acetate, filtered through 10.0 g Celite 545, the solids washed with 20.0 mL ethyl acetate, and the filtrate concentrated under reduced pressure at room temperature to yield a syrupy residue. The crude syrup was dissolved in 5.0 mL dichloromethane, loaded onto a silica gel (100.0 g) column and eluted initially with a 1:4 (v/v) mixture of ethyl acetate::hexanes to remove reagent residues and then with a 1:2 (v/v) mixture of ethyl acetate:hexanes. Evaporation of solvent from the product-containing fractions (as identified by thin layer chromatographic analysis) under reduced pressure at room temperature and drying overnight under vacuum at room temperature provided 1.82 g (1.04 mmol) of Compound 67 {$R_f$: 0.54 [dichloromethane:methyl alcohol, 95:5 (v/v)]} in 71% yield.

To a magnetically stirred solution of 8.0 mL 6 M hydrogen fluoride in acetonitrile in a Teflon reaction vessel was added 390.0 mg (0.224 mmol) of Compound 67 dissolved in 0.5 mL of dichloromethane, at room temperature. The mixture was stirred for one and a half hours, diluted with 20.0 mL saturated aqueous sodium bicarbonate solution, and extracted with 100.0 mL. dichloromethane. The organic layer extract was washed first with 20.0 mL water, and then with 10.0 mL saturated aqueous sodium chloride solution, dried over 25.0 g sodium sulfate, filtered and concentrated under reduced pressure at room temperature. The residue was purified on a silica gel [50.0 g] column and eluted with dichloromethane:methyl alcohol [98:2 (v/v)]. Evaporation of solvent from the product-containing fractions (as identified by thin layer chromatographic analysis) under reduced pressure at room temperature and drying overnight under vacuum at room temperature provided 325.0 mg (0.20 mmol) of Compound 68 {$R_f$: 0.52 [dichloromethane and methyl alcohol, 95:5 (v/v)]} in 89% yield.

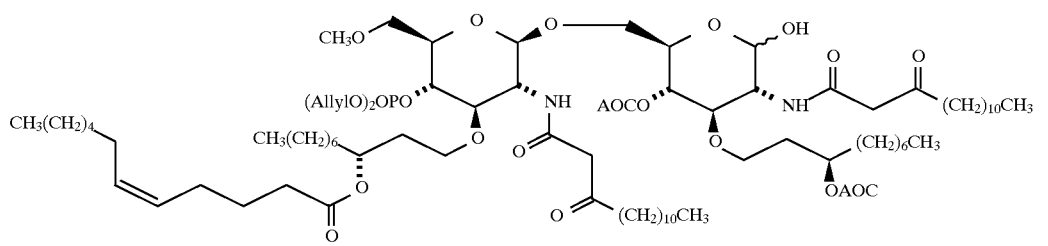

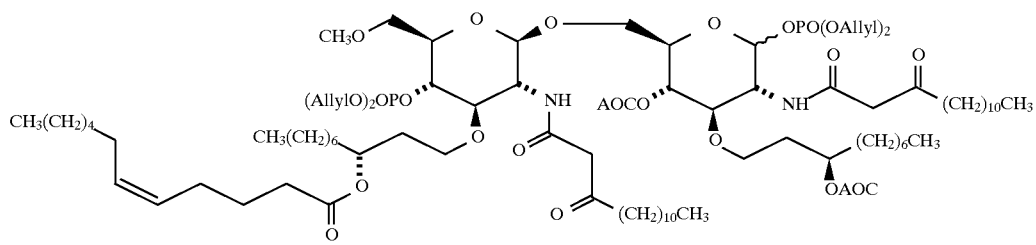

69

To a magnetically stirred solution of 50.0 mg (0.03 mmol) of Compound 68 in 1.0 mL anhydrous dichloromethane was first added 11.3 mg (0.045 mmol) bis(allyloxy) (diisopropylamino) phosphine followed by 9.4 mg (0.135 mmol) 1H-tetrazole at 0° C., under a nitrogen atmosphere. The resulting mixture was warmed to room temperature, stirred 20 minutes, cooled to −78° C., and a solution of 9.5 mg (0.036 mmol) 3-chloroperoxybenzoic acid dissolved in 100.0 μL dichloromethane was added, and the mixture was stirred for 20 additional minutes. A 0.5 mL saturated aqueous sodium bicarbonate solution was then added, and the resultant mixture extracted with 10.0 mL dichloromethane. The organic layer was separated and washed first with 10.0 mL water and then with 5.0 mL saturated aqueous sodium chloride solution, and dried over 5.0 g sodium sulfate. Concentration of the dried organic extract under reduced pressure at room temperature provided the crude product which was purified on a silica gel (10.0 g) column and eluted with ethyl acetate:chloroform [1:1 (v/v)]. Evaporation of solvent from the product-containing fractions (as identified by thin layer chromatographic analysis) under reduced pressure at room temperature and drying for one hour under vacuum at room temperature provided 41.7 mg (0.023 mmol) of Compound 69 {$R_f$: 0.40 [dichloromethane:methyl alcohol, 95:5 (v/v)]} in a 78% yield.

reduced pressure at room temperature to a thick paste, suspended in 10.0 mL methyl alcohol, and hydrogen sulfide gas bubbled through the solution for several minutes. The solvent was removed by evaporation under reduced pressure at room temperature and the crude product was taken up in 10.0 mL of a 3:2:1 (v/v/v) mixture of methyl alcohol:chloroform:water and filtered through a 0.2μ Teflon HPLC filter (Rainin Instrument Co.). The filtrate was loaded onto a DEAE-celluose [100.0 g (Sigma Chemical Co.)] column and eluted with 2.0 L of a 3:2:1 (v/v/v) mixture of methyl alcohol:chloroform:water, using a 0 to 0.1 M ammonium acetate linear salt gradient. The purified product-containing fractions (as identified by thin layer chromatographic analysis) were combined and an equal volume of chloroform was added. The organic layer was separated and concentrated under reduced pressure at room temperature to yield the purified product as the ammonium salt. The product was taken up in 100.0 mL water and lyophilized to remove remaining traces of ammonium acetate. The lyophilized product was suspended in 40.0 mL of water, stirred with 6.0 g of Chelex-100 resin [sodium form (Bio-Rad Laboratories, Hercules, Calif.], passed through a 10.0 g column of Chelex-100 resin [sodium form], and eluted with 20.0 mL of water. The solution was filtered through a 0.2μ Teflon HPLC filter (Rainin Instrument Co.) and lyophilized to provide 98.0 mg

70

To a solution of Compound 69 (130.0 mg, 0.072 mmol) dissolved in 10.0 mL tetrahydrofuran: 96% formic acid [10:1 (v/v)], under a nitrogen atmosphere, in the absence of light, was added 843.0 mg (0.72 mmol) tetrakis (triphenylphosphine)palladium(O) and 575.0 mg (2.19 mmol) triphenylphosphine. The resulting mixture was stirred for a total of one hour, and concentrated under reduced pressure at room temperature. The resulting residue was mixed with 5.0 mL of toluene and evaporated under (0.063 mmol) of the tetra sodium salt, i.e., Compound 70 {$R_f$: 0.60 [chloroform:methyl alcohol:glacial acetic acid:water, 125:75:10:20 (v/v/v/v)]}, as a white hygroscopic foam in 87% yield.

Compound 70 is the Lipid A Analog B531–35. Lipid A Analog B531–32 was obtained by preparing the free acid form of the analog and reacting it with L-lysine as generally described above for their preparation of Compound 31 and Analog B214–32.

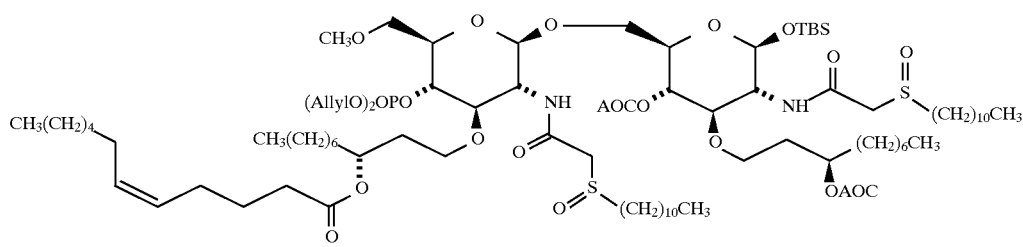

71

To a magnetically stirred solution of 510.0 mg (0.358 mmol) of Compound 66 in 6.0 mL anhydrous dichloromethane, at 0° C., was added 245.0 mg (0.895 mmol) of Compound E3 (see below) and 740.0 mg (1.79 mmol) of 1,3-dicyclohexylcarbodiimide. After 30 minutes, when thin layer chromatographic analysis [dichloromethane:methyl alcohol, 95:5 (v/v)] indicated completion of the reaction had occurred, the reaction mixture was diluted with 50.0 mL ethyl acetate, filtered through 10.0 g Celite 545, the solids obtained washed with 20.0 mL ethyl acetate and the filtrate concentrated under reduced pressure at room temperature to yield a syrupy residue. The crude syrup was dissolved in 5.0 mL dichloromethane, loaded on to a silica gel (100.0 g) column and eluted, initially with a 1:3 (v/v) mixture of ethyl acetate:hexanes to remove reagent residues, and then with a 2:1 (v/v) mixture of ethyl acetate:hexanes. Evaporation of solvent from the product-containing fractions (as identified by thin layer chromatographic analysis) under reduced pressure at room temperature and drying overnight under vacuum at room temperature provided 447.0 mg (0.24 mmol) of Compound 71 {$R_f$: 0.40 [dichloromethane:methyl alcohol, 95:5 (v/v)]} in 67% yield.

extracted with 100.0 mL dichloromethane. The organic layer extract was washed first with 20.0 mL water, and then with 10.0 mL saturated aqueous sodium chloride solution, dried over 25.0 g sodium sulfate, filtered and concentrated under reduced pressure at room temperature. The residue was purified on a silica gel (100.0 g) column and eluted with dichloromethane:methyl alcohol [100:4 (v/v)]. Evaporation of solvent from the product-containing fractions (as identified by thin layer chromatographic analysis) under reduced pressure at room temperature and drying overnight under vacuum at room temperature provided 404.0 mg (0.23 mmol) of Compound 72 {$R_f$: 0.37 [dichloromethane:methyl alcohol, 95:5 (v/v)]} in 96% yield.

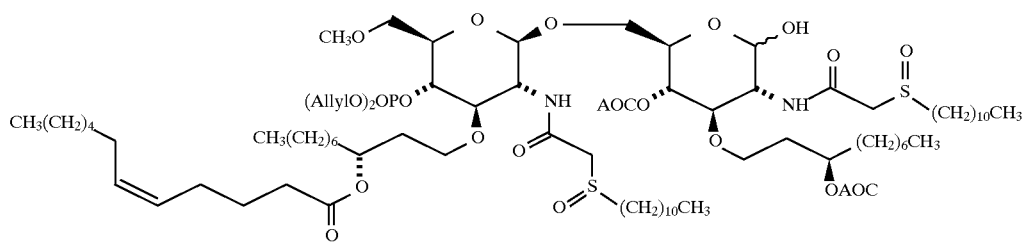

72

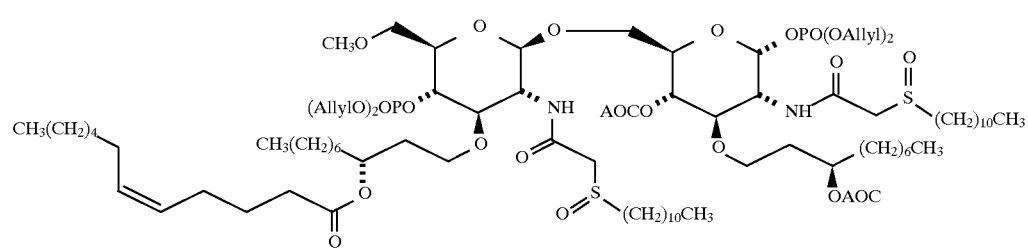

73

To a magnetically stirred solution of 6.0 HL 6 M hydrogen fluoride in acetonitrile in a Teflon reaction vessel was added 447.0 mg (0.24 mmol) of Compound 71 dissolved in 2.3 mL of dichloromethane at room temperature. The resulting mixture was stirred for two hours, diluted with 20.0 mL saturated aqueous sodium bicarbonate solution, and To a solution of 20.0 mg (0.011 mmol) of Compound 72 in 1.0 mL anhydrous tetrahydrofuran, 12.5 μL (0.012 mmol) of 1.0 M lithium bis(trimethylsilyl)amide in tetrahydrofuran was added slowly under a nitrogen atmosphere, at −78° C., with stirring. After five minutes, 34.0 μL (0.017 mmol) of 0.5 M diallyl chlorophosphate in anhydrous toluene was added and stirred for 10 min. The mixture was warmed to 0° C., stirred 10 additional minutes, and quenched with 40.0 μL of glacial acetic acid. The reaction mixture was poured into 10.0 mL of a saturated aqueous sodium bicarbonate solution and extracted with 50.0 mL dichloromethane. The organic layer was washed first with 10.0 mL saturated aqueous sodium bicarbonate solution and then with 10.0 mL saturated aqueous sodium chloride solution, dried over 30.0 g sodium sulfate, filtered, and concentrated under reduced pressure at room temperature. The residue obtained was purified on a silica gel (10.0 g) column and eluted with a mixture of dichloromethane:methyl alcohol [100:4 (v/v)]. Evaporation of solvent from the product-containing fractions (as identified by thin layer chromatographic analysis) under reduced pressure at room temperature and drying overnight under vacuum at room temperature provided 15.0 mg (0.008 mmol) of Compound 73 {$R_f$: 0.29 [dichloromethane:methyl alcohol, 95:5 (v/v)]} in 69% yield.

separated, washed with 5.0 mL saturated aqueous sodium chloride solution, dried over 5.0 g sodium sulfate, and filtered. The crude reaction mixture was loaded directly onto a silica gel (10.0 g) column and eluted with dichloromethane:methyl alcohol [98:2 (v/v)]. Evaporation of solvent from the product-containing fractions (as identified by thin layer chromatographic analysis) under reduced pressure at room temperature and drying overnight under vacuum at room temperature provided 40.0 mg (0.03 mmol) of Compound 74 {$R_f$: 0.36 [hexanes:ethyl acetate, 2:1 (v/v)]} in 87% yield.

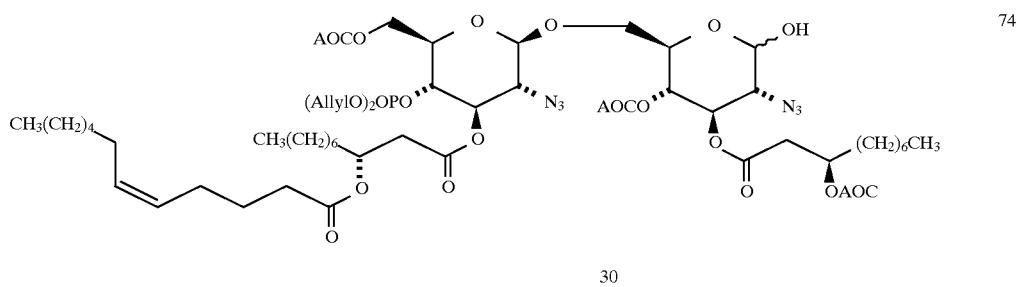

74

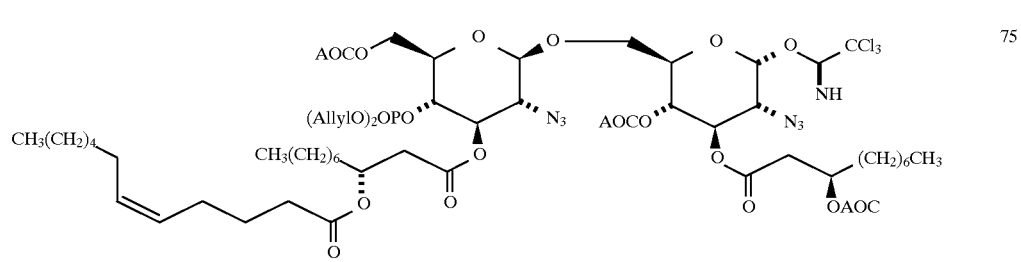

75

Compound 24 (51.5 mg; 0.035 mmol) was dissolved in 1.0 mL of dichloromethane, 0.1 mL of t-butyl alcohol and 0.1 mL of pH 7.0 phosphate buffer concentrate. To this heterogeneous mixture was added 100.0 mg (0.43 mmol) of 2,3-dichloro-5, 6-dicyano-1,4-benzoquinone. The mixture was e magnetically stirred, under a nitrogen atmosphere, in the dark until thin layer chromatographic analysis [hexanes:ethyl acetate, 1:2 (v/v)] indicated complete consumption of starting material (approximately four hours). At that time, the reaction was quenched with 2.0 mL 10% aqueous sodium thiosulfate solution, diluted with 10.0 mL dichloromethane an,d poured into 5.0 mL saturated aqueous sodium bicarbonate solution. The organic layer was To a mechanically stirred solution of 93.6 mg (0.07 mmol) of Compound 74 in 1.0 mL trichloroacetonitrile 58.0 mg (0.175 mmol) of cesium carbonate was added at room temperature under a nitrogen atmosphere. After one hour, the mixture was filtered through 5.0 g Celite 545, the filtered solids washed with 10.0 mL dichloromethane, and the combined filtrates concentrated under reduced pressure at room temperature. The crude product obtained was purified on a silica gel (10.0 g) column and eluted first with dichloromethane:diethyl ether [9:1 (v/v)] to remove reagent-related impurities and then with ethyl acetate. Evaporation of solvent from the product-containing fractions (as identified by thin layer chromatographic analysis) under reduced pressure at room temperature and drying overnight under vacuum at room temperature provided 43.2 mg (0.029 mmol) of Compound 75 {$R_f$: 0.56 [dichloromethane:diethyl ether, 9:1 (v/v)]} in 42% yield.

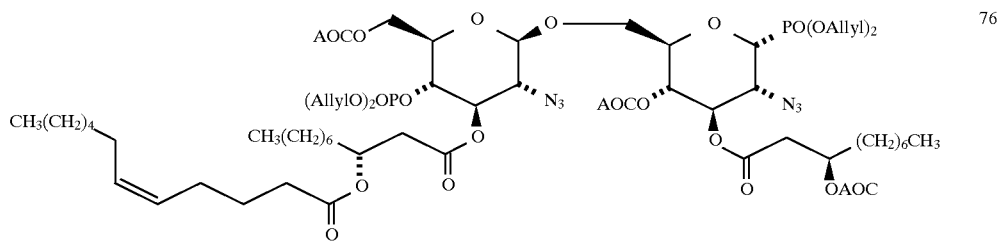

To a mixture of 68.2 mg (0.046 mmol) of Compound 75 and 19.0 μL (0.092 mmol) triallyl phosphite (Alfa Products) dissolved in 2.0 mL of anhydrous dichloromethane, at 0° C., under a nitrogen atmosphere, was added 11.0 μL trimethylsilyl trifluoromethanesulfonate. After stirring for one hour at 0° C., the reaction mixture was quenched with 1.0 mL saturated sodium bicarbonate solution and extracted with 50.0 mL dichloromethane. The organic layers were dried over 25.0 g sodium sulfate, filtered, and concentrated under reduced pressure at room temperature. Purification on a silica gel (25.0 g) column and eluted with a 4:1 (v/v) mixture of hexanes:ethyl acetate and evaporation of solvent from the product-containing fractions (as identified by thin layer chromatographic analysis) provided 37.0 mg (0.025 mmol) of Compound 76 {$R_f$: 0.45 [hexanes:ethyl acetate, 2:1 (v/v)]} in 30% yield.

loaded directly into a silica gel (5.0 g) column and eluted first with a 4:1 (v/v) mixture of hexanes:ethyl acetate to remove reagent by-products, and then with 100% ethyl acetate. Evaporation of solvent from the product-containing fractions (as identified by thin layer chromatographic analysis) under reduced pressure at room temperature and drying under vacuum at room temperature for 30 minutes provided 31.9 mg (0.023 mmol) of partially purified Compound 77 {$R_f$: 0.42 [dichloromethane:methyl alcohol), 95:5 (v/v)]}, which was suitable for use in the subsequent synthetic reaction, in 90% yield.

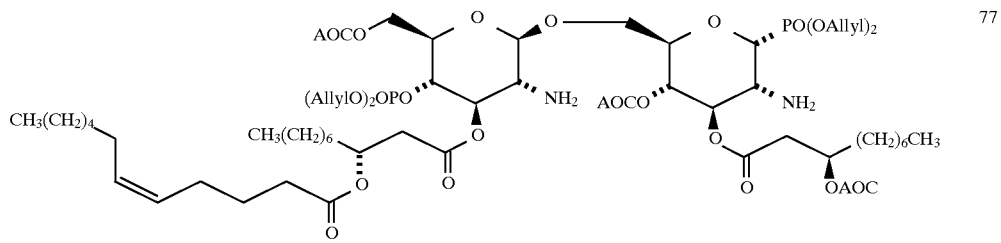

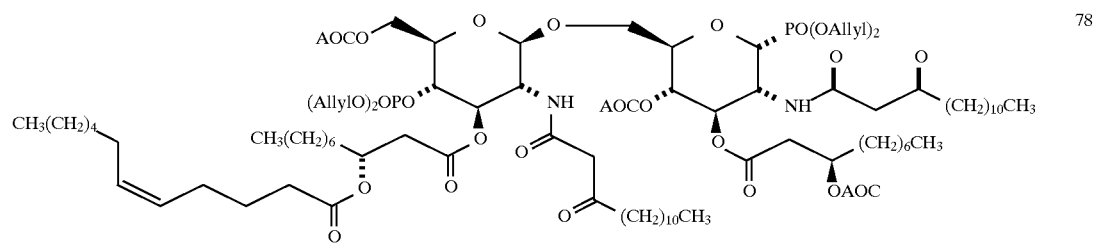

To a magnetically stirred solution of 37.0 mg (0.025 mmol)of Compound 76 dissolved in 0.5 mL of anhydrous dichloromethane was added 42.0 mg (0.076 mmol) of tin (II)tris-benzenethiolate triethylamine complex and the resulting mixture stirred at room temperature under a nitrogen atmosphere in the dark for 30 minutes, at which time thin layer chromatographic analysis [dichloromethane:methyl alcohol, 95:5 (v/v)] showed consumption of the starting material. The reaction mixture was To a magnetically stirred solution of 31.9 mg (0.23 mmol) of Compound 77 in 0.5 mL anhydrous dichloromethane, at 0° C., was added 18.0 mg (0.92 mmol) of Compound D2 (see below) and 23.0 mg (1.38 mmol) of 1,3-dicyclohexylcarbodiimide. After 30 minutes, when thin layer chromatographic analysis [dichloromethane:methyl alcohol, 95:5 (v/v)] indicated completion of the reaction had occurred, the reaction mixture was diluted with 10.0 mL ethyl acetate, filtered through 1.0 g Celite 545, the solids obtained washed with 5.0 mL ethyl acetate, and the filtrate concentrated under reduced pressure at room temperature to give a syrupy residue. The crude syrup was dissolved in 1.0 mL dichloromethane, loaded onto a silica gel (10.0 g) column and eluted, initially with a 1:4 (v/v) mixture of ethyl acetate:hexanes to remove reagent residues and then with a 1:2 (v/v) mixture of ethyl acetate:hexanes. Evaporation of solvent from the product-containing fractions (as identified by thin layer chromatographic analysis) under reduced pressure at room temperature and drying overnight under vacuum at room temperature provided 15.1 mg (1.04 mmol) of Compound 78 {$R_f$: 0.48 [dichloromethane:methyl alcohol, 95:5 (v/v)]} in 32% yield.

To produce the Lipid A Analog B380–32, Compound 78 was deprotected generally as described above for the preparation of Compound 31, and the product was reacted with L-lysine as described above for analog B214–32.

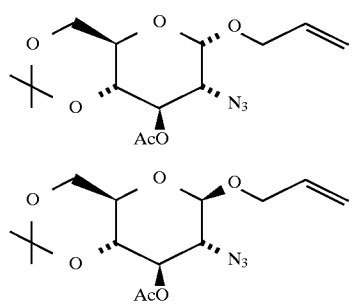

To a mixture of 1.13 g (2.58 mmol) of Compound 10b and 500.0 μL (0.45 mmol) allyl alcohol dissolved in 50.0 mL of anhydrous dichloromethane was added 1.0 g of finely powdered AW-300 molecular sieves. After stirring one hour at room temperature, the mixture was cooled to −78° C., and 15.0 mL of a 0.02 M dichloromethane solution of trimethylsilyl trifluoromethanesulfonate was added over one hour. The reaction mixture was quenched with 10.0 mL saturated sodium bicarbonate solution and extracted with 100.0 mL dichloromethane. The organic layers were dried over 25.0 g sodium sulfate, filtered, and concentrated under reduced pressure at room temperature. Purification on a silica gel (100.0 g) column, elution with a 4:1 (v/v) mixture of hexanes:ethyl acetate, and evaporation of solvent from the product-containing fractions (as identified by thin layer chromatographic analysis) provided 380.0 mg (0.85 mmol) of pure Compound 79b {$R_f$: 0.58 [hexanes:ethyl acetate, 3:1 (v/v)]} in 33% yield and 143.0 mg (0.34 mmol) of Compound 79a {$R_f$: 0.54 [hexanes:ethyl acetate,3:1 (v/v)]} in 13% yield.

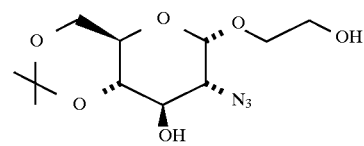

To a solution of 3.25 g (17.2 mmol) of Compound 79a in 220.0 mL (10:1,v/v) acetone:water was first added 6.0 g (51.2 mmol) 4-methylmorpholine N-oxide (Aldrich Chemical Co.), followed by 20.0 mg (0.08 mmol) osmium tetroxide (Aldrich Chemical Co.). The reaction mixture was stirred for two and a half days at room temperature in the absence of light. The reaction was then quenched by addition of 100.0 mL of a saturated aqueous solution of sodium thiosulfate, stirred for an additional hour, and then extracted with 200.0 mL dichloromethane. The organic layers were washed first with 100.0 mL water, then with 100.0 mL of a saturated aqueous solution of sodium chloride, dried over 50.0 g sodium sulfate, filtered, and concentrated under reduced pressure at room temperature to give the crude product.

The crude product was dissolved in 200.0 mL of a 1:1 (v/v) mixture of methyl alcohol and water. To the resulting solution was added 6.0 g (28.1 mmol) sodium periodate (Aldrich Chemical Co.), at 0° C. with vigorous stirring. After one hour, the reaction was diluted with dichloromethane. The organic layer was washed first with 100.0 mL water, then with 100.0 mL of a saturated aqueous solution of sodium chloride, dried over 50.0 g sodium sulfate, filtered, and concentrated under reduced pressure at room temperature to again give the crude product a yellowish oil.

The crude product was then dissolved in 50.0 mL methyl alcohol, cooled to 0° C. and 1.5 g (39.7 mmol) sodium borohydride (Aldrich Chemical Co.) was added portionwise. After one hour, the reaction was quenched by addition of 50.0 mL saturated aqueous ammonium chloride and extracted with 200.0 mL dichloromethane. The organic layers were washed with 50.0 mL saturated aqueous solution of sodium chloride, dried over 20.0 g sodium sulfate, filtered, and concentrated under reduced pressure at room temperature to yield the crude product as a yellow brown oil.

The crude product was then dissolved in 50.0 mL methyl alcohol, and 100.0 μL (25%, wt/wt) sodium methoxide was added. After two and a half days, the reaction was quenched by the addition of 50.0 mL saturated aqueous ammonium chloride solution and extracted with 200.0 mL dichloromethane. The organic layers were washed with 50.0 mL saturated aqueous solution of sodium chloride solution, dried over 50.0 g sodium sulfate, filtered, and concentrated under reduced pressure at room temperature to give the crude product. The crude product was purified by column chromatography on a silica gel (100.0 g), eluting with a 1:1 (v/v) mixture of hexanes and ethyl acetate to provide 3.0 g (9.06 mmol) of Compound 80 {$R_f$: 0.27 [hexanes:ethyl acetate, 1:1 (v/v)]} in 53% overall yield.

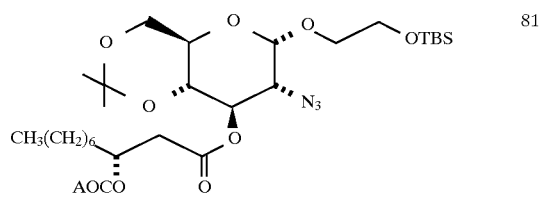

To a solution of 1.0 g (3.02 mmol) of Compound 80 dissolved in 10.0 mL anhydrous dichloromethane, at 0° C., was added 411 mg (6.04 mmol) imidazole, followed by the addition of 0.55 g (3.62 mmol) t-butyldimethylsilyl chloride. After stirring for 30 minutes, the reaction was quenched with 10.0 mL of a saturated aqueous ammonium chloride solution and extracted with 100.0 mL ethyl acetate. The organic layers were dried over 50.0 g sodium sulfate, filtered, and concentrated under reduced pressure at room temperature to give the crude product as a colorless oil. The crude product was then dissolved in 30.0 mL anhydrous dichloromethane, cooled to 0° C., and 0.97 g (3.62 mmol) of A6 was added, followed by the addition of 0.75 g (3.63 mmol) of 1,3-dicyclohexylcarbodiimide, 20 mg (163.7 μmol) 4-dimethylaminopyridine. After two hours, the reaction mixture was warmed to room temperature and stirred for an additional two hours, quenched with 50.0 mL saturated aqueous ammonium chloride solution, and extracted with 100.0 mL dichloromethane. The organic layers were dried over 50.0 g sodium sulfate, filtered, and concentrated under reduced pressure at room temperature to an oil. The crude oil was purified by column chromatography on a silica gel (100.0 g), eluting with 1:6 (v/v) mixture of ethyl acetate and hexanes. Evaporation of the product containing fractions under reduced pressure at room temperature gave 1.25 g (1.90 mmol) of Compound 81 {R$_f$: 0.88 [hexanes:ethyl acetate, 2:1 (v/v)]} in 63% yield.

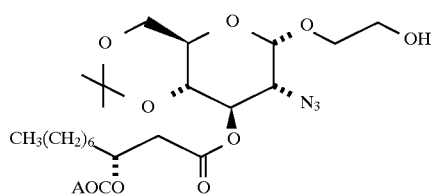

To a solution of 11.2 mg (17.0 μmol) of Compound 81 dissolved in 4.0 mL of anhydrous tetrahydrofuran, at room temperature, was first added 10 μl (173 μmol) acetic acid, followed by the addition of 20 mg (76.5 μmol) solid tetrabutylammonium fluoride (Aldrich Chemical Co.). After one hour, an additional portion of 20 mg (76.5 μmol) tetrabutyl-ammonium fluoride was added. The reaction was stirred for one hour longer, then quenched by the addition of 2.0 mL of a saturated aqueous ammonium chloride solution and extracted with 50.0 mL ethyl acetate. The organic layers were washed with 20.0 mL of a saturated aqueous sodium chloride solution, dried over 10.0 g sodium sulfate, filtered, and concentrated under reduced pressure at room temperature to provide 8.1 mg (14.9 μmol) of Compound 82 {R$_f$: 0.28 [hexanes:ethyl acetate, 2:1 (v/v)]} in 87% yield.

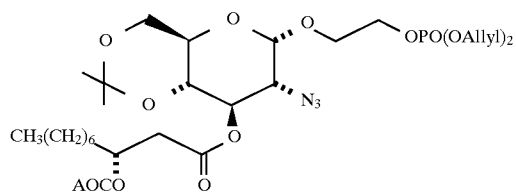

To a solution of 8.1 mg (14.9 μmol) of Compound 82, dissolved in 1.0 mL anhydrous dichloromethane, at 0° C., was added 7.4 mg (30.2 μmol) bis(allyloxy) (diisopropylamino) phosphine and then added 6.5 mg (92.8 μmol) 1H-tetrazole. After 30 minutes, the reaction mixture was warmed to room temperature, an additional quantity of 7.4 mg (30.2 mmol) bis(allyloxy) (diisopropylamino) phosphine was added, and the mixture was stirred for an additional 30 minutes. The mixture was then cooled to −78° C., a solution of 6.6 mg (38.2 μmol) 3-chloroperoxybenzoic acid dissolved in 300.0 μL anhydrous dichloromethane was added, and the resulting mixture stirred for 10 minutes longer. The reaction mixture was then quenched by the addition of 2.0 mL of a 1:1 (v/v) mixture of a saturated aqueous sodium thiosulfate solution and a saturated aqueous sodium bicarbonate solution. The resulting mixture was warmed to room temperature and extracted with 10.0 mL dichloromethane. The organic extracts were washed with 5.0 mL of a saturated aqueous sodium chloride solution, and dried over 5.0 g sodium sulfate. Filtration and concentration of the dried extract under reduced pressure at room temperature, gave 8.9 mg (12.6 μmol) of Compound 83 {R$_f$: 0.28 [hexanes:ethyl acetate, 1:1 (v/v)]} in 85% yield.

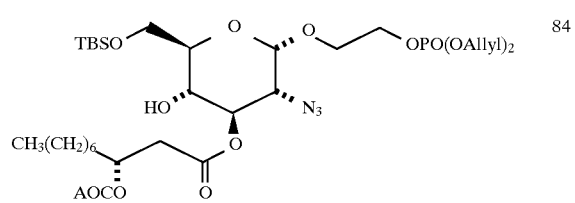

A solution of 0.82 g (1.165 mmol) of Compound 83 dissolved in 100.0 mL of a 1:1 (v/v) mixture of glacial acetic acid and water was stirred at room temperature for eight hours. The reaction mixture was then concentrated, under reduced pressure at room temperature. The resulting oil was dissolved in 50.0 mL toluene and dried by azeotropic removal of the added toluene under reduced pressure at room temperature.

The crude oil was then dissolved in 20.0 mL anhydrous dichloromethane, cooled to 0° C., and to the oil was added 1.0 g (14.7 mmol) imidazole followed by 0.2 g (1.3 mmol) of tert-butyldimethylsilyl chloride. After stirring for 30 minutes, the reaction mixture was quenched by addition of 20.0 mL of a saturated aqueous ammonium chloride solution and extracted with 100.0 mL ethyl acetate. The organic layers were dried over 20.0 g sodium sulfate, filtered, and concentrated under reduced pressure at room temperature to yield the crude product as a colorless oil. The crude oil was purified on a silica gel column (100.0 g) by elution with a 2:1 (v/v) mixture of hexanes:ethyl acetate. Concentration of the product-containing fractions under reduced pressure at room temperature gave 0.65 g (0.835 mmol) of Compound 84 in 72% yield.

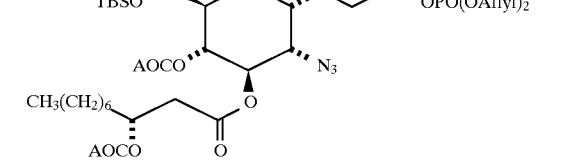

A solution of 0.58 g (0.746 mmol) of Compound 84 dissolved in 10.0 mL anhydrous toluene was cooled to 0 ° C., then 1.0 mL (12.4 mmol) anhydrous pyridine, followed by 1.0 mL (1.93 mmol) of a 1.93 M solution of phosgene in toluene were added. The resulting mixture was stirred for 30 minutes and then 400.0 μL (5.88 mmol) of allyl alcohol was added. After an additional 30 minutes of stirring at room temperature, 5.0 mL of a saturated aqueous ammonium chloride solution was added. The mixture was then extracted with 50.0 mL dichloromethane and the organic layers washed with 10.0 mL of a saturated aqueous sodium chloride solution, dried over 10.0 g sodium sulfate, filtered, and concentrated under reduced pressure at room temperature yielding 0.7 g (0.81 mmol) of Compound 85 {R$_f$: 0.85 [dichloromethane:diethyl ether, 4:1 (v/v)]}.

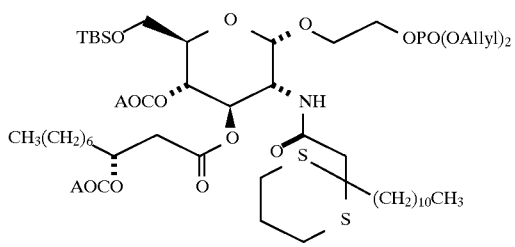

To a solution of 0.60 g (0.696 mmol) of Compound 85 dissolved in 5.0 mL anhydrous dichloromethane was added 0.5 g (1.1 mmol) tin (II)tris-benzenethiolate triethylamine complex. After stirring for five minutes, an additional 0.5 g (1.1 mmol) of tin (II)tris-benzenethiolate triethylamine complex was added, and the mixture was stirred for an additional five minutes. The reaction was then applied directly to a short silica gel column (20.0 g) and eluted first with 4:1 (v/v) hexanes:ethyl acetate and then with 1:19 (v/v) methyl alcohol:dichloromethane to provide the crude amine.

The crude amine was dissolved in 3.0 mL anhydrous dichloromethane, cooled to 0° C., and 290 mg (0.872 mmol) of C8 was added, followed by 200.0 mg (0.969 mmol) of 1,3-dicyclohexyl carbodiimide. After one hour, the reaction mixture was allowed to warm to room temperature, stirred for an additional two hours, diluted with 10.0 mL hexanes, filtered, and concentrated to an oil under reduced pressure at room temperature. Purification on a silica gel column (100.0 g), by elution with a 8:1 (v/v) mixture of hexanes:ethyl acetate provided 380 mg (0.330 mmol) of Compound 86.

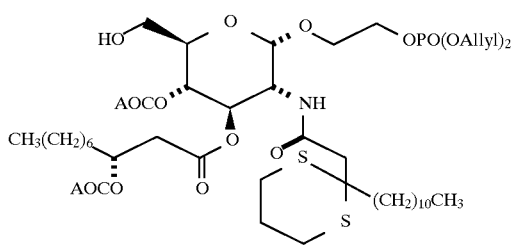

To a solution of 3.0 mL 6 M hydrogen fluoride dissolved in 30.0 mL acetonitrile, contained in a Teflon reaction vessel, was added dropwise at 0° C. a solution of 300.5 mg (0.261 mmol) of Compound 86 dissolved in 2.0 mL acetonitrile. After stirring for one hour, the reaction mixture was poured into 100.0 mL of a saturated aqueous sodium bicarbonate solution and extracted with 100.0 mL dichloromethane. The organic layers were washed with 50.0 mL a saturated aqueous sodium bicarbonate solution, dried over 10.0 g sodium sulfate, filtered, and concentrated under reduced pressure at room temperature to an oil. Purification by silica gel column chromatography by elution with 1:1 (v/v) mixture of hexanes:ethyl acetate provided 200 mg (0.193 mmol) of Compound 87.

Compounds 88 and 89 were synthesized by the general methods described above for the synthesis of Compounds 33 and 34.

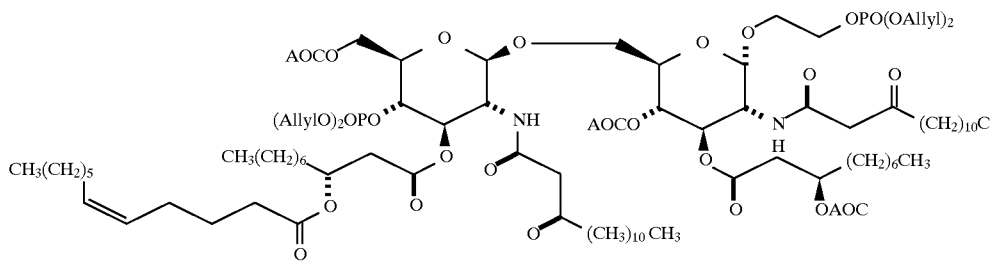

To a stirred room temperature suspension of Compound 89 (102.5 mg, 48.6 μmol) in a mixture of acetonitrile (1.5 mL) and water (100 μL) was added mercuric oxide (96 mg, 443 μmol) and mercuric chloride (61 mg, 224 μmol). After one hour, the mixture was diluted with 1:1 (v/v) methyl alcohol:dichloromethane to induce precipitation. The mixture was filtered through Celite 545, the filtrate collected, and hydrogen sulfide bubbled through it for one hour. The mixture was again filtered and the combined filtrates washed with saturated aqueous sodium bicarbonate, dried with saturated aqueous sodium chloride, dried over sodium sulfate, filtered, and concentrated under reduced pressure to an oil. The oil was purified by a direct application of the oil to a silica gel column (10.0 g) and elution with 1:19 (v/v) methyl alcohol:chloroform, followed by a second silica gel column (10.0 g) chromatography eluting with 1:4 (v/v) hexanes:ethyl acetate. 54.5 mg (28.3 μmol) of Compound 90 was obtained.

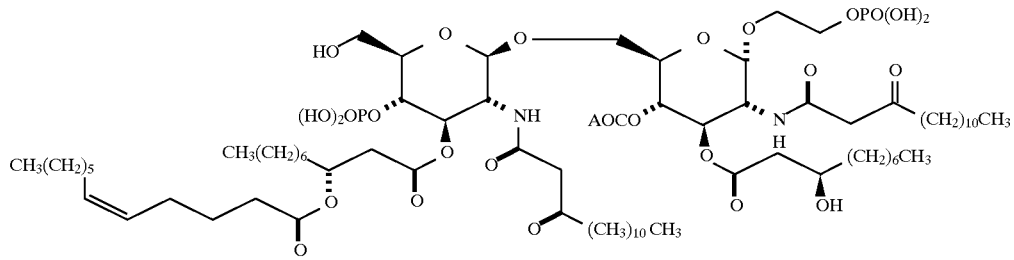

Compound 90 (37.5 mg, 19.5 μmol) was dissolved in 10:1 (v/v) tetrahydrofuran: 96% formic acid under a nitrogen atmosphere in the dark, and to the solution was added tetrakis (triphenylphosphine)palladium(O) and triphenylphosphine. The reaction was carried out as generally described above for Compound 30 (procedure a) and provided 15.0 mg (9.91 μmol) of Compound 91 as a free acid. To produce the Lipid A Analog B377–34, Compound 91 was reacted with L-lysine generally as described above for analog B214–32.

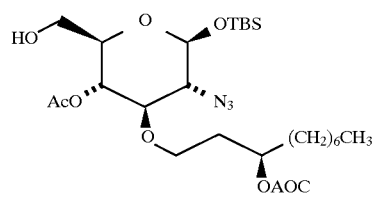

Compound 54 was first acylated using a standard condition of 1:1 [v/v] acetic anhydride:pyridine and a catalytic amount of 4-dimethylaminopyridine added; the reaction was carried out at room temperature. Evaporation of the excess acylating reagents at room temperature under vacuum yielded the crude 4-position acylated product. This product was used in the subsequent transformation without any further purification.

The crude 4-position acylated product was subjected to the synthetic and purification steps generally described above for the transformation of Compound 55 to 56 to provide Compound 92 {$R_f$: 0.23 [hexanes:ethyl acetate, 4:1 (v/v)]}.

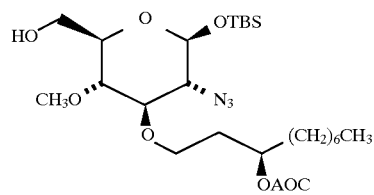

Compound 47 was methylated and treated as described above, except that tert-butylchlorodimethylsilane was used as the silylation reagent. A 2.2 g (2.8 mmol) portion of isolated 4-methylated 6-silylated product was then dissolved in 20.0 mL of a 9:1 (v/v) mixture of acetone and water. To this mixture was added 0.7 g (5.7 mmol) 4-methylmorpholine N-oxide and 10.0 mg (0.04 mmol) osmium tetroxide, and the resulting reaction mixture was stirred for 2.5 hours. The reaction was then quenched by the addition of 100.0 mL of saturated sodium thiosulfate solution and extracted with 100.0 mL dichloromethane. The organic layer was dried over 20.0 g sodium sulfate and evaporated under reduced pressure at room temperature to provide the crude product.

The crude product (obtained in the previous step) was then dissolved in 20.0 mL methyl alcohol and stirred with 2.0 g potassium carbonate for 25 minutes. The reaction mixture was then diluted with 100.0 mL dichloromethane, filtered thru 10.0 g Celite, and washed with 100.0 mL 0.1 N hydrochloric acid. The organic layer was washed with 25.0 mL saturated sodium chloride solution, dried over 30.0 g sodium sulfate, and concentrated under reduced pressure at room temperature to yield the crude product. The product thus obtained was purified on 200.0 g silica gel by elution with a mixture of 9:1 hexanes and ethyl acetate. The desired product was obtained in 80% yield {$R_f$: 0.46 [hexanes:ethyl acetate, 4:1 (v/v)]}. The above-obtained intermediate was then subjected to the synthetic steps generally described above for the transformation of Compound 45 to 52, followed by the synthetic steps generally described above for the transformation of Compound 55 to 56 to provide the final desired intermediate, Compound 93 {$R_f$: 0.33 [hexanes:ethyl acetate, 4:1 (v/v)]}.

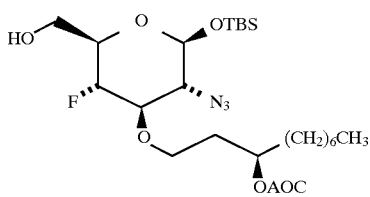

3,4,6-triacetoxygalactose (Pfanstiehl Labs., Inc.) was subjected to the synthetic steps generally described above for the transformation of Compound 7 to 9. The resulting product was then protected at the anomeric position as generally described above for Compound 36. Treatment of this product for the removal of the 3-,4-, and 6-acetate protecting groups and the subsequent protection of the 4 and 6 positions with acetonide was carried out as generally described above for the synthesis of Compounds 36 and 5, respectively. This product was then subjected to the synthetic steps as generally described above for the preparation of Compounds 37 to 45, followed by the synthetic steps for the preparation of Compounds 45 to 54.

A 10.5 g (15.6 mmol) portion of this product was dissolved in 500 mL anhydrous dichloromethane at room temperature under nitrogen, and 18.6 mL (140.7 mmol) 2,4,6-collidine (Aldrich Chemical Co.) was added. To this mixture was next added a solution of 4.8 mL (36.3 mmol) diethylaminosulfur trifluoride (Aldrich Chemical Co.) dissolved in 120.0 mL anhydrous dichloromethane over 1.5 hours dropwise. The resulting mixture was stirred 2 hours longer, then quenched by the addition of 100 mL anhydrous methyl alcohol. The reaction mixture was then poured into 200 mL saturated sodium bicarbonate solution and extracted with 500 mL dichloromethane. The organic extract was then washed with 200 mL saturated aqueous sodium chloride solution, then dried over 100 g sodium sulfate. The crude product was purified on 500 g silica gel by elution with a 10 to 1 (v/v) mixture of hexanes and ethyl acetate yielding the desired 4-position fluorinated product in 65% yield {$R_f$: 0.77 [hexanes:ethyl acetate, 10:1 (v/v)]}.

This product was then subjected to the synthetic steps generally described above for the preparation of Compound 55 to 56 to provide Compound 94 {$R_f$: 0.78 [hexanes: ethyl acetate, 2:1 (v/v)]} in good yield.

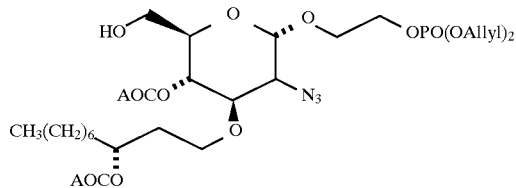

Compound 95 was obtained by treatment of Compound 80 using the silylation conditions described above for the synthesis of Compound 54, followed by alkylation with sidechain A10 (see below) using the conditions described above for the synthesis of Compound 45. The alkylated product was then subjected to the synthetic steps generally described above for the preparation of Compound 80 to 85, followed by the synthetic steps generally described above for the preparation of Compound 86 to 87, to provide the intermediate Compound 95 {$R_f$: 0.09 [hexanes:ethyl acetate, 1:1 (v/v)]}.

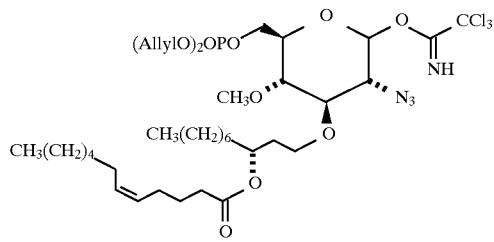

Compound 47 was methylated and treated as described above, except that tert-butylchlorodimethylsilane was used as the silylation reagent. The isolated 4-methylated 6-silylated product was then subjected to the synthetic steps generally described above for the preparation of Compound 56 from 55, followed by phosphorylation of the free 6 position by the method described above for the synthesis of Compound 49. This product was then transformed to the desired intermediate Compound 96 (as an αβ mixture) by the two step sequence described above for the synthesis of Compounds 51A and 51B (from Compound 49 via Compound 50). Compound 96 (an αβ mixture) {$R_f$: 0.50 and 0.83 [hexanes:ethyl acetate, 1:1 (v/v)]}.

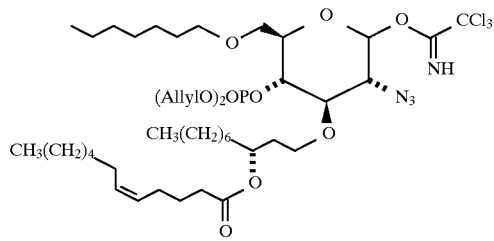

Intermediate Compound 97 was synthesized from Compound 47 in the following manner. A mixture of 2.0 g (3.1 mmol) of Compound 47, 1.0 g powdered 300 AW molecular sieves, 300.0 mg (1.29 mmol) (±)-10-camphorsulfonic acid, 1.0 g (8.7 mmol) heptaldehyde and 6.0 mL anhydrous toluene were stirred for 45 minutes at room temperature under nitrogen. The reaction mixture was then diluted with 50.0 mL dichloromethane, washed first with 20.0 mL saturated aqueous sodium bicarbonate solution, and then with 20 mL saturated aqueous sodium chloride solution. The organic layer was dried over 30.0 g sodium sulfate, the solvent removed under reduced pressure at room temperature, and the resulting crude product purified on 200.0 g silica gel by elution with 1.0 L hexanes followed by 1 L 99:1 (v/v) hexanes:ethyl acetate and finally with 1 L 97:3 (v/v) hexanes:ethyl acetate. The desired product was obtained in a 85% yield (1.96 g, 2.6 mmol), $R_f$: 0.47 [hexanes:ethyl acetate, 19:1 (v/v)].

The above-obtained product was dried under vacuum overnight, then dissolved in 10.0 mL anhydrous dichloromethane. To this mixture was first added 625.0 μL (3.9 mmol) triethylsilane (Aldrich Chemical Co.), and next was added 2.8 mL (2.8 mmol) of a 1.0 M titanium (IV) chloride dichloromethane solution (Aldrich Chemical Co.) over 5 minutes at room temperature under nitrogen. The reaction mixture was then diluted with 50.0 mL dichloromethane, and washed first with 50 mL saturated aqueous sodium bicarbonate solution and then with 20 mL saturated aqueous sodium chloride solution. The organic layer was dried over 10.0 g sodium sulfate, the solvent removed under reduced pressure, at room temperature, and the resulting crude product purified on 200.0 g silica gel by elution with 19:1 (v/v) hexanes: ethyl acetate. The desired product was obtained in a 74% yield (1.4 g, 1.9 mmol), $R_f$: 0.14 [hexanes:ethyl acetate, 19:1 (v/v)].

This 6-position alkylated product was then subjected to the synthetic steps generally described above for the three step synthetic transformation of Compounds 60A and 60B from 57A (via 58 and 59) to provide Compound 97 (as an αβ mixture) {$R_f$: 0.55 and 0.67 [hexanes:ethyl acetate, 2:1 (v/v)]} in comparable yields.

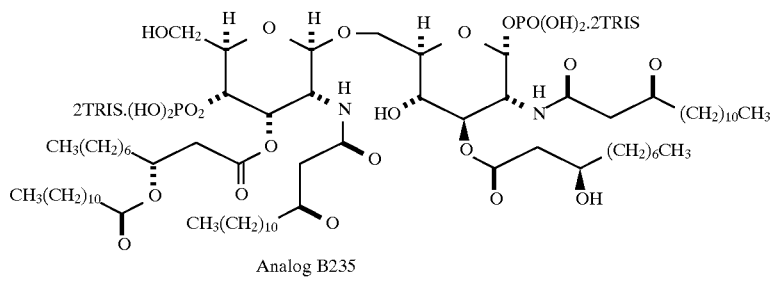

Analog B235

Compound 12 was first reacted with Compound A25 (generally as described above for the synthesis of Compound 13), and the resultant product was sequentially subjected to the synthetic steps generally described above for the preparation of Compounds 13–21. The resultant α-isomeric product was then reacted with Compound 17 (as generally described above for the synthesis of Compound 24), and the resultant product was subjected to the synthetic steps generally described above for the preparation of Compounds 25, 32–34, 30 (Procedure b), and 31. Lipid A Analog B235–32 was produced by reacting the free acid product with L-lysine as described above for analog B214–32. Analog B235–31 was produced by reacting the free acid product with Tris as described above for B214–31.

the synthesis of Compound 24), and the resultant product was sequentially subjected to the synthetic steps generally described above for the preparation of Compounds 25–30 (Procedure a), with the exception that Compound 26 was first reacted with one equivalent of an allylcarbonate protected side chain (prepared as described below for side chains A4–A6 using C4 as starting material), followed by condensation with C6. The resultant product was then deprotected as generally described above for the synthesis of Compound 31. Lipid A Analog B272–32 was produced by reacting the free acid product with L-lysine as described above for analog B214–32.

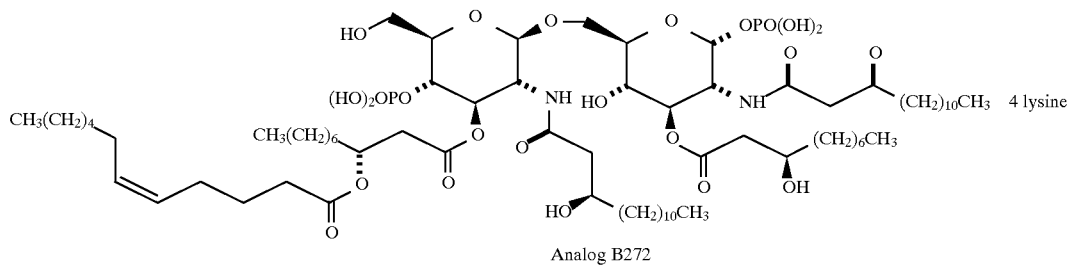

Analog B272

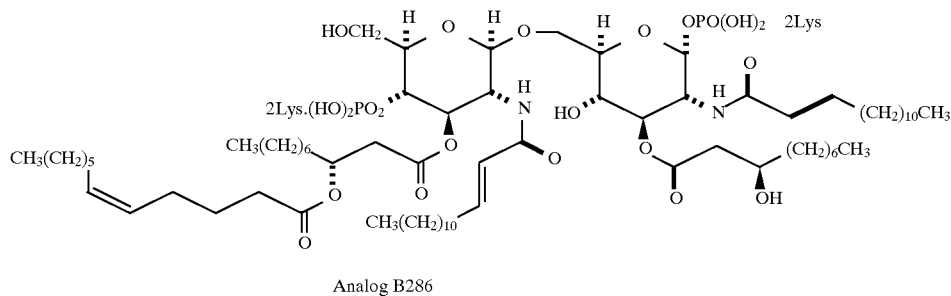

Analog B286

Compound 12 was reacted with Compound A6 (generally as described above for the synthesis of Compound 18), and the resultant product was sequentially subjected to the synthetic steps generally described above for the preparation of Compounds 19–23. The resultant α-isomeric product was reacted with Compound 17 (generally as described above for Compound 25 was reacted with E-2-tetradecenoic acid [described in Mimura et al., J Pharmacobio-Dyn 1983 6 (8):527, 1983] generally as described above for the synthesis of Compound 26, and the resultant product was sequentially subjected to the synthetic steps generally described above for the preparation of Compounds 27, 28, and 31. Lipid A analog B286–32 was produced by reacting the free acid product with L-lysine as described above for analog B214–32.

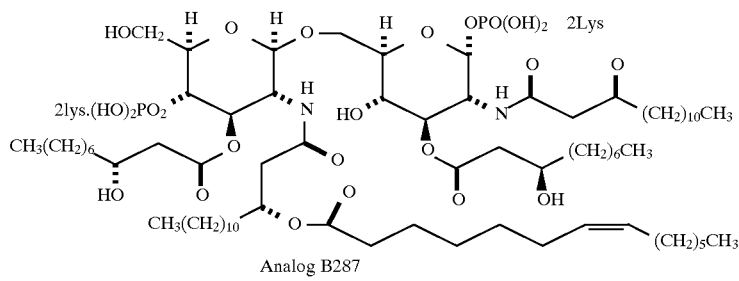

Analog B287

Compound 25 was reacted first with Compound C6 and then with Compound H1 (see below) by selective condensation generally as described above for the preparation of Compound 26, and the resultant product was sequentially subjected to the synthetic steps generally described above for the preparation of Compounds 27–30 (Procedure a), 31. Lipid A analog B287–32 was produced by reacting the free acid product with L-lysine as described above for analog B214–32.

Compound H1 was prepared generally as described for B6 by condensing Compound C4 with Z-7-tetradecenoic acid, itself made by the same general procedure used to make Compound B4.

B288–32 was produced by reacting the free acid product with L-lysine as described above for analog B214–32.

Compound H2 is identical in structure to Compound 23A, except that the allyloxy-protected phosphate group (of 23A) was replaced by an allyloxycarbonate-protected hydroxyl group (in H2); Compound H2 was prepared essentially as described above for Compound 23A.

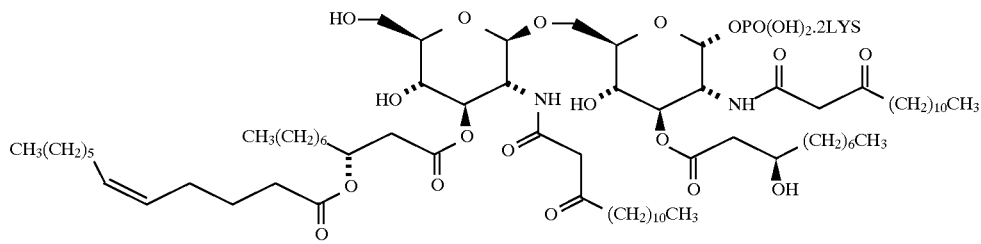

Analog B288

Compound H2 (below) was reacted with Compound 17 (generally as described above for the synthesis of Compound 24), and the resultant product was sequentially subjected to the synthetic steps generally described above for the preparation of Compounds 25–31. Lipid A analog

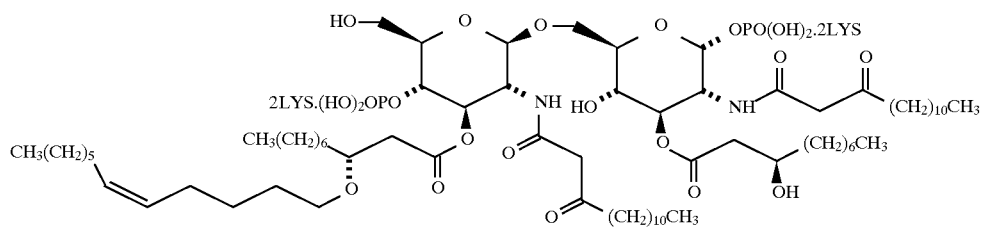

Analog B294

Compound 12 was reacted with Compound A17 (see below) generally as described above for the preparation of Compound 18, and the resultant product was sequentially subjected to the synthetic steps generally described above for the preparation of Compounds 19–23. The resultant α-isomeric product was then reacted with Compound 17 (generally as described above for the preparation of Compound 24), and the product was sequentially subjected to the synthetic steps generally described above for the preparation of Compounds 25–31. Lipid A analog B294–32 was produced by reacting the free acid product with L-lysine as described above for analog B214–32.

Compound 25 was reacted first with Compound H3 (by selective condensation) and then with Compound C6 (see below) by selective condensation generally as described above for the synthesis of Compound 26, and the resultant product was sequentially subjected to the synthetic steps

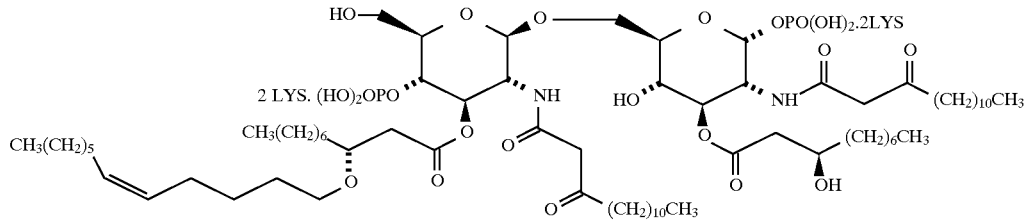

Analog B300

Compound 12 was reacted with Compound A17 (see below) generally as described above for the synthesis of Compound 18. The resultant product was sequentially subjected to the synthetic steps generally described above for the preparation of Compounds 19–29 and then deprotected generally as described above for Compound 31. Lipid A analog B300–32 was produced by reacting the free acid product with L-lysine as described above for analog B214–32.

generally described above for Compounds 27–31. Lipid A analog B314–32 was produced by reacting the free acid product with L-lysine as described above for analog B214–32.

Compound H3 was prepared generally as described below for Compound B6 except Compound C4 was condensed with decanoic acid (Aldrich Chm. Co.).

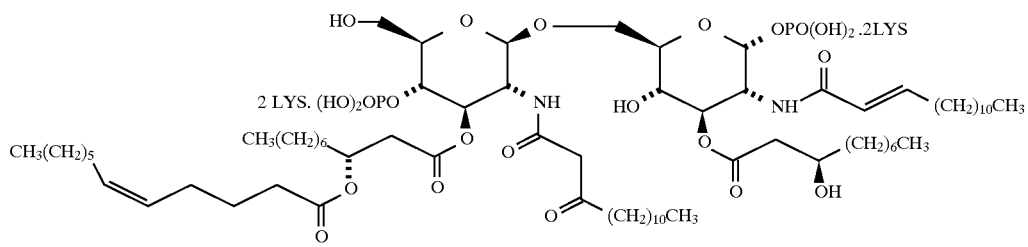

Analog B313

Compound 25 was reacted first with E-2-tetradecenoic acid [described in Mimura et al., *J Pharmacobio-Dyn* 6 (8):527, 1983 ] and then with Compound C5 by selective condensation (generally as described above for Compound 26, and the resultant product was sequentially subjected to the synthetic steps generally described above for the preparation of Compounds 27, 28, and 31. Lipid A analog B313–32 was produced by reacting the free acid product with L-lysine as described above for analog B214–32.

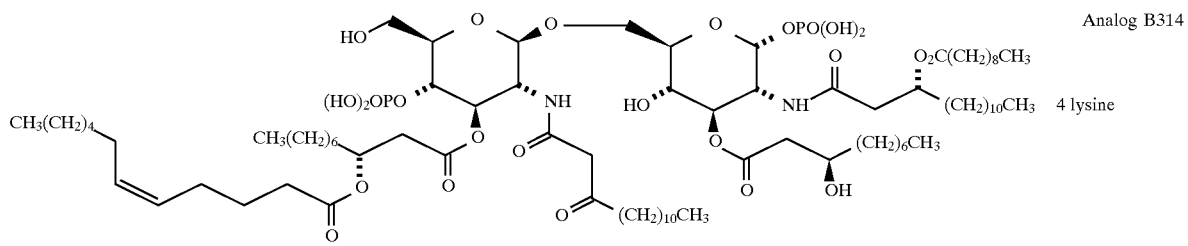

Analog B314

4 lysine

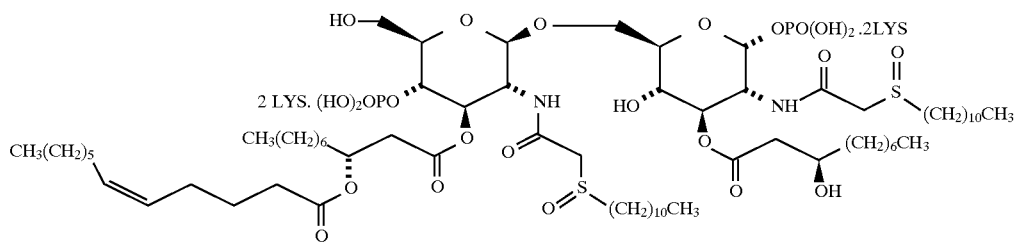

Analog B318

Compound 25 was reacted with a racemic mixture of E3 and E5 generally as described above for the synthesis of Compound 26, and the resultant product was sequentially subjected to the synthetic steps generally described above for the preparation of Compounds 27, 28, 31. Lipid A analog B318–32 was produced by reacting the free acid product with L-lysine as described above for analog B214–32.

Compound 12was reacted with Compound A23 (see below) generally as described above for the synthesis of Compound 18, and the resultant product was sequentially subjected to the synthetic steps generally described above for the preparation of Compounds 19–23. The resultant α-isomeric product was then reacted with Compound 17

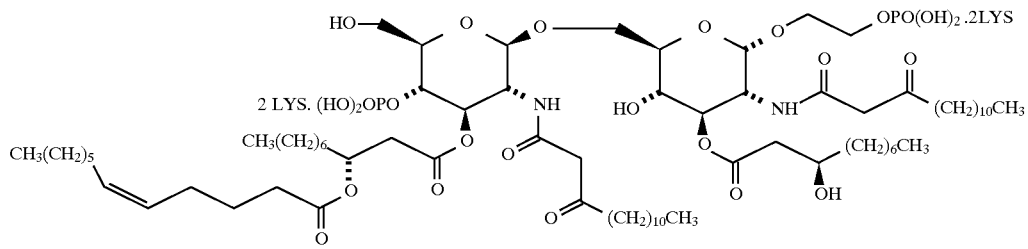

Analog B377

Compound 23A was reacted with Compound 87 generally as described above for the synthesis of Compound 24. The resultant product was then subjected first to the synthetic steps generally described above for the preparation of Compounds 32–34, 30 (Procedure b), and 31 (in that order) and then deprotected generally as described above for Compound 31. Lipid A analog B377–34was prepared by reacting the free acid product with L-lysine generally as described above for analog B214–32, except that a dilysine (rather than a tetralysine) salt is produced.

generally as described above for the synthesis of Compound 24, and the product was subjected to the synthetic steps generally described above for the preparation of Compounds 32–34, 30 (Procedure b), and 31 (in that order). Lipid A analog B379–32 was produced by reacting the free acid product with L-lysine as described above for analog B214–32.

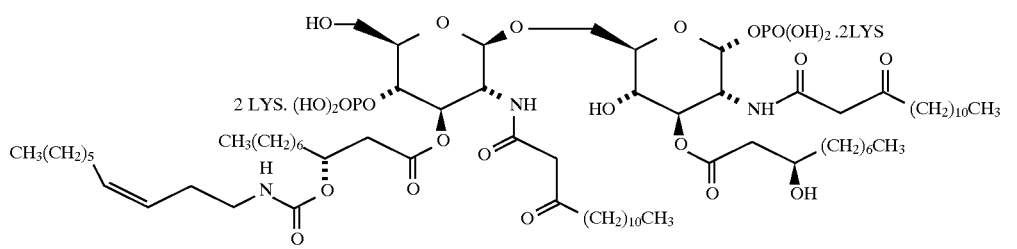

Analog B379

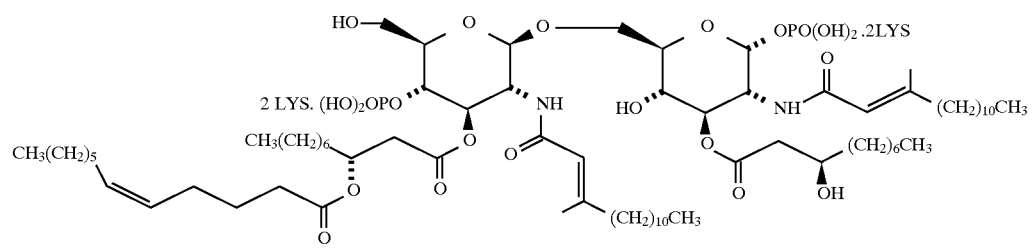

Analog B385

Compound 25 was reacted with Compound A30 (below) generally as described above for Compound 26. The resultant product was first sequentially subjected to the synthetic steps generally described above for the preparation of Compounds 27 and 28 and then deprotected as described above for the preparation of Compound 31. Lipid A analog B385–32 was produced by reacting the free acid product with L-lysine as described above for analog B214–32.

Compound 25 was reacted with Compound G2 generally as described above for the synthesis of Compound 32. The resultant product was first sequentially subjected to the synthetic steps generally described above for the preparation of Compounds 33 and 34, and then the oxythiolane groups were deprotected by the method described for the prepara-

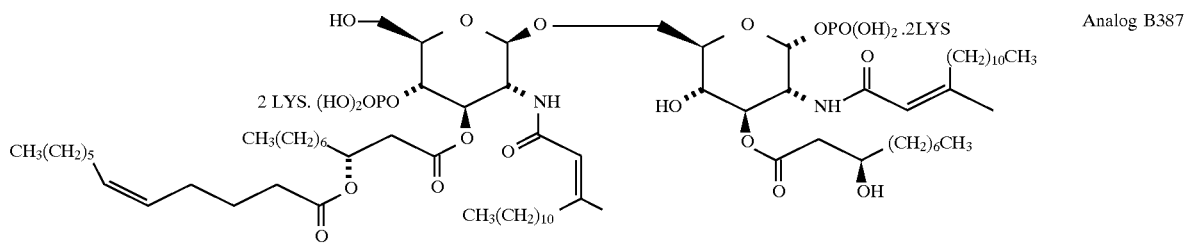

Analog B387

Compound 25 was first reacted with Compound A31 (below) generally as described above for Compound 26. The resultant product was first sequentially subjected to the synthetic steps generally described above for the preparation of Compounds 27 and 28 and then deprotected as described above for the preparation of Compound 31. Lipid A analog B387–32 was produced by reacting the free acid product with L-lysine as described above for analog B214–32.

tion of Compound 30 (Procedure b) above, and the phosphate and hydroxyl groups were deprotected by the method described for Compound 31 above. Lipid A analog B398–32 was produced by reacting the free acid product with L-lysine as described above for analog B214–32.

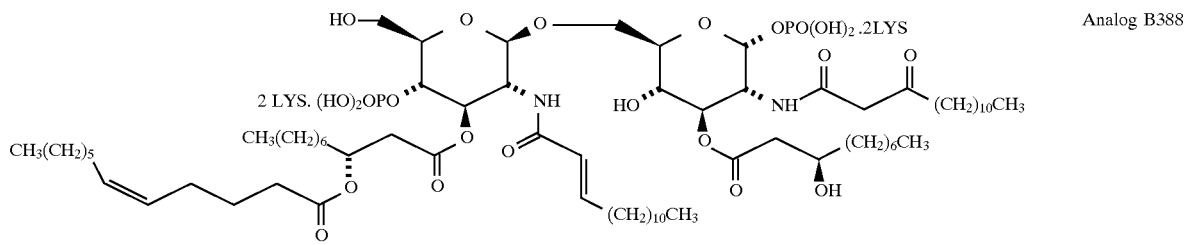

Analog B388

Compound 25 was first reacted with Compound C8 and then reacted with E-2-tetradecenoic acid [described in Mimura et al., *J Pharmacobio-Dyn* 6 (8):527, 1983] generally as described above for the synthesis of Compound 26. The resultant product was sequentially subjected to the synthetic steps generally described above for the preparation of Compounds 27, 28, 30 (Procedure b), and 31. Lipid A analog B388–32 was produced by reacting the free acid product with L-lysine as described above for analog B214–32.

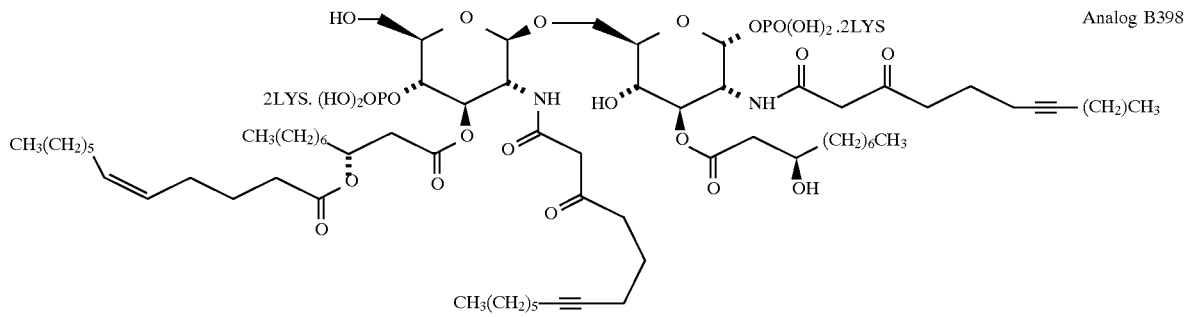

Analog B398

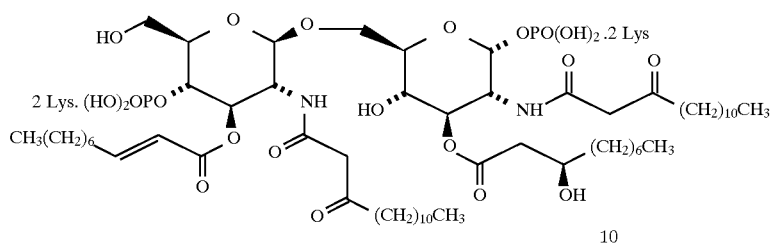

Analog B400

Compound 12 was first reacted with trans-2-decenoic acid (Lancaster Synthesis Inc.) generally as described above for the synthesis of Compound 18, and the resultant product sequentially subjected to the synthetic steps generally described above for the preparation of Compounds 19–23 . The resultant α-isomeric product was next reacted with Compound 17 (generally as described above for the preparation of Compound 24), and the product subjected to the synthetic step generally described above for the preparation of Compound 25. The product obtained was then reacted generally as described above for the synthesis of Compound 32, the resultant product subjected to the synthetic steps generally described above for the preparation of Compounds 33, 34, and 30 (Procedure b) (in that order), and the phosphate and hydroxyl groups deprotected generally as described above for the preparation of Compound 31. Lipid A analog B400–32 was produced by reacting the free acid product with L-lysine as described above for analog B214–32.

synthesis of Compound 13, and the product subjected first to the synthetic steps generally described above for the preparation of Compound 19, and then to the synthetic steps generally described above for the preparation of Compounds 15–17 (in that order). The product was termed H13.

H12A was reacted with H13 generally as described for the preparation of Compound 24, and the product was subjected first to the synthetic step generally described above for the preparation of Compound 25, then to the synthetic steps generally described above for the preparation of Compounds 32–34 (in that order). Finally, the dithiane groups of the product were deprotected as generally described above for Compound 30 (Procedure b), and the phosphate and hydroxyl groups were deprotected as generally described above for the synthesis of Compound 31. Lipid A Analog B406–32 was produced by reacting the free acid product with L-lysine as described above for analog D214–32.

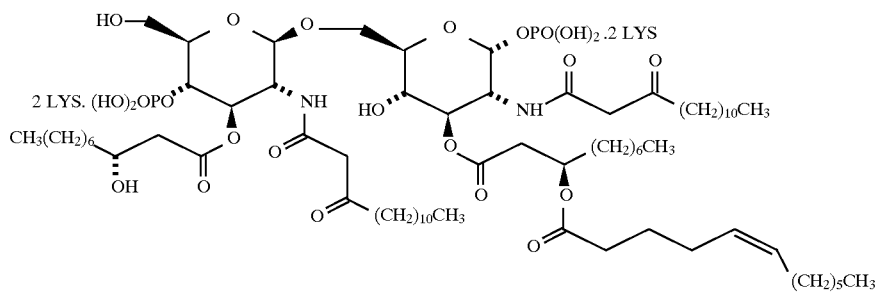

Analog B406

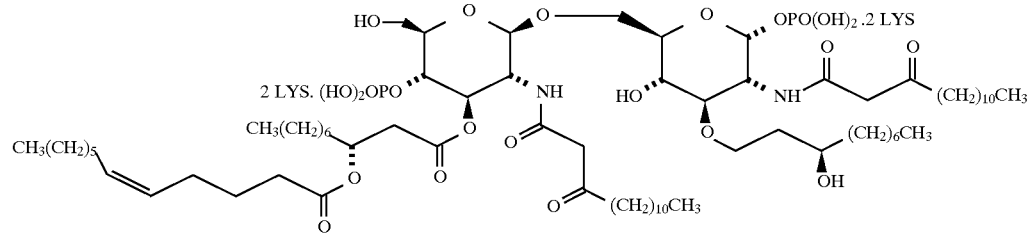

Analog B410

Compound 12 was reacted with Compound A6 (generally as described above for the synthesis of Compound 18), and the resultant product was sequentially subjected to the synthetic steps generally described above for the preparation of Compounds 19–23. The α-isomeric product was termed H12A.

Compound 12 was reacted with H1 (see preparation of Compound B287) generally as described above for the Compound 53 was first reacted with Compound 23A (generally as described above for the synthesis of Compound 40), and the resultant product sequentially subjected to the synthetic steps generally described above for the preparation of Compounds 41–44. The product obtained was then phosphorylated as generally described above for the preparation of Compound 30 (Procedure b), and the phosphate and hydroxyl groups deprotected generally as described for the preparation of Compound 31. Lipid A analog B410–32 was produced by reacting the free acid product with L-lysine as described above for analog B214–32.

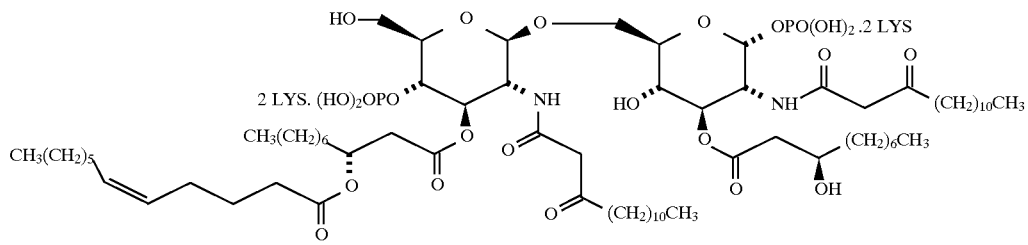

Analog B415

Compound 51A was first reacted with Compound 39 (generally as described above for the synthesis of Compound 40, and the resultant product sequentially subjected to the synthetic steps generally described above for the preparation of Compounds 41–44. The product obtained was then phosphorylated as generally described above for the preparation of Compound 30 (Procedure b), and the phosphate and hydroxyl groups deprotected generally as described for the preparation of Compound 31. Lipid A analog B415–32 was produced by reacting the free acid product with L-lysine as described above for analog B214–32.

A minor anomeric glycosidation product of the synthetic reaction producing Compound 40 (above) was first sequentially subjected to the synthetic steps generally described above for the preparation of Compounds 41–44, phosphorylated as generally described above for Compound 30 (Procedure c), and deprotected as generally described above for Compound 31. The analog B426–32 was then produced by reacting the free acid product with L-lysine as described above for analog B214–32.

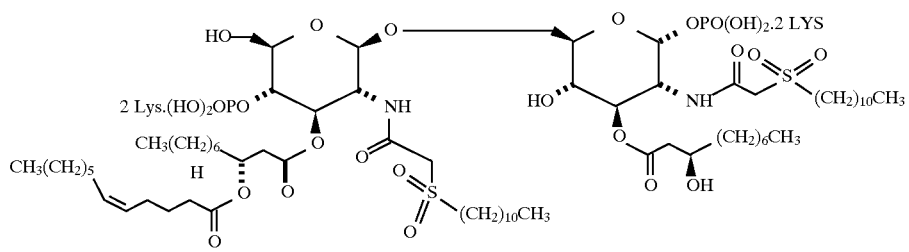

Analog B425

Compound 42 was reacted with 1,3-dicyclohexylcarbodiimide and E7 generally as described above for the preparation of Compound 43, and the resultant product first subjected to the synthetic step generally described above for the preparation of Compound 44, then phosphorylated as generally described above for the preparation of Compound 30 (Procedure b), and finally deprotected as generally described above for the synthesis of Compound 31. The analog B425–32 was then produced by reacting the free acid product with L-lysine as described above for analog B214–32.

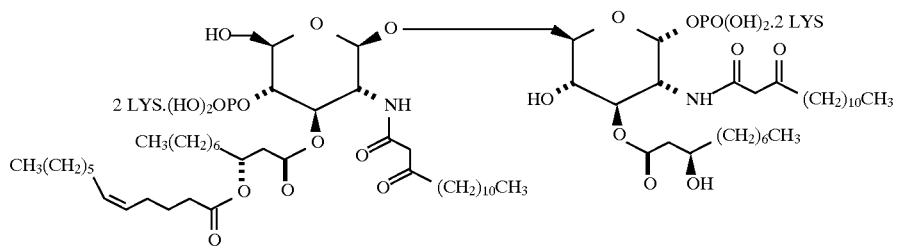

Analog B426

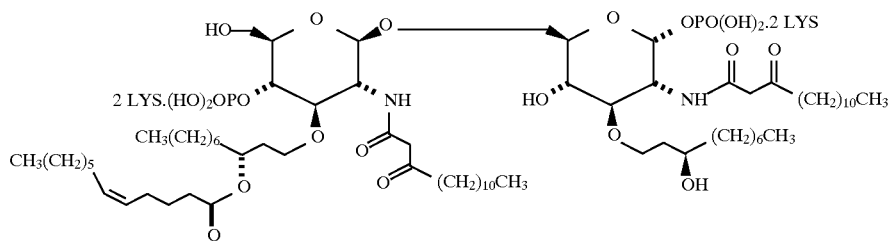

Analog B427

Compound 51A was first reacted with Compound 56 (generally as described above for the synthesis of Compound 65), and the resultant product sequentially subjected to the synthetic steps generally described above for the preparation of Compounds 66–69. The product obtained was then deprotected generally as described for the preparation of Compound 31. Lipid A analog B427–32 was produced by reacting the free acid product with L-lysine as described above for analog p214–32.

Compound 19 was subjected to the same synthetic steps as for the synthesis of Compound 58 from Compound 47. The resulting product was deprotected as generally described above for Compound 22 and then activated as generally described above for the synthesis of Compound 23A. This product was first reacted with Compound 56 (generally as described above for the synthesis of Compound 65), and the resultant product subjected to the syn-

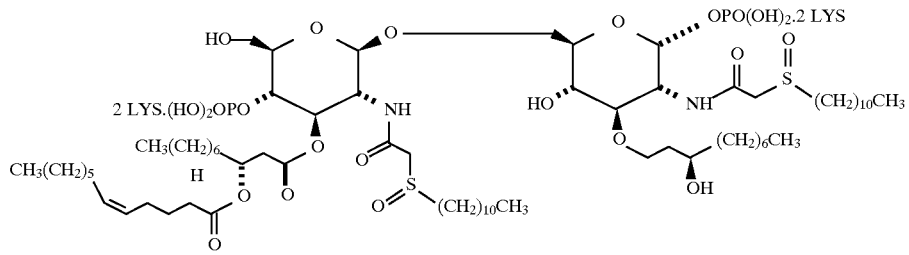

Analog B442

Compound 56 was first reacted with Compound 23A (generally as described above for the synthesis of Compound 24), and the resultant product subjected to the synthetic step generally described above for the preparation of Compound 25. The resultant product was then reacted with a mixture of Compounds E3 and E5 (see below) generally as described above for Compound 43. The product was then subjected to the synthetic steps generally described above for the preparation of Compounds 44, phosphorylated as generally described above for the preparation of Compound 28, and the product deprotected generally as described for the preparation of Compound 31. Lipid A analog B442–32 was produced by reacting the free acid product with L-lysine as described above for analog B214–32.

thetic step generally described above for the preparation of Compound 66. The product was then reacted with Compound E3 (see below) generally as described for the preparation of Compound 67 and the product subjected to the synthetic steps generally described above for the preparation of Compounds 68, 69, 31 (in that order). Lipid A analog B451–32 was produced by reacting the free acid product with L-lysine as described above for analog B214–32.

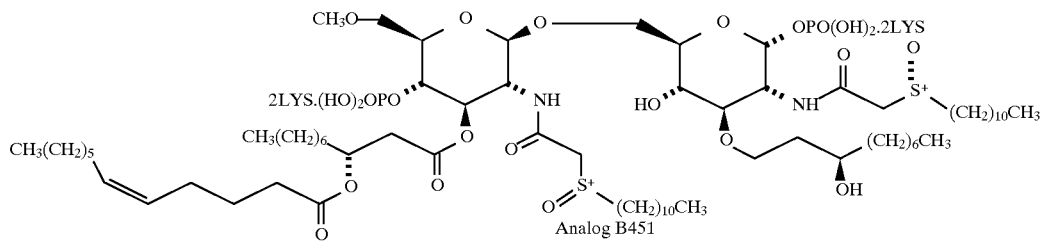

Analog B451

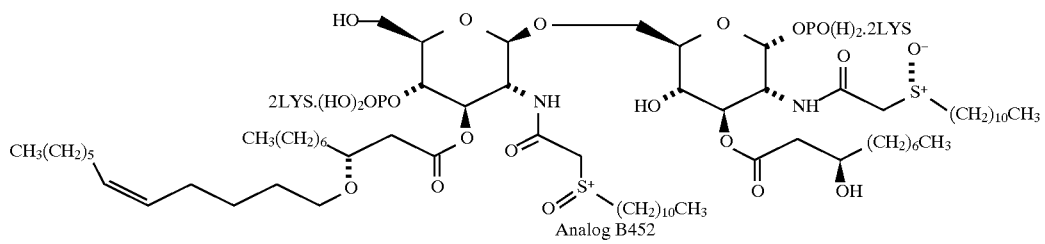
Analog B452

Compound 25 a was first reacted with Compound E3 (generally as described above for the synthesis of Compound 26), and the resultant product subjected to the synthetic steps generally described above for the preparation of Compounds 27, 28, 31 (in that order). Lipid A analog B452–32 was produced by reacting the free acid product with L-lysine as described above for analog B214–32.

Compound 51A was first reacted with Compound 56 (as generally described above for the synthesis of Compound 65, and the resultant product subjected to the synthetic step generally described above for the preparation of Compound 66. The resultant product was then reacted with Compound E3 (see below) as generally described for the synthesis of

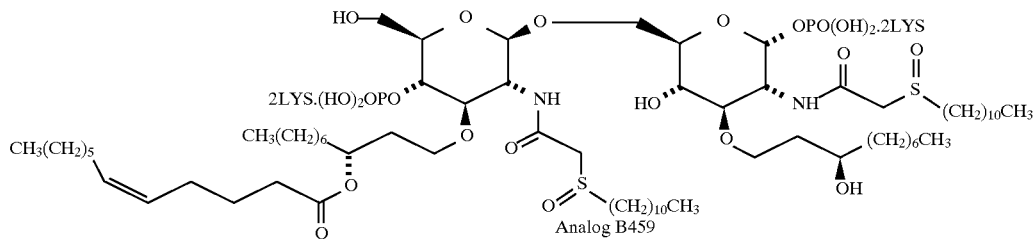
Analog B459

Compound 51A was first reacted with Compound 56 (generally as described above for the synthesis of Compound 65), and the resultant product subjected to the synthetic step generally described above for the preparation of Compound 66. The product was then reacted with a mixture of Compounds E3 and E5 as generally described above for the synthesis of Compound 67, and the product subjected to the synthetic steps generally described for the preparation of Compounds 68, 69, 31 (in that order). Lipid A analog B459–32 was produced by reacting the free acid product with L-lysine as described above for analog B214–32.

Compound 67, and the product sequentially subjected to the synthetic steps generally described above for the preparation of Compounds 68 and 69. The product obtained was then deprotected generally as described for the preparation of Compound 31. Lipid A analog B460–32 was produced by reacting the free acid product with L-lysine as described above for analog B214–32.

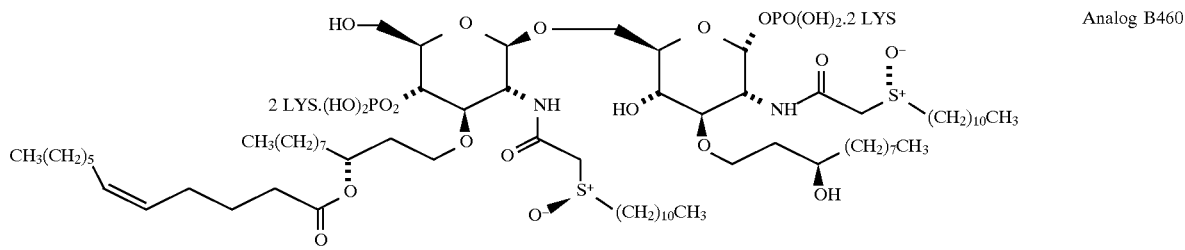
Analog B460

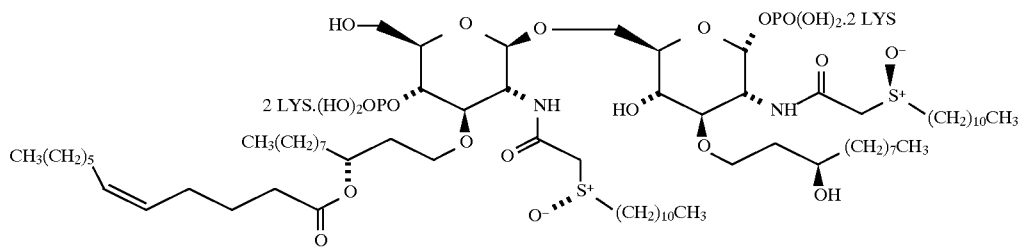

Analog B465

Compound 51A was first reacted with Compound 56 (as generally described above for the synthesis of Compound 62, and the resultant product subjected to the synthetic step generally described above for the preparation of Compound 66. The resultant product was then reacted with Compound E5 (see below) as generally described for the synthesis of Compound 67, and the product sequentially subjected to the synthetic steps generally described above for the preparation of Compounds 68 and 69. The product obtained was then deprotected generally as described for the preparation of Compound 31. Lipid A analog B465–32 was produced by reacting the free acid product with L-lysine as described above for analog B214–32.

A mixture of Compounds 60A and 60B was first reacted with Compound 56 (generally as described above for the synthesis of Compound 65), and the resultant product subjected to the synthetic step generally described above for the preparation of Compound 66. The product was then reacted with Compound E5 as generally described above for the synthesis of Compound 67, and the product subjected to the synthetic steps generally described for the preparation of Compounds 68, 69, and 31 (in that order). Lipid A analog B477–32 was produced by reacting the free acid product with L-lysine as described above for analog B214–32.

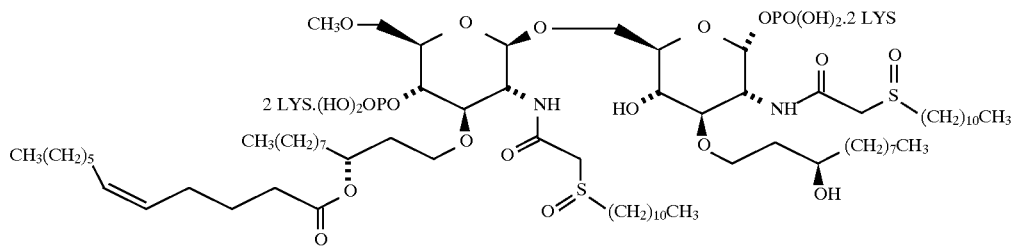

Analog B466

A mixture of Compounds 60A and 60B was first reacted with Compound 56 (as generally described above for the synthesis of Compound 65), and the resultant product subjected to the synthetic step generally described above for Compound 66. The resultant product was then reacted with Compound E3 (see below) as generally described for the synthesis of Compound 67, and the product subjected to the synthetic steps generally described above for the preparation of Compounds 68, 69, and 31 (in that order). Lipid A analog B466–32 was produced by reacting the free acid product with L-lysine as described above for analog B214–32.

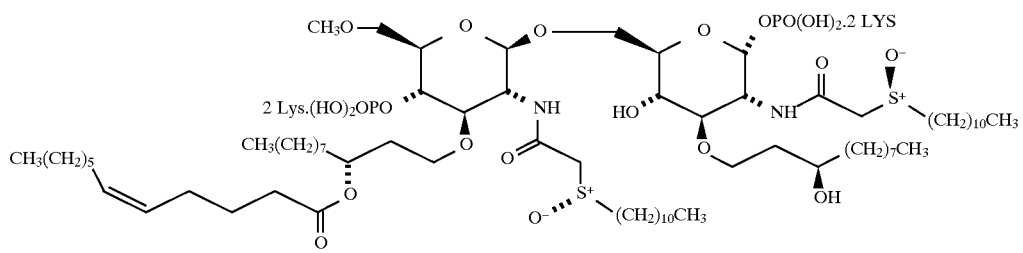

Analog B477

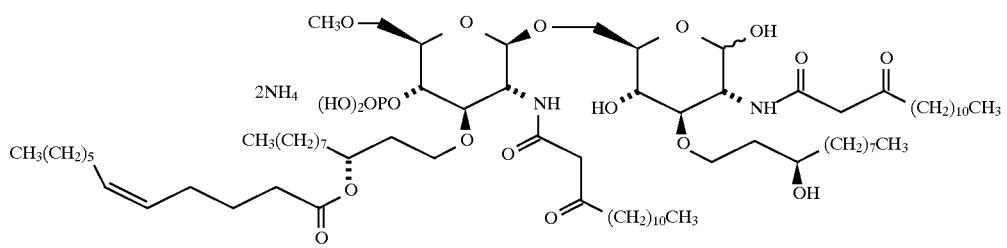

Analog B479

A mixture of Compounds 60 A and 60B was first reacted with Compound 56 (generally as described above for the synthesis of Compound 65), and the resultant product sequentially subjected to the synthetic steps generally described above for the preparation of Compounds 66–68. The product (corresponding to Compound 68 above) was then deprotected generally as described for the synthesis of Compound 31. Lipid A analog B479–33 was produced by reacting the free acid product with L-lysine as described above for analog B214–32.

Analog B464 is identical in structure to Compound 70 with the exception that in the preparation of Compound 45 a one carbon extended sidechain analog of A10 was used (the preparation of A10 was modified by the use of octyl cyanide).

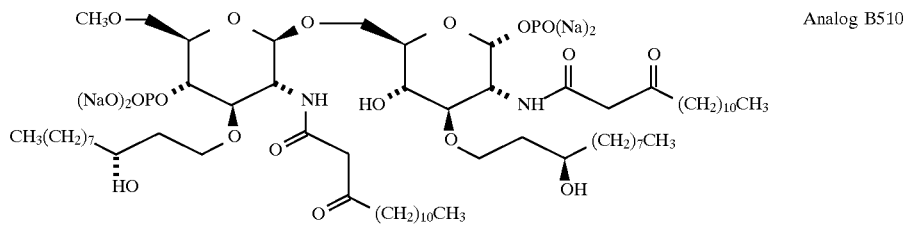

Analog B510

Compound 52 was first sequentially subjected to the reactions generally described above for the preparation of Compounds 46 and 47 and then sequentially subjected to the reactions generally described above for the preparation of Compounds 57–60. The resultant product was then reacted with Compound 56 (as generally described above for the synthesis of Compound 65), and the resultant product was sequentially subjected to the synthetic steps as generally described above for the preparation of Compounds 66–70 to produce Analog B510–35.

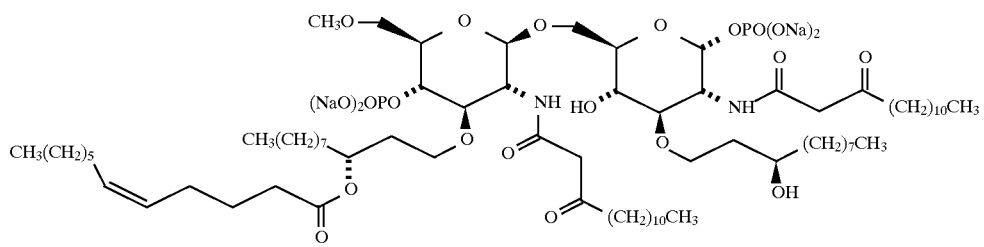

Analog B464

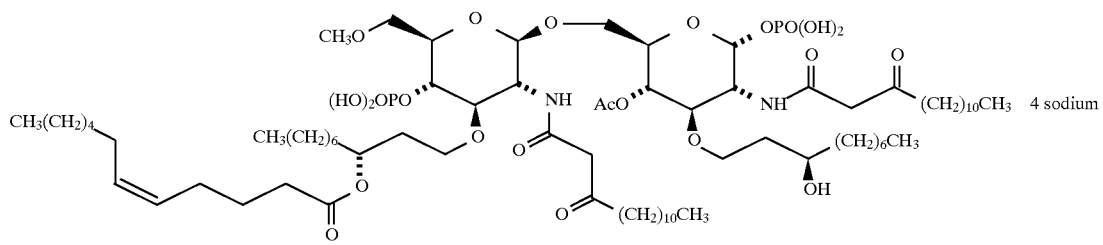

Analog B718

Compound 92 was coupled with Compound 60 (as generally described above for the synthesis of Compound 65). The resultant product was then sequentially subjected to the synthetic steps generally described above for the preparation of Compounds 66–70 to produce Analog B718–35.

Compound 95 was coupled with Compound 60 (as generally described above for the synthesis of Compound 65). The resultant product was then sequentially subjected to the synthetic steps generally described above for the preparation of Compounds 66–70 to produce Analog B736–35.

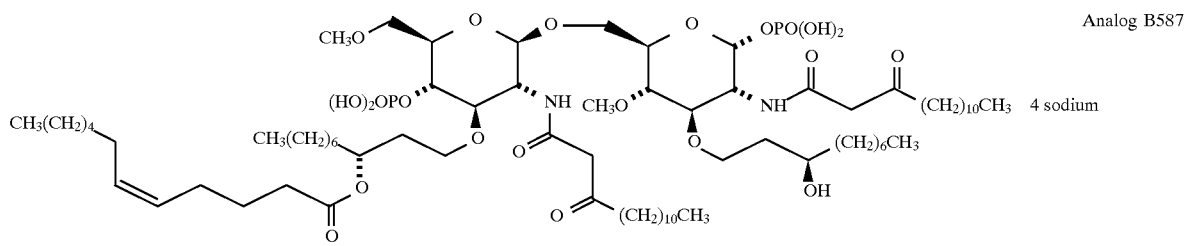

Analog B587

Compound 93 was coupled with Compound 60 (as generally described above for the synthesis of Compound 65). The resultant product was then sequentially subjected to the synthetic steps generally described above for the preparation of Compounds 66–70 to produce Analog B587–35.

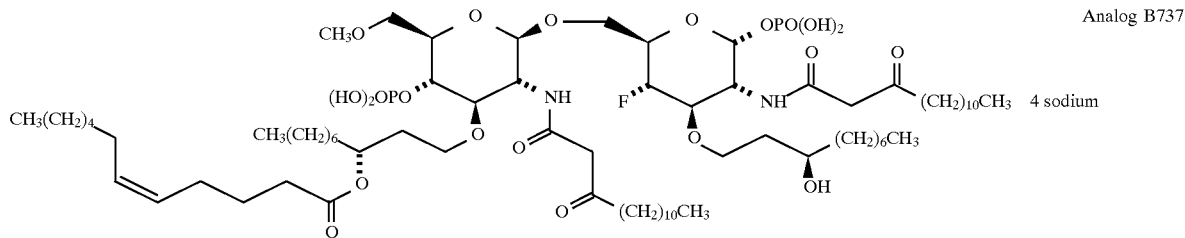

Analog B737

Compound 94 was coupled with Compound 60 (as generally described above for the synthesis of Compound 65). The resultant product was then sequentially subjected to the synthetic steps generally described above for the preparation of Compounds 66–7 to produce Analog B737–35.

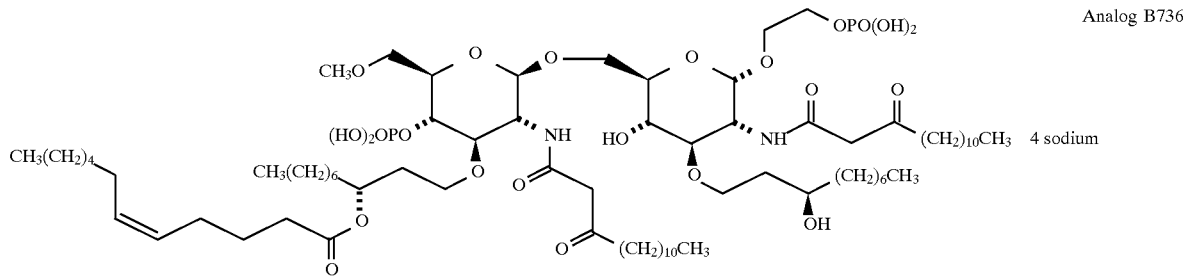

Analog B736

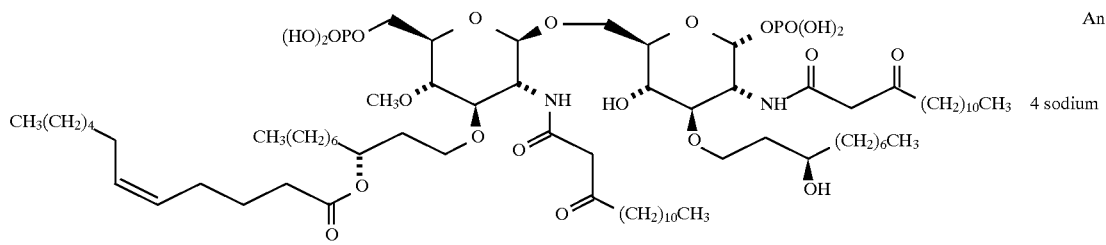

Analog B725

Compound 96 was coupled with Compound 56 (as generally described above for the synthesis of Compound 65). The resultant product was then sequentially subjected to the synthetic steps generally described above for the preparation of Compounds 66–70 to produce Analog B725–35.

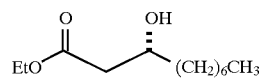

A2

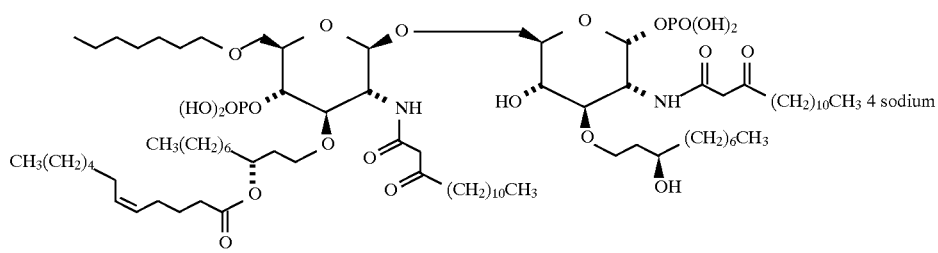

Analog B763

Compound 97 was coupled with Compound 56 (as generally described above for the synthesis of Compound 65). The resultant product was then sequentially subjected to the synthetic steps generally described above for the preparation of Compounds 66–70 to produce Analog B763–35.

PART B

Preparation of Sidechains

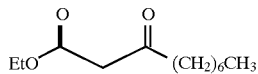

A1

To refluxing anhydrous tetrahydrofuran (500.0 mL) was sequentially added: activated zinc (101.0 g, 1.54 mol; Fisher Scientific), ethyl bromoacetate (3.0 mL; Aldrich Chemical Co.), and, in one portion, heptyl cyanide (47.4 mL, 0.308 mol; Aldrich Chemical Co.). To the resulting mixture, 134.0 mL (1.232 mol) of ethyl bromoacetate was then added dropwise, over three hours. The mixture was refluxed for an additional 10 min, cooled to room temperature, and quenched by the slow addition of saturated aqueous potassium carbonate solution (160.0 mL). Following rapid stirring for 30 minutes, the solution was filtered through 500.0 g Celite 545 to yield a clear yellow solution of crude enamino ester. The solution was acidified with 1.0 N hydrochloric acid (300.0 mL), stirred for three hours, diluted with 2.0 L hexanes, and neutralized by the addition of 300.0 mL saturated aqueous sodium hydrogen carbonate. The organic layer was washed with saturated aqueous sodium chloride solution (400.0 mL), dried over 500.0 g sodium sulfate, filtered, and evaporated. The residue was purified by application to a silica gel (1.0 kg) and elution with 6:1 (v/v) hexanes/ethyl acetate. Evaporation of solvent from the product-containing fractions (as determined by thin layer chromatographic analysis) under reduced pressure at room temperature provided 64.0 g (0.298 mol) of Compound A1. {$R_f$: 0.7 [hexanes:ethyl acetate, 4:1 (v/v)]} in 97% yield.

[R]-(+)-2,2'-Bis(diphenylphosphino)-1,1'-binaphthyl (653.5 mg, 1.05 mmol; Aldrich Chemical Co.) and cyclooctadienyl ruthenium dichloride (279.8 mg, 1.0 mmol; Alfa Chemical Co., Ward Hill, Mass.) were combined in a 125 mL stopcock sidearm round bottom flask fitted with a magnetic stirrer and cold finger water condenser in a dry box. The flask was removed from the dry box and placed under argon. Anhydrous toluene (40.0 mL) and triethylamine (1.7 mL, 10.0 mmol; Aldrich Chemical Co.), both of which had been deoxygenated by sparging with nitrogen, were injected into the flask, and the mixture was refluxed under argon, with stirring, for 15 hours. The deep crimson solution was allowed to cool to 20° C. and formed a reddish gel. Excess solvent was removed from the mixture using a 12-inch, 22-gauge needle, and the residual volatiles were removed by application of a vacuum, over several hours (using great care to exclude air). The residual red-black solid was dissolved in anhydrous, oxygen-free tetrahydrofuran by stirring under a nitrogen atmosphere at 25° C. for one hour. The resultant clear orange-brown solution of [R]-2,2'-Bis (diphenylphosphino)-1,1'-binaphthyl ruthenium dichloride hemi triethylamine complex was used directly in the next reaction.

Compound A1 (334.2 g, 1.15 mol) was dissolved in anhydrous methyl alcohol (330.0 mL) and was deoxygenated by three freeze-thaw vacuum degassing cycles, using liquid nitrogen and a nitrogen atmosphere. The solution of [R]-2,2'-Bis (diphenylphosphlno)-1,1'-binaphthyl ruthenium dichloride hemi triethylamine complex catalyst (prepared above), was added to the reaction solution using a syringe. The reaction mixture was pumped into an argon-flushed 2.0 L hydrogenation bomb containing methyl alcohol-washed Dowex 50×8–200 H⁺resin (3.0 g; Aldrich Chemical Co.) using a catheter under argon. The bomb was charged to 1480 psi with hydrogen gas (Liquid Carbonic, Tewskbury, Mass.) and the reaction mixture was stirred at 25° C. for 66 hours. When the pressure in the bomb had dropped 300 psi, excess hydrogen gas was released, the reaction mixture was filtered, and volatile substances were removed, under reduced pressure, to provide 334.0 g (1.15 mol) of Compound A2 {R_f: 0.31 [hexanes:ethyl acetate, 4:1 (v/v)]} in 99% yield.

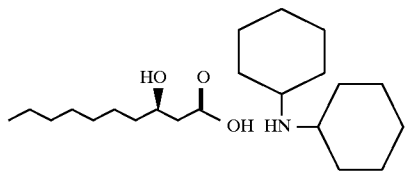
A3

Compound A2 (89.6 g, 0.347 mol) was dissolved in tetrahydrofuran (800.0 mL). To this solution was added 2.5 M aqueous sodium hydroxide (300.0 mL, 0.75 mol), and the resulting mixture vigorously stirred, under a nitrogen atmosphere, at 25° C., for one and a half hours. The reaction mixture was diluted with 1.0 L of 1:1 (v/v) diethyl ether/hexanes, and the aqueous layer was separated. The organic phase was extracted further with 200.0 mL of water, and the combined aqueous phases acidified with concentrated hydrochloric acid 67 mL. The acidified mixture was then extracted with 2.0 L diethyl ether and the extract washed first with 1.0 L water, then with 1.0 L saturated aqueous sodium chloride solution, and finally dried over 500.0 g magnesium sulfate. The solvent was removed under reduced pressure, and the resultant grayish solid dissolved in 2.0 L 80° C. acetonitrile. To the solution at 80° C. was added dicyclohexylamine (80.0 mL, 0.40 mol; Aldrich Chemical Co.). The mixture was cooled to −20° C., providing 104.7 g (0.24 mol) of Compound A3{R_f: 0.38 [hexanes:ethyl acetate:glacial acetic acid, 1:1:0.1 (v/v/v)]} as slightly off-white fine needles, in 71% yield.

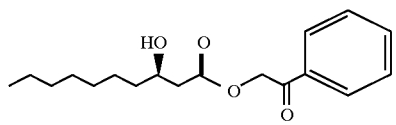
A4

Compound A3 (104.7 g, 246.0 mmol) was suspended in ethyl acetate (2.0 L), and, to the suspension, triethylamine (37.2 g, 369.0 mmol) was first added, followed by 2-bromoacetophenone (48.9 g, 246.0 mmol, in one portion; Aldrich Chemical Co.); additions were made under a nitrogen atmosphere, at 0° C. After three-hours, the reaction mixture was warmed to room temperature, stirred for six hours, and then vacuum filtered. The residue was washed with 400.0 mL ethyl acetate, and the filtrate was washed first with 500.0 mL of 0.8 M hydrochloric acid, then with 500 mL of water, and finally with 1.0 mL saturated aqueous sodium chloride solution, and then dried over 500.0 g magnesium sulfate. The solvent was evaporated under reduced pressure at 50° C. to yield a congealed gray solid which was recrystallized from 1.1 L hexanes and dried in a vacuum oven at 50° C. to provide 81.05 g (223.9 mmol) of Compound A4 {R_f: 0.65 [chloroform:methyl alcohol, 95:5 (v/v)]} as an off-white solid in 91% yield.

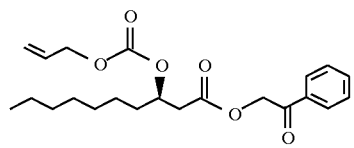
A5

Compound A4 (20.2 g, 65.9 mmol) was dissolved in anhydrous toluene (300.0 mL) and anhydrous pyridine (30.0 mL) at 0° C. and, to this solution, was added 1.93 M phosgene in toluene (50.0 mL, 96.5 mmol), dropwise. The reaction mixture was stirred for 10 minutes, and then allyl alcohol (20.2 mL, 297.0 mmol) was added dropwise. After an additional 10 minutes of stirring, the reaction was quenched, at 0° C., by the addition of 100.0 mL saturated sodium bicarbonate solution. The solution was subsequently warmed to 25° C. and extracted with 1.0 L ethyl acetate. The organic layer was washed with 500.0 mL saturated aqueous sodium chloride solution, dried over 500.0 g sodium sulfate, filtered, and evaporated. The residue was purified on a silica gel (2.0 kg) column, eluting with 1:9 (v/v) ethyl acetate/hexanes. Evaporation of solvent from the product-containing fractions (as determined by thin layer chromatographic analysis) under reduced pressure at room temperature provided 16.1 g (41.2 mmol) of Compound A5 {R_f: 0.9 [hexanes:ethyl acetate, 2:1 (v/v)]} in 62% yield.

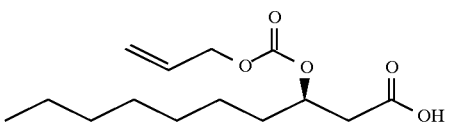
A6

Compound A5 (16.07 g, 41.17 mmol) was dissolved in glacial acetic acid (150.0 mL), in a Morton flask, at 0° C. and, to the solution, was added zinc dust (24.2 g, 371.0 mmol). The solution was warmed to 25° C., stirred for one hour, and then filtered through a 50.0 g Celite 545 plug and evaporated. The residue was purified on a silica gel column, eluting first with 4:1 (v/v) ethyl acetate/hexanes and then with 10:40:1 (v/v/v) methyl alcohol/chloroform/acetic acid. Evaporation of solvent from the product-containing fractions (as determined by thin layer chromatographic analysis) under reduced pressure at room temperature provided A6 {10.8 g; 39.65 mmol; R_f: 0.34 [hexanes:ethyl acetate, 2:1 (v/v)]} in 96% yield.

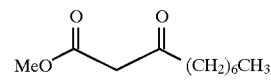
A7

To a mechanically stirred suspension of 1003.0 g (15.33 mol) of activated zinc powder in 2.5 L of anhydrous tetrahydrofuran under a nitrogen atmosphere at room temperature was added dropwise 56.0 mL (0.59 mol) of methyl bromoacetate (Lancaster Chemical Co., Windham, N.H.) over a 10-minute period. The reaction mixture was warmed to reflux temperature and 496.3 g (3.96 mol) of n-heptyl cyanide (Aldrich Chemical Co.) was added dropwise over a five-minute period, and an additional 700.0 mL (7.39 mol) of methyl bromoacetate was then added (dropwise) over a four-hour period. The mixture was refluxed for one additional hour, allowed to cool to room temperature, slowly poured into 3.0 L of a stirred, saturated aqueous solution of potassium carbonate, and 1.0 kg of Celite 545 was added. The heterogeneous mixture was filtered over a pad of 200.0 g of Celite 545 and eluted with four 1.0 L portions of ethyl acetate. The filtrate was separated, and the aqueous layer extracted with two 500.0 mL portions of ethyl acetate. The combined organic layers were washed with 500.0 mL of a saturated aqueous solution of sodium chloride, dried over 2.0 kg of sodium sulfate, filtered, and concentrated under reduced pressure, at room temperature. The crude orange oil was vigorously stirred at room temperature in a two phase system of 1.5 L of hexanes and 500.0 mL of a 1.0 N aqueous solution of hydrochloric acid with a dropwise addition of 250 mL concentrated hydrochloric acid over a forty minute period. After stirring the final heterogeneous solution for an additional 20 minutes, the layers were separated and the aqueous layer was extracted with two 200.0 mL portions of hexanes. The combined organic layers were washed with 500.0 mL of a saturated aqueous solution of sodium hydrogen carbonate, dried over 500.0 g of sodium sulfate, filtered, and concentrated under reduced pressure, at room temperature. The crude orange liquid was distilled using a brush rotary distillation apparatus at a bath temperature of 110° C., under 1.0 mm Hg vacuum. The partially purified clear yellow oil was fractionally vacuum-distilled to provide 652.8 g [3.26 mol, 82.3%, boiling point (b.p.) 86°–88° C./0.4 mm Hg] of Compound A7 {$R_f$: 0.65 [hexanes:ethyl acetate, 4:1 (v/v)]} as a clear, colorless liquid.

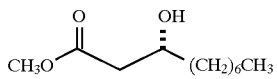

In an oxygen-free dry box, 1.54 g (2.47 mmol) of [R]-(+)-2.2'-bis(diphenylphosphino)-1,1'-binaphthyl and 662.0 mg (2.36 mmol) dichloro(cycloocta-1,5-diene)ruthenium (II) polymer were suspended in 100.0 mL of degassed toluene and 4.0 mL oxygen-free triethylamine in a 250 mL Schlenk flask equipped with a magnetic stirring bar and a condenser. The reaction vessel was sealed under the inert atmosphere, removed from the dry box, and refluxed under an argon atmosphere until an orange solid was obtained (approximately 24 hours). The reaction mixture was cooled slowly to 0° C. over a two-hour period, after which time the gelatinous red semisolid was suspended in 50.0 mL of dry, degassed toluene. The suspension was lightly swirled to wash the crystaline-like sheets, allowed to stand 10 minutes, and the excess solvent was decanted from the solid using a 50 mL syringe with a 20-gauge needle. The above trituration was repeated one additional time, and this was followed by evaporating the final catalyst to dryness under a 1 mm Hg vacuum over a two-hour period. The orange-red solid was suspended in 100.0 mL anhydrous, oxygen-free tetrahydrofuran and stirred under an argon atmosphere for one hour during which time the mixture became a clear red solution. This catalyst solution was transferred via a canula, under an argon atmosphere, to the degassed Compound A7 solution described below.

Compound A7 (365.3 g; 1.824 mol) was dissolved in 500.0 mL of a freshly opened bottle of HPLC grade methyl alcohol, under an argon atmosphere, in a 2 L three-necked round bottom flask. The flask was sealed with a vacuum adapter and two rubber septa, and the solution was cooled, with liquid nitrogen, to a white solid during which time the flask was evacuated under reduced pressure. The solid was then placed under an argon atmosphere and warmed to room temperature with the aid of a heat gun. Such a cooling, evacuation, and warming process was repeated three additional times. After the final degassing process, the chiral catalyst in 100.0 mL of anhydrous, oxygen-free tetrahydrofuran was added as described above. The final reaction mixture was transferred using a Teflon canula under an argon atmosphere into a 2.0 L reaction bomb which contained 1.0 g (5.21 mmol) of para-toluenesulfonic acid monohydrate (Aldrich Chemical Co.) and which had been purged with argon for two hours. (The reaction bomb was equipped with a mechanical stirrer and pressure gauge.) The reaction bomb was evacuated using water aspiration and purged twice with 100 psi of hydrogen gas. The reaction was pressurized to 1500 psi with hydrogen gas and allowed to stir for 72 hours; the system was repressurized after the first 15 minutes of stirring. After the loss of 360 psi of hydrogen gas, the completed reaction was slowly depressurized and purged three times with argon. The methanolic solution was evaporated under reduced pressure, and the resulting residue was dissolved in ethyl acetate and stirred with 300.0 mL of a saturated aqueous solution of sodium bicarbonate for 15 minutes. The layers were separated, and the organic layer was washed with 100.0 mL of a saturated aqueous solution of sodium chloride, dried over 100.0 g of sodium sulfate, filtered, and concentrated under reduced pressure, at room temperature. The residue was purified over 2.5 kg of silica gel eluting first with 32.0 L of hexanes, then with 8.0 L of 19:1 (v/v) hexanes:ethyl acetate, then with 16.0 L of 9:1 (v/v) hexanes:ethyl acetate, and finally with 8.0 L of 3:1 (v/v) hexanes:ethyl acetate. Evaporation of the solvent from the product-containing fractions (as identified by thin layer chromatographic analysis) under reduced pressure, at room temperature, and drying overnight, under vacuum, at room temperature provided 325.0 g (1.61 mol, 88.1% yield, 98+% enantiomeric excess) of Compound A8 {$R_f$: 0.46 [hexanes:ethyl acetate, 3:1 (v/v)]} as a clear and colorless oil.

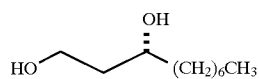

To a stirred suspension of 31.5 g (0.83 mol) of lithium aluminum hydride (Aldrich) in 500.0 g of anhydrous diethyl ether, under a nitrogen atmosphere, at 0° C., was added dropwise 159.0 g (0.78 mol) of Compound A8 in 200.0 g anhydrous diethyl ether over a three and a half-hour period. After stirring for an additional 15 minutes at room temperature, the completed reaction was cooled to 0° C. and quenched with a dropwise addition of 1.0 L of a 1.0 N aqueous solution of hydrochloric acid, followed by addition of 200.0 mL of concentrated hydrochloric acid. The resulting clear layers were separated, and the aqueous layer was extracted three times with 300.0 mL portions of diethyl ether. The combined extracts were washed first with 200.0 mL of water and then with 200.0 mL of a saturated aqueous solution of sodium chloride. The aqueous layers were back extracted three times with 300.0 mL portions of chloroform. The combined organic layers were dried over 500.0 g of sodium sulfate, filtered, and concentrated under reduced pressure at room temperature to provide a clear yellow oil. The crude product was purified on 500.0 g of silica gel eluting first with 5.0 L of 9:1 (v/v) hexanes:ethyl acetate, then with 20.0 L of 4:1 (v/v) hexanes:ethyl acetate, then with 8.0 L of 3:1 (v/v) hexanes:ethyl acetate, then with 1.0 L of chloroform, then with 6.0 L of 9:1 (v/v) chloroform:methyl alcohol, and finally with 4.0 L of 4:1 (v/v) chloroform:methyl alcohol. Evaporation of the solvent from the product-containing fractions (as identified by thin layer chromatographic analysis) under reduced pressure at room temperature and drying overnight under vacuum at room temperature provided 94.2 g (0.54 mol, 69% yield) of Compound A9 {$R_f$: 0.33 [ethyl acetate:hexanes, 1:1 (v/v)]} as a clear colorless oil.

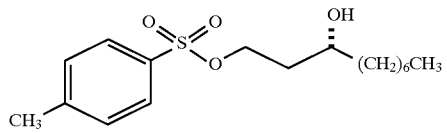

To a stirred solution of 114.1 g (0.65 mol) of Compound A9 in 3.6 L of anhydrous pyridine, at 2.0° C., under a nitrogen atmosphere, was added 136.6 g (0.72 mol) of paratoluenesulfonyl chloride (99+%, Aldrich Chemical Co.) in 10.0 g portions over a 15-minute period. The reaction was allowed to warm slowly to room temperature, was stirred for eight hours under a nitrogen atmosphere, was concentrated under vacuum evaporating conditions, and azeotroped to dryness with three 500.0 mL portions of toluene using vacuum evaporation. The crude syrup was dissolved in 2.5 L of ethyl acetate and 500.0 mL of a saturated aqueous solution of sodium chloride. The layers were separated and the organic layer was washed with 500.0 mL of a saturated aqueous sodium chloride solution. The combined aqueous layers were extracted twice with 500.0 mL portions of chloroform. The combined organic layers were dried over 500.0 g of sodium sulfate, filtered and concentrated under reduced pressure, at room temperature. The residue was purified over 1.5 kg of silica gel eluting first with 12.0 L of 9:1 (v/v) hexanes:ethyl acetate, then with 12.0 L of 17:3 (v/v). hexanes:ethyl acetate, then with 20.0 L of 4:1 (v/v) hexanes:ethyl acetate, then with 4.0 L of dichloromethane, and finally with 16.0 L of 9:1 (v/v) dichloromethane:methyl alcohol. Evaporation of the solvent from the product-containing fractions (as identified by thin layer chromatographic analysis) under reduced pressure at room temperature and drying overnight under vacuum at room temperature provided 96.9 g (0.29 mol) of Compound A10 {$R_f$: 0.45 [hexanes:ethyl acetate, 2:1 (v/v)]} as a yellow oil in 45% yield.

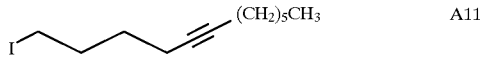

A11

To a stirred solution of 20.0 mL (0.136 mol) of 1-octyne (Aldrich Chemical Co.) in 300.0 mL of anhydrous tetrahydrofuran was added dropwise 70.5 mL (0.177 mol) of a 2.5 M solution of n-butyl lithium in hexanes (Aldrich Chemical Co.), under a nitrogen atmosphere, at 0° C., over a 30-minute period. The mixture was allowed to warm to room temperature over a one hour period, after which time the reaction mixture was cooled to 0° C. and 35.9 mL (0.272 mol) of 1,4-diiodobutane (Aldrich Chemical Co.) was added dropwise over a 20-minute period. The mixture was allowed to warm to room temperature, stirred for an additional 16 hours, diluted with 300.0 mL hexanes, poured over 400 g of ice, and the resulting layers separated. The organic layer was washed with 300.0 mL a saturated aqueous solution of sodium chloride, dried over 150.0 g of sodium sulfate, filtered, and concentrated under reduced pressure at room temperature. The crude product was rendered free of excess diiodobutane by distillation under 0.1 mm Hg of vacuum at 70°–80° C., and the remaining residue was purified on 500.0 g of silica gel by eluting with 2.0 L of hexanes. Evaporation of the solvent from the product-containing fractions (as identified by thin layer chromatographic analysis) under reduced pressure, at room temperature, and drying overnight, under vacuum, at room temperature provided 23.0 g (0.078 mol) of Compound A11 {$R_f$: 0.6 (hexanes]} in 58% yield.

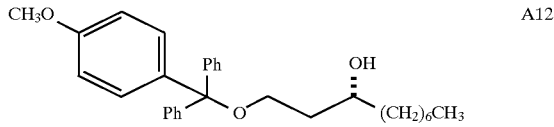

A12

To a stirred solution of 6.53 g (37.5 mmol) of Compound A9 in 45.0 mL of anhydrous pyridine was added 11.53 g (37.5 mmol) of 4-methoxy-triphenylmethyl chloride (Aldrich Chemical Co.), under a nitrogen atmosphere at room temperature. The reaction mixture was stirred at room temperature for four and a half hours, diluted with 200.0 mL of dichloromethaney an d the organic solution washed with 100.0 mL water, dried over 150.0 g of sodium sulfate, filtered, concentrated under reduced pressure at room temperature, and azeotroped to dryness with three 100 mL portions of toluene under vacuum evaporation. The crude product was purified on 300.0 g of silica gel eluting with 2.0 L of 6:1 (v/v) hexanes:ethyl acetate. After evaporation of the solvent from the product-containing fractions (as identified by thin layer chromatographic analysis) under reduced pressure at room temperature the product was dissolved in 200 mL of hexanes, filtered, and the filtrate was concentrated under reduced pressure at room temperature and dried overnight under vacuum at room temperature to provide 16.5 g (36.9 mmol) of Compound A12 {$R_f$: 0.49 [hexanes:ethyl acetate, 4:1 (v/v)]} in 98% yield.

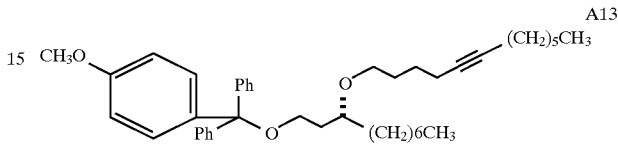

A13

To a stirred solution of 17.1 g (0.038 mol) of Compound A12 in 60.0 mL anhydrous N,N-dimethylformamide, under a nitrogen atmosphere, at 0° C., was added (in small portions) 2.94 g (0.076 mol) of sodium hydride (60% in oil, Aldrich Chemical Co., washed with hexanes). The mixture was stirred at 0° C. for an additional 15 minutes, 12.3 g (0.042 mol) of Compound A11 was added dropwise over a 30-minute period, the reaction mixture was allowed to warm to room temperature, stirred for an additional 16 hours, and quenched with the slow addition of 10.0 mL of methyl alcohol at 0° C. The mixture was stirred for an additional 30 minutes, diluted with 300.0 mL dichloromethane, and the resulting organic solution washed with 200.0 mL of a saturated aqueous solution of sodium chloride, dried over 150.0 g of sodium sulfate, filtered, and concentrated under reduced pressure, at room temperature. The residue was purified on 500.0 g of silica gel eluting first with 1.5 L of hexanes and then with 2.5 L of 30:1 (v/v) hexanes:ethyl acetate. Evaporation of the solvent from the product-containing fractions (as identified by thin layer chromatographic analysis) under reduced pressure at room temperature and drying overnight under vacuum at room temperature provided 2.5 g (4.1 mmol) of Compound A13 {$R_f$: 0.5 [hexanes:ethyl acetate), 10:1 (v/v)]} in 11% yield.

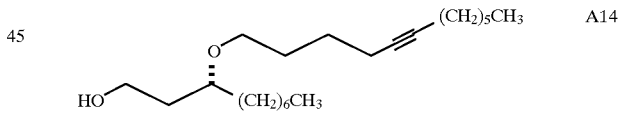

A14

To a stirred solution of 2.6 g (4.26 mmol) of Compound A13 in 80.0 mL of dichloromethane was added 1.0 mL concentrated hydrochloric acid. The solution was stirred at room temperature for one hour, diluted with 400.0 mL ethyl acetate, the organic solution washed four times with 100.0 mL portions of a saturated aqueous solution of sodium chloride, dried over 60.0 g of sodium sulfate, filtered, and concentrated under reduced pressure, at room temperature. The residue was purified on 300.0 g of silica gel eluting with 2.0 L of 5:1 (v/v) hexanes:ethyl acetate. Evaporation of the solvent from the product-containing fractions (as identified by thin layer chromatographic analysis) under reduced pressure at room temperature and drying overnight under vacuum at room temperature provided 1.69 g (>4.26 mmol) of Compound A14 {$R_f$: 0.4 [hexanes :ethyl acetate, 4/1 (v/v)]} that also contained a small amount of 4-methoxytriphenylmethyl chloride. The product was used in subsequent synthetic reactions without further purification.

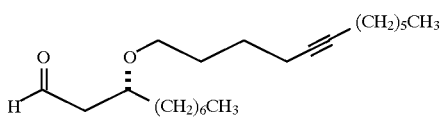

To a stirred solution of 0.55 g (1.62 mmol) of Compound A14 in 50.0 mL of anhydrous dichloromethane, under a nitrogen atmosphere, was added 3.0 g of flame dried 3 Å molecular sieves (Aldrich Chemical Co.). The solution was stirred at room temperature for 15 minutes, 3.05 g (1.62 mmol) of pyridinium dichromate (Aldrich Chemical Co.) was added in one portion, the reaction mixture was stirred for an additional 40 minutes, the suspension was diluted with 50.0 mL of dichloromethane, and the organic suspension was washed first with 50 mL of a 10% (w/v) aqueous solution of sodium thiosulfate and then with 50 mL of a saturated aqueous solution of sodium chloride, dried over 60.0 g of sodium sulfate, filtered over 20.0 g of Celite 545, and concentrated under reduced pressure at room temperature. The residue was purified on 50.0 g of silica gel eluting with 300 mL of 7:1 (v/v) hexanes:ethyl acetate. Evaporation of the solvent from the product-containing fractions (as identified by thin layer chromatographic analysis) under reduced pressure at room temperature and drying for 30 minutes under vacuum at room temperature provided 0.46 g (1.37 mmol) of Compound A15 {$R_f$: 0.88 [hexanes:ethyl acetate, 2/1 (v/v)]} in 84% yield that was used directly in the next reaction.

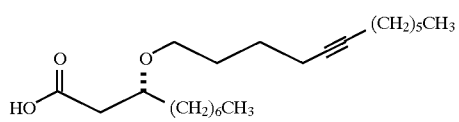

To a stirred solution of 0.46 g (1.37 mmol) of Compound A15 in 12.0 mL of tert-butyl alcohol and 3.0 mL (28.3 mmol) of 2-Methyl-2-butene (Aldrich Chemical Co.) at 0° C. was added dropwise 10.0 mL of an aqueous solution containing 1.04 g (8.22 mmol) of sodium chlorite dihydrate (Eastman Kodak. Co., Rochester, N.Y.) and 1.11 g (8.04 mmol) of sodium phosphate monobasic (Fisher Scientific Co.). The suspension was stirred at 0° C. for 20 minutes, the reaction mixture was quenched with 30.0 mL of a 10% (w/v) aqueous solution of sodium thiosulfate, diluted with 100.0 mL of diethyl ether, and the resulting layers separated. The organic layer was washed with 50 mL of a saturated aqueous solution of sodium chloride, dried over 60.0 g of sodium sulfate, filtered, and concentrated under reduced pressure, at room temperature. The residue was purified on 100.0 g of silica gel eluting first with 300 mL of 4:1 (v/v) hexanes:ethyl acetate, then with 300 mL of 2:1 (v/v) hexanes:ethyl acetate, and finally with 500 mL of 1:1 (v/v) hexanes:ethyl acetate. Evaporation of the solvent from the product-containing fractions (as identified by thin layer chromatographic analysis) under reduced pressure, at room temperature, and drying overnight, under vacuum, at room temperature provided 342.0 mg (0.97 mmol) of Compound A16 {$R_f$: 0.28 [hexanes:ethyl acetate, 2:1 (v/v)]}{$R_f$: 0.45 [hexanes:ethyl acetate, 2:1 (v/v)]} in 70.8% yield.

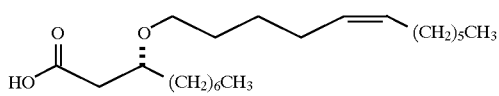

To a stirred solution of 342.0 mg (0.97 mmol) of Compound A16 in 16.0 mL of methyl alcohol and 0.5 mL (4.23 mmol) of quinoline (Aldrich Chemical Co.) at room temperature was added 100.0 mg of 5% (wt/wt) palladium on calcium carbonate, poisoned with lead (Aldrich Chemical Co.) under a nitrogen atmosphere. The reaction mixture was evacuated under reduced pressure at room temperature, purged with hydrogen gas three times, and stirred under an atmosphere of hydrogen gas at atmospheric pressure for two and a half hours. The resulting reaction mixture was purged with nitrogen and filtered over 50.0 g of Celite 545 eluting with three 10.0 mL portions of methyl alcohol. The filtrate was concentrated under reduced pressure at room temperature and diluted with 100.0 mL of dichloromethane. The organic solution was washed twice with 60.0 mL portions of a 1.0 N aqueous solution of hydrochloric acid and then once with 50.0 mL of a saturated aqueous solution of sodium chloride, dried over 60.0 g of sodium sulfate, filtered, and concentrated under reduced pressure at room temperature and dried over night under vacuum at room temperature to provide 340.0 mg (0.96 mmol) of crude Compound A17 {$R_f$: 0.50 [hexanes:ethyl acetate, 2/1 (v/v)]} in 99% yield. Compound A17 was used in the next reaction without further purification.

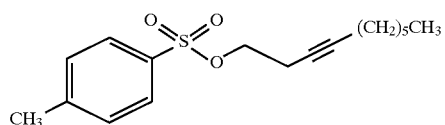

To a stirred solution of 10.0 g (64.8 mmol) of decyn-1-ol (Farchan Chemical Co., Gainesville, Fla.) in 10 mL of anhydrous pyridine, at 0° C., under a nitrogen atmosphere, was slowly added 18.5 g (97.0 mmol) of para-toluenesulfonyl chloride (99+%, Aldrich Chemical Co.) over a five-minute period. The reaction was allowed to warm slowly to room temperature, stirred for four hours, and diluted with 200.0 mL of ethyl acetate. The organic solution was washed with 50.0 mL of a saturated aqueous solution of sodium chloride, dried over 50.0 g of sodium sulfate, filtered, concentrated under reduced pressure at room temperature and azeotroped to dryness with three 50.0 mL portions of toluene using vacuum evaporation to provide 23.0 g of crude Compound A18 {$R_f$: 0.60 [hexanes:ethyl acetate, 4:1 (v/v)]} which was used in the next reaction without further purification.

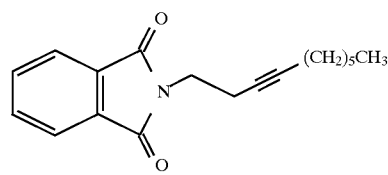

To a stirred solution of 18.0 g (~50.7 mmol) of Compound A18 in 240.0 mL of anhydrous dimethylsulfoxide (Fisher Scientific Co.) was added 36.0 g (194.6 mmol) of potassium phthalimide (Aldrich Chemical Co.) at room temperature under a nitrogen atmosphere. The reaction mixture was warmed to 50° C., stirred for three hours, and diluted with 1.0 L of ethyl acetate. The resulting organic solution was washed first with 200.0 mL of a saturated aqueous solution of sodium bicarbonate and then with 200.0 mL of a saturated aqueous solution of sodium chloride, dried over 150.0 g of sodium sulfate, filtered, and concentrated under reduced pressure, at room temperature. The residue was purified on 300.0 g of silica gel eluting with 3.0 L of 6:1 (v/v) hexanes:ethyl acetate. Evaporation of the solvent from the product-containing fractions (as identified by thin layer chromatographic analysis) under reduced pressure at room temperature and drying overnight under vacuum at room temperature provided 13.0 g (45.8 mmol) of Compound A19 {R$_f$: 0.39 [hexanes:ethyl acetate, 6/1 (v/v)]} in 84% yield.

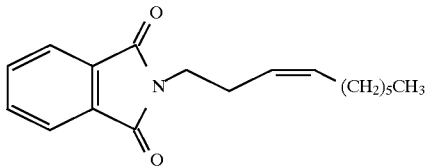

To a stirred solution of 13.0 g (45.8 mmol) of Compound A19 in 200.0 mL of methyl alcohol and 8.1 mL (68.5 mmol) of quinoline at room temperature was added 1.0 g of 5% (wt/wt) palladium on calcium carbonate, poisoned with lead under a nitrogen atmosphere. The reaction mixture was evacuated under reduced pressure, purged with hydrogen gas at room temperature three times, and stirred under an atmosphere of hydrogen gas at atmospheric pressure for one hour. The resulting reaction mixture was purged with nitrogen and filtered over 100.0 g of Celite 545 eluting with three 50.0 mL portions of methyl alcohol. The filtrate was concentrated under reduced pressure at room temperature and diluted with 500.0 mL of dichloromethane. The organic solution was washed with two 100.0 mL potions of a 1.0 N aqueous solution of hydrochloric acid and then with 100.0 mL of a saturated aqueous solution of sodium chloride, dried over 150.0 g of sodium sulfate, filtered, concentrated under reduced pressure at room temperature and dried overnight under vacuum at room temperature to provide 13.0 g (45.6 mmol) of crude Compound A20 {R$_f$: 0.39 [hexanes:ethyl acetate, 6/1 (v/v)]} in 99.6% yield. Compound A20 was used in the next reaction without further purification.

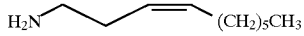

To a stirred solution of 6.0 g (21.0 mmol) of Compound A20 in 200.0 mL of absolute ethyl alcohol (Quantum Chemical Co., Cincinnati, Ohio), at room temperature was added in 5.1 mL (105.0 mmol) of hydrazine hydrate (98%, Lancaster Chemical Co.). The reaction mixture was warmed to 75° C., stirred for 75 minutes, cooled to room temperature, and diluted with 300.0 mL of dichloromethane and 100 mL of water. The resulting layers were separated, and the aqueous layer was extracted with two 50.0 mL portions of dichloromethane. The combined organic layers were dried over 50.0 g of sodium sulfate, filtered, and concentrated under reduced pressure, at room temperature to provide 3.2 g of crude Compound A21 {R$_f$: 0.08 [chloroform:methyl alcohol, 10:1 (v/v)]} in 100% yield. The crude product was used in the next reaction without further purification.

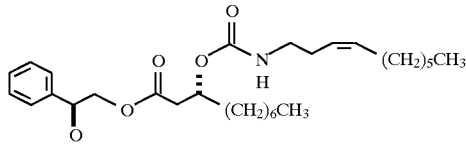

To a mechanically stirred solution of 4.8 g (15.6 mmol) of Compound A4 in 60.0 mL of anhydrous toluene, under a nitrogen atmosphere, at 0° C., was added 6.0 mL (74.2-mmol) of anhydrous pyridine followed by the dropwise addition of 8.9 mL (17.2 mmol) of a 1.93 M solution of phosgene in toluene over a 20-minute period. The mixture was stirred at 0° C. for an additional 15 minutes after which time 2.7 g (17.2 mmol) of Compound A21 in 30.0 mL of anhydrous toluene was added dropwise over a five-minute period. The reaction mixture was stirred for an additional 15 minutes, quenched with 30.0 mL of a saturated aqueous solution of sodium bicarbonate, and diluted with 100.0 mL ethyl acetate. The organic suspension was washed with 50.0 mL of a saturated aqueous solution of sodium chloride, dried over 50.0 g of sodium sulfate, filtered, and concentrated under reduced pressure at room temperature. The residue was purified on 200.0 g of silica gel eluting with 3.0 L of 6:1 (v/v) hexanes:ethyl acetate. Evaporation of the solvent from the product-containing fractions (as identified by thin layer chromatographic analysis) under reduced pressure at room temperature and drying overnight under vacuum at room temperature provided 5.2 g (10.6 mmol) of Compound A22 {R$_f$: 0 0.55 [hexanes:ethyl acetate), 10:1 (v/v)]} in 68.3% yield.

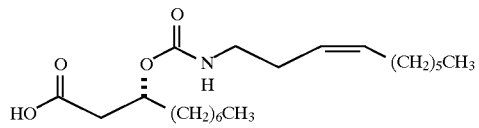

To a mechanically stirred solution of 5.2 g (10.7 mmol) of Compound A22 in 200 mL of glacial acetic acid in a three-necked Morton reaction flask was added 14.0 g (214.1 mmol) of activated zinc powder under a nitrogen atmosphere at room temperature. The reaction was stirred for 30 minutes, the suspension filtered through a pad of 60.0 g of Celite 545, and eluted with four 50.0 mL portions of methyl alcohol. The filtrate was concentrated under reduced pressure, at room temperature, and azeotroped to dryness with three 50 mL portions of toluene under vacuum evaporation. The crude yellow oil was purified on 200.0 g of silica gel by eluting with 2.0 L of 6:1 (v/v) hexanes:ethyl acetate and then with 5.0 L of 1:1 (v/v) hexanes:ethyl acetate. Evaporation of the solvent from the product-containing fractions (as identified by thin layer chromatographic analysis) under reduced pressure, at room temperature, and drying overnight, under vacuum, at room temperature provided 3.55 g (9.63 mmol) of Compound A23 {R$_f$: 0.08 [hexanes:ethyl acetate, 2:1 (v/v)]} in 90% yield.

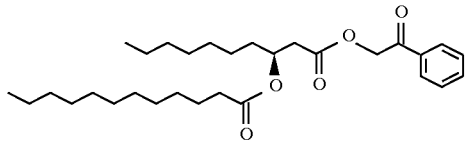

To a stirred solution of 23.7 g (0.118 mol) dodecanoic acid (Aldrich Chemical Co.) and 32.9 g (0.107 mol) of Compound A4 dissolved in 250.0 mL anhydrous dichloromethane, at 0° C., was added 0.03 g (0.2 mmol) 4-dimethylaminopyridine, then 29.2 g (0.143 mol) 1,3-dicyclohexylcarbodimide. After being stirred for two and a half hours at 25° C. the reaction mixture was diluted with 100.0 mL hexanes (200.0 mL), filtered and concentrated under reduced pressure at room temperature. The residue obtained was purified on a silica gel (2.0 Kg) column by elution with a 1:9 (v/v) mixture of ethyl acetate:hexanes. Evaporation of solvent from the product containing fractions (identified by use of thin layer chromatographic analysis) under reduced pressure at room temperature and drying overnight under vacuum at room temperature yielded 48.7 g (0.10 mol) of Compound A24 {R$_f$: 0.6 [hexanes:ethyl acetate, 4:1 (v/v)]} in 84% yield.

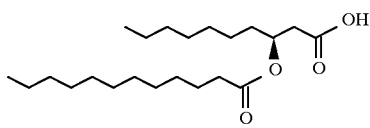
A25

To a mechanically stirred solution of Compound A24 (16.07 g, 32.99 mmol) dissolved in 150.0 mL of glacial acetic acid in a Morton flask at 0° C. was added 24.2 g (371.0 mmol) of zinc dust. After being warmed to 25° C. and stirred one hour, the reaction mixture was filtered through 50.0 g of Celite 545 and concentrated under reduced pressure at room temperature. The residue obtained was purified on silica gel (1.0 Kg) eluting first with ethyl acetate:hexanes [4:1 (v/v)], and then methyl alcohol:chloroform:acetic acid [10:40:1 (v/v/v)]. Evaporation of solvent from the product containing fractions (identified by use of thin layer chromatographic analysis) under reduced pressure at room temperature and drying overnight under vacuum at room temperature gave (10.8 g, 39.35 mmol) of Compound A25 {$R_f$: 0.34 [hexanes:ethyl acetate, 2:1 (v/v)]} in 96% yield.

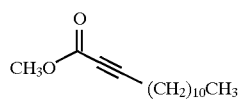
A26

To a stirred solution of 1.0 mL (3.39 mmol) of 1-tridecyne (Lancaster Synthesis) in 20.0 mL of anhydrous tetrahydrofuran at 0° C. under a nitrogen atmosphere was added dropwise 1.5 mL (3.73 mmol) of 2.51 M solution of n1-butyl lithium in hexanes over a five-minute period. The reaction was stirred at 0° C. for one hour after which time the combined solution was transferred via a canula into a stirred solution of 0.46 mL (6.74 mmol) of methyl chloroformate (Aldrich Chemical Co.) in 10.0 mL of anhydrous tetrahydrofuran at room temperature under a nitrogen atmosphere. The resulting reaction mixture was stirred for an additional 30 minutes after which time the mixture was quenched with 10.0 mL of a saturated solution of ammonium chloride. The resulting mixture was extracted with three 20 mL portions of ethyl acetate, and the combined organic layers were washed with one 10 mL portion of saturated sodium chloride, dried over 20.0 g of anhydrous sodium sulfate, filtered and concentrated under reduced pressure at room temperature. The crude product, 0.69 g (2.89 mmol) of Compound A26 in 85.4% yield, was used in the next step without further purification after drying overnight under vacuum at room temperature {$R_f$: 0.78 [hexanes:ethly acetate, 4:1 (v/v)]}.

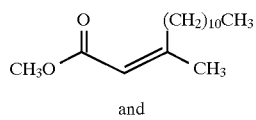
A27 and

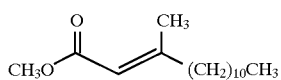
A28

To a stirred suspension of 4.39 g (23.07 mmol) of copper (I) iodide (99.9%, Aldrich Chemical Co.) in 40.0 mL of anhydrous diethyl ether at 0° C. under a nitrogen atmosphere was added dropwise 30.0 mL (46.2 mmol) of a 1.5 M solution of methyl lithium in diethyl ether (Aldrich Chemical Co.) over a 15-minute period until a clear, colorless solution was obtained. The reaction solution was quickly transferred via a canula into a stirred solution of 5.0 g (20.97 mmol) of Compound A26 in 50.0 mL of anhydrous diethyl ether at room temperature under a nitrogen atmosphere. After stirring for an additional five minutes, the resulting reaction mixture was quenched with 60.0 mL of a saturated solution of ammonium chloride and stirred for one hour. The resulting mixture was diluted with 50.0 mL of hexanes, filtered over a 50 g pad of Celite 545 eluting with 50 mL of hexanes, and the layers separated. The aqueous layer was extracted with two 50 mL portions of hexanes, and the combined organic layers were washed with one 50 mL portion of saturated sodium chloride, dried over 100.0 g of anhydrous sodium sulfate, filtered and concentrated under reduced pressure, at room temperature. The residue was purified on two PrepPAK 500/silica cartridges (Waters Associates) connected in tandem, eluting with 10.0 L of a 98.5 to 2.5 (v/v) diethyl ether:hexanes solution at a 200 mL/minute flow rate using the PrepLC/System 500 liquid chromatography device (Waters Associates) as the pumping and detection system. Evaporation of solvent from the product containing fractions (identified by use of thin layer chromatographic analysis) under reduced pressure at room temperature and drying overnight under vacuum,at room temperature yielded 1.25 g (4.93 mmol) of Compound A27 {$R_f$: 0.28 [diethyl ether:hexanes, 1:19 (v/v)]} in 23.5% yield and 2.55 g (10.08 mmol) of Compound A28 {$R_f$: 0.22 [diethyl ether:hexanes, 1:19 (v/v)]} in 48.1% yield.

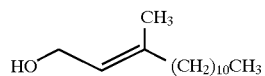
A29

To a stirred solution of 2.30 g (9.08 mmol) of Compound A27 in 8.0 mL of anhydrous dichloromethane at 0° C. under a nitrogen atmosphere was added dropwise 18.1 mL (18.1 mmol) of a 1.0 M solution of diisobutylaluminum hydride in hexanes (Aldrich Chemical Co.) over a 15-minute period. The reaction mixture was quenched with 60.0 mL of a saturated solution of ammonium chloride and stirred for an additional 45 minutes. The resulting mixture was extracted with three 50 mL portions of ethyl acetate, and the combined organic layers were washed with one 50 mL portion of a saturated solution of sodium chloride, dried over 100.0 g of anhydrous sodium sulfate, filtered and concentrated under reduced pressure, at room temperature. The residue was purified on 150.0 g of silica gel, eluting with 2.0 L of a 7:3 (v/v) mixture of hexanes and diethyl ether. Evaporation of solvent from the product containing fractions (identified by use of thin layer chromatographic analysis) under reduced pressure at room temperature and drying overnight under vacuum at room temperature yielded 1.29 g (5,70 mmol) of Compound A29 {$R_f$: 0.19 [diethyl ether:hexanes, 3:7 (v/v)]} in 62.8% yield.

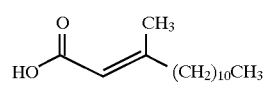
A30

To a stirred solution of 1.20 g (5.30 mmol) of Compound A28 in 6.0 mL of chloroform at room temperature under a nitrogen atmosphere was added 4.6 g (53.00 mmol) of activated manganese dioxide (Aldrich Chemical Co.) in one portion. The reaction suspension was refluxed for 30 minutes after which time the mixture was cooled to room temperature, filtered over a 50 g pad of Celite 545, eluting with 20 mL of chloroform. The combined filtrates were concentrated under reduced pressure, at room temperature. The resulting crude intermediate was dissolved in 50 mL of tetrahydrofuran and cooled to 0° C., after which time 4.0 mL of 2-methyl-2-butene was added in one portion. The reaction solution was treated with a dropwise addition of 10.0 mL of a 1:0.09:1 ratio (w/w/v) of sodium phosphate dibasic (Fisher Scientific Co.), sodium chlorite (Eastman Kodak Co.), and water over a five-minute period. The reaction mixture was stirred for an additional 30 minutes at 0° C. after which time the mixture was quenched with 50.0 mL of a 10% solution of sodium thiosulfate and stirred for an additional 10 minutes. The resulting mixture was acidified to a pH of 3.0 using 1.0 N aqueous hydrochloric acid and extracted with three, 50 mL portions of ethyl acetate. The combined organic layers were washed with one, 50 mL portion of a saturated solution of sodium chloride, dried over 100.0 g of anhydrous sodium sulfate, filtered and concentrated under reduced pressure, at room temperature. The residue was purified on 200.0 g of silica gel, eluting with 2.0 L of a 3:1 (v/v) mixture of hexanes and diethyl ether. Evaporation of solvent from the product-containing fractions (identified by use of thin layer chromatographic analysis) under reduced pressure, at room temperature and drying overnight under vacuum at room temperature yielded 1.01 g (4.22 mmol) of Compound A30 {$R_f$: 0.21 [diethyl ether:hexanes, 3:7 (v/v)]} in 79.6% yield.

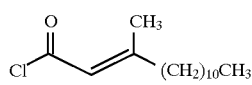

To a stirred solution of 20.8 mg (0.09 mmol) of Compound A30 in 5.0 mL of anhydrous dichloromethane at 0° C. under a nitrogen atmosphere was added 15.7 µL (0.18 mmol) of oxalyl chloride (Aldrich Chemical Co.) dropwise over a two minute period. The reaction mixture was stirred for 40 minutes at 0° C. after which time the mixture was concentrated under reduced pressure at room temperature under anhydrous conditions and dried for one hour under vacuum at room temperature to provide Compound A31 as a crude syrup which was used in the next reaction without further purification.

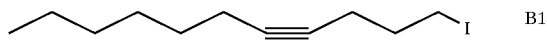

To a stirred solution of 1-octyne (31.6 g, 0.287 mol; Aldrich Chemical Co.) in anhydrous tetrahydrofuran (250.0 mL), n-butyllithium (163.5 mL, 0.315 mol) was added dropwise at 0° C. under a nitrogen atmosphere over a 40-minute period. The solution was stirred at 25° C. for one hour, 1,3-diiodopropane (103.0 g, 0.349 mol; Aldrich Chemical Co.) was added dropwise over a 10-minute period, and the resulting mixture was stirred for 20 hours. The completed reaction mixture was diluted with 250.0 mL hexanes and poured into 400.0 mL of ice water. The product was washed twice with 300.0 mL portions of saturated aqueous sodium chloride solution, dried over 500.0 g sodium sulfate, filtered, and concentrated under reduced pressure at room temperature. The residue was purified on a silica gel (1.0 kg) column, eluting with hexanes. Evaporation of solvent from the product-containing fractions (as determined by thin layer chromatographic analysis) under reduced pressure at room temperature provided 59.5 g (0.21 mol) of Compound B1 {$R_f$: 0.8 [hexanes]} in 78% yield.

To a stirred solution of potassium cyanide (55.0 g, 0.845 mol; Aldrich Chemical Co.) in dimethylsulfoxide (750.0 mL) was added dropwise 135.0 g (0.485 mol) of Compound B1 over a 30-minute period. The solution was then stirred five hours at 50° C., diluted with 250.0 mL hexanes, and washed with 250.0 mL water. The organic layer was dried over 50.0 g magnesium sulfate, filtered, and concentrated at room temperature under reduced pressure. The residue was purified on a silica gel (2.0 kg) column, eluting with 95:5 (v/v) hexanes/ethyl acetate. Evaporation of solvent from the product-containing fractions (as determined by thin layer chromatographic analysis) under reduced pressure at room temperature provided 51.4 g (0.29 mol) of Compound B2 {$R_f$: 0.3 [ethyl acetate:hexanes, 5:95 (v/v)]} in 81% yield.

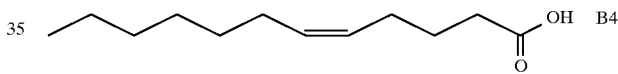

Compound B2 (9.36 g, 0.053 mol) was dissolved in ethylene glycol (90.0 mL; Aldrich Chemical Co.) and, to the solution, was added 8.89 g (0.158 mol) potassium hydroxide (Fisher Scientific). After stirring for four hours at 140° C. and then cooling to 25° C., the reaction mixture was diluted with 90.0 mL water and then washed twice with 90.0 mL portions of dichloromethane. The aqueous layer was acidified with 200.0 mL 1N hydrochloric acid, and the product was extracted with hexanes (250.0 mL). The extract was dried over 50 g magnesium sulfate, filtered, and concentrated under reduced pressure at room temperature to provide 8.58 g (0.04 mol) of Compound B3 {$R_f$: 0.2 [hexanes:ethyl acetate, 4:1 (v/v)]} in 82% yield.

Compound B3 (20.0 g, 0.102 mol) and Lindlar catalyst (i.e., 5% palladium on calcium carbonate, poisoned with lead; 86.0 g) were added to a solution of quinoline (10.0 mL, 0.084 mol) in hexanes (190.0 mL). The reaction mixture was stirred under hydrogen gas for five hours, filtered, and evaporated. The residue was diluted with 10.0 mL dichloromethane, made basic with 150.0 mL of 1N sodium hydroxide, and the aqueous layer was washed with 50.0 mL of dichloromethane. The aqueous layer was then acidified with 20.0 mL 6N hydrochloric acid, and extracted with ethyl acetate (200.0 mL). The extract was washed with 200.0 mL saturated aqueous sodium chloride solution, dried over 100.0 g sodium sulfate, filtered, and concentrated under reduced pressure to provide 19.8 g (0.1 mol) of Compound B4 {$R_f$: 0.2 [hexanes:ethyl acetate, 4:1 (v/v)]} in 98% yield.

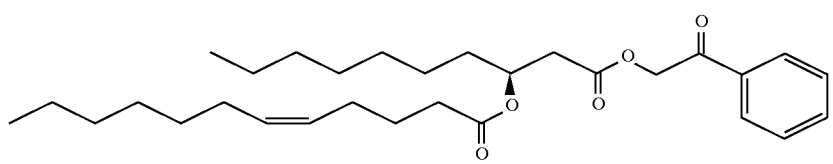

Compound B4 (23.7 g, 0.119 mol) and Compound A4 (32.9 g, 0.107 mol) were dissolved in 250.0 mL anhydrous dichloromethane at 0° C. and to the solution was first added 0.03 g (0.2 mmol) 4-dimethylaminopyridine followed by 29.2 g (0.143 mol) 1,3-dicyclohexylcarbodimide. The solution was stirred for two and a half hours at 25° C., diluted with hexanes (100.0 mL), filtered, and concentrated under reduced pressure at room temperature. The residue was purified on a silica gel (2.0 kg) column, eluting with 1:9 (v/v) ethyl acetate/hexanes. Evaporation of solvent from the product-containing fractions (as determined by thin layer chromatographic analysis) under reduced pressure at room temperature provided 48.7 g (0.10 mol) of Compound B5 ({R$_f$: 0.6 [hexanes:ethyl acetate, 4:1 (v/v)]} in 84% yield.

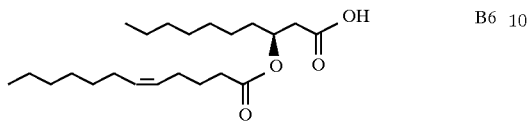

Compound B5 (16.1 g, 0.412 mol) was dissolved in 150.0 mL glacial acetic acid and to the solution was added 24.2 g (0.370 mol) zinc metal powder at 0° C. The reaction mixture was stirred vigorously for 40 minutes at 25° C., diluted with 150.0 mL ethyl acetate, filtered, and concentrated under reduced pressure at room temperature. The residue was purified on a silica gel (1.0 kg) column and eluted with 9:1 (v/v) hexanes/ethyl acetate. Evaporation of solvent from the product-containing fractions (as determined by thin layer chromatographic analysis) under reduced pressure at room temperature provided 10.8 g (0.04 mol) of Compound B6 {R$_f$: 0.3 [hexanes:ethyl acetate, 4:1 (v/v)]} in 96% yield.

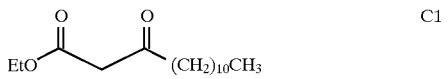

To 101.0 g (1.54 mol) of activated zinc in 500.0 mL refluxing anhydrous tetrahydrofuran was added 3.0 mL of ethyl bromoacetate and 67.5 mL (0.308 mol) of undecyl cyanide (in one portion; Aldrich Chemical Co.). To the resulting mixture was added dropwise 134.0 mL (1.232 mol) of ethyl bromoacetate over three hours. The mixture was refluxed for an additional 10 minutes, cooled to room temperature, and the reaction quenched by the slow addition of 160.0 mL of saturated aqueous potassium carbonate solution. The resultant heterogeneous mixture was rapidly stirred for 30 minutes and then filtered through 500.0 g Celite 545, yielding a clear, yellow solution of crude enamino ester. The solution was then acidified with 300.0 mL of 1.0 N hydrochloric acid, stirred for three hours, diluted with 1.0 L hexanes, and neutralized by addition of 1.0 L saturated aqueous sodium hydrogen carbonate. The organic layer was then washed with 400.0 mL saturated aqueous sodium chloride solution, dried over 1.0 kg sodium sulfate, filtered, and concentrated under reduced pressure. The residue was purified on silica gel (1.0 kg), eluting with 6:1 (v/v) hexanes/ethyl acetate to provide 80.6 g (0.298 mol) of Product C1 {R$_f$: 0.7 [hexanes:ethyl acetate, 4:1 (v/v)]} in 97% yield.

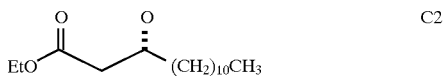

[R]-2,2'-Bis(diphenylphosphino)-1,1'-binaphthyl ruthenium dichloride hemi triethylamine complex, as a clear orange-brown solution, was prepared from [R]-(+)-2,2'-Bis (diphenylphosphino)-1,1'-binaphthyl and cyclooctadienyl ruthenium dichloride as described above.

A solution of 311.0 g (1.15 mol) of Compound C1 in 330.0 mL anhydrous methyl alcohol was deoxygenated by three freeze-thaw vacuum degassing cycles in liquid nitrogen under a nitrogen atmosphere. The solution of [R]-2,21'-Bis (diphenylphosphino)-1,1'-binaphthyl ruthenium dichloride hemi triethylamine complex catalyst was added to the Compound C1-containing solution using a syringe. Using a catheter under argon, the reaction mixture was pumped into an argon-flushed 2.0 L hydrogenation bomb containing 3.0 g methyl alcohol-washed Dowex 50x8–200 H$^+$resin. The bomb was charged to 1480 psi with hydrogen gas, and the reaction mixture was stirred, at 25° C., for 66 hours. When the pressure had dropped 300 psi, excess hydrogen gas was vented, the reaction mixture was filtered, and the volatiles were removed under reduced pressure to provide 310.2 g (1.14 mol) of Compound C2 in 99% yield.

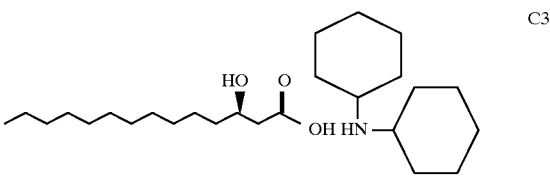

Compound C2 (94.4 g, 0.347 mol) was dissolved in tetrahydrofuran (800.0 mL) and, to the solution, was added 2.5 M aqueous sodium hydroxide (300.0 mL, 0.75 mol). The resultant mixture was stirred vigorously under a nitrogen atmosphere, at 25° C., for one and a half hours. The reaction mixture was diluted with 1.0 L of 1:1 (v/v) diethyl ether/ hexanes and the aqueous layer separated. The organic phase was further extracted with 200.0 mL of water, the aqueous phases combined, and the combined aqueous phases acidified with 20.0 mL of 6N hydrochloric acid. The acidified mixture was then extracted with 2.0 L diethyl ether and the extract washed first with 1.0 L water, and then with 500.0 mL saturated aqueous sodium chloride solution, and dried over 200.0 g magnesium sulfate. Solvent was concentrated under reduced pressure at room temperature, and the grayish solid obtained was dissolved in 2.0 L hot 60° C. acetonitrile. To the solution at 60° C. was added dicyclohexylamine (80.0 mL, 0.40 mol), and the resultant mixture cooled to –20° C., to-provide 102.1 g (0.24 mol) of Compound C3 {R$_f$: 0.38 [hexanes:ethyl acetate:glacial acetic acid, 1:1:0.1 (v/v/v)]}, as slightly off-white, fine needles in 71% yield.

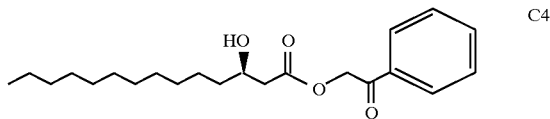

Compound C3 (102.1 g, 0.24 mol) was suspended in 2.0 L ethyl acetate, under a nitrogen atmosphere, at 0° C. To the suspension was added 37.2 g (369.0 mmol) triethylamine, followed by 48.9 g (246.0 mmol) 2-bromoacetophenone (in one portion). After three hours, the reaction mixture was warmed to room temperature and stirred for an additional six hours. The reaction mixture was then vacuum-filtered. The residue was washed with 400.0 mL ethyl acetate. The filtrate was washed first with 500 mL 0.8 M hydrochloric acid, then with 500.0 mL water, and finally with 200.0 mL saturated aqueous sodium chloride solution, and dried over 300.0 g magnesium sulfate. The solvent was evaporated at 50° C., under reduced pressure, to yield a gray congealed solid which was recrystallized from 1.1 L hexanes and dried in a vacuum oven at 50° C. to provide 81.09 g (223.9 mmol) of Compound C4 {R$_f$: 0.65 [chloroform:methyl alcohol, 95:5 (v/v)]} as an off-white solid in 91% yield.

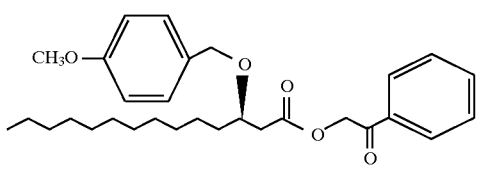

C5

To a suspension of 2.5 g (9.18 mmol) C4 and 1.0 g 4A molecular sieves in 28.0 mL of 3:1 (v/v) hexanes/ dichloromethane, under a nitrogen atmosphere, was added 3.8 mL (13.4 mmol) of 4-methoxybenzyltrichloroimidate (prepared by the method of Audia et al., J Org Chem. 1989 54:3738). The reaction mixture was cooled to 0° C., and 63.0 μL (0.51 mmol) neat boron trifluoride etherate was added dropwise. After five minutes the reaction was quenched with 2.0 mL saturated aqueous sodium bicarbonate solution and the reaction mixture warmed to 25° C. The mixture was then extracted with 100.0 mL ethyl acetate, washed with 50.0 mL saturated aqueous sodium chloride solution, dried over 50.0 g sodium sulfate, filtered, and the solvent concentrated under reduced pressure at room temperature. The residue was purified on a silica gel (300.0 g) column, eluting with 1:9 (v/v) ethyl acetate/hexanes. Evaporation of solvent from the product-containing fractions (as determined by thin layer chromatographic analysis) under reduced pressure at room temperature provided 3.1 g (7.97 mmol) of Compound C5 {R$_f$: 0.7 [ethyl acetate:hexanes, 3:17 (v/v)]} in 87% yield.

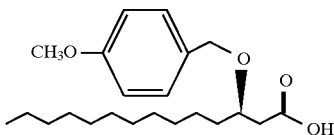

C6

Compound C5 (3.1 g) was dissolved in tetrahydrofuran (30.0 mL) and to the solution was added 16.0 mL (40.0 mmol) 2.5 N sodium hydroxide. The reaction mixture was stirred for six days at 25° C., diluted with 100.0 mL hexanes, and the pH adjusted to 5.0 with 40.0 mL 1 N hydrochloric acid. The reaction mixture was then extracted with 300.0 mL ethyl acetate, washed with 100.0 mL saturated aqueous sodium chloride solution, dried over 200.0 g sodium sulfate, filtered, and the solvent concentrated under reduced pressure at room temperature. The residue was purified on a silica gel (300.0 g) column, eluting with a gradient of methyl alcohol/ chloroform [3:17 (v/v) to 1:9 (v/v)] Each gradient mixture also contained two drops of glacial acetic acid per 100.0 mL solvent. A total of 1.46 g (4:0 mmol) of Compound C6 {R$_f$: 0.14 [hexanes:ethyl acetate, 2:1 (v/v)]} was provided in 50% yield.

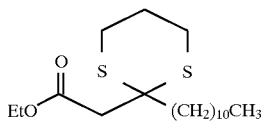

C7

Compound C1 (2.04 g, 7.96 mmol) was dissolved in 25.0 mL dry diethyl ether. To this solution, 1,3-propanedithiol (0.8 mL, 7.97 mmol; in one portion; Aldrich Chemical Co.) was added, under a nitrogen atmosphere, at 0° C. Next, 1.0 mL (8.13 mmol) of boron trifluoride etherate was added dropwise over a two minute period. The reaction mixture was stirred at 0° C. for 30 minutes at room temperature for 48 hours, poured into a saturated aqueous sodium bicarbonate (200.0 mL) solution, and stirred for an additional 30 minutes. The solution was extracted three times with 50.0 mL portions of hexanes. The combined organic fractions were washed with 50.0 mL of saturated aqueous sodium chloride solution, dried over 50.0 g magnesium sulfate, filtered, and concentrated under reduced pressure at room temperature. The product was purified on a silica gel (200.0 g) column, eluting with 2.0 L of a 0 to 5:95 (v/v) gradient of ethyl acetate/hexanes. The fractions containing purified Compound C7 {R$_f$: 0.44 [hexanes:ethyl acetate, (95:5)]} were concentrated and used in subsequent synthetic reactions.

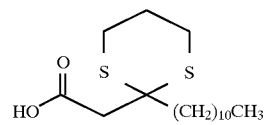

C8

Compound C7 2.88 g (8.01 mmol) was dissolved in tetrahydrofuran (20.0 mL) and, to the solution, 10.0 mL of 2.5 M aqueous sodium hydroxide solution was added. The reaction mixture was warmed to 100° C., stirred for 16 hours, cooled to room temperature, adjusted to pH 2.0 with 10.0 mL 1.0 N hydrochloric acid, and extracted with 200.0 mL ethyl acetate. The organic layer was washed with 50.0 mL saturated aqueous sodium chloride solution, dried over 50.0 g sodium sulfate, filtered, and concentrated under reduced pressure at room temperature. Purification was accomplished on a silica gel (300.0 g)column, eluting first with 1.0 L of 4:1 (v/v) hexanes/ethyl acetate and then with 1.0 L of 9:1:0.1 (v/v/v) chloroform/methyl alcohol/glacial acetic acid. Evaporation of solvent from the product-containing fractions (as determined by thin layer chromatographic analysis) under reduced pressure at room temperature provided 2.10 g (6.33 mmol) of Compound C8 {R$_f$: 0.20 [hexanes:ethyl acetate, 2:1 (v/v)]} in 79% yield.

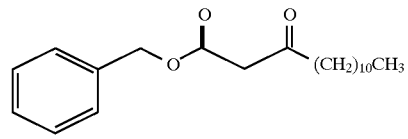

D1

To a mechanically stirred suspension of 1004.0 g (15.4 mol) of activated zinc powder in 2.5 L of anhydrous tetrahydrofuran under a nitrogen atmosphere at room temperature was added dropwise 30.0 mL (0.19 mol) of benzyl bromoacetate over a 10-minute period. The reaction mixture was warmed to reflux, 712.0 mL (3.25 mol) of n-undecyl cyanide (Aldrich Chemical Co.) added dropwise over a 15-minute period, and an additional 1.00 L (6.3 mol) of benzyl bromoacetate (Aldrich Chemical Co.) added over a four-hour period. After an additional hour of refluxing, the reaction mixture was cooled to room temperature and slowly poured into 3.0 L of a stirred saturated aqueous solution of potassium carbonate. To the resulting solution was added 1.0 kg of Celite 545 and the heterogeneous mixture filtered through a pad of 200.0 g of Celite 545 by elution with four 1.0 L portions of ethyl acetate. The filtrate was separated, and the aqueous layer extracted with two 500.0 mL portions of ethyl acetate. The combined organic layers were washed with a 500.0 mL portion of a saturated aqueous solution of sodium chloride, dried over sodium sulfate 100 g, filtered, and concentrated under vacuum to dryness. The crude orange oil was vigorously stirred at room temperature in a two-phase system of 1.0 L of hexanes and 1.0 L of 1.0 N hydrochloric acid with a dropwise addition of 80 mL concentrated hydrochloric acid over a three-hour period. After stirring the final heterogeneous solution for an additional 20 minutes, the layers were separated, and the aqueous layer was extracted with two 200.0 mL portions of hexanes. The combined organic layers were washed first with 500.0 mL of a saturated aqueous solution of sodium hydrogen carbonate and then with 500.0 mL of a saturated aqueous solution sodium chloride, dried over sodium sulfate 100 g (filtered, and concentrated under vacuum to dryness. The crude orange liquid was purified over 2.5 kg of silica gel eluting with 12.0 L of 9:1 (v/v) hexanes:ethyl acetate. Evaporation of solvent from the product-containing fractions (as identified by thin layer chromatographic analysis) under reduced pressure at room temperature and drying overnight under vacuum at room temperature provided 884.7 g (2.66 mol) of Compound D1 {$R_f$: 0.67 [hexanes:ethyl acetate, 4:1 (v/v)]} as a yellow solid in 82% yield.

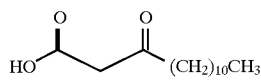

D2

To a stirred solution of 17.9 g (53.9 nmol) of Compound D1 in 110.0 mL of methyl alcohol, under a nitrogen atmosphere, was added 0.9 g of 20% palladium hydroxide on carbon (Aldrich Chemical Co.). The resulting suspension was purged with hydrogen gas and evacuated under reduced pressure three times followed by stirring under an atmosphere of hydrogen gas at atmospheric pressure and room temperature for one hour. The completed reaction mixture was diluted with 100 mL of dichloromethane, filtered over a 50.0 g pad of Celite 545 and the resulting filter cake washed with two 50.0 mL portions of dichloromethane. The combined filtrates were concentrated under reduced pressure, at room temperature. The crude product was quickly purified over 200.0 g of silica gel eluting with 2.0 L of 9:1 (v/v) chloroform:methyl alcohol. Evaporation of the solvent from the product-containing fractions (as identified by thin layer chromatographic analysis) under reduced pressure at room temperature and drying for 30 minutes under vacuum at room temperature provided 11.5 g (47.5 mmol) of Compound D2 {$R_f$: 0.56 [chloroform:methyl alcohol:acetic acid, 9:1:0.1 (v/v/v)]} as a white solid in 88% yield. Compound D2 was used immediately in the next reaction to avoid decomposition.

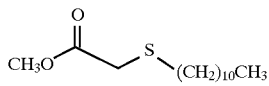

E1

To a vigorously stirred solution of 1000.0 g (9.42 mol) of methylthioglycolate (Aldrich Chemical Co.) in 2.0 L of anhydrous tetrahydrofuran, under a nitrogen atmosphere, at 0° C., was added 1312.0 ml (9.41 mol) of triethylamine followed by the dropwise addition of 2138.0 mL (9.42 mol) of 1-iodoundecane (Aldrich Chemical Co.) over a 12 hour period. The reaction mixture was warmed to room temperature, stirred for an additional 24 hours, diluted with 2.0 L of ethyl acetate, and washed first with 1.0 L of a 1.0 N aqueous solution of hydrochloric acid, then with 1.0 L of a saturated aqueous solution of sodium bicarbonate, and finally with 1.0 L of a saturated aqueous solution of sodium chloride. The organic layer was dried over 500.0 g of sodium sulfate, filtered, and concentrated under reduced pressure, at room temperature to provide 2230.0 g of Compound E1 {$R_f$: 0.69 [hexanes:ethyl acetate, 4:1 (v/v)]} which was used in the next step without further purification.

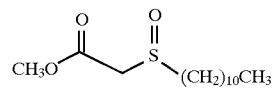

E2

To a stirred solution of 2100.0 g (~8.07 mol) of crude Compound E1 in 5.2 L of acetone and 5.2 L of water at −10° C. was added portion-wise 5.0 kg (8.13 mol) of potassium peroxymonosulfate (OXONE, Aldrich Chemical Co.) over a three-hour period using a powder addition funnel. The mixture was warmed to 0° C., stirred for an additional two hours, and slowly quenched at 0° C. with 3.0 L of a 3.0 M aqueous solution of sodium thiosulfate. The mixture was diluted with 8.0 L of dichloromethane and 4.0 L of water, filtered through a 500.0 g pad of Celite 545, and the resulting filter cake eluted with three 500.0 mL portions of chloroform. The combined filtrates were washed first with 10.0 L of a saturated aqueous solution of sodium bicarbonate and then with 20.0 L of a saturated aqueous solution of sodium chloride, and the organic layer dried over 2.5 kg of sodium sulfate, filtered, and concentrated under reduced pressure at room temperature. The crude product was purified by washing the resulting solid with 8.0 L of hexanes to provide 1541.0 g (5.58 mol) of Compound E2 [melting point (m.p.) 62.6°–63.5° C.] {$R_f$: 0.2 [hexanes:ethyl acetate), 1:1 (v/v)]} as a white solid in 69% yield.

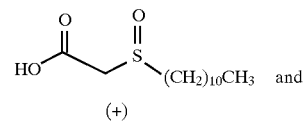

To a stirred mixture of 1644.0 g (5.95 mol) of Compound E2 in 6.0 L of toluene and 48.0 L of an aqueous solution of 0.05 M phosphate buffer was added 12.0 g of lipase (PS-800, Amano Intl. Enzyme Co., Troy, Va.) at room temperature. The reaction mixture was stirred at room temperature for 24 hours, an additional 11.9 g of lipase (PS-800) added, and the final suspension stirred for 96 hours. The resulting mixture was acidified to pH 1.0 with approximately 4.0 L of an aqueous solution of 1.0 N hydrochloric acid, diluted with 6.0 L of chloroform, and the layers separated. The aqueous layer was extracted with five 1.0 L portions of chloroform and the combined organic layers were dried over 500.0 g of sodium sulfate, filtered, and concentrated under reduced pressure at room temperature. The crude product was suspended in 6.0 L of ethyl acetate, warmed to 60° C., cooled to room temperature, filtered, and the resulting solid washed with two 500.0 mL portions of ethyl acetate. The crude solid was recrystallized twice from 10.0 L of ethyl acetate to provide 305.0 g (1.16 mol, m.p. 80.4°–81.8° C.) of Compound E3 in 19.5% yield. The combined mother liquors were concentrated under reduced pressure at room temperature and purified over 2.0 kg of silica gel eluting first with 4.0 L of hexanes, then with 6.0 L of 4:1 (v/v) hexanes:ethyl acetate, then with 4.0 L of chloroform, and finally with 10.0 L of 9:1:0.1 (v/v/v) chloroform :methyl alcohol:acetic acid. Evaporation of the solvent from the product-containing fractions (as identified by thin layer chromatographic analysis) under reduced pressure at room temperature and drying overnight under vacuum at room temperature provided 90.0 g (0.34 mol, 5.8% yield) of E3 {$R_f$: 0.12

[chloroform:methyl alcohol:acetic acid, 9:1:0.1 (v/v/v)]}, 300.0 g of a mixture of E3 and E4, and 500.0 g (1.81 mol, 30.4% yield) of E4 {$R_f$: 0.63 [chloroform:methyl alcohol:acetic acid, 9:1:0.1 (v/v/v)]}.

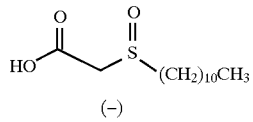

E5

(−)

To a solution of 500.0 g (1.81 mol) of Compound E4 in 5.0 L of methyl alcohol at room temperature was added dropwise 2.0 L of a 2.0 N aqueous solution of sodium hydroxide until a pH range of 11 to 12 was reached. The mixture was stirred for one hour, the mixture acidified to a pH of 2.0–3.0 with 2.0 L of a 2.0 N aqueous solution of hydrochloric acid, and diluted with 4.0 L of chloroform. The layers were separated, and the aqueous layer was extracted with three 1.0 L portions of chloroform. The combined organic layers were dried over 500.0 g of sodium sulfate, filtered, and concentrated under reduced pressure, at room temperature. The crude solid was recrystallized four times from 6.0 L of ethyl acetate to provide 167.0 g (0.64 mol, m.p. 81.2°–82.1° C.) of pure E5 {$R_f$: 0.12 [chloroform:methyl alcohol:acetic acid, 9:1:0.1 (v/v/v)]} in 35.2% yield. Concentration of the mother liquors under reduced pressure at room temperature provided an additional 250.0 g of crude E5.

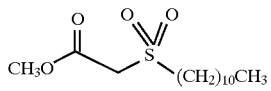

E6

To a stirred solution of 1.07 g (3.85 mmol) of crude Compound E1 in 20.1 mL of anhydrous dichloromethane at 0° C. was added portionwise 2.86 g (7.7 mmol of 3-chloroperoxybenzoic acid over a 10-minute period. The mixture was stirred for one hour and slowly quenched at 0° C. with 10.0 mL of a 3.0 M aqueous solution of sodium thiosulfate. The mixture was then diluted with 100.0 mL of dichloromethane, and the organic layer washed with 100.0 mL of a saturated aqueous solution of sodium bicarbonate, 100.0 mL of a saturated aqueous solution of sodium chloride, and the resulting organic layer was dried over 100.0 g of sodium sulfate, filtered, and concentrated under reduced pressure at room temperature. The crude product was purified by crystallization from hexanes to provide 970.0 mg (3.32 mmol) of Compound E6 {$R_f$: 0.67 [hexanes:ethyl acetate, 1:1 (v/v)]}.

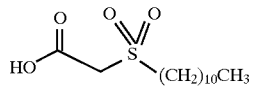

E7

To the solution of 970.0 mg (3.32 mmol) of Compound E6 in 15.0 mL of methyl alcohol at room temperature was added 4.0 mL of a 1.0 N aqueous solution of sodium hydroxide. The mixture was stirred for one hour after which time the resulting mixture was acidified with 4.0 mL of a 2.0 N aqueous solution of hydrochloric acid. The final mixture was diluted with 100.0 mL of chloroform, the layers were separated, and the aqueous layer was extracted with three 100.0 mL portions of chloroform. The combined organic layers were dried over 100.0 g of sodium sulfate, filtered, and concentrated under reduced pressure at room temperature. The crude solid Compound E7 was used without further purification.

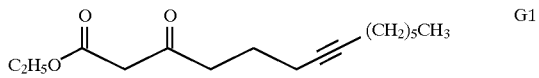

G1

To a refluxing, mechanically stirred suspension of 5.5 g (84.1 mmol) of activated zinc powder in 50 mL of anhydrous tetrahydrofuran was added dropwise 1.0 mL (9.0 mmol) of ethyl bromoacetate over a one-minute period, under a nitrogen atmosphere. 3.0 g (16.9 mmol) of Compound B2 was then added in one portion followed by the dropwise addition of 7.4 mL (66.7 mmol) of ethyl bromoacetate over a 45 minute period. After 10 minutes of refluxing, the reaction mixture was cooled to room temperature, diluted with 170.0 mL of tetrahydrofuran, and quenched with the dropwise addition of 22.0 mL of a 50% saturated aqueous solution of potassium carbonate over a 10-minute period. The resulting suspension was stirred for 30 minutes (after which time stirring was discontinued), the tetrahydrofuran solution decanted from the zinc solid, and the zinc solid washed with four additional 50.0 mL portions of tetrahydrofuran. The resulting product solutions were combined and vigorously stirred with 17.0 mL of 1.0 N hydrochloric acid, stirred for two hours, and concentrated under reduced pressure, at room temperature. The residue was dissolved in 200.0 mL of dichloromethane and the organic solution washed with a 50.0 mL portion of a saturated aqueous solution of sodium bicarbonate, dried over 50.0 g of sodium sulfate, filtered, and concentrated under reduced pressure, at room temperature. The crude product was purified over 200.0 g of silica gel eluting with 3.0 L of 10:1 (v/v) hexanes:ethyl acetate. Evaporation of solvent from the product-containing fractions (as identified by thin layer chromatographic analysis) under reduced pressure at room temperature and drying overnight under vacuum at room temperature provided 3.52 g (13.2 mmol) of Compound G1 {$R_f$: 0.65 [hexanes:ethyl acetate, 4:1 (v/v)]} as a clear, colorless oil in 78.2% yield.

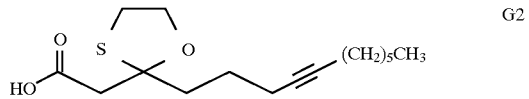

G2

To a stirred solution of 1.5 g (5.64 mmol) of Compound G1 in 7.0 mL of anhydrous diethyl ether and 434.0 μL (6.22 mmol) mercaptoethanol (Aldrich Chemical Co.), at 0° C., under a nitrogen atmosphere, was added dropwise 762.0 μL (6.20 mmol) boron trifluoroetherate over a five-minute period. The mixture was warmed to room temperature, stirred at room temperature for 16 hours, cooled to 0° C., quenched with 10.0 mL of a saturated aqueous solution of sodium bicarbonate, and stirred for an additional five minutes. The resulting mixture was extracted with three 50.0 mL portions of diethyl ether, and the combined organic layers were washed with 50.0 mL saturated aqueous sodium chloride, dried over 50.0 g of sodium sulfate, filtered, and concentrated under reduced pressure at room temperature. The crude product was dissolved in 14.0 mL of tetrahydrofuran, mixed with 7.0 mL of a 2.5 M aqueous solution of sodium hydroxide, and stirred at 80° C. for 16 hours. The final reaction mixture was cooled to room temperature, extracted with three 10.0 mL portions of diethyl ether, and the aqueous layer acidified to a pH of 2.0 with a 1.0 N aqueous solution of hydrochloric acid. The resulting aqueous suspension was extracted three 10.0 mL portions of diethyl ether, and the combined organic layers were washed with 10.0 mL saturated aqueous sodium chloride, dried over 20.0 g of sodium sulfate, filtered, concentrated under reduced pressure at room temperature and dried overnight under vacuum at room temperature to provide 1.40 g (4.68 mmol) of crude Compound G2 {$R_f$: 0.6 [hexanes]} in 83% yield. The product was used in the next reaction without further purification.

There now follow a characterization of the compounds described herein and a description of assays which are used to test their efficacy. These examples are provided to illustrate, not limit, the invention.

EXAMPLE 2

Compound Characterization

Compound 2

$^1$H NMR (CDCl$_3$) δ: 6.08 ppm (1H$_\alpha$,d,J=1.71 Hz), 5.8 (1H$_\beta$,d,J=1.22 Hz), 5.48–5.10(3H,m), 4.32–3.80(3H,m), 2.33–1.92 (15H,m.s).

Compound 3

$^1$H NMR (CDCl$_3$) δ: 7.52–7.30 ppm (5H,m), 5.52(2H,d), 5.32(2H, m), 4.61(1H,m), 4.33(1H,dd), 4.12(1H,dd), 2.18 (3H,s), 2.09(3H,s), 2.05(3H,s), 2.03(3H,s).

Compound 4

$^1$H NMR (CD$_3$OD) δ: 7.48–7.12 ppm (5H,m), 5.51(1H,s), 4.20(1H,s), 4.02(1H,s), 3.97–3.68 (4H,m).

Compound 5

$^1$H NMR (CDCl$_3$) δ: 7.49–7.39 ppm (5H,m), 5.78(1H,s) 4.39(1H,d), 4.26(1H,dd), 4.01(1H,ddd), 3.81(1H,dd), 3.77 (2H,m), 1.52(3H,s), 1.50(3H,s), 1.43(3H,s), 1.37(3H,s).

Compound 6

$^1$H NMR (CDCl$_3$) δ: 6.30 ppm (1H,dd, J=1.50,6.11 Hz), 4.72(1H,dd,J=1.79,6.07 Hz), 4.34(1H,d,J=7.39 Hz), 3.94 (1H,dd,J=5.48,10.92 Hz), 3.84–3.71(3H,m), 1.53(3H,s), 1.43(3H,s).

Compound 7

$^1$H NMR (CDCl$_3$) δ: 6.33 ppm (1H,dd,J=1.46,6.1 Hz), 5.32(1H,dt,J=1.7,1.7,7.8 Hz), 4.76(1H,dd,J=2.0,6.1 Hz), 4.03(1H,dd,J=1.71,7.81 Hz), 3.97(1H,m), 3.87–3.76(2H,m), 2.09(3H,s), 1.52(3H,s), 1.41(3H,s).

Compound 8

$R_f$: 0.21 [methyl alcohol:chloroform, 5:95 (v/v)]

$^1$H NMR (CDCl$_3$) δ: 5.61 (1H,d,J=8.79 Hz), 5.13 (1H,t,J=9.5 Hz), 3.91(1H,dd,J=5.37,10.98 Hz), 3.75(1H,t,J=10.25 Hz), 3.68(1H,t,J=9.76 Hz), 3.56(1H,dd,J=8.79.9.52 Hz), 3.49(1H,m), 2.15(3H,s), 1.46(3H,s), 1.38(3H,s).

Compound 9

$^1$H NMR (CDCl$_3$) 67 : 5.46 ppm (1H$_\beta$,t,J=10.0 Hz), 5.34(1H$_\alpha$,t), 5.00(1H$_\beta$,t,J=9.7 Hz), 4.78(1H$_\alpha$,dd,J=5.1,7.8 Hz), 4.04–3.64(mH), 3.41–3.23(mH),2.12(3H,s), 1.45(3H$_\alpha$, s), 1.44(3H$_\alpha$,s), 1.39(1H$_\beta$,s), 1.35(3H$_\beta$,s).

Compound 10a $^1$H NMR (CDCl$_3$) δ: 8.78 ppm (1H,s), 6.42(1H,d,J=3.9 Hz), 5.48(1H,t,J=9.52 Hz), 3.95–3.86(2H,m), 3.82–3.79 (2H,m), 3.59(1H,dd,J=3.67,10.3 Hz), 2.15(3H,s), 1.47(3H, s), 1.39(3H,s).

Compound 10b $^1$H NMR (CDCl$_3$) δ: 8.80 ppm (1H,s), 5.88(1H,d,J=7.9 Hz), 5.09(1H,t, J=10.0 Hz), 3.95(1H,dd), 3.75(2H,m), 3.48 (1H,ddd), 2.05(3H,s), 1.68(3H,s), 1.39(3H,s).

Compound 11a $^1$H NMR (CDCl$_3$) δ: 7.43ppm (1H,m),6.76(2H,m), 5.46 (1H,t), 4.99(1H,d), 4.75(1H,d), 4.70(1H,d), 4.51(1H,t), 3.97 (3H,s) 3.94(3H,s), 3.81(1H,m),3.76(1H,m), 3.10(1H,dd), 2.10(3H,s), 1.46(3H,s), 1.35(3H,s).

Compound 11b $^1$H NMR (CDCl$_3$) δ: 6.95–6.80 ppm (3H,m), 5.92(1H,t, J=10.0 Hz), 4.85(1H,d), 4.61(1H,d), 4.50(1H,d,J=8.0 Hz), 3.95(1H,dd), 3.88(1H,t,J=10.4 Hz), 3.80(1H,t,J=9.3 Hz), 3.63(1H,t,J=9.0 Hz), 3.46(1H,dd,J=9.0,10.0 Hz), 3.29(1H, m), 2.11(3H,s), 1.46(3H,s), 1.35(3H,s).

Compound 12

$^1$H NMR (CDCl$_3$) δ: 6.98–6.84 ppm (3H,m), 4.86(1H,d), 4.62(1H,d), 4.46(1H,d), 3.96(1H,dd), 3.90(6H,s), 3.83(1H, t), 3.60(1H,t), 3.50–3.40(2H,m), 3.23(1H,m ), 1.52(3H,s), 1.42(3H,s).

Compound 13

$^1$H NMR (CDCl$_3$) δ: 6.94–6.82 ppm (3H,m), 5.93(1H,m), 5.35(1H,d,J=17.09 Hz), 5.25(1H,d,J=10.26 Hz), 5.09(1H, m), 4.92(1H,t,J=9.53 Hz), 4.84(1H,d,J=11.23 Hz), 4.60(2H, m), 4.50(1H,d,J=7.81 Hz), 3.95(1H,dd, J=5.35,10.99 Hz), 3.88(3H,s), 3.87(3H,s), 3.79(1H,t,J=4.88 Hz), 3.62(1H,t,J=9.77 Hz), 3.21(1H,m), 2.78(1H,m), 2.62(1H,m), 1.7–1.56 (mH), 1.45(3H,s), 1.35(3H,s), 1.27–1.24(mH), 0.86(3H,t).

Compound 14

$^1$H NMR (CDCl$_3$) δ: 6.98–6.82 ppm (3H,m), 5.91(1H,m), 5.37(1H,dd), 5.29(1H,d), 5.10(1H,m), 4.88–4.79(2H,m), 4.68–4.60(2H,m), 4.50(1H,d), 3.94(1H,m), 3.89(3H,s), 3.88 (3H,s), 3.84(1H,m), 3.64(1H,m), 3.48–3.35(2H,m), 2.75–2.62(2H,m), 1.80–1.62(2H,m), 1.42–1.20(mH), 0.86 (3H,t).

Compound 15

$^1$H NMR (CDCl$_3$) δ: 6.95–6.81 ppm (3H,m), 5.90(1H,m), 5.35(1H,dd,J=1.46,17.33 Hz), 5.30(1H,dd,J=1.22,10.49 Hz), 5.08(1H,m), 4.86(1H,d,J=11.47 Hz), 4.82(1H,t,J=9.1Hz), 4.60(3H,d), 4.43(1H,d,J=7.65 Hz), 3.91(1H,m), 3.88(3H,s), 3.87(3H,s), 3.52(1H,dt,J=2.0,9.28,9.28 Hz), 3.42(1H,dd,J=8.05,10.5 Hz), 3.35(1H,m), 2.75(1H,dd,J=7.57,15.39 Hz), 2.66(1H,dd,J=4.88,15.38 Hz), 1.78–1.62 (mH), 1.40–1.20(mH), 0.91(9H,S), 0.86(3H,t), 0.10(3H,s), 0.09(3H,s).

Compound 16

$^1$H NMR (CDCl$_3$) δ: 6.94–6.82 ppm (3H,m), 5.99–5.84 (2H,m), 5.33(2H,m), 5.26(2H,m), 5.06(1H,m), 5.00(1H,t), 5.88(1H,d), 5.81(1H,t), 4.66–4.56(5H,m), 4.44(1H,d,J=8.05 Hz), 3.88(3H,s), 3.87(3H,s), 3.80(1H,m), 3.56–3.48(2H,m), 2.71–2.59(2H,m), 1.65(mH), 1.49–1.29(mH), 0.90(9H,s), 0.89–0.86(3H,m), 0.86(6H,s).

Compound 17

$^1$H NMR (CDCl$_3$) δ: 6.94–6.82 ppm (3H,m), 5.95–5.86 (2H,m), 5.36(2H,d), 5.25(2H,t), 5.04(2H,m), 4.86(2H,m), 4.62(5H,m), 4.50(1H,d,J=8.05 Hz), 3.88(3H,s), 3.87(3H,s), 3.84(1H,m), 3.67(1H,dd,J=4.15,12.7 Hz), 3.48(1H ,m), 2.72–2.60(2H,m ), 1.73–1.50(mH), 1.40–1.28(mH), 0.91–0.82(3H,m).

Compound 18

$^1$H NMR (CDCl$_3$) δ: 6.96–6.80 ppm (3H,m), 5.39( 1H,m), 5.30(1H,m), 5.20(1H,m), 4.90(1H,t), 4.84(1H,d), 4.61(1H,d), 4.51(1H,d), 3.96(1H,dd), 3.89(3H,s), 3.88(3H, s), 3.80(1H,t), 3.65(1H,t), 3.46(1H,dd), 3.29(1H,m), 2.69 (1H,dd), 2.58(1H,dd), 2.28(1H,t), 2.10–1.96(2H,m), 1.72–1.58(2H,m), 1.42(3H,s), 1.35(3H,s), 1.32–1.18(mH), 0.89–0.82(6H,m).

Compound 19

$^1$H NMR (CDCl$_3$) δ: 6.98–6.82 ppm (3H,m), 5.42(1H,m), 5.30(1H,m), 5.12(1H,m), 4.88(1H,d), 4.82(1H,t), 4.65(1H, d), 4.49(1H,d), 3.94(1H,m), 3.90(3H,s), 3.89(3H,s), 3.83 (1H,m), 3.60(1H,t), 3.46–3.35(2H,m), 2.30(2H,t), 2.09–1.98 (4H,m), 1.67(mH), 1.40–1.22(mH), 0.91–0.85(6H,m).

Compound 20

$^1$H NMR (CDCl$^3$) δ: 6.94–6.81 ppm (3H,m), 5.94(1H,m), 5.39–5.26 (4H,m), 5.13(1H,m), 4.86(1H,d), 4.79(1H,m), 4.68–4.59(m,H), 4.52(1H,d), 4.42(2H,m), 3.88(3H,s), 3.87 (3H,s), 3.52(2H,m), 3.45(1H,t,J=8.06 Hz), 2.60(2H,m), 2.30 (2H,t), 2.10–1.95(4H,m), 1.70–1.53(mH), 1.40–1.27(mH), 0.88–0.84(6H,m).

Compound 21

$^1$H NMR (CDCl$_3$) δ: 6.94–6.80 ppm (3H,m), 5.97–5.83 (3H,m), 5.40–5.22(8H,m), 4.96(1H,dd,J=9.28,10.26 Hz), 4.84(1H,d,J=11.48 Hz), 4.68–4.29(11H,m), 3.87(3H,s), 3.86 (3H,s), 3.60(1H,m), 3.49(1H,dd,J=8.06,10.26 Hz),2.68(2H, t), 2.26(2H,q), 2.08–1.90(4H,m), 1.70–1.65(mH), 1.32–1.18 (mH), 0.84(6H,m).

Compound 22

$^1$H NMR (CDCl$_3$) 67 : 5.95–5.84 ppm (3H,m), 5.59(1H$_{3\beta}$, t), 5.40–5.21(9H,m), 5.03(1H$_{3\alpha}$,t), 4.76–4.22(10H,m), 3.42 (1H$_{2\beta}$,dd,J=8.05,10.5 Hz), 3.20(1H$_{2\alpha}$,dd,J=3.17,10.5Hz), 2.76–2.62(2H,m), 2.30–2.23(2H,m), 2.09–1.95(4H,m), 1.70–1.65(mH), 1.35–1.18(mH), 0.90–0.80(6H,m).

Compound 23A $^1$H NMR (CDCl$_3$) δ: 8.85 ppm (1H,s), 6.45(1H,d,J=3.66 Hz), 5.96–5.84(3H,m), 5.57(1H,dd,J=9.03,10.74 Hz), 5.41–5.22(9H,m), 4.60–4.42(8H,m), 4.32(1H,dd,J=3.91, 11.97 Hz), 4.18(1H,d,J=8.79 Hz), 3.58(1H,dd,J=3.0,10.0 Hz), 2.80–2.67(2H,m), 2.29(2H,t), 2.06–1.95(4H,m), 1.70–1.59(mH), 1.35–1.25(mH), 1.81–1.90(6H,m).

Compound 23B $^1$H NMR (CDCl$_3$) δ: 8.80 ppm (1H,s), 5.98–5.82(3H,m), 5.72(1H,d), 5.42–5.22(9H,m), 5.15(1H,t), 4.62–4.41(8H,m), 4.23(2H,m), 3.72(1H,t), 2.81–2.68(2H,m), 2.30(2H,m), 2.10–1.96(4H,m), 1.71–1.52(mH), 1.37–1.15(mH), 0.88 (6H,m).

Compound 24

$^1$H NMR (CDCl$_3$) δ: 5.95–5.86 ppm (3H,m), 5.99–5.83 (5H,m), 5.40–5.22(12H,m), 5.10–5.22(2H,m), 4.91(1H,d,J= 10.7 Hz), 4.68(1H,dd), 4.64–4.43(10H,m), 4.33(1H,q), 4.27 (1H,dd,J=4.9,12.8 Hz), 4.00(1H,d,J=9.9 Hz), 3.89(3H,s), 3.88(3H,s), 3.75(2H,m), 3.60(1H,m), 3.54(1H,dd,J=7.9,9.8 Hz), 3.47(1H,dd,J=8.6.11.0 Hz), 2.78–2.58(4H,m), 2.30–2.23(2H,t), 2.03–1.95(4H,m), 1.70–1.59(2H,m), 1.39–1.25(mH), 0.90–0.82(9H,m).

Compound 25

$^1$H NMR (CDCl$_3$) δ: 7.23 ppm (1H,m), 6.92–6.82(2H,m), 5.98–5.85(5H,m), 5.40–5.21(12H,m), 5.08–4.99(2H,m), 4.85(1H,m), 4.62–4.42(10H,m), 4.38–4.23(2H,m), 3.89(6H, s), 3.75–3.61(2H,m), 2.96(1H,dd), 2.72(1H,dd), 2.61(2H, m), 2.29–2.15(2H,m),2.02–1.94(4H,m), 1.70–1.52(mH), 1.38–1.20(mH), 0.91–0.82(9H,m).

Compound 26

$^1$H NMR (CDCl$_3$) δ: 7.29 ppm (2H,d), 7.16(2H,d), 6.91–6.85(7H,m), 6.40(1H,d), 6.08(1H,d), 5.98–5.85(5H, m), 5.40–5.15(13H,m), 5.07(1H,t), 4.98(1H,m), 4.76–4.23 (mH), 3.98(1H,q), 3.84(3H,s), 3.83(2H,m), 3.82(3H,s), 3.79 (3H,s), 3.77(3H,s), 3.82(3H,m), 3.60–3.50(2H,m), 2.70–2.42(4H,m), 2.36–2.22(4H,m), 2.07–1.96(2H,m), 1.68–1.36(mH), 1.33–1.15(mH), 0.91–0.82(15H,m).

Compound 27

$^1$H NMR (CDCl$_3$) δ: 6.35 ppm (1H,d), 6.12(1H,d), 5.98–5.82(5H,m), 5.44–5.21(13H,m), 5.00(1H,m), 4.94(1H, d), 4.68–4.48 (mH), 4.32(1H,dd), 4.26–4.15(2H,m), 4.00 (1H,m), 3.92–3.82(2H,m), 3.79–3.65(2H,m), 3.58(1H,dd), 2.68–2.49(4H,m), 2.41–2.22(6H,m), 2.09–1.97(4H,m), 1.70–1.19(mH),0.91–0.80(15H,m).

Compound 28

$^1$H NMR (CDCl$_3$) δ: 6.80 ppm (1H,d,J=8.2 Hz), 6.52(1H, d,J=7.6 Hz), 6.01–5.84(5H,m), 5.72(1H,dd,J=2.7,5.4 Hz), 5.45–5.17(13H,m), 5.02–4.90(2H,m), 4.94(1H,d,J=8.1 Hz), 4.67–4.33(mH), 4.39–4.28(3H,m), 4.12(1H,m), 3.99–3.85 (3H,m), 3.89–3.68(4H,m), 2.64–2.52(4H,m), 2.36–2.12(6H, m), 2.10–1.95(4H,m), 1.70–1.15(mH), 0.91–0.81(15H,m).

Compound 29

$^1$H NMR (CDCl$_3$) δ: 7.30 ppm (1H,d), 6.55(1H,d), 6.00–5.85(5H,m), 5.78(1H,dd), 5.44–5.19(13H,m), 5.10–4.82(3H,m), 4.67–4.46(mH), 4.38–4.28(2H,m), 4.15 (1H,m), 4.00–3.86(2H,m), 3.86–3.60(mH), 3.40–3.34(4H, m), 2.66–2.42(6H,m), 2.37–2.22(6H,m), 2.08–1.96(4H,m), 1.69–1.20(mH), 0.87 (15H,m).

Compound 30

$^1$H NMR (CDCl$_3$) δ: 7.38 ppm (1H,d), 7.09(1H,d), 6.00–5.83(5H,m), 5.71(1H,m), 5.43–5.19(13H,m), 5.01(1H, m), 4.87(2H,m), 4.68–4.44(mH), 4.40–4.36(mH), 4.18(1H, m), 3.93(1H,dd), 3.76(1H,q), 3.71–3.62(2H,m), 3.38(2H,q), 3.32(2H,q), 2.68–2.41(8H,m), 2.28–2.20(2H,t), 2.07–1.95 (4H,m), 1.68–1.48(mH), 1.35–1.12(mH), 0.90–0.81(15H, m).

Analog B214 (Compound 31)

R$_f$: 0.43 [chloroform:methyl alcohol:acetic acid:water, 125:75:10:20 (v/v/v/)]RT(HPLC) 12.22 min $^1$H NMR (CDCl$_3$:CD$_3$OD, 3:1, v/v) δ: 5.40 ppm (1H,m), 5.17(1H,m), 5.09(1H,m), 5.00(2H,m), 4.96(1H,t,J=10.0 Hz), 4.48(1H,d), 4.02(2H,m), 3.90–3.60(mH), 3.45(1H,m), 3.34(1H,t,J=9.6 Hz), 3.26–3.13(mH), 2.48–2.20(mH), 2.06 (2H,t), 1.84(4H,m), 1.45–1.00(mH), 0.65(15H,m).

$^{13}$C NMR (CDCl$_3$:CD$_3$OD, 3:1, v/v) δ: 205.26 ppm, 205.16, 173.71, 172.57, 170.52, 168.10, 167.45, 130.63, 127.93, 100.63, 94.55, 74.64, 72.74, 72.42, 71.60, 69.82, 67.95, 67.64, 59.95, 53.57, 43.03, 42.79, 41.74, 38.26, 36.78, 34.63, 33.91, 33.47, 31.51, 31.46, 31.43, 31.38, 29.25, 29.21, 29.15, 29.12, 29.08, 29.06, 28.96, 28.93, 28.86, 28.74, 28.65, 28.56, 26.79, 26.12, 25.15, 24.78, 24.53, 23.00, 22.91, 22.24, 22.22, 13.51.

$^{31}$P NMR (CDCl$_3$:CD$_3$OD 3:1, v/v) δ: 1.31 ppm, −1.40.

Compound 32

$^1$H NMR (CDCl$_3$) δ: 6.89–6.80 ppm (3H,m), 6.68(1H,d, J=8.79 Hz), 6.56(1H,d,J=8.05 Hz), 5.95–5.86(5H,m), 5.41–5.28(13H,m), 4.97(1H,m), 4.80(1H,t,J=9.7 Hz), 4.72 (1H,d,J=8.5 Hz), 4.60(mH), 4.48(2H,m), 4.30(2H,m), 3.97 (2H,t), 3.89(3H,s), 3.85(3H,s), 3.77–3.74(2H,m), 3.68–3.60 (2H,m), 3.00–2.56 (mH), 2.26(2H,t), 2.09–1.04(mH), 0.88–0.84(15H,m).

Compound 33

$^1$H NMR (CDCl$_3$) δ: 6.83 ppm (1H,d,J=7.33 Hz), 6.59 (1H,d,J=9.03 Hz), 5.94–5.86(5H,m), 5.47(1H,t,J=7.1 Hz), 5.40–5.30(12H,m), 5.00(1H,m), 4.68–4.45(mH), 4.38(1H, q), 4.32–4.20(2H,m), 3.83–3.69(2H,m), 3.41(1H,q), 2.98–2.56(8H,m), 2.27(2H,t), 2.07–1.90(mH), 1.67–1.52 (mH), 1.35–1.15(mH), 0.89–0.85(15H,m).

Compound 34

$^1$H NMR (CDCl$_3$) δ: 7.39 ppm (1H,d), 7.08(1H,d), 6.00–5.83(7H,m), 5.70(1H,dd), 5.43–5.20(13H,m), 5.01 (1H,m), 4.88 (1H,m), 4.65–4.45(mH), 4.40–4.25(2H,m), 4.18(1H,m), 3.92(1H,dd), 3.75(1H,q), 3.67 (1H,m), 3.39 (2H,d), 3.32(2H,q), 2.67–2.42(4H,m), 2.24(2H,t), 2.07–1.92 (2H,m), 1.74–1.46(mH), 1.35–1.24(mH), 0.91–0.82(15H, m).

Compound 36

R$_f$: 0.77 [hexanes:ethyl acetate, 1:1 (v/v)]

$^1$H NMR (CDCl$_3$) δ: 4.92 ppm (1H,t,J=9.0 Hz), 4.62(1H, d, J=7.9 Hz), 3.88(1H,dd), 3.77(1H,t), 3.64(1H,t), 3.30(2H, m), 2.21(3H,s), 1.44(3H,s), 1.35(3H,s), 0.89(9H,s), 0.12 (3H,s). 0.11(3H,s).

Compound 37

R$_f$: 0.37 [hexanes:ethyl acetate, 3:1 (v/v)]

$^1$H NMR (CDCl$_3$) δ: 4.70 ppm (1H,d,J=7.5 Hz), 3.86 (1H,dd,J=3.0,8.35 Hz), 3.77(1H,t,J=10.3 Hz), 3.57(1H,t,J= 9.29 Hz), 3.45(1H,m), 3.30(2H,m), 1.50(3H,s), 1.42(3H,s), 0.91(9H,s), 0.14(3H,s), 0.13(3H,s).

Compound 38

$^1$H NMR (CDCl$_3$) δ: 5.90 ppm (1H,m), 5.35(1H,dd,J= 1.46,17.36 Hz), 5.23(1H,d,J=10.49 Hz), 5.08(1H,m), 4.90 (1H,t,J=10.01 Hz), 4.60(3H,m), 3.86(1H,dd,J=5.61,10.98 Hz), 3.74(1H,t,J=10.5 Hz), 3.62(1H,t,J=9.52 Hz), 3.30(2H, m), 2.75(1H,dd,J=7.0,15.8 Hz), 2.63(1H,dd,J=6.35,15.63 Hz), 1.65(mH), 1.42(3H,s), 1.32(3H,s), 1.24(mH), 0.89(9H, s), 0.86(3H,t), 0.12(3H,s), 0.10(3H,s).

Compound 39

$^1$H NMR (CDCl$_3$) δ: 5.90 ppm (1H,m), 5.38(1H,dd), 5.29(1H,d), 5.07(1H,m), 4.81(1H,t), 4.62(2H,m), 3.88(1H,m), 3.80(1H,m), 3.62(1H,m), 3.40(1H,m), 3.31(1H,dd), 2.79 (2H,m), 1.98(1H,t), 1.72(1H,m), 1.65(1H,m), 1.27(mH), 0.91(9H,s), 0.88(3H,t), 0.18(3H,s), 0.17(3H,s).

Compound 40

$^1$H NMR (CDCl$_3$) δ: 5.96–5.85 ppm (4H,m), 5.42–5.22 (11H,m), 5.05(1H,m), 5.00(1H,t), 4.80(1H,dd), 4.66–4.42 (mH), 4.35–4.22(2H,m), 4.10(1H,d), 3.61(1H,m), 3.52(1H,m), 3.42(1H,dd), 3.31(1H,dd), 2.78–2.62(4H,m), 2.28(2H,t), 2.09–1.95(4H,m), 1.69–1.87(4H,m), 1.38–1.19(mH), 0.92(9H,s), 0.85(15H,m), 0.16(6H,s).

Compound 41

$^1$H NMR (CDCL$_3$) δ: 5.94–5.86 ppm (5H,m), 5.38–5.21 (12H,m), 5.19–4.97(2H,m), 4.72–4.42(mH), 4.38(1H,d,J=8.06 Hz), 4.32–4.23(2H,m), 3.88(1H,m), 3.75(1H,dd), 3.60 (1H,m), 3.40(2H,m), 2.76(6H,m), 2.28(2H,t), 2.09–1.95 (4H,m), 1.70–1.63(4H,m), 1.35–1.19(mH), 0.92(9H,s), 0.87–0.86(15H,m), 0.17(3H,s), 0.16(3H,s).

Compound 43

$^1$H NMR (CDCl$_3$) δ: 7.20 ppm (1H,d), 7.00(1H,d), 5.95 (5H,m), 5.30(mH), 4.95(1H,q), 4.75(1H,t), 4.55(mH), 4.30 (mH), 3.90(1H,dd), 3.70(mH), 3.45(mH), 3.35(2H,s), 3.28 (2H,s), 2.60(1H,dd), 2.45(mH), 2.25(2H,t), 1.95(mH), 1.65 (mH), 1.50(mH), 1.20(mH), 0.85(15H,m), 0.80(9H,s) 0.08 (6H,2s).

Compound 44

$^1$H NMR (CDCl$_3$) δ: 7.20 ppm (1H,d), 6.82(1H,d), 5.95 (5H,m), 5.30(mH), 5.10(mH), 4.58(mH), 4.47(mH), 4.30 (mH), 3.70(mH) 3.35(mH), 2.50(mH), 2.25(2H,t), 2.09 (mH), 1.50(mH), 1.25(mH) 0.85(15H,m).

Compound 45

R$_f$:0.53 [hexanes:ethyl acetate, 4:1 (v/v)]
$^1$H NMR (CDCl$_3$) δ: 4.53 ppm (1H,d,J=7.42 Hz), 3.99 (1H,m), 3.87–3.73(2H,m), 3.60(1H,t,J=9.2 Hz), 3.26–3.14 (2H,m), 1.70–1.63(2H,m), 1.48(3H,s), 1.40(3H,s), 1.27 (mH,br.s), 0.91(9H,s), 0.90–0.85(3H,m), 0.13(3H,s), 0.21 (3H,s).

Compound 46

R$_f$: 0.80 [hexanes:ethyl acetate, 4:1 (v/v)]
$^1$H NMR (CDCl$_3$) δ: 5.43–5.28 ppm (2H,m), 5.03(1H,m), 4.49(1H,d,J=7.46 Hz), 3.86–3.73(2H,m), 3.66–3.56(2H,m), 3.22–3.10(2H,m), 2.30–2.26(2H,t), 2.09–1.97(mH), 1.83–1.54(mH), 1.48(3H,s), 1.38(3H,s), 1.26(mH,br.s), 0.91 (9H,s), 0.89–0.85(6H,m), 0.13(3H,s), 0.12(3H,s).

Compound 47

R$_f$: 0.13 [hexanes:ethyl acetate, 4:1 (v/v)]
$^1$H NMR (CDCl$_3$) δ: 5.44–5.28 ppm (2H,m), 5.10–5.04 (1H,m), 4.53(1H,d,J=7.6 Hz), 3.91–3.85(2H,m), 3.77–3.66 (2H,m), 3.43(1H,m), 3.33(1H,m), 3.18(1H,dd,J=7.6,9.9 Hz), 3.01(1H,dd,J=9.3,9.8 Hz), 2.32–2.26(2H,t), 2.10–1.48 (mH), 1.34–1.25(mH), 0.92(9H,s), 0.92–0.85(6H,m), 0.15 (3H,s), 0.14(3H,s).

Compound 48

R$_f$:0.45 [hexanes:ethyl acetate, 4:1 (v/v)]
$^1$H NMR (CDCl$_3$) δ: 5.95 ppm (1H,m), 5.33(2H,m), 5.30(2H,m), 5.07(1H,m), 4.62(2H,d), 4.48(1H,d,J=7.8 Hz), 4.44(1H,dd,J=2.2,11.3 Hz), 4.33(1H,dd,J=6.1,11.7 Hz), 3.85 (1H,m), 3.68(1H,m), 3.58(1H$_{OH}$,d,J=3.2 Hz) 3.45(1H,m), 3.37(1H,m), 3.18(1H,t,J=9.1 Hz), 2.98(1H,t,J=10.1 Hz), 2.28(2H,t), 2.06(mH), 1.82(mH), 1.65 (mH), 1.25(mH), 0.91(9H,s), 0.85(6H,m), 0.13(6H,2s).

Compound 49

R$_f$: 0.29 [hexanes:ethyl acetate, 4:1 (v/v)]
$^1$H NMR (CDCl$_3$) δ: 5.95 ppm (3H,m), 5.41–5.26(8H,m), 5.00(1H,m), 4.63–4.47(mH), 4.30(1H,dd,J=6.6,11.7 Hz), 4.18(1H,q), 3.72(1H,m), 3.55(1H,m), 3.25(2H,t,J=7.9,10.3 Hz), 3.15(1H,t,J=8.8,10.8 Hz), 2.25(2H,t), 2.00(4H,m), 1.65 (mH), 1.50(mH), 1.25(mH), 0.91(9H,s), 0.85(6H,m), 0.01 (6H,2s).

Compound 50

R$_f$: 0.25 & 0.20 [diethyl ether:dichloromethane, 1:9 (v/v)]
$^1$H NMR (CDCl$_3$) δ: 5.95 ppm (3H,m), 5.35(mH), 5.25 (mH), 4.95(mH), 4.59(mH), 4.30(mH), 3.75(mH), 3.60 (mH), 3.35(mH), 2.25(2H,t), 2.00(mH), 1.65(mH), 1.25 (mH), 0.85(6H,m).

Compound 51A

R$_f$: 0.50 [diethyl ether:dichloromethane, 1:9 (v/v)]
$^1$H NMR (CDCl$_3$) δ: 8.77 ppm (1H,s), 6.38(1H,d,J=2.41 Hz), 5.95(3H,m), 5.30(mH), 4.98(1H,m), 4.55(mH), 4.40 (mH), 4.05(1H,m), 3.85(1H,m), 3.75(1H,m), 3.60(1H,dd,J=3.42,9.5 Hz), 2.27(2H,t), 2.00(mH), 1.65(mH), 1.25(mH), 0.85(6H,m).

Compound 51B

R$_f$: 0.37 [diethyl ether:dichloromethane, 1:9 (v/v)]
$^1$H NMR (CDCl$_3$) δ: 8.80 ppm (1H,s), 5.95(3H,m), 5.72 (1H,d), 5.30(mH), 5.15(1H,t), 4.62(1H,d), 4.50(mH), 4.32 (1H,dd), 3.80(1H,m), 3.70(1H,t), 2.70(2H,t), 2.25(2H,t), 1.95(mH), 1.60(mH), 1.25(mH), 0.85(6H,m).

Compound 52

R$_f$: 0.38 [ethyl acetate:hexanes, 1:9 (v/v)]
$^1$H NMR (CDCl$_3$) δ: 5.98–5.88 ppm (1H,m), 5.32(1H,m), 5.25(1H,m), 4.88(1H,m), 4.62(2H,d), 4.48(1H,d,J=7.46 Hz), 3.86–3.66(mH), 3.59(1H,t,J=9.4 Hz), 3.23–3.10(mH), 1.87–1.80(2H,m), 1.64–1.56(2H,m), 1.48(3H,S), 1.38(3H,s), 0.91(9H,s), 0.90–0.86(3H,t), 0.13(3H,s), 0.12(3H,s).

Compound 53

R$_f$:0.12 [ethyl acetate:hexanes, 1:4 (v/v)]
$^1$H NMR (CDCl$_3$) δ: 5.93 ppm (1H,m), 5.37(1H,m), 5.27(1H,m), 4.90(1H,m), 4.67–4.58(2H,m), 4.54(1H,d,J=7.5 Hz), 4.12(1H,q), 3.94(1H,m), 3.87(1H,dd,J=3.4,11.5 Hz), 3.78–3.69(2H,m), 3.50–3.43(2H,m), 3.34–3.30(1H,m), 3.21(1H,dd,J=7.6,10.0 Hz), 3.03(1H,t,J=9.2 Hz), 2.05–2.01 (1H,m), 1.96–1.50(mH), 1.36–1.23(mH), 0.92(9H,s), 0.88–0.85(3H,m), 0.15(3H,s), 0.14(3H,s).

Compound 54

$^1$H NMR (CDCl$_3$) δ: 5.91 ppm (1H,m), 5.37–5.32 (1H,m), 5.26–5.23(1H,m), 4.92–4.87(1H,m), 4.65–4.55(2H,m), 4.47(1H,d,J=7.64 Hz), 3.90–3.74(mH), 3.48(1H,ddd,J=2.1, 9.3,11.2 Hz), 3.42(1H$_{OH}$,d,J=2.1 Hz), 3.28(1H,m), 3.18(1H, dd,J=7.6,9.9 Hz), 3.00(1H,dd,J=8.7,9.8 Hz), 1.89(mH), 1.60–1.20(mH), 0.91(18H,s), 0.90–0.84(3H,m), 0.065(6H, s), 0.059(6H,s).

Compound 55

$^1$H NMR (CDCl$_3$) δ: 5.97–5.87 ppm (2H,m), 5.37–5.31 (2H,m), 5.28–5.23(2H,m), 4.81(1H,m), 4.69(1H,t,J=10.0 Hz), 4.68–4.57(2H,m), 4.48(1H,d,J=7.5 Hz), 3.79(1H,q), 3.75–3.65(2H,d), 3.64–3.58(1H,m), 3.36(1H,m), 3.27(1H, dd,J=7.7,10.1 Hz), 3.17(1H,t,J=9.3 Hz), 1.80(2H,q), 1.61–1.52(mH), 1.31–1.25(mH), 0.91(18H,m), 0.92–0.84 (3H,m), 0.025(6H,s), 0.010(6H,s).

Compound 56

$^1$H NMR (CDCl$_3$) δ: 5.96–5.87 ppm (2H,m), 5.38–5.20 (4H,m), 4.80(1H,m), 4.69–4.56(mH), 4.52(1H,d,J=7.4 Hz), 3.81–3.59(3H,m), 3.36(1H,m), 3.30–3.26(1H,dd,J=7.64, 9.88 Hz), 3.20(1H,t,J=9.25 Hz), 2.19(1H$_{OH}$,t,J=5.71 Hz), 1.82(2H,q), 1.68–1.50(mH), 1.24(mH,br.s), 0.92(9H,s), 0.85 (3H,m), 0.14(6H,s).

Compound 57A $^1$H NMR (CDCl$_3$) δ: 5.43–5.28 ppm (2H,m), 5.06(1H,m), 4.47(1H,d, J=7.68 Hz), 3.83(1H,m), 3.73(1H,m), 3.66–3.56 (2H,m), 3.47(1H,m), 3.38(3H,s), 3.34(1H,m), 3.20(1H,t,J=7.9 Hz), 2.98(1H,t,J=8.9 Hz), 2.29(2H,t), 2.09–1.50(mH), 1.34–1.25(mH), 0.92(9H,s), 0.91–0.85(6H,m), 0.14(6H,s).

Compound 57B

¹H MNR (CDCl₃) δ: 7.89–7.34 ppm (10H,m), 5.43–5.29 (2H,m), 5.00(1H,m), 4.44(1H,d,J=7.74 Hz), 3.84–3.70(3H, m), 3.46(3H,s), 3.28(1H,q), 3.18(2H,m), 3.04(1H,t,J=9.5 Hz), 2.30(2H,t), 2.11–2.00(4H,m), 1.89(2H,m), 1.70(2H,m), 1.58(2H,m), 1.27(mH), 1.07(9H,s), 0.95(9H,s), 0.87(6H,m), 0.16(3H,s), 0.15(3H,s).

Compound 58

¹H NMR (CDCl₃) δ: 5.96–5.87 ppm (2H,m), 5.41–5.23 (mH), 5.00(1H,m), 4.58(4H,m), 4.46(1H,d,J=7.50 Hz), 4.23 (1H,q), 3.77–3.68(mH), 3.57(1H,dd,J=5.13,10.91 Hz), 3.41 (1H,m), 3.35(3H,s), 3.24(1H,dd,J=7.7,10.1 Hz), 3.12(1H, dd,J=8.8,9.7 Hz), 2.28–2.26(2H,t), 2.07–1.52(mH), 1.32–1.12(mH), 0.91(9H,s), 0.90–0.85(6H,m), 0.13(6H,s).

Compound 59

¹H NMR (CDCl₃) δ: 5.97–5.90 ppm (2H,m), 5.41–5.25 (4H,m), 4.97(1H,m), 4.61–4.54(4H,m), 4.27–4.07(2H,m), 3.81–3.40(mH), 3.38(3H,s), 3.32(2H,m), 3.22(1H,t,J=9.9 Hz), 2.29–2.24(2H,m), 2.08–1.52(mH), 1.33–1.23(mH), 0.88–0.84(6H,m).

Compound 60A and B

R$_{f\alpha/\beta}$:05.3 [hexanes:ethyl acetate, 1:1 (v/v)]

¹H NMR (CDCl₃) δ: 8.74 ppm (H1$_{\alpha,\beta}$,2s), 6.39(1H$_\alpha$,d, J=3.46 Hz), 6.00–5.91(2H,m), 5.58(1H$_\beta$,d,J=8.46 Hz), 5.42–5.25(mH), 5.00(1H,m), 4.63–4.36(mH), 3.99–3.50 (mH), 3.37(3H$_\beta$,s), 3.36(3H$_\alpha$,s), 3.34–3.30(mH), 2.35–2.25 (2H,m), 2.08–1.80(mH), 1.70–1.54(mH), 1.27–1.23(mH), 0.89–0.85(6H,m).

Compound 62

¹H NMR (CDCl₃) δ: 6.96 ppm (1H,s), 6.85(2H,m), 5.95 (5H,m), 5.30(mH), 5.00(mH), 4.60(mH), 4.35(1H,d), 4.27 (1H,dd), 4.20(1H,q), 3.98(1H,d), 3.85(6H,2s), 3.75(mH), 3.52(2H,m), 3.35(1H,t) 3.15(1H,t), 2.60(2H,m), 2.25(2H,t), 2.00(4H,m), 1.60(mH), 1.25(mH), 0.85(9H,m).

Compound 63

¹H NMR (CDCl₃) δ: 6.98 ppm (1H,d,J=1.71 Hz), 6.90 (1H,d,J=8.30 Hz), 6.85(1H,d,J=8.30 Hz), 5.95(4H,m), 5.30 (mH), 5.00(1H,t,J=9.03 Hz), 4.90(mH), 4.55(mH), 4.30 (mH), 3.85(6H,2s), 3.70(mH), 3.62(1H,m), 3.50(mH), 3.35 (mH), 3.00(1H,t,J=9.8 Hz), 2.69(2H,t,), 2.25(2H,t), 2.00 (mH), 1.60(mH), 1.25(mH), 0.85(9H,m)

Compound 64

¹H NMR (CDCl₃) δ: 5.95 ppm (4H,m), 5.40–5.22(10H, m), 4.96(1H,m), 4.90(1H,m), 4.55(mH), 4.32(1H,d), 4.30–4.22(2H,m), 4.18( 1H, q), 4.10(1H,dd), 3.90(mH), 3.75(mH), 3.50(mH), 3.33(2H,m), 3.20(mH), 3.00(1H,t), 2.25(2H,t), 2.00(4H,m), 1.80(mH), 1.50(mH), 1.25(mH), 0.91(9H,s), 0.85(9H,m), 0.15(6H,s).

Compound 65

¹H NMR (CDCl₃) δ: 5.98–5.87 ppm (4H,m), 5.42–5.23 (mH), 4.95(1H,m), 4.80(2H,m), 4.65–4.50(mH), 4.49(1H,d, J=7.6 Hz), 4.27(1H,d,J=8.1 Hz), 4.26(1H,m),3.87(1H,d,J= 9.95 Hz), 3.83–3.54(mH), 3.36(3H,s), 3.30–3.13(4H,m), 2.28–2.23(2H,t), 2.07–1.78(mH), 1.73–1.53(mH), 1.40–1.23(mH), 0.92(9H,s), 0.91–0.77(9H,m), 0.17(6H,s).

Compound 67

¹H NMR (CDCl₃) δ: 7.32 ppm (1H,d,J=8.2 Hz), 7.24(1H, d,J=9.8 Hz), 5.97–5.89(4H,m), 5.37–5.23(mH), 4.91(2H,m), 4.81(1H,m), 4.71(1H,m), 4.63–4.54(mH), 4.24(1H,q), 3.88–3.43(mH), 3.39(3H,s), 2.53–2.50(4H,m), 2.26–2.23 (2H,t), 2.06–1.54(mH), 1.2(mH), 0.88–0.83(mH), 0.08(3H, s), 0.05(3H,s).

Compound 68

R$_f$: 0.52 [dichloromethane:methyl alcohol, 95:5 (v/v)]

¹H NMR (CDCl₃) δ: 7.25 ppm (1H,d,J=7.6 Hz), 7.22(1H, d,J=8.4 Hz), 5.97–5.85(4H,m), 5.41–5.20(mH), 5.05(1H,d, J=8.0 Hz), 4.93(1H,m), 4.78(1H,m), 4.65–4.51(mH), 4.28 (1H,q), 4.11(1H,m), 3.79–3.57(mH), 3.52–3.39(mH), 3.37 (3H,s), 2.50(4H,t), 2.25(2H,t), 2.07–1.96(4H,m), 1.78–1.48 (mH), 1.24(mH), 0.86(15H,m).

Compound 69

¹H NMR (CDCl₃) δ: 7.55 ppm (1H,d), 7.05(1H,d), 6.00–5.86(6H,m), 5.79(1H,m), 5.42–5.20(mH), 4.91(1H, m), 4.84(2H,m), 4.75(1H,t), 4.67–4.52(mH), 4.28(1H,q), 4.13(1H,m), 4.05(1H,m), 3.91(1H,d), 3.80–3.40(mH), 3.39 (3H,s), 2.52(4H,m), 2.26(2H,t), 2.10–1.95(4H,m), 1.82–1.43(mH), 1.38–1.24(mH),0.87(15H,m).

Analog B531 (Compound 70)

RT(HPLC):13.87 min.

¹H NMR (CDCl₃:CD₃OD,3:1, v/v) δ: 5.29 ppm (1H,dd, J=3.3,6.3 Hz), 5.20(1H,m), 5.10(1H,m), 4.70(1H,m), 4.46 (1H,d,J=8.2 Hz), 3.86(2H,m), 3.72–3.30(mH), 3.20(3H,s), 3.18(1H,t), 2.38(4H,m), 2.10(2H,t), 1.82(4H,m), 1.72–0.95 (mH), 0.68(15H,t).

¹³C NMR (CDCl₃:CD₃OD,3:1, v/v) δ: 205.9 ppm, 174.1, 168.0, 167.6, 130.6, 127.8, 100.3, 94.6, 80.1, 78.9; 74.6, 73.6, 72.8, 71.1, 70.6, 69.7, 69.2, 69.1, 69.08, 67.3, 58.3, 54.9, 52.2, 52.1, 48.8, 47,5, 43.0, 42.9, 37.3, 36.6, 34.4, 34.1, 33.6, 31.4, 31.3, 29.3, 29.2, 29.1, 29.0, 28.9, 28.8, 28.7, 28.6, 28.5, 26.7, 26.1, 25.3, 24.8, 24.6, 22.9, 22.8, 22.2, 13.4.

³¹P NMR (CDCl₃:CD₃OD,3:1, v/v) δ: –0.58 ppm, –1.24.

Compound 71

¹H NMR (CDCl₃) δ: 7.10 ppm (1H,d), 6.95(1H,d), 5.95 (4H,m), 5.25(mH), 4.92(1H,d), 4.82(1H,d), 4.75(1H,m), 4.65(mH), 4.50(mH), 4.38(1H,q), 3.85(1H,m), 3.45(mH), 3.35(3H,s), 2.80(4H,m), 2.63(2H,m), 2.20(2H,t), 1.95(mH), 1.65(mH), 1.20(mH), 0.80(24H,m), 0.05(6H,2s).

Compound 72

¹H NMR (CDCl₃) δ: 7.22 ppm (1H,d), 6.65(1H,d), 5.90 (4H,m), 5.40–5.23(mH); 4.90(1H,m), 4.83(1H,m), 4.70(1H, d), 4.60–4.50(mH), 4.40(1H,q), 4.10(1H,m), 4.02(1H,m), 3.95(1H,q), 3.80–3.62(mH), 3.47(3H,m), 3.39(3H,s), 3.36 (1H,t), 2.98–2.83(4H,m), 2.24(2H,t), 2.00(4H,m), 1.80–1.20 (mH), 0.85(15H,m).

Compound 73

¹H NMR (CDCl₃) δ: 7.55 ppm (2H,m), 5.95(6H,m), 5.80(1H,m), 5.35(mH), 4.90(1H,m), 4.60(mH), 4.32(1H,q), 4.15(1H,m), 3.65(mH), 3.45(1H,m), 3.35(3H,s), 2.85(4H, m), 2.25(2H,t), 2.00(4H,m), 1.80(mH), 1.25(mH), 0.85 (15H,m).

Compound 74

¹H NMR (CDCl₃) δ: 5.95 ppm (5H,m), 5.60(1H,t), 5.30 (mH), 5.05(3H,m), 4.75(2H,m), 4.60(mH), 4.50(mH), 4.40 (mH), 4.30(mH), 3.90(1H,m), 3.75(mH), 3.60(mH), 3.47 (mH), 3.28(1H,dd), 2.68(4H,m), 2.25(2H,t), 2.00(4H,m), 1.60(mH), 1.25(mH), 0.85(9H,m).

Compound 75

¹H NMR (CDCl₃) δ: 8.85 ppm (1H,s), 6.45(1H,d,J=3.6 Hz), 5.92(5H,m), 5.60(1H,t,J=10.2 Hz), 5.30(mH), 5.10 (mH), 5.03(1H,dt,J=4.3,10.1,10.1 Hz), 4.62(mH), 4.50 (mH), 4.30(1H,q), 4.25(1H,m), 4.00(1H,d,J=10.8 Hz), 3.75 (1H,dd,J=4.3,11.5 Hz), 3.70(1H,dd,J=3.6,11.0 Hz), 3.61 (1H,m), 3.40(1H,dd,J=7.9,9.7 Hz), 2.65(4H,m), 2.25(2H,t), 2.00(4H,m), 1.60(mH), 1.25(mH), 0.85(9H,t).

Compound 76

¹H NMR (CDCl₃) δ: 5.98 ppm (7H,m), 5.75(1H,t,J=8.2 Hz), 5.35(mH), 5.07(1H,m), 5.04(1H,dd,J=9.2,10.1 Hz), 4.95(1H,t,J=9.8 Hz), 4.62(mH), 4.50(mH), 4.47(1H,d,J=7.5 Hz), 4.30(mH), 4.00(2H,m), 3.70(1H,dd,J=3.9,11.4 Hz), 3.60(1H,m), 3.42(1H,dd,J=7.5,9.8 Hz), 2.70(4H,m), 2.25 (2H,t), 2.00(4H,m), 1.62(mH), 1.30(mH), 0.85(9H,t).

Compound 77 ¹H NMR (CDCl₃) δ: 5.95 ppm (7H,m), 5.55(1H,t), 5.35(mH), 5.05(mH), 4.90(1H,t), 4.62(mH), 4.50(mH), 4.28(mH), 4.20(mH), 4.05 (mH), 3.65(mH), 3.35

(1H,q), 2.92(1H,t), 2.70(mH), 2.60(2H,d), 2.25(2H,t), 2.00 (mH), 1.75(mH), 1.60(mH), 1.30(mH), 0.85(9H,t).

Compound 78

$^1$H NMR (CDCl$_3$) δ: 7.36 ppm (1H,d,J=8.5 Hz), 7.28(1H, d), 5.90(7H,m), 5.60(1H,dd,J=10.6,11.6 Hz), 5.30(mH), 5.05(1H,m), 4.90(2H,m), 4.75(1H,t,J=9.5 Hz), 4.55(mH), 4.30.(mH), 4.08(2H,m), 3.85(mH), 3.68(mH), 3.35(mH), 2.65(mH), 2.50(2H,t), 2.45(2H,t), 2.25(2H,t), 2.00(mH), 1.60(mH), 1.30(mH), 0.85(15H,m).

Compound 79a $^1$H NMR (CDCl$_3$) δ: 5.94 ppm (1H,m), 5.45(1H,d,J=9.5 Hz), 5.35(1H,dd,J=1.47,17.1 Hz), 5.25(1H,d,J=10.0 Hz), 4.98(1H,d,J=3.66 Hz), 4.97(1H,m), 4.25(1H,dd,J=5.2,12.7 Hz), 4.06(1H,dd,J=1.2,14.7 Hz), 3.90–3.60(mH), 3.14(1H, dd,J=3.4,10.2 Hz), 2.12(3H,s), 1.45(3H,s), 1.37(3H,s).

Compound 79b $^1$H NMR (CDCl$_3$) δ: 5.94 ppm (1H,m), 5.35(1H,dd,J= 1.5,17.1 Hz), 5.25(1H,dd,J=1.2,17.1 Hz), 4.95(2H,t,J=9.76 Hz), 4.47(1H,d,J=7.81 Hz), 4.40(1H,dd,J=5.1,11.7 Hz), 4.16 (1H,dd,J=6.5,12.4 Hz), 3.95(1H,dd,J=5.4,10.8 Hz), 3.80 (1H,t,J=10.7 Hz), 3.65(1H,t,J=9.76 Hz), 3.43(1H,dd,J=8.1, 10.0 Hz), 3.27(1H,m), 2.12(3H,s), 1.45(3H,s), 1.37(3H,s).

Compound 80

$^1$H NMR (CDCl$_3$) δ: 4.95 ppm (1H,d,J=3.9 Hz), 4.12(1H, m), 3.80(mH), 3.60(mH), 3.28(1H,dd,J=3.66,10.0 Hz), 2.62 (1H,d,J=2.44 Hz), 2.22(1H$_{OH}$,t) 1.51(3H,s), 1.44(3H,s).

Compound 81

$^1$H NMR (CDCl$_3$) δ: 5.92 ppm (1H,m), 5.44(1H,t,J=9.52 Hz), 5.37(1H,dd,J=1.46,17.4 Hz), 5.27(1H,dd,J=1.2,10.5 Hz), 5.11(mH), 5.02(1H,d,J=3.42 Hz), 4.61(2H,m), 3.85 (mH), 3.65(mH), 3.05(1H,dd,J=3.66,10.5 Hz), 2.79(1H,dd, J=7.08,14.5 Hz), 2.65(1H,dd,J=6.35,15.4 Hz), 1.65(mH), 1.45(3H,s), 1.36(3H,s), 1.25(mH), 0.90(12H,m), 0.08(6H, 2s).

Compound 82

$^1$H NMR (CDCl$_3$) δ: 5.95 ppm (1H,m), 5.45(1H,t,J=9.3 Hz), 5.37(1H,dd,J=1.47,15.8 Hz), 5.27(1H,dd,J=1.22,10.5 Hz), 5.12(1H,m), 4.99(1H,d,J=3.66 Hz), 4.62(2H,m), 3.80 (mH), 3.65(mH), 3.16(1H,dd,J=3.62,10.5 Hz), 2.78(1H,dd, J=7.02,15.4 Hz), 2.63(1H,dd,J=6.30,15.6 Hz), 1.65(mH), 1.46(3H,s), 1.37(3H,s), 1.26(mH), 0.86(3H,t).

Compound 83

$^1$H NMR (CDCl$_3$) δ: 5.95 ppm (3H,m), 5.41(mH), 5.27 (mH), 5.12(1H,m), 5.02(1H,d,J=3.4 Hz), 4.55(mH), 4.25 (mH), 3.90(mH), 3.65(1H,t,J=8.8 Hz), 3.10(1H,dd,J=3.67, 10.5 Hz), 2.79(1H,dd,J=5.4,14.4 Hz), 2.63(1H,dd,J=6.6, 15.6 Hz), 1.65(mH), 1.45(3H,s), 1.36(3H,s), 1.26(mH), 0.86 (3H,t).

Compound 84

R$_f$: 0.6 [methylene chloride:diethyl ether, 4:1 (v/v)]

$^1$H NMR (CDCl$_3$) δ: 5.95 ppm (3H,m), 5.40(mH), 5,25 (1H,dd), 5.13(1H,m), 4.98(1H,d,J=3.4 Hz), 4.55(mH), 4.25 (mH), 3.80(mH), 3.65(1H,t), 3.38(mH), 3.13(1H,dd), 2.75 (1H,dd), 2.65(1H,dd), 1.68(mH), 1.45(2H,q), 1.25(mH), 0.85(12H,m), 0.10(6H,s).

Compound 85

$^1$H NMR (CDCl$_3$) δ: 5.95 ppm (4H,m), 5.55(2H,m), 5.35(8H,m), 5.10(1H,m), 5.01(2H,m), 4.95(1H,t), 4.90(1H, t), 4.55(mH), 4.23(2H,m), 3.90(2H,m), 3.68(mH), 3.25(1H, dd), 2.68(1H,dd), 2.58(1H,dd), 2.15(2H,q), 1.25(mH), 0.85 (mH), 0.10(6H,s).

Compound 86

R$_f$: 0.80 [methylene chloride:diethyl ether, 4:1 (v/v)]

$^1$H NMR (CDCl$_3$) δ: 7.55 ppm (1H,d,J=8.8 Hz), 5.95(4H, m), 5.30(mH), 4.95(mH), 4.85(1H,t,J=10.0 Hz), 4.78(1H,d, J=3.6 Hz), 4.55(mH), 4.35(1H,m), 4.25(mH), 3.85(mH), 3.71(2H,d), 3.62(1H,m), 3.20(1H,d,J=13.9 Hz), 3.16(1H, m), 2.85(1H,d,J=13.9 Hz), 2.60(2H,m), 2.01(2H,m), 1.55 (mH), 1.20(mH), 0.85(mH), 0.10(6H,2s).

Compound 87

R$_f$: 0.08 [hexanes:ethyl acetate, 1:1 (v/v)]

$^1$H NMR (CDCl$_3$) δ: 7.51 ppm (1H,d,J=9.52 Hz), 5.95 (4H,m), 5.30(mH), 4.95(1H,m), 4.82(2H,m), 4.55(mH), 4.35(1H,m), 4.25(2H,m), 3.85(mH), 3.65(mH), 3.16(mH), 2.84(1H,d,J=14.41 Hz), 2.55(mH), 2.01(mH), 1.55(mH), 1.20(mH), 0.85(6H,t).

Compound 90

R$_f$: 0.39 [methylene chloride:methyl alcohol, 95:5 (v/v)]

$^1$H NMR (CDCl$_3$) δ: 7.62 ppm (1H,d,J=8.0 Hz), 7.20(1H, d,J=8.1 Hz), 5.90(7H,m), 5.46(1H,t,J=10.0 Hz), 5.40–5.15 (mH), 5.05(1H,m), 4.85(mH), 4.50(mH), 4.30(mH), 4.25 (mH), 4.15(mH), 3.90(mH), 3.70(1H,m), 3.60(1H,m), 3.53 (1H,dd), 3.35(mH), 2.70–2.42(8H,m), 2.25(2H,t), 2.00 (mH), 1.80–1.45(mH), 1.37–1.07(mH), 0.85(15H,m).

Analog B235

R$_{f:\ 0.47}$ [chloroform:methyl alcohol:acetic acid:water, 125:75:10:20 (v/v/v/v)]

RT(HPLC):13.43 min.

$^1$H NMR (CDCl$_3$:CD$_3$OD, 1:1, v/v) δ: 5.15 ppm (2H,m), 5.00–4.80(3H,m), 3.94–3.45(mH), 3.20–3.00(mH), 2.40–1.95(10H,m), 1.31–0.75(mH), 0.55(15H,br.s).

$^{13}$C NMR (CDCl$_3$:CD$_3$OD, 1:1, v/v) δ: 208.3 ppm, 207.8, 175.6, 174.1, 172.4, 170.0, 169.4, 102.8, 95.2, 76.8, 74.8, 74.3, 72.6, 71.8, 70.0, 61.5, 55.0, 52.2, 43.8, 43.5, 43.0, 40.2, 38.5, 35.7, 33.2, 30.8,.30.6, 30.4, 30.2, 26.9, 26.5, 26.4, 26.3, 24.8, 23.9, 23.7, 15.0.

Analog B235 (fully protected)

R$_f$: 0.39 [methylene chloride:methyl alcohol, 19:1 (v/v)]

$^1$H NMR (CDCl$_3$) δ: 7.40 ppm (1H,d), 7.13(1H,d), 5.93 (7H,m), 5.70(1H,m), 5.46–5.16(mH), 5.00(1H,m), 4.86(2H, m), 4.67–4.46(mH), 4.38–4.27(mH), 4.18(1H,m), 3.93(1H, d), 3.80–3.60(mH), 3.40–3.30(mH), 2.68–2.42(mH), 2.22 (2H,t), 1.80–0.80(mH).

Analog B272

R$_f$: 0.48 [chloroform:methyl alcohol:acetic acid:water, 125:75:10:20 (v/v/v/v)]

RT(HPLC):14.13 min.

Analog B272 (fully protected)

R$_f$: 0.66 [methylene chloride:methyl alcohol, 19:1 (v/v/v/ v)]

$^1$H NMR (CDCl$_3$) δ: 7.13 ppm (1H,d), 7.05(1H,d), 5.92 (8H,m), 5.69(1H,dd), 5.32(mH), 5.09(1H,m), 4.88(1H,d), 4.80(1H,t), 4.65–4.45(mH), 4.38–4.20(mH), 3.88–3.62 (mH), 3.32(2H,q), 2.58(mH), 2.43(2H,m), 2.25(2H,t), 2.00 (4H,m), 1.58(mH), 1.23(mH), 0.85(15H,m).

Analog B286

R$_f$: 0.43 [chloroform:methyl alcohol:acetic acid:water, 125:75:10:20 (v/v/v/v)]

RT(HPLC):14.70 min.

$^1$H NMR (CDCl$_3$:CD$_3$OD, 3:1, v/v) δ: 6.58 ppm (2H,m), 5.61(2H, d, J=15.3 Hz), 5.28(1H,dd,J=2.9,5.7 Hz), 5.20–5.07(2H,m), 5.00–4.88(3H,m), 4.52(1H,d,J=8.2 Hz), 4.20–4.05(mH), 3.85–3.20(mH), 2.48–1.75(mH), 1.40 (mH), 1.20–1.00(mH), 0.67(15H,m)

$^{31}$P NMR (CDCl$_3$:CD$_3$OD 3:1, v/v) δ: 1.24 ppm, −1.61.

Analog B286 (fully protected)

R$_f$: 0.60 [methylene chloride:methyl alcohol, 95:5 (v/v)]}

$^1$H NMR (CDCl$_3$) δ: 6.88–6.73 ppm (4H,m), 5.98–5.85 (7H,m), 5.83(1H,d), 5.71(2H,m), 5.42–5.20(16H,m), 5.16 (1H,t), 4.98(1H,m), 4.85(2H,dd), 4.67–4.45(mH), 4.41–4.29 (2H,m), 4.18(1H,m), 3.95(1H,dd), 3.88(1H,d), 3.75(1H,m), 3.67(1H,m), 2.63–2.46(3H,m), 2.22(2H,t), 2.12(2H,t), 2.00 (2H,m), 1.78–1.15(mH), 0.84(15H,m)

Analog B287.

R$_f$: 0.49 [chloroform:methyl alcohol:acetic acid:water, 125:75:10:20 (v/v/v/v)]

RT(HPLC):13.70 min.

$^1$H NMR (CDCl$_3$:CD$_3$OD, 3:1, v/v) δ: 5.28 ppm (1H,dd, J=3.6,6.0 Hz), 5.12(2H,m), 4.96(2H,m), 4.87(1H,m), 4.50 (1H,d,J=8.7 Hz), 4.05 (mH), 3.80(mH), 3.60–3.24(mH), 2.40–2.10(mH), 1.80(mH), 0.65(15H,m)

$^{31}$P NMR (CDCl$_3$:CD$_3$OD 3:1, v/v) δ: 0.31 ppm, −1.66.

Analog B287 (fully protected)

R$_f$: 0.68 [methylene chloride:methyl alcohol, 95:5 (v/v)]

$^1$H NMR (CDCl$_3$) δ: 7.14 ppm (1H,d,J=7.9 Hz), 6.80(1H, d,J=8.0 Hz), 5.92(8H,m), 5.70(1H,m), 5.45–5.17(mH), 5.05 (1H,m), 5.02(1H,m), 4.93(1H,d,J=7.9 Hz), 4.86(1H,t), 4.67–4.47(mH), 4.32(mH), 4.19(1H,dd), 3.87(1H,d), 3.66 (mH), 3.32(2H,q), 2.70–2.24(mH), 2.00(mH), 1.55(mH), 1.25(mH), 0.85(15H,m).

Analog B288

R$_f$: 0.82 [chloroform:methyl alcohol:acetic acid:water, 125:75:10:20 (v/v/v/v)]

RT(HPLC):13.48 min. $^1$H NMR (CDCl$_3$:CD$_3$OD, 3:1, v/v) δ: 5.30 ppm (1H,br.s), 5.25–5.10(2H,m), 4.99(1H,t,J= 9.5 Hz), 4.74(1H,t,J=9.4 Hz), 4.39(1H,d,J=8.3 Hz), 4.02 (1H,m), 3.82(2H,m), 3.71–3.10(mH), 2.50–2.10(mH), 1.90–1.70(6H,m), 1.50–0.90(mH), 0.70(15H,t).

$^{13}$C NMR (CDCl$_3$:CD$_3$OD, 3:1, v/v) δ: 205.13 ppm, 205.02, 173.56, 172.44, 170.78, 167.76, 167.32, 130.64, 130.54, 100.68, 94.57, 75.75, 74.65, 72.58, 72.26, 70.10, 68.01, 67.83, 67.55, 60.74, 53.24, 51.04, 42.87, 41.62, 38.46, 38.31, 36.64, 33.74, 33.60, 33.33, 33.18, 32.02, 31.71, 31.63, 31.37, 31.32, 31.27, 31.20, 31.04, 30.86, 29.15, 29.11, 29.08, 29.00, 28.97, 28.93, 28.88, 28.83, 28.80, 28.70, 28.59, 28.51, 28.43, 28.30, 26.67, 25.00, 24.59, 24.37, 22.85, 22.78, 22.11, 21.97, 13.37.

$^{31}$P NMR (CDCl$_3$:CD$_3$OD 3:1, v/v) δ: −1.49 ppm.

Analog B294

R$_f$: 0.69 [chloroform:methyl alcohol:acetic acid:water, 125:75:10:20 (v/v/v/v)]

Analog B294 (fully protected)

R$_f$: 0.40 [methylene chloride:methyl alcohol, 95:5 (v/v)]

RT(HPLC):15.07 min.

$^1$H NMR (CDCl$_3$) δ: 7.41 ppm (1H,d,J=8.2 Hz), 7.09(1H, d,J=8.5 Hz), 6.00–5.82(7H,m), 5.70(1H,m), 5.43–5.20(mH), 5.02(1H,m), 4.87(2H,m), 4.69–4.44(mH), 4.40–4.28(3H, m), 4.18(1H,dd), 3.94(1H,d), 3.78–3.61(4H,m), 3.46(2H, m), 3.38–3.28(5H,m), 2.65–2.42(mH), 2.00(5H,m), 1.64–1.25(mH), 0.86(15H,m).

Analog B300

R$_f$: 0.51 [chloroform:methyl alcohol:acetic acid:water, 125:75:10:20 (v/v/v/v)]

RT(HPLC):13.65 min.

Analog B300 (fully protected)

R$_f$: 0.36 [methylene chloride:methyl alcohol, 95:5 (v/v)]

$^1$H NMR (CDCl$_3$) δ: 7.31 ppm (1H,d,J=8.0 Hz), 6.50(1H, d,J=8.1 Hz), 6.00–5.83(7H,m), 5.78(1H,m), 5.46–5.20(14H, m), 5.00–4.84(3H,m), 4.64–4.46(mH), 4.39–4.28(2H,m), 4.13(1H,m), 3.99(1H,d), 3.90(1H,m), 3.75–3.60(3H,m), 3.47(1H,m), 3.38–3.30(2H,m), 2.65–2.43(6H,m), 2.30(1H, dd), 2.18(1H,dd), 2.00(2H,t), 1.60–1.20(mH), 0.87(15H,m).

Analog B313

R$_f$: 0.57 [chloroform:methyl alcohol:acetic acid:water, 125:75:10:20 (v/v/v/v)]

RT(HPLC):11.75 min.

Analog B313 (fully protected)

R$_f$: 0.71 [methylene chloride:methyl alcohol, 19:1 (v/v)]

$^1$H NMR (CDCl$_3$) δ: 7.37 ppm (1H,d), 6.82(2H,m), 5.91(7H,m), 5.75(1H,t), 5.7(1H,d), 5.41–5.19(mH), 4.96–4.87(2H,m), 4.63–4.48(mH), 4.45–4.30(mH), 4.18 (1H,m), 3.95(1H,d), 3.80–3.60(mH), 3.38(2H,q), 2.65–2.48 (6H,m), 2.24(2H,t), 2.17–1.95(6H,m), 1.70–1.10(mH), 0.85 (15H,m).

Analog E314

R$_f$: 0.48 [chloroform:methyl alcohol:acetic acid:water, 125:75:10:20 (v/v/v/v)]

RT(HPLC):27.93 min.

$^1$H NMR (CDCl$_3$:CD$_3$OD, 3:1, v/v) δ: 5.26 ppm (1H,m), 5.17(1H,m), 5.08(1H,m), 5.00(1H,m), 4.93(2H,m), 4.48 (1H,d,J=7.9 Hz), 4.00(mH), 3.85–3.20(mH), 1.80(4H,m), 1.40–1.00(mH), 0.70(18H,m).

Analog B314 (fully protected)

R$_f$: 0.46 [methylene chloride:methyl alcohol, 19:1 (v/v)]

$^1$H NMR (CDCl$_3$) δ: 7.38 ppm (1H,d,J=7.8 Hz), 6.14(1H, d,J=8.0 Hz), 6.05–5.82(7H,m), 5.70(1H,t), 5.45–5.20(mH), 5.11–4.98(1H,m), 4.90–4.82(2H,m), 4.67–4.42(mH), 4.39–4.22(mH), 4.10(1H,dd), 3.98–3.85(2H,m), 3.83–3.62 (mH), 3.38(2H,q), 2.68–2.30(mH), 2.25(mH), 2.00(4H,m), 1.55(mH), 1.25(mH), 0.85(15H,m).

Analog B318

R$_f$: 0.48 [chloroform:melhyl alcohol:acetic acid:water, 125:75:10:20 (v/v/v/v)]

RT(HPLC):14.05 min.

Analog B318 (fully protected)

R$_f$: 0.44 [methylene chloride:methyl alcohol, 19:1 (v/v)]

$^1$H NMR (CDCl$_3$) δ: 7.40 ppm (1H,d), 6.99(1H,d), 6.05–5.82(7H,m), 5.78(1H,q), 5.46–5.15(mH), 5.02(1H,m), 4.91–4.80(3H,m), 4.70–4.42(mH), 4.38–4.20(mH), 3.90–3.25(mH), 2.93–2.50(mH), 2.25(2H,t), 2.00(mH), 1.90–1.10(mH), 0.85(15H,m).

Analog B377

R$_f$: 0.52 [chloroform:methyl alcohol:acetic acid:water, 125:75:10:20 (v/v/v/v)]

Analog B377 (fully protected)

R$_f$: 0.39 [methylene chloride:methyl alcohol, 19:1 (v/v)]

$^1$H NMR (CDCl$_3$) δ: 7.62 ppm (1H,d,J=8.0 Hz), 7.20(1H, d,J=8.1 Hz), 5.90(7H,m), 5.46(1H,t,J=10.0 Hz), 5.40–5.15 (mH), 5.05(1H,m), 4.85(mH), 4.50(mH), 4.30(mH), 4.25 (mH), 4.15(mH), 3.90(mH), 3.70(1H,m), 3.60(1H,m), 3.53 (1H,dd), 3.35(mH), 2.70–2.42(8H,m), 2.25(2H,t), 2.00 (mH), 1.80–1.45(mH), 1.37–1.07(mH), 0.85(15H,m).

Analog B379

R$_f$: 0.55 [chloroform:methyl alcohol:acetic acid:water, 125:75:10:20 (v/v/v/v)]

RT(HPLC):9.12 min.

$^1$H NMR (CDCl$_3$:CD$_3$OD, 3:2, v/v) δ: 5.14 ppm (2H,m), 5.05(1H,m), 4.92(1H,t), 4.78(2H,m), 4.43(2H,m), 3.92–3.44 (mH), 3.13(2H,m), 2.93(1H,m), 2.70(1H,m), 2.35(3H,m), 2.22(4H,m), 2.12(1H,dd), 1.94(2H,m), 1.74(2H,m), 1.30–0.90(mH), 0.58(15H,t)

Analog B379 (fully protected)

R$_f$: 0.28 [methylene chloride:methyl alcohol, 100:3 (v/v)]

$^1$H NMR (CDCl$_3$) δ: 7.62 ppm (1H,d), 7.08(1H,d), 5.90 (7H,m), 5.70(1H,dd), 5.40–5.20(17H,m), 5.00(1H,m), 4.82 (2H,m), 4.65–4.46(15H,m), 4.35(2H,m), 4.20(1H,dd), 3.90 (1H,m), 3.67(1H,m), 3.35(3H,m), 3.20(1H,m), 3.10(1H,m), 2.70(1H,dd), 2.58(2H,m), 2.47(3H,m), 2.26(2H,m), 2.03 (2H,m), 1.65–1.10(mH), 0.85(15H,t).

Analog B385

R$_f$: 0.58 [chloroform:methyl alcohol:acetic acid:water, 125:75:10:20 (v/v/v/v)]

RT(HPLC):18.55 min.

Analog B385 (fully protected)

R$_f$: 0.40 [methylene chloride:methyl alcohol, 97:3 (v/v)]

$^1$H NMR (CDCl$_3$) δ: 6.52 ppm (1H,d), 5.93–5.85(7H,m), 5.71(1H,m), 5.59(1H,br.s), 5.47(1H,br.s), 5.45–5.21(mH), 5.18(1H,m), 4.99(1H,m), 4.83(2H,m), 4.66–4.45(mH), 4.40–4.25(mH), 4.18(1H,m), 3.95–3.65(mH), 2.70–2.46 (mH), 2.25(2H,t), 2.15–1.99(mH), 1.67–1.20(mH), 0.85 (15H,m).

Analog B387

R$_f$: 0.50 [chloroform:methyl alcohol:acetic acid:water, 125:75:10:20 (v/v/v/v)]
RT(HPLC):19.05 min.

Analog B387 (fully protected)

R$_f$: 0.75 [methylene chloride:methyl alcohol, 95:5 (v/v)]
$^1$H NMR (CDCl$_3$) δ: 6.60 ppm (1H,d), 5.99–5.86(7H,m), 5.70(1H,m), 5.44(1H,m), 5.42–5.21(mH), 5.12(1H,d), 4.65–4.44(mH), 4.35–4.26(mH), 4.05(mH), 3.90(mH), 2.72–2.48(mH), 2.35(mH), 2.25(mH), 2.14–1.94(mH), 1.58–1.18(mH), 0.89(15H,m).

Analog B388

R$_f$: 0.60[chloroform:methyl alcohol:acetic acid:water, 125:75:10:20 (v/v/v/v)]RT(HPLC):13.92 min.

Analog B388 (fully protected)

R$_f$: 0.80 [methylene chloride:methyl alcohol, 19:1 (v/v)]
$^1$H NMR (CDCl$_3$) δ: 7.09 ppm (1H,d), 6.84(2H,m), 6.00–5.86(7H,m), 5.84(1H,dd,J=3.0,17.0 Hz), 5.69(1H,dd, J=3.9,5.2 Hz), 5.46–5.22(mH), 5.18(1H,dd), 5.01(1H,m), 4.86(1H,d,J=7.4 Hz), 4.80(1H,t,J=9.4 Hz), 4.68–4.46(mH), 4.40–4.25(2H,m), 4.20(1H,m), 3.99(1H,q), 3.87(1H,d,J= 11.5 Hz), 3.75(1H,dd), 3.68(1H,m), 3.58(2H,dd), 3.34(2H, d), 2.69–2.50(4H,m), 2.45(2H,t), 2.23(2H,t), 2.12(2H,m), 2.08–1.98(4H,m), 1.67–1.16(mH), 0.88(15H,m).

Analog B398

R$_f$: 0.49 [chloroform:methyl alcohol:acetic acid:water, 125:75:10:20 (v/v/v/v)]
RT(HPLC):7.12 min.
$^1$H NMR (CD$_3$OD) δ: 5.42 ppm (1H,m), 5.37(1H,t), 5.38(1H,m), 5.26(1H,m), 5.18(1H,m), 4.70(1H,d,J=8.6 Hz), 4.22–3.82(mH), 3.76(1H,d,J=11.4 Hz), 3.55(1H,t,J=11.0 Hz), 3.42(1H,d,J=10.3 Hz), 2.72–2.60(5H,m), 2.42(1H,dd, J=8.6,17.1 Hz), 2.31(2H,t), 2.18–2.00(6H,m), 1.77–1.58 (4H,m), 1.50–1.23(mH), 0.87(15H,m).
$^{13}$C NMR (CD$_3$OD) δ: 207.2 ppm, 206.8, 176.0, 174.7, 173.0, 170.8, 170.2, 133.0, 130.8, 103.6, 96.2, 82.5, 82.4, 81.0, 80.8, 78.0, 77.9, 77.8, 75.7, 75.6, 75.5, 74.8, 74.7, 73.3, 72.4, 72.1, 70.4, 70.2, 69.9, 62.4, 56.8, 54.2, 44.5, 44.2, 44.0, 41.0, 39.7, 36.4, 35.6, 33.8, 33.5, 32.0, 31.7, 31.2, 30.8, 29.0, 28.5, 27.8, 27.4, 27.3, 25.3, 25.1, 24.8, 20.3, 20.0, 19.9, 15.5.

Analog B400

R$_f$: 0.36 [chloroform:methyl alcohol:acetic acid:water, 125:75:10:20 (v/v/v/v)]
RT(HPLC):14.27 min.

Analog B400 (fully protected)

R$_f$: 0.21 [methylene chloride:methyl alcohol, 98:2 (v/v)]
$^1$H NMR (CDCl$_3$) δ: 7.43 ppm (1H,d), 7.08(1H,d), 6.98 (1H,ddd), 6.92(7H,m), 6.80(1H,dd), 6.70(1H,dd), 5.43–5.18 (17H,m), 5.00(1H,m), 4.87(2H,m), 4.65–4.30(mH), 4.18 (1H,ddd), 3.93(1H,dd), 3.82(1H,q), 3.70(2H,m), 3.33(4H, m), 2.58(2H,m), 2.46(4H,q), 2.17(2H,q), 1.64–1.20(mH), 0.85(12H,t).

Analog B406

R$_f$: 0.35 [chloroform:methyl alcohol:acetic acid:water, 125:75:10:20 (v/v/v/v)]
RT(HPLC):13.95 min.

Analog B406 (fully protected)

R$_f$: 0.33 [methylene chloride:methyl alcohol, 19:1 (v/v)]
$^1$H NMR (CDCl$_3$) δ: 7.32 ppm (1H,d), 7.17(1H,t), 6.05–5.85(7H,m), 5.73(1H,m), 5.45–5.20(mH), 5.22(1H, m), 4.91–4.8(2H,m), 4.68–4.43(mH), 4.40–4.28(mH), 4.20 (1H,m), 3.91(1H,dd), 3.82–3.75(mH), 3.59 (1H,q), 3.42–3.29(mH), 2.72(2H,d), 2.35–2.20(mH), 2.25(2H,t), 2.10–1.91(mH), 1.65(2H,t), 1.50(mH), 1.25(mH), 0.85 (15H,m).

Analog B410

R$_f$: 0.51 [chloroform:methyl alcohol:acetic acid:water, 125:75:10:20 (v/v/v/v)]
RT(HPLC):13.70 min.
$^1$H NMR (CDCl$_3$:CD$_3$OD, 3:1, v/v) δ: 5.28 ppm (1H, br.s), 5.17(1H,m), 5.09(1H,m), 5.00(1H,m), 4.95(1H,t,J=9.6 Hz), 4.46 (1H,d,J=8.1 Hz), 4.09(1H,m), 3.85–3.46(mH), 3.25(3H,m), 2.45–2.25(6H,m), 2.06(2H,t), 1.80(4H,m), 0.65 (15H,m).
$^{31}$P NMR (CDCl$_3$:CD$_3$OD, 3:1, v/v) δ: 1.32 ppm, −1.12.

Analog B410 (fully protected)

R$_f$: 0.41 [methylene chloride:methyl alcohol, 97:3 (v/v)]
$^1$H NMR (CDCl$_3$) δ: 7.50 ppm (2H,dd), 5.92(7H,m), 5.80(1H,m), 5.42–5.23(17H,m), 4.80(2H,m), 4.74(1H,t), 4.62–5.00(15H,m), 4.33(2H,m), 4.11(2H,m), 3.85(1H,t), 3.68(2H,m), 3.42(2H,d), 3.36(2H,s), 2.78(2H,d), 2.50(4H, q), 2.22(2H,t), 2.00(4H,m), 1.80–1.50(1H,m), 1.25(mH), 0.85(15H,m).

Analog B415

R$_f$: 0.50 [chloroform:methyl alcohol:acetic acid:water, 125:75:10:20 (v/v/v/v)]
RT(HPLC):12.62 min.

Analog B415 (fully protected)

R$_f$: 0.20 [methylene chloride:methyl alcohol, 98:2 (v/v)]
$^1$H NMR (CDCl$_3$) δ: 7.53 ppm (1H,d), 7.04 (1H,d), 5.94 (7H,m) 5.73(1H,m), 5.43–5.20(17H,m), 5.02(1H,m), 4.88 (2H,m), 4.58(15H,m), 4.37(1H,m), 4.28(1H,dd), 4.18(1H,t), 4.12(1H,t), 3.95(1H,dd), 3.86(1H,t), 3.78(1H,dd), 3.67(1H, m), 3.59(2H,m), 3.44(3H,m), 3.32(2H,q), 2.55(4H,m), 2.45 (2H,t), 2.02(4H,m), 1.78(2H,m), 1.68–1.20(mH), 0.87(15H, m).

Analog B425

R$_f$: 0.62 [chloroform:methyl alcohol:acetic acid:water, 125:75:10:20 (v/v/v/v)]
RT(HPLC):14.05 min.
$^1$H NMR (CD$_3$OD:CDCl$_3$, 2:1, v/v) δ: 5.40–5.12 ppm (mH), 4.18–3.70(mH), 3.45–3.19(mH), 2.60(mH), 2.25(2H, t), 2.00(mH), 1.80(mH), 1.65–1.15(mH), 0.85(15H,m).

Analog B425 (fully protected)

R$_f$: 0.75 [methylene chloride:methyl alcohol, 95:5 (v/v)]
$^1$H NMR (CDCl$_3$) δ: 7.45 ppm (1H,d), 6.84(1H,d), 5.95 (7H,m), 5.80(1H,m), 5.46–5.22(mH), 5.05(1H,m), 4.85 (mH), 4.67–4.48(mH), 4.30(mH), 3.95–3.80(mH), 3.75(2H, d), 3.65(1H,m), 3.25(mH), 3.15(2H,t), 2.65(mH), 2.60(1H, d), 2.55(1H,d), 2.25(2H,t), 2.00(mH), 1.80(mH), 1.65–1.20 (mH), 0.85(15H,m).

Analog B426

R$_f$: 0.44 [chloroform:methyl alcohol:acetic acid:water, 125:75:10:20 (v/v/v/v)]
RT(HPLC):14.63 min.

Analog B426 (fully protected)

R$_f$: 0.50 [methylene chloride:methyl alcohol, 95:5 (v/v)]
$^1$H NMR (CDCl$_3$) δ: 7.38 ppm (1H,d), 7.11(1H,d), 5.95 (7H,m), 5.72(1H,m), 5.65(mH), 5.42–5.18(mH), 5.05(mH), 4.95(1H,t), 4.85(1H,d), 4.68–4.25(mH), 3.95(1H,m), 3.79 (mH), 3.55–3.30(mH), 2.68(2H,t), 2.58(2H,t), 2.45(mH), 2.25(2H,t), 2.00(mH), 1.69–1.45(mH), 1.30–1.15(mH), 0.85 (15H,m).

Analog B427

R$_f$: 0.62 [chloroform:methyl alcohol:acetic acid:water, 125:75:10:20 (v/v/v/v)]
RT(HPLC):14.17 min.
$^1$H NMR (CDCl$_3$:CD$_3$OD, 3:1, v/v) δ: 5.37 ppm (1H,m), 5.27(1H,m), 5.17(1H,m), 4.78(1H,m), 4.53(1H,d,J=6.3 Hz), 4.04–3.20(mH), 2.43(4H,m), 2.15(2H,t), 1.95–1.83(4H,m), 1.70–0.95(mH), 0.75(15H,t).
$^{31}$P MMR (CDCl$_3$:CD$_3$OD, 3:1, v/v) δ: 1.24 ppm, −1.40.

Analog B442

¹H NMR (CDCl₃:CD₃OD, 2:1, v/v) δ: 5.20 ppm (mH), 5.13(mH), 4.95(mH), 4.75(mH), 3.85–3.28(mH), 2.68(mH), 2.40(mH), 2.10(2H,t), 1.80(mH), 1.65–1.00(mH), 0.70 (15H,m).

Analog B442 (fully protected)

¹H NMR (CDCl₃) δ: 7.60–7.50 ppm (2H,2d), 5.95(7H, m), 4.88(1H,m), 4.70–4.45(mH), 4.35(2H,m), 4.15(mH), 3.85–3.45 (mH), 2.88(mH), 2.65(2H,t), 2.25(2H,t), 2.00 (mH), 1.78–1.23(mH), 0.85(15H,m).

Analog B451

$R_f$: 0.45 [chloroform:methyl alcohol:acetic acid:water, 125:75:10:20 (v/v/v/v)]

RT(HPLC):12.37 min.

¹H NMR (CDCl₃:CD₃OD, 3:1, v/v) δ: 5.35 ppm (1H,dd, J=3.4,6.6 Hz), 5.17(1H,m), 5.09(1H,m), 4.92(1H,t,J=10.3 Hz), 4.90(1H,m), 4.56(1H,J=8.4 Hz), 4.00(2H,m), 3.80–3.20(mH), 3.18(3H,s), 3.17(1H,t), 2.68(4H,m), 2.36 (2H,ABX,J=4.5,8.4,16.1 Hz), 2.10(2H,t), 1.80(4H,m), 1.55–1.05(mH), 0.67(15H,m).

³¹P NMR (CDCl₃:CD₃OD, 3:1, v/v) δ: –0.51 ppm, –1.41.

Analog B451 (fully protected)

$R_f$: 0.19 [methylene chloride:methyl alcohol, 95:5 (v/v)]

¹H NMR (CDCl₃) δ: 7.74 ppm (1H,d), 7.54(1H,d), 5.92 (6H,m), 5.85(1H,m), 5.44–5.20(16H,m), 4.86(2H,m), 4.70 (1H,t), 4.63(9H,m), 4.50(4H,m), 4.38(1H,q), 4.17(1H,m), 4.08(1H,m), 3.82–3.46(8H,m), 3.38(3H,s), 2.96–2.73(4H, m), 2.62(2H,m), 2.26(2H,m), 2.00(4H,m), 1.80–1.18(mH), 0.85(15H,m).

Analog B452

$R_f$: 0.44 [chloroform:methyl alcohol:acetic acid:water, 125:75:10:20 (v/v/v/v)]

RT(HPLC):10.30 min.

¹H NMR (CDCl₃:CD₃OD, 3:1, v/v) δ: 5.34 ppm (1H,m), 5.18(1H,m), 4.95(1H,t,J=9.6 Hz), 4.93(1H,m), 4.50(1H,d,J= 8.3 Hz), 4.05(1H,m), 3.92–3.60(mH), 3.50–3.20(mH), 2.65 (2H,m), 2.40–2.10(mH), 1.85(4H,m), 1.55–1.00(mH), 0.70 (15H,m).

¹³C NMR (CDCl₃:CD₃OD, 3:1, v/v) δ: 173.52 ppm, 172.22, 170.24, 164.80, 164.62, 130.71, 127.87, 100.08, 94.05, 74.49, 73.09, 72.26, 71.68, 69.72, 68.01, 67.49, 66.94, 59.99, 57.58, 56.96, 55.94, 53.83, 51.80, 42.15, 38.61, 36.90, 34.07, 33.43, 32.03, 31.49, 31.40, 29.25, 29.20, 28.93, 28.83, 28.58, 28.37, 28.27, 26.81, 26.12, 25.20, 24.70, 24.54, 23.68, 22.24, 21.37, 13.52.

³¹P NMR (CDCl₃:CD₃OD, 3:1, v/v) δ: 1.24 ppm, –1.65.

Analog B452 (fully protected)

$R_f$: 0.47 [methylene chloride:methyl alcohol, 95:5, (v/v)]

¹H NMR (CDCl₃) δ: 7.48 ppm (1H,d), 7.03(1H,d), 5.95 (7H,m), 5.79(1H,m), 5.45–5.18(mH), 5.03(1H,m), 4.85 (mH), 4.75–4.50(mH), 4.30(mH), 4.25(1H,m), 3.91(1H,dd), 3.78–3.60(mH), 3.55(mH), 3.30(2H,d), 2.90–2.50(mH), 2.25(2H,t), 2.00(mH), 1.80–1.15(mH), 0.85(15H,m).

Analog B459

$R_f$: 0.49 [chloroform:methyl alcohol:acetic acid:water, 125:75:10:20 (v/v/v/v)]

RT(HPLC):13.37–14.13 min (multiple peaks)

¹H NMR (CDCl₃:CD₃OD, 3:1, v/v) δ: 5.42 ppm(1H,br.s), 5.25(1H,m), 5.17(1H,m), 4.75(1H,m), 4.64(1H,d,J=7.7 Hz), 4.53(1H,m), 4.00(1H,m), 3.90–3.20(mH), 2.80(4H,m), 2.15 (2H,t), 1.90–1.80(4H,m), 1.70–1.00(mH), 0.75(15H,br.s).

³¹P NMR (CDCl₃:CD₃OD, 3:1, v/v) δ: 1.39 ppm, –1.51.

Analog B459 (fully protected)

$R_f$: 0.43 [methylene chloride, 95:5 (v/v)]

¹H NMR (CDCl₃) δ: 7.68–7.50 ppm (2H,m), 5.95(7H,m), 5.85(1H,m), 5.42–5.23(12H,m), 4.93(1H,m), 4.82(1H,m), 4.76(1H,m), 4.66–4.55(mH), 4.31(1H,m), 4.26(1H,q), 4.12 (2H,m), 3.83–3.42(mH), 2.95–2.84(4H,m), 2.26(2H,t), 2.00 (4H,m), 1.80–1.18(mH), 0.85(15H,m).

Analog B460

$R_f$: 0.63 [chlcroform:methyl alcohol:acetic acid:water, 125:75:10:20 (v/v/v/v)]

RT(HPLC):14.52 min.

¹H NMR (CDCl₃:CD₃OD, 3:1, v/v) δ: 5.34 ppm (1H,m), 5.19(1H,m), 5.11(1H,m), 4.68(1H,m), 4.41(1H,d,J=8.1 Hz), 3.90(1H,m), 3.81–3.12(mH), 2.70(4H,q), 2.10(2H,t), 1.80 (4H,m), 1.58–0.90(mH), 0.65(15H,t).

³¹P NMR (CDCl₃:CD₃OD, 3:1, v/v) δ: 1.38 ppm, –1.30.

Analog B460 (fully protected)

¹H NMR (CDCl₃) δ: 7.68 ppm (1H,d), 7.53(1H,d), 5.95 (7H,m), 5.83(1H,m), 5.45–5.21(mH), 4.95(1H,m), 4.82 (mH), 4.72(2H,q), 4.55(mH), 4.28(mH), 4.10(mH), 3.80 (1H,d), 370–3.55(mH), 3.51–3.45 (mH), 2.95–2.81( H), 2.25(2H,t), 2.00 (mH), 1.75(mH) 1.45(mH), 1.25(mH), 0.85 (15H,m).

Analog B465

$R_f$: 0.83 [chloroform:methyl alcohol:acetic acid:water, 125:75:10:20 (v/v/v/v)]

RT(HPLC):13.53 min.

¹H NMR (CDCl₃:CD₃OD, 2:1, v/v) δ: 5.34 ppm (1H,dd, J=3.3,6.7 Hz), 5.19(1H,m), 5.11(1H,m), 4.69(1H,m), 4.54 (1H,d,J=7.9 Hz), 3.92(1H,m), 3.83–3.24(mH), 2.70(4H,m), 2.10(2H,t), 1.80(4H,m), 1.60–0.95(mH), 0.65(15H,m).

³¹P NMR (CDCl₃:CD₃OD, 2:1, v/v) δ: 1.32 ppm, –1.40.

Analog B465 (fully protected)

¹H NMR (CDCl₃) δ: 7.55ppm (2H,m), 5.93(7H,m), 5.80 (1H,m), 5.50–5.25(mH), 4.90(2H,m), 4.75–4.50(mH), 4.30 (2H,m), 4.13(1H,m), 3.85–3.40(mH), 2.95–2.80(4H,m), 2.26(2H,t), 2.00(4H,m), 1.80–0.80(mH).

Analog B466

$R_f$: 0.51 [chloroform:methyl alcohol:acetic acid:water, 125:75:10:20 (v/v/v/v)]

RT(HPLC):14.45 min

¹H NMR (CDCl₃:CD₃OD, 3:1, v/v) δ: 5.36 ppm (1H,dd, J=3.2,6.7 Hz), 5.18(1H,m), 5.09(1H,m), 4.65(1H,m), 4.48 (1H,d,J=8.3 Hz), 3.90–3.24(mnH), 3.17(3H,s), 2.70(4H,q), 2.10(2H,t), 1,8-(4H,m), 1.55–1.00(mH), 0.65(15H,t).

³¹P NMR (CDCl₃:CD3OD, 3:1, v/v) δ: –0.67 ppm, –1.50.

Analog B466 (fully protected)

¹H NMR (CDCl₃) δ: 7.67 ppm (1H,d), 7.55(1H,d), 6.03–5.88(6H,m), 5.84(1H,m), 5.46–5.21(mH), 4.92(1H, m), 4.88–4.50(mH), 4.32(1H,q), 4.10(1H,m), 3.88–3.43 (mH), 3.37(3H,s), 3.0–2.79(2H,m), 2.30(2H,t), 2.10–1.25 (mH), 0.85(15H,m).

Analog B477

$R_f$: 0.53 [chloroform:methyl alcohol:acetic acid:water, 125:75:10:20 v/v/v/v)]

RT(HPLC):13.48 min

¹H NMR (CDCl₃:CD₃OD, 3:1, v/v) δ: 5.36 ppm (1H,dd, J=3.3,6.8 Hz), 5.18(1H,m), 5.10(1H,m), 4.70(1H,m), 4.57 (1H,d,J=8.2 Hz), 3.90–3.25(mH), 3.20(3H,s), 2.73(4H,m), 2.10(2H,t), 1.80(4H,m), 1.65–0.90(mH), 0.70(15H,t).

³¹P NMR (CDCl₃:CD₃OD, 3:1, v/v) δ: –0.64 ppm, –1.44.

Analog B477 (fully protected)

$R_f$: 0.41 [methylene chloride:methyl alcohol, 95:5 (v/v)]

¹H NMR (CDCl₃) δ: 7.56 ppm (2H,m), 5.93(6H,m), 5.82(1H,m), 5.44–5.24(12H,m), 4.90(1H,m), 4.70(1H,t), 4.66–4.53(mH), 4.32(1H,q), 4.12(1H,m), 3.85–3.42(mH), 3.38(3H,s), 2.93–2.82(mH), 2.26(2H,t), 2.00(4H,m), 1.80–1.20(mH), 0.85(15H,m).

Analog B479

$R_f$: 0.97 [chloroform:methyl alcohol:acetic acid:water, 125:75:10:20 (v/v/v/v)]

Analog B510

R$_f$: 0.47 [chloroform:methyl alcohol:acetic acid:water, 125:75:10:20 (v/v/v/v)].

RT(HPLC):6.37 min.

$^1$H NMR (CDCl$_3$:CD$_3$OD, 3:1, v/v) δ: 5.36 ppm (1H, br.s), 4.55(1H,d,J=8.2 Hz), 4.00–3.20(mH), 3.23(3H,s), 2.40 (4H,br.s), 1.60–0.70(mH).

$^{13}$C NMR (CDCl$_3$:CD$_3$OD, 3:1, v/v) δ: 205.96 ppm, 205.80, 167.85, 167.19, 100.14, 94.74, 80.13, 78.70, 74.03, 73.61, 73.18, 70.50, 69.56, 69.16, 68.85, 67.08, 58.21, 54.45, 52.20, 52.13, 42.89, 42.76, 37.26, 37.23, 36.62, 36.36, 31.36, 30.42, 29.21, 29.09, 29.01, 28.95, 28.78, 28.57, 28.51, 25.20, 25.10, 22.79, 22.09, 13.25.

$^{31}$P NMR (CDCl$_3$:CD$_3$OD, 3:1, v/v) δ: −0.72 ppm, −1.49.

Analog B464

R$_f$: 0.51 [chloroform:methyl alcohol:acetic acid:water, 125:75:10:20 (v/v/v/v)]

RT(HPLC):17.62 min.

$^1$H NMR (CDCl$_3$:CD$_3$OD, 3:1, v/v) δ: 5.29 ppm (1H,m), 5.18(1H,m), 5.09(1H,m), 4.70(1H,m), 4.44(mH), 3.88(2H, m), 3.72–3.12(mH), 3.16(3H,s), 2.36(4H,m), 2.07(2H,t), 1.87–1.76(4H,m), 1.60–0.92(mH), 0.65(15H,m).

$^{13}$C NMR (CDCl$_3$:CD$_3$OD, 3:1, v/v) δ: 206.07 ppm, 206.00, 174.15, 167.99, 167.15, 130.69, 127.82, 100.22, 94.98, 80.12, 78.86, 74.88, 74.82, 73.72, 72.84, 71.81, 70.70, 69.74, 69.17, 67.28, 58.38, 55.12, 54.21, 52.12, 43.08, 42.98, 42.78, 37.37, 36.65, 34.47, 34.19, 33.63, 32.14, 31.48, 31.35, 29.41, 29.25, 29.22, 29.14, 29.08, 29.05, 28.93, 28.91, 28.87, 28.72, 28.62, 28.54, 26.78, 26.13, 25.32, 24.82, 24.63, 22.94, 22.88, 22.22, 13.47.

$^{31}$P NMR (CDCl$_3$:CD$_3$OD, 3:1, v/v) δ: −0.629 ppm, −1.431.

Analog B587

R$_f$: 0.62 [chloroform:methyl alcohol:acetic acid:water, 125:75:10:20 (v/v/v/v)]

RT(HPLC):14.80 min.

$^1$H NMR (CDCl$_3$:CD$_3$OD, 3:1, v/v) δ: 5.26 ppm (1H,m), 5.17(1H,m), 5.10(1H,m), 4.70(1H,m), 4.49(1H,d,J=8.10 Hz), 3.91–3.29(mH), 3.28(3H,s), 3.24–3.20(mH), 3.17(3H, s), 3.12(mH), 2.89(1H,t,J=9.30 Hz), 2.34(4H,m), 2.08(2H,t), 1.89–1.75(4H,m), 1.62–0.92(mH), 0.64(15H,m).

$^{13}$C NMR (CDCl$_3$:CD$_3$OD, 3:1, v/v) δ: 206.41 ppm, 205.56, 174.17, 167.80, 167.18, 130.69, 127.83, 99.93, 94.62, 80.18, 79.50, 78.92, 74.78, 73.84, 72.31, 71.83, 70.77, 69.84, 69.06, 68.27, 67.88, 66.93, 64.48, 61.86, 59.96, 58.49, 54.98, 52.53, 50.60, 43.15, 42.89, 37.30, 36.99, 34.44, 34.17, 33.64, 31.48, 31.40, 31.35, 29.34, 29.22, 29.13, 29.08, 28.93, 28.84, 28.70, 28.61, 28.54, 26.79, 26.14, 25.29, 24.81, 24.62, 22.92, 22.86, 22.22, 13.49.

$^{31}$P NMR (CDCl$_3$:CD$_3$OD, 3:1, v/v) δ: −0.67 ppm, −1.509.

Analog B718

R$_f$: 0.40 [chloroform:methyl alcohol:acetic acid:water, 125:75:10:20 (v/v/v/v)]

RT(HPLC):13.65 min.

$^1$H NMR (CDCl$_3$:CD$_3$OD, 3:1 v/v) δ: 5.34 ppm (1H,br.s), 5.20(1H,m), 5.12(1H,m), 4.70(2H,m), 4.32(1H,d,J=8.0 Hz), 4.0–3.85(mH), 3.70–3.20(mH), 3.18(3H,s), 3.22–3.13(mH), 2.35(mH), 2.08(2H,t), 1.90(3H,s), 1.90–1.77(4H,m), 1.63–1.00(mH), 0.67(mH).

$^{13}$C NMR (CDCl$_3$:CD$_3$OD, 3:1 v/v) δ: 206.35 ppm, 205.88, 174.23, 169.94, 168.25, 167.20, 130.80, 127.94, 100.45, 94.44, 80.48, 74.68, 74.38, 73.93, 71.89, 70.65, 69.70, 69.28, 69.20, 68.39, 67.02, 58.59, 54.85, 52.19, 43.23, 43.07, 37.31, 36.97, 34.50, 34.26, 33.74, 31.50, 31.45, 31.08, 29.43, 29.37, 29.32, 29.28, 29.20, 29.17, 29.14, 29.04, 29.01, 28.94, 28.84, 28.71, 28.64, 26.89, 26.25, 25.37, 24.89, 24.72, 23.03, 22.97, 22.33, 22.30, 20.43., 13.78, 11.98.

$^{31}$P NMR (CDCl$_3$:CD$_3$OD, 3:1, v/v) δ: −0.63 ppm, −1.59.

Analog B725

R$_f$: 0.58 [chloroform:methyl alcohol:acetic acid:water, 125:75:10:20 (v/v/v/v)]

RT(HPLC):17.58 min.

$^1$H MMR (CDCl$_3$:CD$_3$OD, 3:1, v/v) δ: 5.32 ppm (1H, br.s), 5.24(1H,m), 5.12(1H,m), 4.78(1H,m), 4.36(1H,d), 4.04–3.00(mH), 3.34(3H,s), 2.36(4H,m), 2.10(2H,t), 1.85 (4H,m), 1.60–1.10(mH), 0.67(15H,t).

$^{13}$C NMR (CDCl$_3$:CD$_3$OD, 3:1, v/v) δ: 206.06 ppm, 205.94, 174.02, 167.82, 167.20, 130.87, 127.82, 101.11, 94.88, 81.24, 79.45, 78.93, 77.30, 73.69, 72.58, 71.53, 70.04, 69.82, 69.40, 69.01, 68.02, 64.72, 59.95, 55.31, 52.30, 49.00, 48.78, 48.57, 48.36, 48.14, 47.93, 47.72, 43.15, 43.07, 37.39, 36.67, 34.89, 34.21, 33.75, 31.54, 31.45, 31.42, 29.41, 29.27, 29.20, 29.15, 28.99, 28.88, 28.77, 28.70, 28.61, 26.87, 26.22, 25.37, 24.89, 24.74, 23.03, 22.96, 22.29, 22.26, 13.57.

$^{31}$P NMR (CDCl$_3$:CD$_3$OD, 3:1, v/v) δ:0.74 ppm, −1.27.

Analog B736

R$_f$: 0.57 [chloroform:methyl alcohol:acetic acid:water, 125:75:10:20 (v/v/v/v)]

RT(HPLC):12.57 min.

$^1$H NMR (CDCl$_3$:CD$_3$OD, 3:1, v/v) δ: 5.20 ppm (1H,m), 5.10(1H,m), 4.70(1H,m), 4.53(1H,d,J=3.5 Hz), 4.40(1H,d, J=7.7 Hz), 3.90–3.20(mH), 3.18(3H,s), 2.34(4H,q), 2.10 (2H,t), 1.85(4H,m), 1.70–0.90(mH), 0.65(15H,m).

$^{13}$C NMR (CDCl$_3$:CD$_3$OD, 3:1, v/v) δ: 206.00 ppm, 205.81, 174.05, 167.52, 167.01, 130.62, 127.71, 100.47, 97.33, 80.00, 79.66, 74.71, 73.69, 71.67, 70.67, 70.56, 69.64, 69.42, 69.24, 69.12, 67.84, 66.51, 65.00, 58.35, 58.34, 55.21, 52.02, 43.05, 42.88, 37.23, 36.60, 34.42, 34.10, 33.55, 31.39, 31.37, 31.30, 31.25, 29.26, 29.17, 29.12, 29.08, 29.03, 28.99, 28.95, 28.86, 28.84, 28.81, 28.74, 28.63, 28.55, 28.45, 26.70, 26.04, 25.23, 24.74, 22.88,22.80, 22.13, 22.10, 13.38.

$^{31}$P NMR (CDCl$_3$:CD$_3$OD, 3:1, v/v) δ: 0.99 ppm, −0.48.

Analog B737

R$_f$: 0.71 [chloroform:methyl alcohol:acetic acid:water, 125:75:10:20 (v/v/v/v)]

RT(HPLC):12.45 min.

$^1$H NMR (CDCl$_3$:CD$_3$OD, 3:1, v/v) δ: 5.31 ppm (1H,m), 5.29(1H,m), 5.10(1H,m), 4.71(1H,m), 4.46(1H,d,J=8.0 Hz), 4.20(1H,t), 4.07(1H,t,J=4.14 Hz), 3.98–3.81(mH), 3.72–3.27(mH), 3.17(3H,s), 3.12(mH), 2.33(4H,m), 2.07 (2H,t), 1.90–1.78(mH), 1.60–0.98(mH), 0.65(15H,m).

$^{13}$C NMR (CDCl$_3$:CD$_3$OD, 3:1, v/v) δ: 206.1 ppm, 179.7, 174.1, 168.0, 167.2, 130.7, 127.8, 100.3, 94.2, 90.3, 84.0, 80.1, 74.8, 73.8, 71.8, 70.6, 70.4, 70.1, 69.5, 69.1, 68.1, 66.9, 66.7, 64.7, 58.2, 55.1, 51.9, 43.0, 42.9, 37.3, 36.7, 34.4, 34.2, 33.6, 32.5, 31.5, 31.4, 31.3, 29.3, 29.2, 29.1, 29.0, 28.9, 28.8, 28.7, 28.6, 28.5, 28.4, 26.8, 26.1, 25.3, 24.8, 24.6, 22.9, 22.2, 13.5.

$^{31}$P NMR (CDCl$_3$:CD$_3$OD, 3:1, v/v) δ: −0.635 ppm, −1.634.

$^{19}$F NMR (CDCl$_3$:CD$_3$OD, 3:1, v/v) δ: 1.62 ppm.

Analog B763

R$_f$: 0.92 [chloroform:methyl alcohol:acetic acid:water, 125:75:10:20 (v/v/v/v)]

RT(HPLC):13.70 min.

Compound 92

R$_f$: 0.26 [hexanes:ethyl acetate, 4:1 (v/v)]

$^1$H NMR (CDCl$_3$) δ: 5.95 ppm (1H,m), 5.32(1H,d,J=17.2 Hz), 5.28(1H,d,J=10.4 Hz), 4.80(mH), 4.58(2H,d), 4.50(1H, d,J=7.40 Hz), 4.08(1H,q), 3.78–3.49(mH), 3.30–3.13 ( mH), 2.30 (1H$_{OH}$,s). 2.06(3H,s), 1.80(mH), 1.55(mH) 1.25(mH), 0.89(9H,s), 0.83(3H,t), 0.11(6H,s).

Compound 93

$^1$H NMR (CDCl$_3$) δ: 5.92 ppm (1H,m), 5.36(1H,dd,J=1.4, 17.3 Hz), 5.28(1H,dd,J=1.2, 10.5 Hz), 4.88(1H,m), 4.62(2H, m), 4.48(1H,d,J=7.6 Hz), 3.87–3.67(mH), 3.50(3H,s), 3.22–3.13(3H,m), 3.07(1H,dd,J=8.3, 9.7 Hz), 1.90(3H,m), 1.60(2H,m), 1.23(mH), 0.90(9H,s), 0.85(3H,t), 0.12(6H,2s).

Compound 94

R$_f$: 0.69 [hexanes:ethyl acetate, 2:1 (v/v)]

$^1$H NMR (CDCl$_3$) δ: 5.94(1H,m), 5.35(1H,d,J=15.5 Hz), 5.25(1H, d,J=9.3 Hz), 4.89(1H,m), 4.62(2H,m), 4.54(1H,d, J=7.4 Hz), 4.46–4.28(1H,ddd,J=7.7,10.1,50.0 Hz), 3.90–3.68(mH), 3.43(1H,m), 3.33–3.19(2H,m), 1.88(2H, m), 1.77(1H,t), 1.26(mH, br.s), 0.88(9H,s), 0.86(3H,t), 0.15 (6H,2s).

Compound 95

R$_f$: 0.06 [hexanes:ethyl acetate, 1:1 (v/v)]

$^1$H NMR (CDCl$_3$) δ: 5.93 ppm (4H,m), 5.27(8H,m), 4.92(1H,d,J=3.5 Hz), 4.78(1H,m), 4.70–4.55(8H,m), 4.21 (1H,m), 3.88–3.60(mH), 3.59(1H,dd,J=4.6,13.0 Hz), 3.30 (1H,dd,J=3.5,10.1 Hz), 1.83(2H,m), 1.54(2H,m), 1.26(mH), 0.85(3H,m).

Compound 96

R$_{fα}$:0.52 [hexanes:ethyl acetate, 1:1 (v/v)]
R$_{fβ}$:0.30 [hexanes:ethyl acetate, 1:1 (v/v)]

$^1$H NMR (CDCl$_3$) δ: 8.69 ppm (1H,s), 6.33(1H$_α$,d,J=3.4 Hz), 5.92(2H,m), 5.56(1H$_β$,d,J=8.5 Hz), 5.30(6H,m), 5.02 (1H,m), 4.53(4H,m), 4.31(1H,m), 4.22(2H,m), 3.82(3H,m), 3.71(1H,t,J=8.5 Hz), 3.57(3H$_α$,s), 3.56(3H$_{62}$,s), 3.49(2H, m), 3.25(3H,m), 2.10(2H,m), 2.04(4H,m), 1.88(2H,m), 1.65 (2H,m), 1.56(1H,s), 1.25(rnH), 0.86(6H,m)

Compound 97

$^1$H NMR (CDCl$_3$) δ: 8.74 ppm (1H,s), 6.40(1H$_{1α}$,d),5.59 (1H$_β$,d,J=8.5 Hz), 5.40–5.23(6H,m), 5.0(1H,m), 4.57(4H, m), 4.50(1H$_{4α}$,q), 4.36(1H$_{4β}$,q), 3.80(3H,m), 3.63(3H,m), 3.42(2H,m), 3.30(1H,t,J=9.3 Hz), 2.28(2H,t), 2.08–1.82 (mH), 1.70–1.20(mH), 0.83(9H,m).

Compound A1

$^1$H NMR (CDCl$_3$) δ: 4.96 ppm (1H$_{enone-H}$,S), 4.19(2H,q), 3.74(2H,s), 3.43(2H,s), 2.52(2H,t), 2.17(2H$_{enone\ form}$, t), 1.68–1.51(2H,m), 1.37–1.18(9H,m), 0.88(3H,t).

Compound A2

$^1$H NMR (CDCl$_3$) δ: 4.16 ppm (2H,q), 3.98(1H,m), 2.95(1H,d), 2.52(1H,dd,J=2.9,5.8 Hz), 2.49(2H,dd), 1.55–1.51(2H,m), 1.47–1.37(2H,m), 1.30–1.11(10H,m), 0.87(3H,t).

Compound A3

MP: 105.6°–106.2° C.

$^1$H NMR (CDCl$_3$) δ: 3.86–3.78 ppm (1H,m), 2.96–2.86 (2H,m), 2.33, 2.16(2H,ABX,J=2.4,9.5,15.6 Hz), 2.03–1.94 (4H,br.d), 1.83–1.74(4H,br.d), 1.66–1.60(2H,br.d), 1.54–1.10(22H,m), 0.86(3H,t).

Compound A4

$^1$H NMR (CDCl$_3$) δ: 7.92 ppm (2H,dd,J=1.1,7.7 Hz), 7.63(1H,td,J$_t$=7.6 Hz,J$_d$=1.2 Hz), 7.50(2H,–J=7.7 Hz), 5.49, 5.38(2H,AB,J=16.5 Hz), 4.14(1H,m), 3.50(1H,br.s), 2.69–2.58(2H,ABX,J=2.9,9.4,15.1 Hz), 1.65–1.45(2H,m), 1.4–1.2 (10H,m), 0.88(3H,t)

Compound A5

$^1$H NMR (CDCl$_3$) δ: 7.91 ppm (2H,dd,J=1.2,6.4 Hz), 7.61(1H,td,J$_t$=7.6 HZ,J$_d$=1.2 Hz), 7.50(2H,t,J=7.8 Hz), 5.99–5.89(1H,m), 5.42,5.38(2H,AB,J=15.1 Hz), 5.27(2H, d), 5.24(1H,m), 4.6(2H,dd), 2.83,2.76(2H,ABX,J=5.37, 7.56,21.7 Hz), 1.75–1.65(2H,m), 1.41–1.26(10H,m), 0.87 (3H,t).

Compound A6

$^1$H NMR (CDCl$_3$:CD$_3$OD, 15:1) δ: 5.90 ppm (1H,m), 5.32(2H,dd), 5.19–5.01(1H,m), 4.57(2H,dt), 2.61–2.56(2H, ABX,J=5.37,7.57,19.7 Hz), 1.65–1.55(2H,m), 1.31–1.21 (121)10H,m), 0.82(3H,t).

Compound A7

$^1$H NMR (CDCl$_3$) δ: 4.90 ppm (1H$_{enone-H}$,S), 3.74(3H,s), 3.45(2H,s), 2.52(2H,t), 2.18(2H$_{enone\ form}$,t), 1.62–1.52(2H, m), 1.35–1.20 (8H,m), 0.88(3H,t)

Compound A8

$^1$H NMR (CDCl$_3$) δ: 4.08 ppm (1H,m), 3.71(3H,s), 2.88 (1H,d,J=3.8 Hz), 2.49(1H,dd,J=3.1,16.4 Hz), 2.41(1H,dd,J= 9.1,16.5 Hz), 1.58–1.47(2H,m), 1.44–1.38(2H,m), 1.37–1.23(10H,m), 0.87(3H,t).

Compound A9

$^1$H NMR (CDCl$_3$) δ: 3.91–3.75 ppm (3H,m), 2.62–2.38 (2H$_{OH}$,m), 1.75–1.61(2H,m), 1.55–1.36(2H,m), 1.35–1.23 (10H,m), 0.87(3H,t).

Compound A10

$^1$H NMR (CDCl$_3$) δ: 7.86 ppm (2H,d,J=8.3 Hz), 7.34(2H, d,J=8.1 Hz), 4.27(1H,m), 4.13(1H,m), 3.72(1H,m), 2.44(3H, s), 1.89–1.81(1H,m), 1.68–1.62(2H,m), 1.39–1.25(12H,m), 0.87(3H,t).

$^{13}$C NMR (CDCl$_3$) δ: 144.44 ppm, 132.59, 129.49, 127.49, 67.60, 37.14, 35.86, 31.39, 29.11, 28.83, 25.11, 22.25, 21.26, 13.70.

Compound A11

$^1$H NMR (CDCl$_3$) δ: 3.21 ppm (2H,t), 2.20–2.10(4H,m), 1.93(2H,m), 1.58(2H,rm), 1.46(2H,m), 1.40–1.22(6H,m), 0.88(3H,t).

Compound A12

$^1$H NMR (CDCl$_3$) δ: 7.43 ppm (2H,d), 7.33–7.20(10H, m), 6.84(2H,d), 3.79 (3H,s), 3.74(1H,br.s), 3.38(1H,m), 3.22 (1H,m), 2.98(1H,d,J=2.9 Hz), 1.72(1H,m), 1.56–1.24(10H, m), 0.87(3H,t).

Compound A13

$^1$H NMR (CDCl$_3$) δ: 7.44 ppm (2H,d), 7.33–7.19 (10H, m), 6.82(2H,d), 3.79(3H,s), 3.40(2H,m), 3.28(1H,m), 3.15 (2H,t), 2.11(4H,q), 1.75(2H,q), 1.55–1.25(29H,m), 0.88(6H, t).

Compound A14

$^1$H NMR (CDCl$_3$) δ: 3.80 ppm (2H,m), 3.52(2H,m), 3.42(1H,m), 2.72(1H,m), 2.17(4H,m), 1.80–1.25(26H,m); 0.88(6H,t).

Compound A16

$^1$H NMR (CDCl$_3$) δ: 3.68 ppm (1H,m), 3.48(2H,t), 2.52 (2H,m), 2.14(4H,m), 1.68–1.26(24H,m), 0.87(6H,t).

Compound A17

$^1$H NMR (CDCl$_3$) δ: 5.33 ppm (2H,m), 3.68 (1H,m), 3.52 (2H,m), 2.56(2H,m), 2.02(2H,m), 1.98–1.27(27H,m), 0.88 (6H,t).

Compound A18

$^1$H NMR (CDCl$_3$) δ: 7.80 ppm (2H,d), 7.34(2H,d), 4.05 (2H,t) 2.51(2H,m), 2.45(3H,s), 2.06(2H,m), 1.41(2H,m), 1.27(6H,m), 0.88(3H,t).

Compound A19

$^1$H NMR (CDCl$_3$) δ: 7.84 ppm (2H,m), 7.72(2H,m), 3.83(2H,t), 2.56(2H,m), 2.06(2H,m), 1.34(2H,m), 1.20(6H, m), 0.84(3H,t).

Compound A20

$^1$H NMR (CDCl$_3$) δ: 7.82 ppm (2H,m), 7.71(2H,m), 5.44(1H,m), 5.37(1H,m), 3.72(2H,r), 2.44(2H,q), 1.95(2H, m), 1.18(8H,m), 0.83(3H,t).

Compound A21

$^1$H NMR (CDCl$_3$) δ: 5.48 ppm (1H,m), 5.34(1H,m), 2.71(2H,t), 2.18(2H,q), 2.03(2H,m), 1.27(8H,m), 0.87(3H, t).

Compound A22
$^1$H NMR (CDCl$_3$) δ: 7.91 ppm (2H,d), 7.61(1H,t,J=7.3 Hz), 7.56(2H,t), 5.50(1H,m), 5.35(2H,s), 5.30(1H,m), 5.15 (1H,t), 4.78(1H,t), 3.17(2H,m), 2.74(2H,t), 2.24(2H,t), 2.01 (2H,q), 1.58(2H,m), 1.57(2H,d), 1.26(16H,m), 0.87(6H,t).
Compound A23
$^1$H NMR (CD$_3$OD) δ: 6.85 ppm (1H,m), 5.45(1H,m), 5.32(1H,m), 5.06(2H,m), 4.92(1H,d), 3.15–3.00(mH), 2.45 (2H,t), 2.32(1H,d), 2.20(mH), 2.03(mH), 1.59(mH), 1.28 (mH), 0.85(6H,m).
Compound A24
$^1$H NMR (CDCl$_3$) δ: 7.90 ppm (2H,d), 7.61(1H,t), 7.49 (2H,t), 5.34(2H,s), 5.30(1H,m), 2.74(2H,m), 2.31(2H,t), 1.69–1.57(4H,m), 1.37–1.20(28H,m), 0.88(6H,t).
Compound A25
$^1$H NMR (CDCl$_3$) δ: 5.21 ppm (1H,m), 2.62(2H,m), 2.29(2H,t), 1.61(4H,m), 1.36–1.18(26H,m), 0.89(6H,t).
Compound A26
$^1$H NMR (CDCl$_3$) δ: 3.76 ppm (3H,s), 2.32(2H,t), 1.56 (2H,m), 1.40–1.35(mH), 1.30–1.22(mH), 0.88(3H,t).
Compound A27
$^1$H NMR (CDCl$_3$) δ: 5.65 ppm (1H,s), 3.67(3H,s), 2.61 (2H,t), 1.88 (3H,s), 1.50–1.40 (mH), 1.35–1.20 (H), 0.88 (3H,t)
Compound A28
$^1$H NMR (CDCl$_3$) δ: 5.66 ppm (1H, s), 3.68(3H, s), 2.15(2H,t) 1.50–1.40(mH), 1.34–1.20(mH), 0.88(3H,t).
Compound A29
$^1$H NMR (CDCl$_3$) δ: 5.40 ppm (1H,t,J=7.1 Hz), 4.15(2H, t), 2.00(2H,t), 1.66(3H,s), 1.40–1.20(18H,m), 0.88(3H,t).
Compound A30
$^1$H NMR (CD$_3$OD) δ: 5.64 ppm (1H,s), 4.91(1H,br.s), 2.15(2H,t), 2.11(3H,s), 1.48(4H,m), 1.29(14H,m), 0.89(3H, t).
Compound A31
R$_f$: 0.76 [hexanes:ethyl acetate, 3:2 (v/v)]
$^1$H NMR (CDCl$_3$) δ: 6.02 ppm (1H,s), 2.19(2H,m), 2.13 (3H,s), 1.48(2H,m), 1.26(16H,m), 0.88(3H,t).
Compound B1
$^1$H NMR (CDCl$_3$) δ: 3.30 ppm (2H,m), 2.26(2H,m), 2.13(1H,m), 1.95(1H,m), 1.47(mH), 1.28(mH), 0.88(3H,t).
Compound B2
$^1$H NMR (CDCl$_3$) δ: 2.50 ppm (2H,t), 2.33(2H,m), 2.13 (2H,m), 1.83(2H,m), 1.45(2H,m), 1.30–1.25(6H,m), 0.89 (3H,t)
Compound B3
$^1$H NMR (CDCl$_3$) δ: 2.49 ppm (2H,t), 2.24(2H,m), 2.13 (2H,m), 1.80(2H,m), 1.45(2H,m), 1.37–1.26(6H,m), 0.88 (3H,t).
Compound B4
$^1$H NMR (CDCl$_3$) δ: 5.42 ppm (1t, m), 5.32(1H,m), 2.37(2H,t), 2.10(2H,m), 2.01(2H,M), 1.70(2H,m), 1.28(8H, m), 0.89(3H,t).
Compound B5
$^1$H NMR (CDCl$_3$) δ: 7.90 ppm (2H,d), 7.61(1H,t), 7.49 (2H,m), 5.38(1H,m), 5.30(2H,m), 2.75(2H,m), 2.31(2H,m), 2.06(2H,m), 1.99(2H,m), 1.68(2H,m), 1.27(m,H), 0.88 (6H, t)
Compound B6
$^1$H NMR (CDCl$_3$) δ: 5.38 ppm (1H,m), 5.21(1H,m), 2.61(2H,m), 2.29(2H,t), 2.05(2H,m), 1.99(2H,m), 1.67(2H, m), 1.62(2H,m). 1.26(15H,m), 0.87(6H,t).
Compound C1
$^1$H NMR (CDCl$_3$) δ: 4.19 ppm (2H,q), 3.43(2H,s), 2.52 (2H,m), 1,60(3H,m) 1.29(18H,m), 0.87(3H,t).
Compound C2
R$_f$: 0.35 [hexanes:ethyl acetate, 4:1(v/v)]
$^1$H NMR (CDCl$_3$) δ: 4.16 ppm (2H,q), 3.97(1H,m), 2.46(1H,dd,J=3.2,16.4 Hz), 2.38(1H,dd,J=9.0,16.4 Hz), 1.54–1.10(23H,m), 0.86(3H,t).
Compound C3
$^1$H NMR (CDCl$_3$) δ: 3.84 ppm (1H,m), 2.96(2H, m), 2.36(1H,dd,J=2.7,15.9 Hz), 2.17(1H,dd,J=9.3,15.6 Hz), 2.02(4H,t), 1.78(4H,m), 1.66(2H,m), 1.41(mH), 1.25(mH), 0.87(3H,t).
Compound C4
$^1$H NMR (CDCl$_3$) δ: 7.93 ppm (2H,d), 7.63(1H,s,J=7.3 Hz), 7.50(2H,m), 5.43(2H,q), 4.14(1H,m), 2.70(1H,dd,J= 2.9,14.9 Hz), 2.53(1H,dd,J=9.3,15.1 Hz), 1.40–1.20(20H, m), 0.88(3H,t)
Compound C5
$^1$H NMR (CDCl$_3$) δ: 7.91 ppm (2H,2d), 7.59(1H,t,J=6.5 Hz), 7.49(2H,t), 7.27(2H,d), 6.86(2H,d), 5.33(2H,q), 4.51 (2H,q), 3.94(1H,m), 3.79(3H,s), 2.79(1H,dd,J=7.0,15.2 Hz), 2.66,1H, dd,J=5.5,15.3 Hz), 1.62(2H,m), 1.40–1.26(16H, m), 0.88(3H,t).
Compound C6
$^1$H NMR (CDCl$_3$) δ: 6.87 ppm (4H,2d), 4.50(2H,s), 3.85(1H,p,J=5.9 Hz), 3.79(3H,s), 2.60–2.55(2H,m), 1.69–1.60(1H,m), 1.59–1.50(1H,m), 140–1.18(18H,m), 0.88(3H,t).
Compound C7
$^1$H NMR (CDCl$_3$) δ: 4.15 ppm (2H,q), 3.05(4H,m), 2.70(2H,m) 2.04(3H,m), 1.87(1H,m), 1.31–1.21(21H,m), 0.87(3H,t).
Compound C8
$^1$H NMR (CDCl$_3$) δ: 3.12 ppm (2H,s), 3.03(2H,t), 2.76 (2H,t), 2.13–2.01(mH), 1.89(mH), 1.54(mH), 1.26(mH), 0.88(3H,t).
Compound D1
$^1$H NMR (CDCl$_3$) δ: 7.36 ppm (5H,s), 5.17(2H,s), 3.48 (2H,s), 2.50(2H,t), 1.56(6H,s), 1.24(12H,m), 0.88(3H,t).
Compound D2
$^1$H NMR (CDCl$_3$) δ:3.52 ppm (2H,s), 2.56(2H,t), 1.16 (2H,m), 1.25(14H,m), 0.88(3H,t).
Compound E1
$^1$H NMR (CDCl$_3$) δ: 3.74 ppm (3H,s), 3.22(2H,s), 2.62 (2H,t), 1.59(2H,m), 1.35(2H,m), 1.25(14H,m), 0.88(3H,t).
Compound E2
$^1$H NMR (CDCl$_3$) δ: 3.80 ppm (3H,s), 3.68(2H,m), 2.82 (2H,m), 1.77(2H,m), 1.50–1.40(2H,m), 1.26(14H,m), 0.88 (3H,t).
Compound E3
$^1$H NMR (CDCl$_3$) δ: 3.84 ppm (1H,d,J=14.6 Hz), 3.49 (1H,d,J=14.4 Hz), 3.08–3.03(1H,m), 2.89–2.81(1H,m), 1.79–1.74(2H,m), 1.51–1.40(2H,m), 1.35–1.25(14H,m), 0.88(3H,t).
Compound E4
$^1$H NMR (CDCl$_3$) δ: 3.80 ppm (3H,s), 3.68(2H,m), 2.84 (2H,m), 1.77(2H,m), 1.50–1.40(2H,m), 1.26(14H,m), 0.88 (3H,t).
Compound E5
$^1$H MMR (CDCl$_3$) δ: 3.82–3.68 ppm (2H,m), 3.07–2.86 (2H,m), 1.75(2H,m), 1.45(2H,m), 1.29(mH), 0.87(3H,t).
Compound E6
$^1$H NMR (CDCl$_3$) δ: 3.96 ppm (2H,s), 3.82(3H,s), 3.24 (2H,m), 1.86(2H,m), 1.44(mH), 1.25(mH), 0.87(3H,t).
Compound E7
R$_f$: 0.33 [methylene chloride:methyl alcohol, 19:1 (v/v)]
$^1$H NMR (CDCl$_3$) δ: 4.01 ppm (2H,s), 3.27(2H,m), 1.87 (2H,m), 1.47–1.26(16H,m), 0.88(3H,t).
Compound G1
$^1$H NMR (CDCl$_3$) δ: 4.19 ppm (2H,q), 3.45(2H,s), 2.67 (2H,t), 2.20(2H,m), 2.12(2H,m), 1.76(2H,m), 1.45(2H,m), 1.35–1.25(9H,m), 0.88(3H,t).

Compound G2

$^1$H NMR (CDCl$_3$) δ: 4.21 ppm (2H,m), 3.06(2H,m), 2.94(2H,q), 2.20–2.01(mH), 1.80–1.50(mH), 1.48–1.43 (mH), 1.39–1.22(mH), 0.88(3H,t).

EXAMPLE 3

In Vitro Inhibition of LPS-Induced Production of Tumor Necrosis Factor (TNF) and IL-1β

Both bacterial LPS and bacterial lipid A elicit production of tumor necrosis factor (TNF) and IL-1β in cultured human monocytes (*J. Immunol.* 13:429, 1987). The lipid A analogs described herein inhibit such LPS- and/or lipid A-mediated induction as demonstrated by the following experiments.

Monocytes were isolated from human blood by Percoll density gradient centrifugation, plated at approximately 1×10$^6$ cells/well on a 48-well plate in RPMI 1640 medium (GIBCO, Grand Island, N.Y.) containing 10% human serum (Sigma Chemical Co., St. Louis, Mo.), and incubated for two to three hours. Bacterial LPS (i.e., from *E. coli* 0111:B4; Sigma Chemicals, St. Louis, Mo.) at 10 ng/ml or lipid A (Daiichi Chemicals, Tokyo, Japan) at 1.0 ng/ml in RPMI 1640 medium were combined with 0.45 ml of RPMI 1640 medium containing 1% human serum and added to the cultured monocytes. In experiments involving a lipid A analog, the analog was added immediately before addition of LPS or lipid A in varying concentrations (e.g., between 0 and 100 μM in a 50 μl aliquot). Following a three-hour incubation period, a 0.1 ml aliquot of the culture supernatant was assayed for the presence of TNF and IL-1β. TNF and IL-1β were assayed using the ELISA assay of R & D Systems (Minneapolis, Minn.) and the instructions of the manufacturer, however, any other standard ELISA kits may be utilized, for example, the kit available from Genzyme, Cambridge, Mass.. Experiments were performed in triplicate.

The lipid A analogs inhibited LPS-induced production of TNF in human monocytes in a concentration dependent manner. Of the lipid A analogs tested, Lipid A Analog B531–35 was found to be one of the most effective compounds to inhibit LPS-induced production of TNF, exhibiting an ED50 of approximately 0.02 nM. Other lipid A analogs found to inhibit LPS-induced TNF production included B214–32, B410–32, B442–32, B451–32, B452–32, B427–32, B459–32, B460–32, B464–32, B464–34, B464–35, B465–32 B466–32, B477–32, B477–35, B718–35, B587–35, B737–35, B736–35, B725–35, and B763–35; these compounds exhibited ED$_{50}$s of between 0.03 nM and 129 nM.

Lipid A analogs similarly inhibited the LPS-induced production of IL-1β in human monocytes. LPS was added at 10 ng/ml, and lipid A analogs were added at a concentration of between 0 and 10 μM. Inhibition of IL-1β production was also found to be concentration dependent.

In a separate set of experiments, LPS-induced TNF production was inhibited by lipid A analogs in macrophages isolated from guinea pigs and mice. Hartley-white guinea pig (Elm Hill Breeders, Chelmsford, Mass.) and C57BL/6 mouse (Jackson Labs, Bar Harbor, Me.) macrophages were isolated from the abdomen of primed animals. Priming was accomplished by intraperitoneal injection of 2 mg of Bacillus calmette guerin (BCG; RIBI Immunochemical Research, Inc., Hamilton, Mont.) at a concentration of 10 mg/ml in physiological saline for mice and 2 mg of BCG at a concentration of 2 mg/7 ml in mineral oil for guinea pigs. Three days post-injection, peritoneal macrophages were isolated from the abdomen of the animals by standard techniques. Cells were allowed to adhere to culture plates for two to three hours and were then contacted with RPMI 1640 medium containing 10% fetal calf serum and LPS (at 10 ng/ml). To test inhibition, lipid A analogs (at a concentration of between 0 and 100 μM) were added to the culture medium just prior to LPS addition. Following a three-hour incubation period, guinea pig and mouse TNF levels were assayed by the cytolytic bioassay described in *Lymphokines* 2:235, 1981. Lipid A analogs B214–32, B410–32, B442–32, B451–32, B452–32, B427–32, B459–32, B460–32, B464–32, B464–34, B464–35, B465–32, B466–32, B477–32, B477–35, and B718–35 (all analogs tested to date) similarly inhibited LPS-induced TNF production in both guinea pigs and mice. Analogs B464–34 and B531–35 provided the most effective inhibition in guinea pigs (ED$_{50'_s}$=0.04 nM and 0.66 nM, respectively); analogs B477–32 and B531–35 provided very effective inhibition in mice (ED$_{50'_s}$=1.3 nM and 2.26 nM, respectively). Lipid A analogs B214–32, B410–32, B442–32, B451–32, B452–32, B427–32, B459–32, B460–32, B464–32, B464–34, B464–35, B465–32, B466–32, B477–32, B477–35, and B718–35 (all analogs tested to date) inhibited LPS-induced TNF production. ED$_{50'_s}$ measured in the experiments involving guinea pig macrophages ranged from approximately 0.04 nM to 18.5 nM. ED$_{50'_s}$ measured in the experiments involving mouse macrophages ranged from approximately 1.0 nM to 1.0 μM.

EXAMPLE 4

In Vivo Assays

BCG-primed mice (as described above) were utilized as an in vivo assay system for monitoring the inhibitory effects of lipid A analogs on (1) LPS-induced TNF production and (2) LPS-induced lethality as follows.

Five week old male C57BL/6 mice (supra) were primed by intravenous tail vein injection with 2 mg of BCG. Ten days post-injection, *E. coli* LPS (supra) in pyrogen-free 5% glucose solution (Otsuka Pharmaceuticals Inc., Tokyo, Japan) was administered intravenously through the tail vein of the BOG-primed mice. LPS was administered at a concentration of 1–3 μg/mouse for both TNF production and mortality studies. In experiments involving a lipid A analog, the analog was administered as a component of the injected LPS solution at a concentration of between 10 and 300 μg/mouse. Plasma was obtained one hour post-LPS injection, and TNF was assayed by the ELISA assay described above. Mortality resulting from septic shock was recorded for 36 hours post-LPS injection.

Lipid A analogs effectively suppressed the production of TNF following administration of LPS. Analogs B318–32 and B531–35 effectively inhibited TNF production in vivo in mice (ED$_{50'_s}$=5.4 μg/mouse and 16.2 μg/mouse, respectively). Analogs B214–31, B214–32, B214–33, B218–32, B231–32, B235–32, B262–32, B274–32, B278–32, B286–32, B294–32, B313–32, B314–32, B318–32, B379–32, B380–32, B398–32, B399–32, B400–32, B406–32, 410 B415–32, B425–32, and B426–32 also inhibited TNF production.

In parallel experiments carried out in guinea pigs, these analogs were also effective inhibitors of LPS-induced TNF production in vivo (optimum ED$_{50'_s}$ =7.5 μg/guinea pig and 5 μg/guinea pig measured for analog B214–32).

EXAMPLE 5

Lipid A Analogs Suppress LPS-Stimulated Virus Production

LPS potently stimulates the production of viruses which reside (in their latent phase) in monocytes or macrophages (see, e.g., Pomerantz et al., *J. Exp. Med.* 127:253, 1990; Masihi et al., *J. of Acquired Imm. Deficiency Syndromes* 3:200, 1990). In the case of HIV-1, increased viral production likely results from activation of cells by both a direct activation by LPS and the LPS-mediated elevation in TNF-α levels. Cellular activation promotes increased binding of trans-acting factors to the HIV-1NF-κB binding site; this, in turn, leads to increased viral transcription and replication (see, e.g., Duh et al., *Proc. Natl. Acad. Sci. USA* 85:5974, 1989).

The lipid A analogs described herein inhibited an LPS-mediated increase in HIV-1 replication. This was demonstrated using an in vitro model system which monitored HIV-1 long terminal repeat (LTR) transcription. Because activation of the transcriptional enhancer of the HIV-1 long terminal repeat (LTR) has been correlated with viral replication (Colman et al., *AIDS* 2:185, 1988;Nabel and Baltimore, *Nature* 325:711, 1987), the assay provides a reliable measure of viral replication, and hence virus production.

Plasmid HIV-1-LTR-CAT (Pomerantz et al., 1990, supra), a construct which includes the HIV-1 LTR fused, in frame, to the chloramphenicol acetyltransferase (CAT) gene, was propagated in HB-101 cells (Gibco-BRL, Grand Island, N.Y.). Plasmid was purified from host cell extract using a Qiagen affinity column and the instructions of the manufacturer (Qiagen Inc., Chatsworth, Calif.) and transiently transfected into U937 cells (ATCC Accession No. CRL 1593; American Type Culture Collection; Rockville, Md.) generally by the method of Pomerantz et al. (1990, supra), except that 80 μM chloroquine (Promega Biotech, Madison, Wis.) was present throughout the transfection procedure, and $10^6$ U937 cells were transfected with either 20 μg of HIV-1-LTR-CAT or 10 μg of pCAT (i.e., a control plasmid carrying only the CAT gene; Promega Biotech, Madison, Wis.). Twenty-four hours post-transfection, cells were incubated with or without a lipid A analog (typically at a concentration of between of 0.0 and 1.0 μM). Following a 30 minute incubation phorbol myristate acetate (PMA; Sigma Chemical Co., St. Louis, Mo.) at 50 ng/ml and *E. coli* 0111:B4 LPS (described above) at 100 ng/ml were added to the cells, and incubation was allowed to proceed for an additional 24 hours. Cells were then harvested and lysed as described in Ausubel et al. (*Current Protocols in Molecular Biology*, John Wiley & Sons, New York, N.Y., 1987), extract protein concentration was determined using the Micro BCA Protein Assay System of Pierce Chemical Co. (Rockford, Ill.), and CAT activity assayed as the rate of acetylation of chloramphenicol (in DPM/min) as described in *Biotech Update* 5(2):28 (Novel Fluor Diffusion CAT Assay Facilitates Sample Processing and Analysis, DuPont Co. Publication, Biotechnology Systems, Wilmington, Del.). Lipid A analog B398–32 inhibited the LPS-mediated induction of LTR-CAT transcription with an average $IC_{50}$ of 85 nM.

Similar results were obtained using U937 cell lines stably transfected with an HIV-1 LTR-CAT fusion gene. Experiments were carried out using one such stably-transfected cell line, i.e., the U938 cell line of Latham et al. (*Cell. Immunol.* 129:513, 1990). Cells were cultured as described in Latham et al. (1990, supra), and $10^6$ cells were treated with a lipid A analog (at a concentration of between 0.0 and 1.0 μM). Thirty minutes after addition of the analog, cells were treated with phorbol myristate acetate (at a concentration of 0.33 ng/ml; described above) and *E. Coli* 0111:B4 LPS (at a concentration of 33 ng/ml; described above). Cells were cultured for an additional 24 hours, harvested, and assayed for CAT activity as described above. Results indicate that B477 suppresses the LPS-stimulated activation of the HIV LTR at an $IC_{50}$ of 15 nM. Analogs B398–32, B400–32, B427–32, B464–32, and B466–32, similarly suppressed LPS-stimulated HIV LTR activation with $IC_{50}$s ranging from 15 to 260 nM. B464–32 similarly inhibited activation of the HIV-LTR mediated by the LPS of other Gram-negative bacteria (for example, Salmonella typhimurium).

NF-κB-regulated transcriptional control is not unique to HIV-1. Other viral genomes, including that of Simian Virus-40 (SV-40), include an NF-κB binding site within an enhancer element of its early promoter (Nakamura et al., *J. Biol Chem.* 264:20189, 1989). A plasmid construct containing an SV40 promoter enhancer-CAT fusion gene, termed pCAT (Promega Biotech), was transiently transfected into U937 cells as described above. $10^6$ cells/plate were treated with a lipid A analog (at a concentration of 0.0, 0.1, or 1.0 μM). Thirty minutes after addition of the analog, cells were treated with phorbol myristate acetate (at a concentration of 50 ng/ml) and *E. coli* 0111:B4 LPS (at a concentration of 100 ng/ml). Cells were cultured for an additional 24 hours, harvested, and assayed for CAT activity as described above. LPS-stimulated CAT expression was inhibited or completely blocked by lipid A analog B398–32. In another "Experiment 4", LPS-stimulated CAT expression was inhibited or completely blocked by lipid A analog B466–32. These results indicated that the lipid A analogs described herein effectively suppressed the LPS-mediated increase in SV-40 replication.

The lipid A analogs described herein may similarly suppress the activation of any-virus whose replication is directly or indirectly controlled by an NF-κB regulatory region. Such viruses include, without limitation, cytomegaloviruses or Herpes viruses (e.g., *Herpes simplex*). In addition, because influenza virus activation (in monocytes and macrophages) is potentiated by LPS (Nain et al., *J. Immunol.* 145:1921, 1990) and an enhanced release of TNF-α has been implicated in observed complications of combined influenza A and bacterial infections, the instant lipid A analogs are likely to suppress influenza virus activation as well.

THERAPY

The lipid A analogs described herein provide useful therapeutics for the treatment or prevention of any LPS-mediated disorder. Such disorders include without limitation:endotoxemia (or sepsis syndrome) resulting from a Gram⁻ bacteremia (with its accompanying symptoms of fever, generalized inflammation, disseminated intravascular coagulation, hypotension, acute renal failure, acute respiratory distress syndrome, hepatocellular destruction, and/or cardiac failure); and LPS-mediated exacerbation of latent or active viral infections (e.g., infection with HIV-1, cytomegaloviruses, herpes simplex viruses, and influenza virus).

The lipid A analog is typically administered in a pharmaceutically-acceptable formulation, e.g., dissolved in physiological saline or physiological saline which may include 5% glucose (for the purpose of increased analog solubility). Administration is by any appropriate route, but, ordinarily, it will be administered intravenously, either by intravenous injection or transfusion. When lipid A analog is provided for the treatment of a viral infection, it may be administered in conjunction with appropriate viricidal agents. The lipid A analogs may be stored as a freeze-dried formulation.

Lipid A analogs are administered in dosages which provide suitable inhibition of LPS activation of target cells; generally, these dosages are, preferably, between 0.001–500 mg/patient, more preferably, between 0.01–100 mg/patient.

What is claimed is:

1. A method for treating sepsis in a mammal, said method comprising administering to said mammal a therapeutic composition containing a compound having the formula:

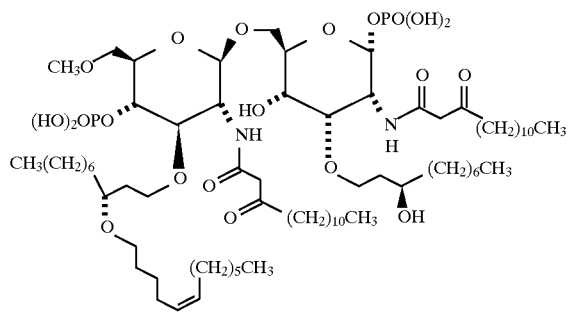

or a pharmaceutically-acceptable salt thereof.

* * * * *